US007288251B2

(12) United States Patent
Bedian et al.

(10) Patent No.: US 7,288,251 B2
(45) Date of Patent: Oct. 30, 2007

(54) ANTIBODIES TO CD40

(75) Inventors: Vahe Bedian, East Lyme, CT (US);
Ronald P. Gladue, Stonington, CT (US); Jose Corvalan, Foster City, CA (US); Xiao-Chi Jia, San Mateo, CA (US); Xiao Feng, Union City, CA (US)

(73) Assignees: Abgenix, Inc., Fremont, CA (US);
Pfizer Inc., New York, NY (US)

( * ) Notice: Subject to any disclaimer, the term of this patent is extended or adjusted under 35 U.S.C. 154(b) by 669 days.

(21) Appl. No.: 10/292,088

(22) Filed: Nov. 8, 2002

(65) Prior Publication Data
US 2003/0211100 A1 Nov. 13, 2003

Related U.S. Application Data

(60) Provisional application No. 60/348,980, filed on Nov. 9, 2001.

(51) Int. Cl.
*A61K 39/395* (2006.01)
*C07K 16/28* (2006.01)

(52) U.S. Cl. .............................. 424/153.1; 424/130.1; 424/133.1; 424/141.1; 424/143.1; 424/144.1; 424/173.1; 530/387.1; 530/387.3; 530/388.2; 530/388.22; 530/388.7; 530/388.73

(58) Field of Classification Search ............... None
See application file for complete search history.

(56) References Cited

U.S. PATENT DOCUMENTS

| | | | |
|---|---|---|---|
| 4,399,216 A | 8/1983 | Axel et al. ....................... 435/6 |
| 4,510,245 A | 4/1985 | Cousens et al. .......... 435/172.3 |
| 4,634,665 A | 1/1987 | Axel et al. ..................... 435/68 |
| 4,740,461 A | 4/1988 | Kaufman ...................... 435/68 |
| 4,912,040 A | 3/1990 | Kaufman et al. ........... 435/69.6 |
| 4,959,455 A | 9/1990 | Clark et al. .................. 530/351 |
| 4,968,615 A | 11/1990 | Koszinowski et al. ... 435/172.3 |
| 5,151,510 A | 9/1992 | Stec et al. ..................... 536/27 |
| 5,168,062 A | 12/1992 | Stinski ..................... 435/240.2 |
| 5,179,017 A | 1/1993 | Axel et al. ............... 435/240.2 |
| 5,223,409 A | 6/1993 | Ladner et al. .............. 435/69.7 |
| 5,545,806 A | 8/1996 | Lonberg et al. ................. 800/2 |
| 5,545,807 A | 8/1996 | Surani et al. .................... 800/2 |
| 5,569,825 A | 10/1996 | Longberg et al. .............. 800/2 |
| 5,587,458 A | 12/1996 | King et al. ................. 530/387.3 |
| 5,591,669 A | 1/1997 | Krimpenfort et al. .......... 800/2 |
| 5,612,205 A | 3/1997 | Kay et al. ................. 435/172.3 |
| 5,625,126 A | 4/1997 | Lonberg et al. ................. 800/2 |
| 5,633,425 A | 5/1997 | Lonberg et al. ................. 800/2 |
| 5,643,763 A | 7/1997 | Dunn et al. ................. 435/91.1 |
| 5,661,016 A | 8/1997 | Lonberg et al. .......... 435/172.3 |
| 5,677,165 A | 10/1997 | de Boer et al. |
| 5,721,367 A | 2/1998 | Kay et al. ....................... 800/2 |
| 5,741,957 A | 4/1998 | Deboer et al. .................. 800/2 |
| 5,747,498 A | 5/1998 | Schnur et al. ............... 514/259 |
| 5,750,172 A | 5/1998 | Meade et al. ................ 426/580 |
| 5,756,687 A | 5/1998 | Denman et al. ............. 530/412 |
| 5,770,429 A | 6/1998 | Lonberg et al. .......... 435/240.2 |
| 5,789,215 A | 8/1998 | Berns et al. .............. 435/172.3 |
| 5,789,650 A | 8/1998 | Lonberg et al. ................. 800/2 |
| 5,792,783 A | 8/1998 | Tang et al. ................... 514/397 |
| 5,814,318 A | 9/1998 | Lonberg et al. ........... 424/184.1 |
| 5,827,690 A | 10/1998 | Meade et al. ............... 435/69.6 |
| 5,834,504 A | 11/1998 | Tang et al. ................... 514/418 |
| 5,861,510 A | 1/1999 | Piscopio et al. ............. 544/131 |
| 5,863,949 A | 1/1999 | Robinson et al. ........... 514/575 |
| 5,874,082 A | 2/1999 | de Boer |
| 5,877,305 A | 3/1999 | Huston et al. ............ 536/23.53 |
| 5,883,113 A | 3/1999 | Tang et al. ................... 514/418 |

(Continued)

FOREIGN PATENT DOCUMENTS

EP 0 216 846 4/1987

(Continued)

OTHER PUBLICATIONS

Bendig, Methods: A Companion to Methods in Enzymology 8: 83-93, 1995.*

(Continued)

*Primary Examiner*—Phillip Gambel
(74) *Attorney, Agent, or Firm*—Jane T. Gunnison; Z. Ying Li; Ropes & Gray LLP

(57) ABSTRACT

The present invention relates to antibodies and antigen-binding portions thereof that specifically bind to CD40, preferably human CD40, and that function as CD40 agonists. The invention also relates to human anti-CD40 antibodies and antigen-binding portions thereof. The invention also relates to antibodies that are chimeric, bispecific, derivatized, single chain antibodies or portions of fusion proteins. The invention also relates to isolated heavy and light chain immunoglobulins derived from human anti-CD40 antibodies and nucleic acid molecules encoding such immunoglobulins. The present invention also relates to methods of making human anti-CD40 antibodies, compositions comprising these antibodies and methods of using the antibodies and compositions for diagnosis and treatment. The invention also provides gene therapy methods using nucleic acid molecules encoding the heavy and/or light immunoglobulin molecules that comprise the human anti-CD40 antibodies. The invention also relates to transgenic animals comprising nucleic acid molecules of the present invention.

22 Claims, 19 Drawing Sheets

U.S. PATENT DOCUMENTS

| | | | |
|---|---|---|---|
| 5,886,020 A | 3/1999 | Tang et al. ................. | 514/418 |
| 5,916,771 A | 6/1999 | Hori et al. ................. | 435/69.6 |
| 5,939,598 A | 8/1999 | Kucherlapati et al. ........ | 800/25 |
| 5,959,177 A | 9/1999 | Hein et al. .................. | 800/288 |
| 5,985,615 A | 11/1999 | Jakobovits et al. ........ | 435/69.6 |
| 5,994,619 A | 11/1999 | Stice et al. .................... | 800/21 |
| 5,998,209 A | 12/1999 | Jokobovits et al. ........ | 435/463 |
| 6,046,037 A | 4/2000 | Hiatt et al. ................ | 435/70.1 |
| 6,051,228 A | 4/2000 | Aruffo et al. | |
| 6,075,181 A | 6/2000 | Kucherlapati et al. ........ | 800/25 |
| 6,091,001 A | 7/2000 | Jakobovits et al. ........... | 800/18 |
| 6,114,598 A | 9/2000 | Kucherlapati et al. ........ | 800/18 |
| 6,130,364 A | 10/2000 | Jakobovits et al. ............ | 800/6 |
| 6,150,584 A | 11/2000 | Kucherlapati et al. ........ | 800/18 |
| 6,162,963 A | 12/2000 | Kucherlapati et al. ........ | 800/18 |
| 6,312,693 B1 | 11/2001 | Aruffo et al. ............ | 424/154.1 |
| 6,417,429 B1 | 7/2002 | Hein et al. .................. | 800/288 |
| 6,440,418 B1 | 8/2002 | Black et al. | |
| 6,482,411 B1* | 11/2002 | Ahuja et al. ............. | 424/185.1 |
| 6,517,529 B1 | 2/2003 | Quinn ........................ | 604/528 |
| 6,713,610 B1* | 3/2004 | Kucherlapati et al. . | 530/388.23 |
| 6,843,989 B1* | 1/2005 | Siegall et al. ............ | 424/130.1 |
| 2001/0026932 A1* | 10/2001 | Thomas et al. .......... | 435/70.21 |
| 2002/0142358 A1 | 10/2002 | Mikayama et al. | |
| 2003/0059427 A1 | 3/2003 | Force et al. | |
| 2003/0118588 A1* | 6/2003 | Diehl et al. .............. | 424/144.1 |

FOREIGN PATENT DOCUMENTS

| | | |
|---|---|---|
| EP | 0 256 055 | 2/1988 |
| EP | 0 323 997 | 7/1989 |
| EP | 0 338 841 | 10/1989 |
| EP | 0 606 046 | 7/1994 |
| EP | 0 780 386 | 6/1997 |
| EP | 0 818 442 | 1/1998 |
| EP | 0 931 788 | 7/1999 |
| EP | 0 945 864 | 9/1999 |
| EP | 1 004 578 | 5/2000 |
| JP | 8012700 A | 1/1996 |
| RU | 2000 124084 | 9/2000 |
| RU | 2000 109255 | 1/2002 |
| WO | WO90/05719 | 5/1990 |
| WO | WO91/10741 | 7/1991 |
| WO | WO91/17271 | 11/1991 |
| WO | WO92/01047 | 1/1992 |
| WO | WO92/09690 | 6/1992 |
| WO | WO92/15679 | 9/1992 |
| WO | WO92/18619 | 10/1992 |
| WO | WO92/20791 | 11/1992 |
| WO | WO93/01288 | 1/1993 |
| WO | WO93/06213 | 4/1993 |
| WO | WO94/02602 | 2/1994 |
| WO | WO95/09653 | 4/1995 |
| WO | WO95/19970 | 7/1995 |
| WO | WO95/21613 | 8/1995 |
| WO | WO96/27583 | 9/1996 |
| WO | WO96/33172 | 10/1996 |
| WO | WO96/33735 | 10/1996 |
| WO | WO96/34096 | 10/1996 |
| WO | WO97/13760 | 4/1997 |
| WO | WO97/22596 | 6/1997 |
| WO | WO97/32856 | 9/1997 |
| WO | WO98/02434 | 1/1998 |
| WO | WO98/02437 | 1/1998 |
| WO | WO98/02438 | 1/1998 |
| WO | WO98/03516 | 1/1998 |
| WO | WO98/07697 | 2/1998 |
| WO | WO98/14451 | 4/1998 |
| WO | WO98/16654 | 4/1998 |
| WO | WO98/24893 | 6/1998 |
| WO | WO98/30566 | 7/1998 |
| WO | WO98/33768 | 8/1998 |
| WO | WO98/34915 | 8/1998 |
| WO | WO98/34918 | 8/1998 |
| WO | WO98/50356 | 11/1998 |
| WO | WO98/50433 | 11/1998 |
| WO | WO98/52976 | 11/1998 |
| WO | WO98/54093 | 12/1998 |
| WO | WO99/07675 | 2/1999 |
| WO | WO99/10349 | 3/1999 |
| WO | WO99/16755 | 4/1999 |
| WO | WO99/24440 | 5/1999 |
| WO | WO99/29667 | 6/1999 |
| WO | WO99/35132 | 7/1999 |
| WO | WO99/35146 | 7/1999 |
| WO | WO99/45031 | 9/1999 |
| WO | WO99/52889 | 10/1999 |
| WO | WO99/52910 | 10/1999 |
| WO | WO99/53049 | 10/1999 |
| WO | WO99/61057 A2 | 12/1999 |
| WO | WO99/61422 | 12/1999 |
| WO | WO99/62890 | 12/1999 |
| WO | WO 00/09560 | 2/2000 |
| WO | WO 00/34317 | 6/2000 |
| WO | WO 00/37504 | 6/2000 |
| WO | WO 01/56603 | 8/2001 |
| WO | WO 01/83755 | 11/2001 |

OTHER PUBLICATIONS

Albert et al., "Dendritic cells acquire antigen from apoptotic cells and induce class I-restricted CTLS," *Nature*, 392:86-89 (1998).

Alderson et al., "CD40 expression by human monocytes: regulation by cytokines and activation of monocytes by the ligand for CD40," *The Journal of Experimental Medicine*, 178:669-674 (1993).

Altenburg et al., "CD40 ligand-CD40 interaction induces chemokines in cervical carcinoma cells in synergism with IFN-$\gamma$," *The Journal of Immunology*, 162:4140-4147 (1999).

Altschul et al., "Basic local alignment search tool," *Journal of Molecular Biology*, 215(1):403-410 (1990).

Altschul et al., "Gapped BLAST and PSI-BLAST: a new generation of protein database search programs," *Nucleic Acids Research*, 25(17):3389-402 (1997).

Armant et al., "Functional CD40 ligand expression on T lymphocytes in the absence of T cell receptor engagement: involvement in interleukin-2-induced interleukin-12 and interferon-$\gamma$ production," *European Journal of Immunology*, 26:1430-1434 (1996).

Banchereau et al., "Functional CD40 antigen on B cells, dendritic cells and fibroblasts," *Dendritic Cells in Fundamental and Clinical Immunology*, 2:79-83 (1995).

Barbas et al., "Assembly of combinatorial antibody libraries on phage surfaces: The gene III site," *PNAS*, 88:7978-7982 (1991).

Bennetti et al., "Help for cytotoxic-T-cell responses is mediated by CD40 signalling," *Nature*, 393:478-480 (1998).

Bennett et al., "Induction of a $CD8^+$ cytotoxic T lymphocyte response by cross-priming requires cognate $CD4^+$ T cell help," *Journal of Experimental Medicine*, 186:65-70 (1997).

Bird et al., "Single-chain antigen-binding proteins," *Science*, 242:423-426 (1988).

Bowie et al., "A method to identify protein sequences that fold into a known three-dimensional structure," *Science*, 253:164-170 (1991).

Brossart et al., "Generation of functional human dendritic cells from adherent peripheral blood monocytes by CD40 ligation in the absence of granulocyte-macrophage colony-stimulating factor," *Blood*, 92(11):4238-4247 (1998).

Buhlmann et al., "In the absence of a CD40 signal, B cells are tolerogenic," *Immunity*, 2:645-653 (1995).

Carbone et al., "A new mechanism of NK cell cytotoxicity activation: the CD40-CD40 ligand interaction," *The Journal of Experimental Medicine*, 185(12):2053-2060 (1997).

Caux et al., "Activation of human dendritic cells through CD40 cross-linking," *The Journal of Experimental Medicine*, 180:1263-1272 (1994).

Cella e al., "Ligation of CD40 on dendritic cells triggers production of high levels of interleukin-12 and enhances T cell stimulatory capacity: T-T help via APC activation," *The Journal of Experimental Medicine*, 184:747-52 (1996).

Chaussabel et al., "CD40 ligand prevents *Trypanosoma cruzi* infection through interleukin-12 Upregulation," *Infection and Immunity*, 67:1929-1934 (1999).

Chothia et al., "Canonical structures for the hypervariable regions of immunoglobulins," *Journal of Molecular Biology*, 196:901-917 (1987).

Chothia et al., "Conformations of immunoglobulin hypervariable regions," *Nature*, 342:877-883 (1989).

Clackson et al., "Making antibody fragments using phage display libraries," *Nature*, 352:624-628 (1991).

Deckers et al., "IL-4 and IL-13 augment cytokine- and CD40-induced RANTES production by human renal tubular epithelial cells in vitro," *Journal of the American Society of Nephrology*, 9:1187-1193 (1998).

Denfeld et al., "CD40 is functionally expressed on human keratinocytes," *European Journal of Immunology*, 26:2329-2234 (1996).

Diehl et al., "CD40 activation in vivo overcomes peptide-induced peripheral cytotoxic T-lymphocyte tolerance and augments anti-tumor vaccine efficacy," *Nature Medicine*, 5(7):774-779 (1999).

Donepudi et al., "Signaling through CD40 enhances cytotoxic T lymphocyte generation by CD8$^+$ T cells from mice bearing large tumors," *Cancer Immunology Immunotherapy*, 48:153-164 (1999).

Evans et al., "Design of nonpeptidal ligands for a peptide receptor: cholecystokinin antagonists," *Journal of Medicinal Chemistry*, 30:1229-1239 (1987).

Fauchere, "Elements for the rational drug design of peptides drugs," *Advances in Drug Research*, 15:29-69 (1986).

Ferlin et al., "The induction of a protective response in *Leishmania major*-infected BALB/c mice with anti-CD40 mAb," *European Journal of Immunology*, 28:525-531 (1998).

Flores-Romo et al., "Anti-CD40 antibody stimulates the VLA-4-dependent adhesion of normal and LFA-1-deficient B cells to endothelium," *Immunology*, 79:445-451 (1993).

Flores-Romo et al., "CD40 ligation on human cord blood CD34$_+$ hematopoietic progenitors induces their proliferation and differentiation into functional dendritic cells," *The Journal of Experimental Medicine*, 185(2):341-349 (1997).

Foy et al., "Immune regulation by CD40 and its ligand GP39," *Annual Review of Immunology*, 14:591-617 (1996).

French et al., "CD40 antibody evokes a cytotoxic T-cell response that eradicates lymphoma and bypasses T-cell help," *Nature Medicine*, 5(5):548-553 (1999).

Fuchs et al., "Targeting recombinant antibodies to the surface of *Escherichia coli*: fusion to a peptidoglycan associated lipoprotein," *Biotechnology*, 9:1369-1372 (1991).

Funakoshi et al., "Differential in vitro and in vivo antitumor effects mediated by anti-CD40 and anti-CD20 monoclonal antibodies against human B-cell lymphomas," *Journal of Immunotherapy with Emphasis on Tumor Immunology*, 19(2):93-101 (1996).

Galfre et al., "Preparation of monoclonal antibodies: stratgies and procedures," *Methods in Enzymology*, 73:3-46 (1981).

Garrard et al., "$F_{AB}$ assembly and enrichment in a monovalent phage display system," *Biotechnology*, 9:1373-1377 (1991).

Gonnet et al., "Exhaustive matching of the entire protein sequence database," *Science*, 256:1443-1445 (1992).

Gram et al., "In vitro selection and affinity maturation of antibodies from a naive combinatorial immunoglobulin library," *PNAS*, 89:3576-3580 (1992).

Grammer et al., "TNF receptor-associated factor-3 signaling mediates activated of p38 and Jun N-terminal kinase, cytokine, secretion, and Ig production following ligation of CD40 on human B cells," *Journal of Immunology*, 161(3):1183-1193 (1998).

Green et al., "Antigen-specific human monoclonal antibodies from mice engineered with human lg heavy and light chain YACs," *Nature Genetics*, 7:13-21 (1994).

Green et al., "Regulation of B cell development by variable gene complexity in mice reconstituted with human immunoglobulin yeast artificial chromosomes," *Journal of Experimental Medicine*, 188(3):483-495 (1998).

Grewal et al., "CD40 and CD154 in cell-mediated immunity," *Annual Review of Immunology*, 16:111-135 (1998).

Grewal et al., "Impairment of antigen-specific T-cell priming in mice lacking CD40 ligand," *Nature*m 378(7):617-620 (1995).

Grewal et al., "Requirement for CD40 ligand in costimulation induction, T cell activation, and experimental allergic encephalomyelitis," *Science*, 273:1864-2867 (1996).

Griffiths et al., "Human anti-self antibodies with high specificity from phage display libraries," *The EMBO Journal*, 12(2):725-734 (1993).

Grousson et al., "Effects of CD40 ligation on human keratinocyte accessory function," *Archives of Dermatological Research*, 290:325-330 (1998).

Gruss et al., "Expression and function of CD40 on Hodgkin and Reed-Sternberg cells and the possible relevance for Hodgkin's disease," *Blood*, 84(7):2305-2314 (1994).

Hawkins et al., "Selection of phage antibodies by binding affinity mimicking affinity maturation," *Journal of Molecular Biology*, 226:889-896 (1992).

Hay et al., "Bacteriophage cloning and *Escherichia coli* expression of a human IgM Fab," *Hum. Antibod. Hybridomas*, 3:81-85 (1992).

Hirano et al., "Inhibition of human breast carcinoma growth by a soluble recombinant human CD40 ligand," *Blood*, 93(9):2999-3007 (1999).

Hollenbaugh et al., "Expression of functional CD40 vascular endothelial cells," *Journal of Experimental Medicine*, 182:33-40 (1995).

Holliger et al., "Diabodies: small bivalent and bispecific antibody fragments," *PNAS*, 90:6444-6448 (1993).

Hoogenboom et al., "Multi-subunit proteins on the surface of filamentous phage: methodologies for displaying antibody (Fab) heavy and light chains," *Nucleic Acids Research*, 19(15):4133-4137 (1991).

Huang et al., "Bone marrow-derived cells present MHC class 1-restricted tumour antigens in priming of antitumor immune responses," *Ciba Foundation Symposium*, 187:229-244 (1994).

Huse et al., "Generation of a large combinatorial library of the immunoglobulin repertoire in phage lambda," *Science*, 246:1275-1281 (1989).

Huston et al., "Protein engineering of antibody binding sites: recovery of specific activity in an anti-digoxin single-chain Fv analogue produced in *Escherichia coli*," *PNAS*, 85:5879-5883 (1988).

Ill et al., "Design and construction of a hybrid immunoglobulin domain with properties of both heavy and light chain variable regions," *Protein Engineering*, 10(8): 949-957 (1997).

Ishida et al., "TRAF5, a novel tumour necrosis factor receptor-associated factor family protein, mediates CD40 signaling," *PNAS*, 93:9437-9442 (1996).

Jeppson et al., "Requirements for dual signals by anti-CD40 and IL-4 for the induction of nuclear factor-κB, IL-6, and IgE in human B lymphocytes," *Journal of Immunolgy*, 161:1738-1742 (1998).

Johnsson et al., "Comparison of methods for immobilization to carboxymethyl dextran sensor surfaces by analysis of the specific activity of monoclonal antibodies," *Journal of Molecular Recognition*, 8:125-131 (1995).

Johnsson et al., "Immobilization of proteins to a carboxymethyldextran-modified gold surface for biospecific interaction analysis in surface plasmon resonance sensors," *Analytical Biochemistry*, 198:268-277 (1991).

Jones et al., "Activated T hybridomas induce upregulation of B7-1 on bystander B lymphoma cells by a conduct-dependent interaction utilizating CD40 ligand," *Cellular Immunology*, 174:42-53 (1996).

Jonsson et al., "Introducing a biosensor based technology for real-time biospecific interaction analysis," *Ann. Biologie Clinique.*, 51:19-26 (1993.

Jonsson et al., "Real-time biospecific interaction analysis using surface plasmon resonance and a sensor chip technology,"0 *BioTechniques*, 11(5):620-627 (1991.

Katada et al., "B cell-B cell interaction through intercellular adhesion molecule-1 and lymphocyte functional antigen-1 regulates immunoglobulin E synthesis by B cells stimulated with interleukin-4 and anti-CD40 antibody," *European Journal of Immunology*, 26:192-200 (1996).

Kiener et al., "Stimulation of CD40 with purified soluble gp39 induces proinflammatory responses in human monocytes," *The Journal of Immunology*, 155(10):4917-1425 (1995).

Koch et al., "High level IL-12 production by murine dendritic cells: Upregulation via MHC class II and CD40 molecules and downregulation by IL-4 and IL10," *Journal of Experimental Medicine*, 184:741-746 (1996).

Kostelny et al., "Formation of a bispecific antibody by the use of leucine zippers," *The Journal of Immunology*, 148:1547-1553 (1992).

Kuniyoshi et al., "Dendritic cell secretion of IL-15 is induced by recombinant huCD40LT and augments the stimulation of antigen-specific cytolytic T cells," *Cellular Immunology*, 193:48-58 (1999).

LaPlanche et al., "Phosphorothiote-modified oligodeoxyribonucleotides, III. NMR and UV spectroscopic studies of the $R_p$-$R_p$, $S_p$-$S_p$, and $R_p$-$S_p$ duplexes, $[d(GG_5AATTCC)]_2$, derived from diastereomeric O-ethyl phosphorothioates," *Nucleic Acids Research*, 14(22):9081-9093 (1986).

Lazaar et al., "CD40-mediated signal transduction in human airway smooth muscle," *Journal of Immunology*, 161:3120-3127 (1998).

Lee et al., "Specificities of CD40 signaling: Involvement of TRAF2 in CD40-induced NF-κB activation and intercellular adhesion molecule-1 up-regulation," *PNAS*, 96:1421-1426 (1999).

Mackey et al., "Cutting edge: Dendritic cells require maturation via CD40 to generate protective antitumor immunity," *Journal of Immunology*, 161:2094-2098 (1998).

Mackey et al., "Protective induced by tumor vaccines requires interaction between CD40 and its ligand, CD154," *Cancer Research*, 57:2569-2574 (1997).

Mackey et al., "The role of CD40/CD154 interactions in the priming, differentiation, and effector function of helper and cytotoxic T cells," *Journal of Leukocyte Biology*, 63:418-428 (1998).

Marks et al., "Oligonucleotide primers for polymerase chain reaction amplification of human immunoglobulin variable genes and design of family-specific oligonucleotide probes." *European Journal of Immunology*, 21:985-991 (1991).

Martin et al., "The affinity-selection of a minibody polypeptide inhibitor of human interleukin-6," *The EMBO Journal*, 13(22):5303-5309 (1994).

Mayumi et al., "Session II: Allergy and intracellular signal transmission mechanisms," *The Journal of Allergy and Clinical Immunology*, 96(6):1136-1144 (1995).

McCafferty et al., "Phage antibodies: filamentous phage displaying antibody variable domains," *Nature*, 348:552-554 (1990).

McDonnell et al., "bcl-2-immunoglobulin transgenic mice demonstrate extended B cell survival and follicular lymphoproliferation," *Cell*, 57:79-88 (1989).

McDyer et al., "Differential effects of CD40 ligand/trimer stimulation on the ability of dendritic cells to replicate and transmit HIV infection: Evidence for CC-chemokine-dependent and independent mechanisms," *Journal of Immunology*, 162:37110-3717 (1999).

Mendez et al., "Functional transplant of megabase human immunoglobulin loci recapitulates human antibody response in mice," *Nature Genetics*, 15:146-156 (1997).

Moody et al., "Growth factor and peptide receptors in small cell lung cancer," *Life Sciences*, 52:1161-1173 (1993).

Naismith et al., "Modularity in the TNF-receptor family," *TIBS*, 23:74-79 (1998).

Noelle, "CD40 and its ligand in cell-mediated immunity," *Agents and Actions Supplements*, 49:17-22 (1998).

Paulie et al., "A p50 surface antigen restricted to human urinary bladder carcinomas and B lymphocytes," *Cancer Immunology Immunotherapy*, 20:23-28 (1985).

Pearson, "Effective protein sequence comparison," *Methods in Enzymology*, 266:227-258 (1996).

Pearson, "Empirical statistical estimates for sequence similarity searches," *Journal of Molecular Biology*, 276:71-84 (1998).

Pearson, "Rapid and sensitive sequence comparison with FASTP and FASTA," *Methods in Enzymology*, 183:63-98 (1990).

Pearson, "Flexible sequence similarity searching with the FASTA3 program package," *Methods in Molecular Biology*, 132:185-219 (2000).

Pearson, "Using the FASTA program to search protein and DNA sequence databases," *Methods in Molecular Biology*, 24:307-331 (1994).

Poljak, "Production and structure of diabodies," *Structure*, 2:1121-1123 (1994).

Pullen et al., "CD40 signaling through tumor necrosis factor receptor-associated factors (TRAFs)," *The Journal of Biological Chemistry*, 274:14246-14254 (1999).

Pullen et al., "CD40-tumor necrosis factor receptor-associated factor (TRAF) interactions: Regulation of CD40 signaling through multiple TRAF binding sites and TRAF hetero-oligomerization," *Biochemistry*, 37:11836-11845 (1998).

Rizo et al., "Constrained peptides: models of bioactive peptides and protein substructures," *Annual Review of Biochemistry*, 61:387-418 (1992).

Roy et al., "Studies on the interdependence of gp39 and B7 expression and function during antigen-specific immune response," *European Journal of Immunology*, 25:596-603 (1995).

Ruggiero et al., "CD40 expressed on thymic epithelial cells provides costimulation for proliferation but not for apoptosis of human thymocytes," *Journal of Immunology*, 156:3737-3746 (1996).

Santos-Argumedo et al., "Antibodies to murine CD40 protect normal and malignant B cells from induced growth arrest," *Cellular Immunology*, 156(2):272-285 (1994).

Schaniel et al., "Activated murine B lymphocytes and dendritic cells produce a novel CC chemokine which acts selectively on activated T cells," *Journal of Experimental Medicine*, 188:451-463 (1998).

Seguin et al., "Sensitized lymphocytes and CD40 ligation augment interleukin-12 production by human dendritic cells in response to *Toxoplasma gondii*," *Journal of Infectious Diseases*, 179(2):467-467-474 (1999).

Songsivilai et al., "Bispecific antibody: a tool for diagnosis and treatment of disease," *Clinical and Experimental Immunology*, 79:315-321 (1990).

Sotomayor et al., "Conversion of tumor-specific $CD4^{30}$ T-cell tolerance to T-cell priming through in vivo ligation of CD40," *Nature Medicine*, 5(7):780-787 (1999).

Stamenkovic et al., "A B-lymphocyte activation molecule related to the nerve growth factor receptor and induced by cytokines in carcinomas," *The EMBO Journal*, 8(5):1403-1410(1989).

Stec et al., "Automated solid-phase synthesis, separation, and stereochemistry of phosphorothioate analogues of oligodeoxyribonucleotides," *Journal of the American Chemical Society*, 106(20):6077-6079 (1984).

Stein et al., "Physiochemical properties of phosphorothioate oligodeoxynucleotides," *Nucleic Acids Research*, 16(8):3209-3221 (1988).

Sutherland et al., An 11—amino acid sequence in the cytoplasmic domain of CD40 is sufficient for activation of c-Jun N-terminal kinase, activation of MAPKAP kinase-2, phosphorylation of IκBα, and protection of WEHI-231 cells from anti-IgM-induced growth arrest, *Journal of Immunology*, 162:4720-4730 (1999).

Thornton et al., "Prediction of progress at last," *Nature*, 354(14):105-106 (1991).

Toes et al., "CD40-CD40Ligand interactions and their role in cytotoxic T lymphocyte priming and anti-tumor immunity," *Seminars in Immunology*, 10:443-448 (1998).

Traunecker et al., "Bispecific single chain molecules (Janusins) target cytotoxic lymphocytes on HIV infected cells," *The EMBO Journal*, 10(12):3655-3659 (1991.

Traunecker et al., "Janusin: new molecular design for bispecific reagents," *International Journal of Cancer*, 7:51-52 (1992).

Trojan et al., "Treatment and prevention of rat glioblastoma by immunogenic C6 cells expressing antisense insulin-like growth factor 1 RNA," *Science*, 259:94-97 (1993).

Tsukamoto et al., "Two differently regulated nuclear factor κB activation pathways triggered by the cytoplasmic tail of CD40," *PNAS*, 96:1234-1239 (1999).

Tutt et al., "Monoclonal antibody therapy of B cell lymphoma: signaling activity on tumor cells appears more important than recruitment of effectors," *Journal of Immunology*, 161(6):3176-3185 (1998).

Uejima et al., "Effect of interleukin-10 on anti-CD40- and interleukin-4-induced immunoglobulin E production by human lymphocytes," *International Archives of Allergy and Immunology*, 110(3):225-232 (1996).

Uhlmann et al., "Antisense oligonucleotides: a new therapeutic principle," *Chemical Reviews*, 90(4):543-584 (1990).

Van Kooten et al., "CD40-CD40 ligand," *Journal of Leukocyte Biology*, 67:2-17 (2000).

Veber et al., "The design of metabolically-stable peptide analogs," *TINS*, 8(9):392-396 (1985).

Von Leoprechting et al., "Stimulation of CD40 on Immunogenic human malignant melanomas augments their cytotoxic T lymphocyte-mediated lysis and induces apoptosis," *Cancer Research*, 59:1287-1294 (1999).

Ward et al., "Binding activities of a repertoire of single immunoglobulin variable domains secreted from *Escherichia coli*," *Nature*, 341:544-546 (1989).

Wing et al., "Ex vivo whole blood cultures for predicting cytokine-release syndrome: dependence on target antigen and antibody isotype," *Therapeutic Immunology*, 2:183-90 (1995).

Yellin et al., "Ligation of CD40 on fibroblasts induces CD54 (ICAM-1) and CD106 (VCAM-1) up-regulation and IL-6 production and proliferation," *Journal of Leukocyte Biology*, 58:209-216 (1995).

Zon et al., "Phosphorothioate oligonulceotides," *Oligonucleotides and Analogues: A Practical Approach*, 87-108 (F. Eckstein, Ed., Oxford University Press, Oxford England (1991).

Alexandroff et al., "Role for CD40-CD40 ligand interactions in the immune response to solid tumours," *Molecular Immunology* 37(9):515-526 (2000).

Francisco et al., "Agonistic properties and in vivo antitumor activity of the anti-CD40 antibody SGN-14," *Cancer Research* 60, 3225-3231 (2000).

Grohmann et al., "CD40 ligation ablates the tolerogenic potential of lymphoid dendritic cells," *Journal of Immunology* 166(1):277-283 (2001).

Mierlo et al., "CD40 stimulation leads to effective therapy of CD40-tumors through induction of strong systemic cytotoxic T lymphocyte immunity," *Proceedings of the National Academy of Sciences USA* 99(8):5561-5566 (2002).

Szocinski et al., "Activation-induced cell death of aggressive histology lymphomas by CD40 stimulation: Induction of bax," *Blood* 100(1):217-223 (2002).

Todryk et al., "CD40 ligation for immunotherapy of solid tumors," *Journal of Immunological Methods* 248:139-147 (2001).

Turner et al., "Anti-CD40 antibody induces antitumor and antimetastatic effects: the role of NK cells," *Journal of Immunology* 166(1):89-94 (2001).

\* cited by examiner

Figure 1 - Alignment of antibody variable domain protein sequences with germline (GL) sequences (CDRs are underlined; mutations from germline are bold/shadow)

Figure 1A
Germline: V=A3/A19, J=JK1
Germline  DIVLTQSPLS LPVTPGEPAS ISCRSSQSLL YSNGYNFLDW YLQKPGQSPQ LLIYLGSNRA SGVPDRFSGS GSGTDFTLKI SRLEAEDVGV YYCMQALQTP RTFGQGTKVE IK
3.1.1     DIVMTQSPLS LPVTPGEPAS ISCRSSQSLL YSNGYNFLDW YLQKPGQSPQ LLIYLGSNRA SGVPDRFSGS GSGTDFTLKI SRVEAEDVGV YYCMQALQTP RTFGQGTKVE IK
7.1.2     DIVMTQSPLS LPVTPGEPAS ISCRSSQSLL YSNGYNFLDW YLQKPGQSPQ LLIYLGSNRA SGVPDRFSGS GSGTDFTLKI SRVEAEDVGV YYCMQALQTP RTFGQGTKVE IK
GL        DIVMTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP WTFGQGTKVE IK Figure 1B
Germline: V=A3/A19, J=JK2
Germline  DIVMTQSPLS LPVTPGEPAS ISCRSSQSLL HTNGYNYFDW YLQKPGQSPQ LLIYLGSNRA SGVPDRFSGS GSGTDFTLKI SRVEAEDVGV YYCMQALQTP YSFGQGTKLE IK
15.1.1    DIVMTQSPLS LPVTPGEPAS ISCRSSQSLL HSNGYNYLDW YLQKPGQSPQ LLIYLGSNRA SGVPDRFSGS GSGTDFTLKI SRVEAEDVGV YYCMQALQTP YTFGQGTKLE IK
GL Figure 1C
Germline: V=L5, J=JK4
Germline  DIQMTQSPSS VSASVGDRVT ITCRASQPIS SWLAWYQQKP GKAPKLLIYS ASGLQSGVPSR FSGSGSGTD FTLTISSLQP EDFATYYCQQ TDSFPLIFGG GTKVEIK
10.8.3    DIQMTQSPSS VSASVGDRVT ITCRASQGIY SWLAWYQQKP GKAPNLLIYT ASTLQSGVPSR FSGSGSGTD FTLTISSLQP EDFATYYCQQ ANIFPLTFGG GTKVEIK
21.4.1    DIQMTQSPSS VSASVGDRVT ITCRASQGIS SWLAWYQQKP GKAPKLLIYA ASSLQSGVPSR FSGSGSGTD FTLTISSLQP EDFATYYCQQ ANSFPLIFGG GTKVEIK
GL Figure 1D
Germline V=3-30+, D=D4+DIR3, J=JH6
Germline  QVQLVESGGG VVQPGRSLRL SCAASGFTFS SYGMHWVRQA PGKGLEWVAV ISKDGGNKYH ADSVKGRFTI SRDNSKNALY LQMNSLRVED TAVYYCVRRG HQLVLGYYY NGLDVWGQGT TVTVSS
3.1.1     QVQLVESGGG VVQPGRSLRL SCAASGFTFS SYGMHWVRQA PGKGLEWVAV ISYDGSNKYY ADSVKGRFTI SRDNSKNTLY LQMNSLRAED TAVYYCAR-G HQL-LGYYYY YGMDVWGQGT TVTVSS
GL Figure 1E
Germline V=3-30+, D=DIR5+D1-26, J=JH6
Germline  QVQLVESGGG VVQPGRSLRL SCAASGFTFS SYGMHWVRQA PCKGLEWVAV ISNDGDNKYH ADSVWGRFTI SRDNSRSTLY LQMNSLRAED TAVYYCARRG MGSSGSRGDY YYYYGLDVWG QGTTVTVSS
7.1.2     QVQLVESGGG VVQPGRSLRL SCAASGFTFS SYGMHWVRQA PCKGLEWVAV ISNDGSNKYY ADSVKGRFTI SRDNSKNTLY LQMNSLRAED TAVYYCAR-- MGSSGS--DY YYYYGMDVWG QGTTVTVSS
GL Figure 1F
Germline V=4.35, D=DIR3, J=JH6
Germline  QVQLQESGPG LVKPSETLSL TCTVSGGSIS SYYWMIRQP AGKGLEWIGR VYTSGSTNYN PSLKSRVTMS VDTSKNQFSL KLSSVTAADT AVYYCARDGL YRG----YGM DVWGQGTTVTVSS
10.8.3    QVQLQESGPG LVKPSETLSL TCTVSGGSIS SYYNSWIRQP AGKGLEWIGR IYTSGSTNYN PSLKSRVTMS VDTSKNQFSL KLSSVTAADT AVYYCAR--- YCGYYYYGM DVWGQGTTVTVSS
GL Figure 1G
Germline V=4.59, D=D4-23, J=JH4
Germline  QVQLQESGPG LVKPSETLSL TCTVSGGSIR SYYYWIRQP PGKGLEWIGY IYYSGSTNY PSLKSRVTIS VDMSKNQFSL KLSSVTAADT AVYYCARIGD YGGNFNYFHQ WGGQTLVTVSS
15.1.1    QVQLQESGPG LVKPSETLSL TCTVSGGSIS SYYNSWIRQP PGKGLEWIGY IYYSGSTNY PSLKSRVTIS VDTSKNQFSL KLSSVTAADT AVYYCAR--D YGGNS-YFDY WGQGTLVTVSS
GL Figure 1H
Germline V=1-02, D=DLR1, J=JH4
Germline  QVQLVQSGAE VKKPGASVKV SCKASGYTFT GYYMHWVRQA PGQGLEWMGW INPDSGGTNY AQKFQGRVTM TRDTSISTAY MELNRLRSDD TAVYYCARDQ PLGYCTNGVC SYFDYWGQGT LVTVSS
21.4.1    QVQLVQSGAE VKKPGASVKV SCKASGYTFT GYYMHWVRQA PGQGLEWMGW INPNSGGTNY AQKFQGRVTM TRDTSISTAY MELSRLRSDD TAVYYCAR-- --GYCTNGVC YYFDYWGQGT LVTVSS
GL Figure 2 - Alignment of antibody variable domain protein sequences with germline (GL) sequences (CDRs are underlined; mutations from germline are bold/shadow)

Figure 2A
Germline V=A3/A19, J=JK1
22.1.1    DIVMTQSPLSLPVTPGEPASISCRSSQSLLYSNGYNYLDWYLQKPGQSPHLLIYLGSNRASGVPDRFSGSGSGTDFTLKISRVEAEDVGVYYCMQALQTPRTFGQGTKVEIK
23.5.1    DIVMTQSPLSLPVTPGEPASISCRSSQSLLPGNGYNYLDWYLQKPGQSPQLLIYLGSNRASGVPDRFSGSGSGTDFTLKISRVEAEDVGVYYCMQALQTPRTFGQGTKVEIK
23.29.1   DIVMTQSPLSLPVTPGEPASISCRSSQSLLPGNGYNYLDWYLQKPGQSPQLLIYLGSNRASGVPDRFSGSGSGTDFTLKISRVEAEDVGVIYYCMQALQTPRTFGQGTKVEIK
Germ      DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPWTFGQGTKVEIK Figure 2B
Germline V=A3/A19, J=JK3
21.2.1    DIVMTQSPLSLPVTPGEPASISCRSSQSVLYSNGYNYLDWYLQKPGQSPQLLIYLGSNRASGVPDRFSGSGSGTDFTLKISRVEAEDVGVYYCMQVLQTPFTFGPGTKVDIK
Germ      DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPFTFGPGTKVDIK Figure 2C
Germline V=A27, J=JK3
23.28.1    EIVLTQSPGTLSLSPGERATLSCRASQSVSSSDLAWHQQKPGQAPRLLIYGASSRATGIPDRFSGSGSGTDFTLTISRLEPEDFAVYYCQHCRS-LFTFGPGTKVDIK
23.28.1L-C92A EIVLTQSPGTLSLSPGERATLSCRASQSVSSSDLAWHQQKPGQAPRLLIYGASSRATGIPDRFSGSGSGTDFTLTISRLEPEDFAVYYCQHARS-LFTFGPGTKVDIK
24.2.1     EIVLTQSPGTLSLSPGERATLSCRASQSVSSTYLAWYQQKPGQAPRLLIYGASSRATGIPDRFSGSGSGTDFTLTISRLEPEDFAVYYCQQYSS-LFTFGPGTKVDIK
Germ       EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPFTFGPGTKVDIK Figure 2D
Germline V=3-30+, D=DIR3+D6-19, J=JH4
21.2.1    QVQLVESGGGVVQPGRSLRLSCAASGFTFSSYVMHWVRQAPGKGLEWVAVMSYDGSSKYYANSVKGRFTISRDNSKNTLYLQINSLRAEDTAVYYCAR-DGGK----AVPGPDYWGQGTLVTVSS
Germ      QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARYCGGDCYGIAVAG---WGQGTLVTVSS Figure 2E
Germline V=3-30+, D=DD1-1, J=JH6
22.1.1     QVQLVESGGGVVQPGRSLRLSCAASGFTFSRYGMHWVRQAPGKGLEWVAVISDGGNKYYADSVKGRFTISRDNSKNTLYLQMNSLRAEDTAVYYCTRGT-GKTYHYCGMDVWGQGTTVTVSS
22.1.1H-C109A QVQLVESGGGVVQPGRSLRLSCAASGFTFSRYGMHWVRQAPGKGLEWVAVISDGGNKYYADSVKGRFTISRDNSKNTLYLQMNSLRAEDTAVYYCTRGT-GKTYHYAGMDVWGQGTTVTVSS
Germ       QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAR-GTTG-TYYYYGMDVWGQGTTVTVSS Figure 2F
Germline V=3-30+, D=D4-17, J=JH6
22.1.1     QVQLVESGGGVVQPGRSLRLSCVASGFTFSNYGMHWVRQAPGKGLEWVAIISYDGSNKYYADSVKGRFTISRDNSKNTLYVQMNSLRAEDTAVYYCARRGHYGRDYYSYGLDVWGQGTTVTVSS
23.5.1     QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAR--DYGDYYYYGMDVWGQGTTVTVSS
Germ       QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAR--DYGDYYYYGMDVWGQGTTVTVSS Figure 2G
Germline V=3-30.3, D=D4-17, J=JH6
23.29.1    QVQLVESGGGVVQPGRSLRLSCAASGFTFSSYAMHWVRQAPGKGLEWVAVISYDGSNKYYADSVKGRFTIYRDNSKNTLYLQMNSLRAEDTAVYYCARRGHYGNNYYSYYGLDVWGQGTTVTVSS
Germ       QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR--DYGDYYYYGMDVWGQGTTVTVSS Figure 2H
Germline V=4-16, D=DIR1+D4-17, J=JH5
23.28.1        QVQLQESGPGLVKPSDTLSLTCTVSGGSIRGYYWSWIRQPPGKGLEWIGYIYYSGSTNYNPSLKSRVTISVDTSKNQFSLKLNSVTAADTAVYYCARKGGLYGDYGWFAPWGQGTLVTVSS
23.28.1H-D16E  QVQLQESGPGLVKPSETLSLTCTVSGGSIRGYYWSWIRQPPGKGLEWIGYIYYSGSTNYNPSLKSRVTISVDTSKNQFSLKLNSVTAADTAVYYCARKGLYGDYGWFAPWGQGTLVTVSS
24.2.1         QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCARRGLYGDYGWFAPWGQGTLVTVSS
Germ           QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCAR    DYGDYNWFDPWGQGTLVTVSS

FIGURE 16

D1
Mouse VTCSDKQYLHDGQCCDLCQPGSRLTSHCTALEKTQCH
Human TACREKQYLINSQCCSLCQPGQKLVSDCTEFTETECL D2
Mouse PCDSGEFSAQWNREIRCHQHRHCEPNQGLRVKKEGTAESDTVCT
Human PCGESEFLDTWNRETHCHQHKYCDPNLGLRVQQKGTSETDTICT D3
Mouse CKEGQHCTSKDCEACAQHTPCIPGFGVMEMATETTDTVCHP
Human CEEGWHCTSEACESCVLHRSCSPGFGVKQIATGVSDTICEP D4
Mouse CPVGFFSNQSSLFEKCYPWTSCEDKNLEVLQKGTSQTNVICG
Human CPVGFFSNVSSAFEKCHPWTSCETKDLVVQQAGTNKTDVVCG

FIGURE 17

Mouse MVSLPRLCALWGCLLTAVHLGQCVTCSDKQYLHDGQCCDLCQPGSRLTSH
Human MVRLPLQCVLWGCLLTAVHPEPPTACREKQYLINSQCCSLCQPGQKLVSD Mouse ALEKTQCHPCDSGEIFSAQWNREIRCHQHRHCEPNQGLRVKKEGTIAESD
Human EFTETECLPCGESEIFLDTWNRETHCHQHKYCDPNLGLRVQQKGTISETD
                    *EcoRI*                              *BanI*

Mouse TVCTCKEGQHCTSKDCEACAQHTPCIPGFGVMEMATETTDTVCHPCPHHHH
Human TICTCEEGWHCTSEACESCVLHRSCSPFGVKQIATGVSDTICEPCPHHHH

SEQUENCE LISTING

<160> NUMBER OF SEQ ID NOS: 147

<210> SEQ ID NO 1
<211> LENGTH: 378
<212> TYPE: DNA
<213> ORGANISM: Homo sapiens

<400> SEQUENCE: 1
caggtgcagc tggtggagtc tgggggaggc gtggtccagc ctgggaggtc cctgagactc      60
tcctgtgcag cctctggatt caccttcagt agttatggca tgcactgggt ccgccaggct     120
ccaggcaagg ggctggagtg ggtggcagtt atatcaaagg atggaggtaa taaataccat     180
gcagactccg tgaagggccg attcaccatc tccagagaca attccaagaa tgcgctgtat     240
ctgcaaatga atagcctgag agttgaagac acggctgtgt attactgtgt gagaagaggg     300
catcagctgg ttctgggata ctactactac aacggtctgg acgtctgggg ccaagggacc     360
acggtcaccg tctcctca                                                   378

<210> SEQ ID NO 2

<211> LENGTH: 126
<212> TYPE: PRT
<213> ORGANISM: Homo sapiens

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Lys Asp Gly Asn Lys Tyr His Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Val Glu Asp Thr Ala Val Tyr Tyr Cys
                85                  90                  95

Val Arg Arg Gly His Gln Leu Val Leu Gly Tyr Tyr Tyr Asn Gly
            100                 105                 110

Leu Asp Val Trp Gly Gln Gly Thr Thr Val Thr Val Ser Ser
        115                 120                 125

<210> SEQ ID NO 3
<211> LENGTH: 336
<212> TYPE: DNA
<213> ORGANISM: Homo sapiens

<400> SEQUENCE: 3

```
gatattgtgc tgactcagtc tccactctcc ctgcccgtca cccctggaga gccggcctcc      60
atctcctgca ggtctagtca gagcctcttg tatagtaatg gatacaactt tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagattgg aggctgagga tgttggggtt tattactgca tgcaagctct acaaactcct     300
cggacgttcg gccaagggac caaggtggaa atcaaa                                336
```

<210> SEQ ID NO 4
<211> LENGTH: 112
<212> TYPE: PRT
<213> ORGANISM: Homo sapiens

<400> SEQUENCE: 4

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
                20                  25                  30

Asn Gly Tyr Asn Phe Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 5
<211> LENGTH: 1416
<212> TYPE: DNA
<213> ORGANISM: Homo sapiens

<400> SEQUENCE: 5

| | |
|---|---|
| atggagtttg ggctgagctg ggttttcctc gttgctcttt taagaggtgt ccagtgtcag | 60 |
| gtgcagctgg tggagtctgg gggaggcgtg gtccagcctg gaggtccct gagactctcc | 120 |
| tgtgcagcct ctggattcac cttcagtagt tatggcatgc actgggtccg ccaggctcca | 180 |
| ggcaaggggc tggagtgggt ggcagttata tcaaaggatg gaggtaataa ataccatgca | 240 |
| gactccgtga aggccgatt caccatctcc agagacaatt ccaagaatgc gctgtatctg | 300 |
| caaatgaata gcctgagagt tgaagacacg gctgtgtatt actgtgtgag aagagggcat | 360 |
| cagctggttc tgggatacta ctactacaac ggtctggacg tctggggcca agggaccacg | 420 |
| gtcaccgtct cctcagcctc caccaagggc ccatcggtct tccccctggc gccctgctcc | 480 |
| aggagcacct ccgagagcac agcggccctg ggctgcctgg tcaaggacta cttccccgaa | 540 |
| ccggtgacgg tgtcgtggaa ctcaggcgct ctgaccagcg gcgtgcacac cttcccagct | 600 |
| gtcctacagt cctcaggact ctactccctc agcagcgtgg tgaccgtgcc ctccagcaac | 660 |
| ttcggcaccc agacctacac ctgcaacgta gatcacaagc ccagcaacac caaggtggac | 720 |
| aagacagttg agcgcaaatg ttgtgtcgag tgcccaccgt gcccagcacc acctgtggca | 780 |
| ggaccgtcag tcttcctctt ccccccaaaa cccaaggaca cccttcatgat ctcccggacc | 840 |
| cctgaggtca cgtgcgtggt ggtggacgtg agccacgaag accccgaggt ccagttcaac | 900 |
| tggtacgtgg acggcgtgga ggtgcataat gccaagacaa agccacggga ggagcagttc | 960 |
| aacagcacgt tccgtgtggt cagcgtcctc accgttgtgc accaggactg gctgaacggc | 1020 |
| aaggagtaca gtgcaaggt ctccaacaaa ggcctcccag cccccatcga gaaaaccatc | 1080 |
| tccaaaacca agggcagcc ccgagaacca caggtgtaca ccctgccccc atcccgggag | 1140 |
| gagatgacca gaaccaggt cagcctgacc tgcctggtca aaggcttcta ccccagcgac | 1200 |
| atcgccgtgg agtgggagag caatgggcag ccggagaaca actacaagac cacacctccc | 1260 |
| atgctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 |
| acgcagaaga gcctctccct gtctccgggt aaatga | 1416 |

<210> SEQ ID NO 6
<211> LENGTH: 471
<212> TYPE: PRT
<213> ORGANISM: Homo sapiens

<400> SEQUENCE: 6

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Lys Asp Gly Gly Asn Lys Tyr His Ala
65                  70                  75                  80

```
Asp Ser Val Lys Gly Arg Phe Thr Ile Ser Arg Asp Asn Ser Lys Asn
                85                  90                  95

Ala Leu Tyr Leu Gln Met Asn Ser Leu Arg Val Glu Asp Thr Ala Val
            100                 105                 110

Tyr Tyr Cys Val Arg Arg Gly His Gln Leu Val Leu Gly Tyr Tyr Tyr
        115                 120                 125

Tyr Asn Gly Leu Asp Val Trp Gly Gln Gly Thr Thr Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 7
<211> LENGTH: 720
<212> TYPE: DNA
```

```
<213> ORGANISM: Homo sapiens

<400> SEQUENCE: 7
atgaggctcc ctgctcagct cctggggctg ctaatgctct gggtctctgg atccagtggg      60
gatattgtgc tgactcagtc tccactctcc ctgcccgtca cccctggaga gccggcctcc     120
atctcctgca ggtctagtca gagcctcttg tatagtaatg gatacaactt tttggattgg     180
tacctgcaga agccagggca gtctccacag ctcctgatct atttgggttc taatcgggcc     240
tccggggtcc ctgacaggtt cagtggcagt ggatcaggca cagattttac actgaaaatc     300
agcagattgg aggctgagga tgttggggtt tattactgca tgcaagctct acaaactcct     360
cggacgttcg gccaagggac caaggtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

<210> SEQ ID NO 8
<211> LENGTH: 239
<212> TYPE: PRT
<213> ORGANISM: Homo sapiens

<400> SEQUENCE: 8

Met Arg Leu Pro Ala Gln Leu Leu Gly Leu Leu Met Leu Trp Val Ser
  1               5                  10                  15

Gly Ser Ser Gly Asp Ile Val Leu Thr Gln Ser Pro Leu Ser Leu Pro
                 20                  25                  30

Val Thr Pro Gly Glu Pro Ala Ser Ile Ser Cys Arg Ser Ser Gln Ser
             35                  40                  45

Leu Leu Tyr Ser Asn Gly Tyr Asn Phe Leu Asp Trp Tyr Leu Gln Lys
         50                  55                  60

Pro Gly Gln Ser Pro Gln Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Leu Glu Ala Glu Asp Val Gly Val Tyr Tyr
            100                 105                 110

Cys Met Gln Ala Leu Gln Thr Pro Arg Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
```

<210> SEQ ID NO 9
<211> LENGTH: 387
<212> TYPE: DNA
<213> ORGANISM: Homo sapiens

<400> SEQUENCE: 9

```
caggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg gtggcagtt atatcaaatg atggagataa taaataccat     180
gcagactccg tgtggggccg attcaccatc tccagagaca attccaggag cacgctttat     240
ctgcaaatga acagcctgag agctgaggac acggctgtat attactgtgc gagaagaggc     300
atggggtcta gtgggagccg tgggattac tactactact acggtttgga cgtctggggc     360
caagggacca cggtcaccgt ctcctca                                          387
```

<210> SEQ ID NO 10
<211> LENGTH: 129
<212> TYPE: PRT
<213> ORGANISM: Homo sapiens

<400> SEQUENCE: 10

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Asp Asn Lys Tyr His Ala Asp Ser Val
    50                  55                  60

Trp Gly Arg Phe Thr Ile Ser Arg Asp Asn Ser Arg Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Met Gly Ser Ser Gly Ser Arg Gly Asp Tyr Tyr Tyr
            100                 105                 110

Tyr Tyr Gly Leu Asp Val Trp Gly Gln Gly Thr Thr Val Thr Val Ser
        115                 120                 125

Ser
```

<210> SEQ ID NO 11
<211> LENGTH: 336
<212> TYPE: DNA
<213> ORGANISM: Homo sapiens

<400> SEQUENCE: 11

```
gatattgtga tgactcagtc tccactctcc ctgcccgtca cccctggaga gccggcctcc      60
atctcctgca ggtctagtca gagcctcttg tatagtaatg gatacaactt tttggattgg     120
tacctgcaga agccagggca gtctccacag ctcctgatct atttgggttc taatcgggcc     180
tccggggtcc ctgacaggtt cagtggcagt ggatcaggca gattttac actgaaaatc       240
agcagagtgg aggctgagga tgttggggtt tattactgca tgcaagctct acaaactcct     300
cggacgttcg gccaagggac caaggtggaa atcaaa                                336
```

<210> SEQ ID NO 12
<211> LENGTH: 112
<212> TYPE: PRT
<213> ORGANISM: Homo sapiens

<400> SEQUENCE: 12

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
             20                  25                  30

Asn Gly Tyr Asn Phe Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
            100                 105                 110
```

<210> SEQ ID NO 13
<211> LENGTH: 1425
<212> TYPE: DNA
<213> ORGANISM: Homo sapiens

<400> SEQUENCE: 13

| | |
|---|---|
| atggagtttg ggctgagctg ggttttcctc gttgctcttt taagaggtgt ccagtgtcag | 60 |
| gtgcagctgg tggagtctgg gggaggcgtg gtccagcctg gaggtccct gagactctcc | 120 |
| tgtgcagcct ctggattcac cttcagtagc tatggcatgc actgggtccg ccaggctcca | 180 |
| ggcaagggc tggagtgggt ggcagttata tcaaatgatg gagataataa ataccatgca | 240 |
| gactccgtgt ggggccgatt caccatctcc agagacaatt ccaggagcac gctttatctg | 300 |
| caaatgaaca gcctgagagc tgaggacacg gctgtatatt actgtgcgag aagaggcatg | 360 |
| gggtctagtg ggagccgtgg ggattactac tactactacg gtttggacgt ctggggccaa | 420 |
| gggaccacgg tcaccgtctc ctcagcctcc accaagggcc catcggtctt ccccctggcg | 480 |
| ccctgctcca ggagcaccc cgagagcaca gcggccctgg gctgcctggt caaggactac | 540 |
| ttccccgaac cggtgacggt gtcgtggaac tcaggcgctc tgaccagcgg cgtgcacacc | 600 |
| ttcccagctg tcctacagtc ctcaggactc tactccctca gcagcgtggt gaccgtgccc | 660 |
| tccagcaact tcggcaccca gacctacacc tgcaacgtag atcacaagcc cagcaacacc | 720 |
| aaggtggaca gacagttga gcgcaaatgt tgtgtcgagt gcccaccgtg cccagcacca | 780 |
| cctgtggcag gaccgtcagt cttcctcttc cccccaaaac ccaaggacac cctcatgatc | 840 |
| tcccggaccc ctgaggtcac gtgcgtggtg gtggacgtga gccacgaaga ccccgaggtc | 900 |
| cagttcaact ggtacgtgga cggcgtggag gtgcataatg ccaagacaaa gccacgggag | 960 |
| gagcagttca cagcacgtt ccgtgtggtc agcgtcctca ccgttgtgca ccaggactgg | 1020 |
| ctgaacggca aggagtacaa gtgcaaggtc tccaacaaag gcctcccagc ccccatcgag | 1080 |
| aaaaccatct ccaaaaccaa aggcagcccc gagaaccac aggtgtacac cctgcccca | 1140 |
| tcccgggagg agatgaccaa gaaccaggtc agcctgacct gcctggtcaa aggcttctac | 1200 |
| cccagcgaca tcgccgtgga gtgggagagc aatgggcagc cggagaacaa ctacaagacc | 1260 |
| acacctccca tgctggactc cgacggctcc ttcttcctct acagcaagct caccgtggac | 1320 |

```
aagagcaggt ggcagcaggg gaacgtcttc tcatgctccg tgatgcatga ggctctgcac   1380
aaccactaca cgcagaagag cctctccctg tctccgggta aatga                  1425
```

<210> SEQ ID NO 14
<211> LENGTH: 474
<212> TYPE: PRT
<213> ORGANISM: Homo sapiens

<400> SEQUENCE: 14

```
Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Asn Asp Gly Asp Asn Lys Tyr His Ala
65                  70                  75                  80

Asp Ser Val Trp Gly Arg Phe Thr Ile Ser Arg Asp Asn Ser Arg Ser
                85                  90                  95

Thr Leu Tyr Leu Gln Met Asn Ser Leu Arg Ala Glu Asp Thr Ala Val
            100                 105                 110

Tyr Tyr Cys Ala Arg Arg Gly Met Gly Ser Ser Gly Ser Arg Gly Asp
        115                 120                 125

Tyr Tyr Tyr Tyr Gly Leu Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350
```

```
Lys Gly Leu Pro Ala Pro Ile Glu Lys Thr Ile Ser Lys Thr Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 15
<211> LENGTH: 720
<212> TYPE: DNA
<213> ORGANISM: Homo sapiens

<400> SEQUENCE: 15

```
atgaggctcc ctgctcagct cctggggctg ctaatgctct gggtctctgg atccagtggg    60
gatattgtga tgactcagtc tccactctcc ctgcccgtca cccctggaga gccggcctcc   120
atctcctgca ggtctagtca gagcctcttg tatagtaatg gatacaactt tttggattgg   180
tacctgcaga agccagggca gtctccacag ctcctgatct atttgggttc taatcgggcc   240
tccggggtcc ctgacaggtt cagtggcagt ggatcaggca cagattttac actgaaaatc   300
agcagagtgg aggctgagga tgttggggtt tattactgca tgcaagctct acaaactcct   360
cggacgttcg gccaagggac caaggtggaa atcaaacgaa ctgtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720
```

<210> SEQ ID NO 16
<211> LENGTH: 239
<212> TYPE: PRT
<213> ORGANISM: Homo sapiens

<400> SEQUENCE: 16

```
Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu Tyr Ser Asn Gly Tyr Asn Phe Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80
```

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
            100                 105                 110

Cys Met Gln Ala Leu Gln Thr Pro Arg Thr Phe Gly Gln Gly Thr Lys
            115                 120                 125

Val Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 17
<211> LENGTH: 357
<212> TYPE: DNA
<213> ORGANISM: Homo sapiens

<400> SEQUENCE: 17
caggtgcagc tgcaggagtc gggcccagga ctggtgaagc cttcggagac cctgtccctc      60
acctgcactg tctctggtgg ctccatcagt agttactact ggatctggat ccggcagccc     120
gccgggaagg gactggaatg gattgggcgt gtctatacca gtgggagcac caactacaac     180
ccctccctca gagtcgagt caccatgtca gtagacacgt ccaagaacca gttctccctg     240
aagctgagct ctgtgaccgc cgcggacacg gccgtgtatt actgtgcgag agatggtctt     300 tacaggggg acggtatgga cgtctgggc aagggacca cggtcaccgt ctcctca        357

<210> SEQ ID NO 18
<211> LENGTH: 119
<212> TYPE: PRT
<213> ORGANISM: Homo sapiens

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ile Trp Ile Arg Gln Pro Ala Gly Lys Gly Leu Glu Trp Ile
        35                  40                  45

Gly Arg Val Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Leu Tyr Arg Gly Tyr Gly Met Asp Val Trp Gly Gln Gly
            100                 105                 110

-continued

Thr Thr Val Thr Val Ser Ser
        115

<210> SEQ ID NO 19
<211> LENGTH: 321
<212> TYPE: DNA
<213> ORGANISM: Homo sapiens

<400> SEQUENCE: 19
gacatccaga tgacccagtc tccatcttcc gtgtctgcat ctgtaggaga cagagtcacc    60
atcacttgtc gggcgagtca gcctattagc agctggttag cctggtatca gcagaaacca   120
gggaaagccc ctaaactcct gatttattct gcctccggtt tgcaaagtgg ggtcccatca   180
aggttcagcg gcagtggatc tgggacagat tcactctca ccatcagcag cctgcagcct    240
gaagattttg caacttacta ttgtcaacag actgacagtt tcccgctcac tttcggcggc   300
gggaccaagg tggagatcaa a                                              321

<210> SEQ ID NO 20
<211> LENGTH: 107
<212> TYPE: PRT
<213> ORGANISM: Homo sapiens

<400> SEQUENCE: 20

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Pro Ile Ser Ser Trp
            20                  25                  30

Leu Ala Trp Tyr Gln Gln Lys Pro Gly Lys Ala Pro Lys Leu Leu Ile
        35                  40                  45

Tyr Ser Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asp Ser Phe Pro Leu
                85                  90                  95

Thr Phe Gly Gly Gly Thr Lys Val Glu Ile Lys
            100                 105

<210> SEQ ID NO 21
<211> LENGTH: 1395
<212> TYPE: DNA
<213> ORGANISM: Homo sapiens

<400> SEQUENCE: 21
atgaaacacc tgtggttctt cctcctgctg gtggcagctc ccagatgggt cctgtcccag    60
gtgcagctgc aggagtcggg cccaggactg gtgaagcctt cggagaccct gtccctcacc   120
tgcactgtct ctggtggctc catcagtagt tactactgga tctggatccg cagcccgcc    180 gggaagggac tggaatggat tgggcgtgtc tataccagtg ggagcaccaa ctacaacccc   240
tccctcaaga gtcgagtcac catgtcagta gacacgtcca agaaccagtt ctccctgaag   300
ctgagctctg tgaccgccgc ggacacggcc gtgtattact gtgcgagaga tggtctttac   360
agggggtacg gtatgacgt ctgggccaa gggaccacgg tcaccgtctc ctcagcctcc    420
accaagggcc catcggtctt ccccctggcg ccctgctcca ggagcacctc cgagagcaca   480
gcggccctgg gctgcctggt caaggactac ttccccgaac cggtgacggt gtcgtggaac   540
tcaggcgctc tgaccagcgg cgtgcacacc ttcccagctg tcctacagtc ctcaggactc   600

-continued

```
tactccctca gcagcgtggt gaccgtgccc tccagcaact tcggcaccca gacctacacc    660
tgcaacgtag atcacaagcc cagcaacacc aaggtggaca agacagttga gcgcaaatgt    720
tgtgtcgagt gcccaccgtg cccagcacca cctgtggcag gaccgtcagt cttcctcttc    780
cccccaaaac ccaaggacac cctcatgatc tcccggaccc ctgaggtcac gtgcgtggtg    840
gtggacgtga gccacgaaga ccccgaggtc cagttcaact ggtacgtgga cggcgtggag    900
gtgcataatg ccaagacaaa gccacgggag gagcagttca acagcacgtt ccgtgtggtc    960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgccccca tcccgggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acacctccca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aatga                                                    1395
```

<210> SEQ ID NO 22
<211> LENGTH: 464
<212> TYPE: PRT
<213> ORGANISM: Homo sapiens

<400> SEQUENCE: 22

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
                 20                  25                  30

Pro Ser Glu Thr Leu Ser Leu Thr Cys Thr Val Ser Gly Gly Ser Ile
             35                  40                  45

Ser Ser Tyr Tyr Trp Ile Trp Ile Arg Gln Pro Ala Gly Lys Gly Leu
         50                  55                  60

Glu Trp Ile Gly Arg Val Tyr Thr Ser Gly Ser Thr Asn Tyr Asn Pro
 65                  70                  75                  80

Ser Leu Lys Ser Arg Val Thr Met Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg Asp Gly Leu Tyr Arg Gly Tyr Gly Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220
```

```
His Lys Pro Ser Asn Thr Lys Val Asp Lys Thr Val Glu Arg Lys Cys
225                 230                 235                 240

Cys Val Glu Cys Pro Cys Pro Ala Pro Pro Val Ala Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 23
<211> LENGTH: 705
<212> TYPE: DNA
<213> ORGANISM: Homo sapiens

<400> SEQUENCE: 23
atgaggctcc ctgctcagct cctggggctc ctgctgctct ggttcccagg ttccagatgc    60
gacatccaga tgacccagtc tccatcttcc gtgtctgcat ctgtaggaga cagagtcacc   120
atcacttgtc gggcgagtca gcctattagc agctggttag cctggtatca gcagaaacca   180
gggaaagccc ctaaactcct gatttattct gcctccggtt tgcaaagtgg ggtcccatca   240
aggttcagcg gcagtggatc tgggacagat ttcactctca ccatcagcag cctgcagcct   300
gaagattttg caacttacta ttgtcaacag actgacagtt tcccgctcac tttcggcggc   360
gggaccaagg tggagatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag cacccctgacg   600 ctgagcaaag cagactacga gaaacacaaa gtctacgcct gcgaagtcac ccatcagggc   660
ctgagctcgc ccgtcacaaa gagcttcaac aggggagagt gttag                    705

<210> SEQ ID NO 24
```

```
<211> LENGTH: 234
<212> TYPE: PRT
<213> ORGANISM: Homo sapiens

<400> SEQUENCE: 24

Met Arg Leu Pro Ala Gln Leu Leu Gly Leu Leu Leu Trp Phe Pro
 1               5                  10                  15

Gly Ser Arg Cys Asp Ile Gln Met Thr Gln Ser Pro Ser Ser Val Ser
                20                  25                  30

Ala Ser Val Gly Asp Arg Val Thr Ile Thr Cys Arg Ala Ser Gln Pro
            35                  40                  45

Ile Ser Ser Trp Leu Ala Trp Tyr Gln Gln Lys Pro Gly Lys Ala Pro
        50                  55                  60

Lys Leu Leu Ile Tyr Ser Ala Ser Gly Leu Gln Ser Gly Val Pro Ser
 65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Thr Asp
               100                 105                 110

Ser Phe Pro Leu Thr Phe Gly Gly Gly Thr Lys Val Glu Ile Lys Arg
           115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 25
<211> LENGTH: 363
<212> TYPE: DNA
<213> ORGANISM: Homo sapiens

<400> SEQUENCE: 25
caggtgcagc tgcaggagtc gggcccagga ctggtgaagc cttcggagac cctgtccctc      60
acctgcactg tctctggtgg ctccatcaga agttactact ggacctggat ccggcagccc     120
ccagggaagg gactggagtg gattggatat atctattaca gtgggagcac caactacaat     180
ccctccctca agagtcgagt caccatatca gtagacatgt ccaagaacca gttctccctg     240
aagctgagtt ctgtgaccgc tgcggacacg gccgtttatt actgtgcgag aaagggtgac     300
tacggtggta atttaacta ctttcaccag tggggccagg gaaccctggt caccgtctcc     360
tca                                                                    363

<210> SEQ ID NO 26
<211> LENGTH: 121
<212> TYPE: PRT
<213> ORGANISM: Homo sapiens
```

<400> SEQUENCE: 26

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Arg Ser Tyr
             20                  25                  30

Tyr Trp Thr Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Met Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Lys Gly Asp Tyr Gly Gly Asn Phe Asn Tyr Phe His Gln Trp Gly
                100                 105                 110

Gln Gly Thr Leu Val Thr Val Ser Ser
            115                 120

<210> SEQ ID NO 27
<211> LENGTH: 336
<212> TYPE: DNA
<213> ORGANISM: Homo sapiens

<400> SEQUENCE: 27
gatattgtga tgactcagtc tccactctcc ctgcccgtca cccctggaga gccggcctcc     60
atctcctgca ggtctagtca gagcctccta catactaatg gatacaacta tttcgattgg    120
tacctgcaga agccagggca gtctccacaa ctcctgatct atttgggttc taatcgggcc    180
tccggggtcc ctgacaggtt cagtggcagt ggatcaggca cagattttac actgaaaatc    240
agcagagtgg aggctgagga tgttgggggtt tattactgca tgcaagctct acaaactccg    300
tacagttttg gccaggggac caagctggag atcaaa                               336

<210> SEQ ID NO 28
<211> LENGTH: 112
<212> TYPE: PRT
<213> ORGANISM: Homo sapiens

<400> SEQUENCE: 28

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Thr
             20                  25                  30

Asn Gly Tyr Asn Tyr Phe Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Leu Gln Thr Pro Tyr Ser Phe Gly Gln Gly Thr Lys Leu Glu Ile Lys
                100                 105                 110

<210> SEQ ID NO 29
<211> LENGTH: 1401
<212> TYPE: DNA

-continued

<213> ORGANISM: Homo sapiens

<400> SEQUENCE: 29

```
atgaaacatc tgtggttctt ccttctcctg gtggcagctc ccagatgggt cctgtcccag    60
gtgcagctgc aggagtcggg cccaggactg gtgaagcctt cggagaccct gtccctcacc   120
tgcactgtct ctggtggctc catcagaagt tactactgga cctggatccg gcagccccca   180
gggaagggac tggagtggat tggatatatc tattacagtg ggagcaccaa ctacaatccc   240
tccctcaaga gtcgagtcac catatcagta gacatgtcca agaaccagtt ctccctgaag   300
ctgagttctg tgaccgctgc ggacacggcc gtttattact gtgcgagaaa gggtgactac   360
ggtggtaatt ttaactactt tcaccagtgg ggccagggaa ccctggtcac cgtctcctca   420
gcctccacca agggcccatc ggtcttcccc ctggcgccct gctccaggag cacctccgag   480
agcacagcgg ccctgggctg cctggtcaag gactacttcc ccgaaccggt gacggtgtcg   540
tggaactcag gcgctctgac cagcggcgtg cacaccttcc cagctgtcct acagtcctca   600
ggactctact ccctcagcag cgtggtgacc gtgccctcca gcaacttcgg cacccagacc   660
tacacctgca acgtagatca caagcccagc aacaccaagg tggacaagac agttgagcgc   720
aaatgttgtg tcgagtgccc accgtgccca gcaccacctg tggcaggacc gtcagtcttc   780
ctcttccccc caaaacccaa ggacaccctc atgatctccc ggacccctga ggtcacgtgc   840
gtggtggtgg acgtgagtca cgaagacccc gaggtccagt tcaactggta cgtggacggc   900
gtggaggtgc ataatgccaa gacaaagcca cgggaggagc agttcaacag cacgttccgt   960
gtggtcagcg tcctcaccgt tgtgcaccag gactggctga acggcaagga gtacaagtgc  1020
aaggtctcca acaaaggcct cccagccccc atcgagaaaa ccatctccaa aaccaaaggg  1080
cagccccgag aaccacaggt gtacaccctg cccccatccc gggaggagat gaccaagaac  1140
caggtcagcc tgacctgcct ggtcaaaggc ttctacccca gcgacatcgc cgtggagtgg  1200
gagagcaatg ggcagccgga gaacaactac aagaccacac tcccatgct ggactccgac  1260
ggctccttct cctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaatg a                                              1401
```

<210> SEQ ID NO 30
<211> LENGTH: 466
<212> TYPE: PRT
<213> ORGANISM: Homo sapiens

<400> SEQUENCE: 30

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Thr Val Ser Gly Gly Ser Ile
         35                  40                  45

Arg Ser Tyr Tyr Trp Thr Trp Ile Arg Gln Pro Pro Gly Lys Gly Leu
     50                  55                  60

Glu Trp Ile Gly Tyr Ile Tyr Tyr Ser Gly Ser Thr Asn Tyr Asn Pro
 65                  70                  75                  80

Ser Leu Lys Ser Arg Val Thr Ile Ser Val Asp Met Ser Lys Asn Gln
                 85                  90                  95

Phe Ser Leu Lys Leu Ser Ser Val Thr Ala Ala Asp Thr Ala Val Tyr
```

```
                100             105             110
Tyr Cys Ala Arg Lys Gly Asp Tyr Gly Asn Phe Asn Tyr Phe His
            115                 120                 125

Gln Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly Lys
465

<210> SEQ ID NO 31
<211> LENGTH: 720
<212> TYPE: DNA
<213> ORGANISM: Homo sapiens

<400> SEQUENCE: 31
```

-continued

```
atgaggctcc ctgctcagct cctggggctg ctaatgctct gggtctctgg atccagtggg      60
gatattgtga tgactcagtc tccactctcc ctgcccgtca cccctggaga gccggcctcc     120
atctcctgca ggtctagtca gagcctccta catactaatg gatacaacta tttcgattgg     180
tacctgcaga agccagggca gtctccacaa ctcctgatct atttgggttc taatcgggcc     240
tccggggtcc ctgacaggtt cagtggcagt ggatcaggca cagattttac actgaaaatc     300
agcagagtgg aggctgagga tgttggggtt tattactgca tgcaagctct acaaactccg     360
tacagttttg gccaggggac caagctggag atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720
```

<210> SEQ ID NO 32
<211> LENGTH: 239
<212> TYPE: PRT
<213> ORGANISM: Homo sapiens

<400> SEQUENCE: 32

```
Met Arg Leu Pro Ala Gln Leu Leu Gly Leu Leu Met Leu Trp Val Ser
 1               5                  10                  15

Gly Ser Ser Gly Asp Ile Val Met Thr Gln Ser Pro Leu Ser Leu Pro
             20                  25                  30

Val Thr Pro Gly Glu Pro Ala Ser Ile Ser Cys Arg Ser Ser Gln Ser
         35                  40                  45

Leu Leu His Thr Asn Gly Tyr Asn Tyr Phe Asp Trp Tyr Leu Gln Lys
     50                  55                  60

Pro Gly Gln Ser Pro Gln Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Met Gln Ala Leu Gln Thr Pro Tyr Ser Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 33

<211> LENGTH: 361
<212> TYPE: DNA
<213> ORGANISM: Homo sapiens

<400> SEQUENCE: 33

| caggtgcagc | tggtggagtc | tgggggaggc | gtggtccagc | ctggagggtc | cctgagactc | 60 |
| tcctgtgcag | cctctggatt | caccttcagt | agctatgtca | tgcactgggt | ccgccaggct | 120 |
| ccaggcaagg | ggctggagtg | ggtggcagtt | atgtcatatg | atggaagtag | taaatactat | 180 |
| gcaaactccg | tgaagggccg | attcaccatc | tccagagaca | attccaagaa | cacgctgtat | 240 |
| ctgcaaataa | acagcctgag | agctgaggac | acggctgtgt | attactgtgc | gagagatggg | 300 |
| ggtaaagcag | tgcctggtcc | tgactactgg | ggccagggaa | tcctggtcac | cgtctcctca | 360 |
| g | | | | | | 361 |

<210> SEQ ID NO 34
<211> LENGTH: 120
<212> TYPE: PRT
<213> ORGANISM: Homo sapiens

<400> SEQUENCE: 34

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ala Val Met Ser Tyr Asp Gly Ser Ser Lys Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Arg Asp Gly Gly Lys Ala Val Pro Gly Pro Asp Tyr Trp Gly Gln
            100                 105                 110

Gly Ile Leu Val Thr Val Ser Ser
        115                 120

<210> SEQ ID NO 35
<211> LENGTH: 337
<212> TYPE: DNA
<213> ORGANISM: Homo sapiens

<400> SEQUENCE: 35

| gatattgtga | tgactcagtc | tccactctcc | ctgcccgtca | cccctggaga | gccggcctcc | 60 |
| atctcctgca | ggtctagtca | gagtgttctg | tatagtaatg | gatacaacta | tttggattgg | 120 |
| tacctgcaga | agccagggca | gtctccacag | ctcctgatct | atttgggttc | taatcgggcc | 180 |
| tccggggtcc | ctgacaggtt | cagtggcagt | ggatcaggca | cagatttac | actgaaaatc | 240 |
| agcagagtgg | aggctgagga | tgttggggtt | tattactgca | tgcaagtttt | acaaactcca | 300 |
| ttcactttcg | gccctgggac | caaagtggat | atcaaac | | | 337 |

<210> SEQ ID NO 36
<211> LENGTH: 112
<212> TYPE: PRT
<213> ORGANISM: Homo sapiens

<400> SEQUENCE: 36

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Val Leu Tyr Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Val
             85                  90                  95

Leu Gln Thr Pro Phe Thr Phe Gly Pro Gly Thr Lys Val Asp Ile Lys
            100                 105                 110
```

<210> SEQ ID NO 37
<211> LENGTH: 1398
<212> TYPE: DNA
<213> ORGANISM: Homo sapiens

<400> SEQUENCE: 37

```
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcct ctggattcac cttcagtagc tatgtcatgc actgggtccg ccaggctcca     180
ggcaaggggc tggagtgggt ggcagttatg tcatatgatg aagtagtaa atactatgca     240
aactccgtga agggccgatt caccatctcc agagacaatt ccaagaacac gctgtatctg     300
caaataaaca gcctgagagc tgaggacacg gctgtgtatt actgtgcgag agatgggggt     360
aaagcagtgc ctggtcctga ctactgggc cagggaatcc tggtcaccgt ctcctcagcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caagggcag    1080
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

<210> SEQ ID NO 38
<211> LENGTH: 465
<212> TYPE: PRT
<213> ORGANISM: Homo sapiens

<400> SEQUENCE: 38

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Val Met His Trp Val Arg Gln Ala Pro Gly Lys Gly Leu
    50                  55                  60

Glu Trp Val Ala Val Met Ser Tyr Asp Gly Ser Lys Tyr Tyr Ala
65                  70                  75                  80

Asn Ser Val Lys Gly Arg Phe Thr Ile Ser Arg Asp Asn Ser Lys Asn
                85                  90                  95

Thr Leu Tyr Leu Gln Ile Asn Ser Leu Arg Ala Glu Asp Thr Ala Val
            100                 105                 110

Tyr Tyr Cys Ala Arg Asp Gly Gly Lys Ala Val Pro Gly Pro Asp Tyr
        115                 120                 125

Trp Gly Gln Gly Ile Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 39
<211> LENGTH: 720
<212> TYPE: DNA
<213> ORGANISM: Homo sapiens

<400> SEQUENCE: 39
atgaggctcc ctgctcagct cctggggctg ctaatgctct gggtctctgg atccagtggg      60
gatattgtga tgactcagtc tccactctcc ctgcccgtca cccctggaga gccggcctcc     120
atctcctgca ggtctagtca gagtgttctg tatagtaatg gatacaacta tttggattgg     180
tacctgcaga agccagggca gtctccacag ctcctgatct atttgggttc taatcgggcc     240
tccggggtcc ctgacaggtt cagtggcagt ggatcaggca cagattttac actgaaaatc     300
agcagagtgg aggctgagga tgttggggtt tattactgca tgcaagtttt acaaactcca     360
ttcactttcg gccctgggac caaagtggat atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

<210> SEQ ID NO 40
<211> LENGTH: 239
<212> TYPE: PRT
<213> ORGANISM: Homo sapiens

<400> SEQUENCE: 40

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Val Leu Tyr Ser Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110
```

```
Cys Met Gln Val Leu Gln Thr Pro Phe Thr Phe Gly Pro Gly Thr Lys
            115                 120                 125
Val Asp Ile Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235
```

<210> SEQ ID NO 41
<211> LENGTH: 378
<212> TYPE: DNA
<213> ORGANISM: Homo sapiens

<400> SEQUENCE: 41

| | | | | | |
|---|---|---|---|---|---|
| caggtgcagc | tggtgcagtc | tggggctgag | gtgaagaagc | ctggggcctc | agtgaaggtc | 60 |
| tcctgcaagg | cttctggata | caccttcacc | ggctactata | tgcactgggt | gcgacaggcc | 120 |
| cctggacaag | ggcttgagtg | gatgggatgg | atcaaccctg | acagtggtgg | cacaaactat | 180 |
| gcacagaagt | tcagggcag | ggtcaccatg | accagggaca | cgtccatcag | cacagcctac | 240 |
| atggagctga | acaggctgag | atctgacgac | acggccgtgt | attactgtgc | gagagatcag | 300 |
| ccccctaggat | attgtactaa | tggtgtatgc | tcctactttg | actactgggg | ccagggaacc | 360 |
| ctggtcaccg | tctcctca | | | | | 378 |

<210> SEQ ID NO 42
<211> LENGTH: 126
<212> TYPE: PRT
<213> ORGANISM: Homo sapiens

<400> SEQUENCE: 42

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asp Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Asn Arg Leu Arg Ser Asp Asp Thr Ala Val Tyr Tyr Cys
                85                  90                  95
Ala Arg Asp Gln Pro Leu Gly Tyr Cys Thr Asn Gly Val Cys Ser Tyr
            100                 105                 110
Phe Asp Tyr Trp Gly Gln Gly Thr Leu Val Thr Val Ser Ser
        115                 120                 125
```

<210> SEQ ID NO 43
<211> LENGTH: 321
<212> TYPE: DNA
<213> ORGANISM: Homo sapiens

<400> SEQUENCE: 43

```
gacatccaga tgacccagtc tccatcttcc gtgtctgcat ctgtaggaga cagagtcacc      60
atcacttgtc gggcgagtca gggtatttac agctggttag cctggtatca gcagaaacca     120
gggaaagccc ctaacctcct gatctatact gcatccactt tacaaagtgg ggtcccatca     180
aggttcagcg gcagtggatc tgggacagat ttcactctca ccatcagcag cctgcaacct     240
gaagattttg caacttacta ttgtcaacag gctaacattt cccgctcac tttcggcgga      300
gggaccaagg tggagatcaa a                                                321
```

<210> SEQ ID NO 44
<211> LENGTH: 107
<212> TYPE: PRT
<213> ORGANISM: Homo sapiens

<400> SEQUENCE: 44

```
Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Tyr Ser Trp
             20                  25                  30

Leu Ala Trp Tyr Gln Gln Lys Pro Gly Lys Ala Pro Asn Leu Leu Ile
         35                  40                  45

Tyr Thr Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ile Phe Pro Leu
                 85                  90                  95

Thr Phe Gly Gly Gly Thr Lys Val Glu Ile Lys
            100                 105
```

<210> SEQ ID NO 45
<211> LENGTH: 1416
<212> TYPE: DNA
<213> ORGANISM: Homo sapiens

<400> SEQUENCE: 45

```
atggactgga cctggaggat cctcttcttg gtggcagcag ccacaggagc ccactcccag      60
gtgcagctgg tgcagtctgg ggctgaggtg aagaagcctg ggcctcagt gaaggtctcc      120
tgcaaggctt ctggatacac cttcaccggc tactatatgc actgggtgcg acaggcccct     180
ggacaagggc ttgagtggat gggatggatc aaccctgaca gtggtggcac aaactatgca     240
cagaagtttc agggcagggt caccatgacc agggacacgt ccatcagcac agcctacatg     300
gagctgaaca ggctgagatc tgacgacacg gccgtgtatt actgtgcgag atcagccc      360
ctaggatatt gtactaatgg tgtatgctcc tactttgact actggggcca gggaaccctg     420
gtcaccgtct cctcagcctc caccaagggc ccatcggtct tccccctggc gccctgctcc     480
aggagcacct ccgagagcac agcggccctg ggctgcctgg tcaaggacta cttccccgaa     540
ccggtgacgg tgtcgtggaa ctcaggcgct ctgaccagcg gcgtgcacac cttcccagct     600
gtcctacagt cctcaggact ctactccctc agcagcgtgg tgaccgtgcc ctccagcaac     660
ttcggcaccc agacctacac ctgcaacgta gatcacaagc ccagcaacac caaggtggac     720
```

-continued

```
aagacagttg agcgcaaatg ttgtgtcgag tgcccaccgt gcccagcacc acctgtggca    780
ggaccgtcag tcttcctctt ccccccaaaa cccaaggaca ccctcatgat ctcccggacc    840
cctgaggtca cgtgcgtggt ggtggacgtg agccacgaag accccgaggt ccagttcaac    900
tggtacgtgg acggcgtgga ggtgcataat gccaagacaa agccacggga ggagcagttc    960
aacagcacgt tccgtgtggt cagcgtcctc accgttgtgc accaggactg gctgaacggc   1020
aaggagtaca agtgcaaggt ctccaacaaa ggcctcccag cccccatcga aaaaccatc    1080 tccaaaacca agggcagcc ccgagaacca caggtgtaca ccctgccccc atcccgggag    1140
gagatgacca agaaccaggt cagcctgacc tgcctggtca aaggcttcta ccccagcgac   1200
atcgccgtgg agtgggagag caatgggcag ccggagaaca actacaagac cacacctccc   1260
atgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatga                             1416
```

<210> SEQ ID NO 46
<211> LENGTH: 471
<212> TYPE: PRT
<213> ORGANISM: Homo sapiens

<400> SEQUENCE: 46

```
Met Asp Trp Thr Trp Arg Ile Leu Phe Leu Val Ala Ala Ala Thr Gly
  1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Gly Tyr Tyr Met His Trp Val Arg Gln Ala Pro Gly Gln Gly Leu
     50                  55                  60

Glu Trp Met Gly Trp Ile Asn Pro Asp Ser Gly Gly Thr Asn Tyr Ala
 65                  70                  75                  80

Gln Lys Phe Gln Gly Arg Val Thr Met Thr Arg Asp Thr Ser Ile Ser
                 85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
```

```
                     245                 250                 255
Pro Pro Val Ala Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Gln Phe Asn Trp Tyr Val Asp
        290                 295                 300
Gly Val Glu Val His Asn Ala Lys Thr Lys Pro Arg Glu Glu Gln Phe
305                 310                 315                 320
Asn Ser Thr Phe Arg Val Val Ser Val Leu Thr Val Val His Gln Asp
                325                 330                 335
Trp Leu Asn Gly Lys Glu Tyr Lys Cys Lys Val Ser Asn Lys Gly Leu
            340                 345                 350
Pro Ala Pro Ile Glu Lys Thr Ile Ser Lys Thr Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Met Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 47
<211> LENGTH: 705
<212> TYPE: DNA
<213> ORGANISM: Homo sapiens

<400> SEQUENCE: 47
atgaggctcc ctgctcagct cctggggctc ctgctgctct ggttcccagg ttccagatgc      60
gacatccaga tgacccagtc tccatcttcc gtgtctgcat ctgtaggaga cagagtcacc     120
atcacttgtc gggcgagtca gggtatttac agctggttag cctggtatca gcagaaacca     180
gggaaagccc ctaacctcct gatctatact gcatccactt tacaaagtgg gtcccatca     240 aggttcagcg gcagtggatc tgggacagat ttcactctca ccatcagcag cctgcaacct     300
gaagattttg caacttacta ttgtcaacag gctaacattt tccgctcac tttcggcgga     360 gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                    705

<210> SEQ ID NO 48
<211> LENGTH: 234
```

<212> TYPE: PRT
<213> ORGANISM: Homo sapiens

<400> SEQUENCE: 48

Met Arg Leu Pro Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Tyr Ser Trp Leu Ala Trp Tyr Gln Gln Lys Pro Gly Lys Ala Pro
50                  55                  60

Asn Leu Leu Ile Tyr Thr Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 49
<211> LENGTH: 373
<212> TYPE: DNA
<213> ORGANISM: Homo sapiens

<400> SEQUENCE: 49
caggtgcagc tggtggagtc tgggggaggc gtggtccagc ctgggaggtc cctgagactc     60
tcctgtgcag cctctggatt caccttcagt cgctatggca tgcactgggt ccgccaggct    120
ccaggcaagg ggctggagtg ggtggcagtt atatcatctg atggaggtaa taaatactat    180
gcagactccg tgaagggccg attcaccatc tccagagaca attccaagaa cacgctgtat    240
ctgcaaatga acagcctgag agctgaggac acggctgtgt attactgtac gagaagaggg    300
actggaaaga cttactacca ctactgtggt atggacgtct ggggccaagg gaccacggtc    360
accgtctcct cag                                                      373

<210> SEQ ID NO 50
<211> LENGTH: 124
<212> TYPE: PRT
<213> ORGANISM: Homo sapiens

<400> SEQUENCE: 50

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Ala Val Ile Ser Ser Asp Gly Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Arg Gly Thr Gly Lys Thr Tyr Tyr His Tyr Cys Gly Met Asp
             100                 105                 110

Val Trp Gly Gln Gly Thr Thr Val Thr Val Ser Ser
         115                 120
```

<210> SEQ ID NO 51
<211> LENGTH: 337
<212> TYPE: DNA
<213> ORGANISM: Homo sapiens

<400> SEQUENCE: 51

```
gatattgtga tgactcagtc tccactctcc ctgcccgtca cccctggaga gccggcctcc      60
atctcctgca ggtctagtca gagcctcctg tatagtaatg gatataacta tttggattgg    120
tacctgcaga agccagggca gtctccacac ctcctgatct atttgggttc taatcgggcc    180
tccggggtcc ctgacaggtt cagtggcagt ggttcaggca ctgatttac actgaaaatc    240
agcagagtgg aggctgagga tgttggggtt tattactgca tgcaagctct acaaactcct    300
cggacgttcg gccaagggac caaggtggaa atcaaac                             337
```

<210> SEQ ID NO 52
<211> LENGTH: 112
<212> TYPE: PRT
<213> ORGANISM: Homo sapiens

<400> SEQUENCE: 52

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Tyr Ser
             20                  25                  30

Asn Gly Tyr Asn Tyr Leu Asp Trp Tyr Leu Gln Lys Pro Gly Gln Ser
         35                  40                  45

Pro His Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
             100                 105                 110
```

<210> SEQ ID NO 53
<211> LENGTH: 1410
<212> TYPE: DNA
<213> ORGANISM: Homo sapiens

<400> SEQUENCE: 53

```
atggagtttg ggctgagctg ggttttcctc gttgctcttt taagaggtgt ccagtgtcag      60
gtgcaactgg tggagtctgg gggaggcgtg gtccagcctg gaggtccct gagactctcc     120
tgtgcagcct ctggattcac cttcagtcgc tatggcatgc actgggtccg ccaggctcca    180
ggcaaggggc tggagtgggt ggcagttata tcatctgatg gaggtaataa atactatgca    240
gactccgtga agggccgatt caccatctcc agagacaatt ccaagaacac gctgtatctg    300
caaatgaaca gcctgagagc tgaggacacg gctgtgtatt actgtacgag aagagggact    360
ggaaagactt actaccacta ctgtggtatg gacgtctggg gccaagggac cacggtcacc    420
gtctcctcag cctccaccaa gggcccatcg gtcttcccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agctgtccta    600
cagtcctcag gactctactc cctcagcagc gtggtgaccg tgccctccag caacttcggc    660
acccagacct acacctgcaa cgtagatcac aagcccagca acaccaaggt ggacaagaca    720
gttgagcgca aatgttgtgt cgagtgccca ccgtgcccag caccacctgt ggcaggaccg    780
tcagtcttcc tcttcccccc aaaacccaag gacaccctca tgatctcccg gacccctgag    840
gtcacgtgcg tggtggtgga cgtgagccac gaagacccg aggtccagtt caactggtac    900
gtggacggcg tggaggtgca taatgccaag acaaagccac gggaggagca gttcaacagc    960
acgttccgtg tggtcagcgt cctcaccgtt gtgccaccag actggctgaa cggcaaggag   1020
tacaagtgca aggtctccaa caaaggcctc ccagccccca tcgagaaaac catctccaaa   1080
accaaagggc agccccgaga accacaggtg tacaccctgc ccccatcccg ggaggagatg   1140
accaagaacc aggtcagcct gacctgcctg gtcaaaggct tctacccag cgacatcgcc   1200
gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                    1410
```

<210> SEQ ID NO 54
<211> LENGTH: 469
<212> TYPE: PRT
<213> ORGANISM: Homo sapiens

<400> SEQUENCE: 54

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
                 20                  25                  30

Pro Gly Arg Ser Leu Arg Leu Ser Cys Ala Ala Ser Gly Phe Thr Phe
             35                  40                  45

Ser Arg Tyr Gly Met His Trp Val Arg Gln Ala Pro Gly Lys Gly Leu
         50                  55                  60

Glu Trp Val Ala Val Ile Ser Ser Asp Gly Gly Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110
```

```
Tyr Tyr Cys Thr Arg Arg Gly Thr Gly Lys Thr Tyr Tyr His Tyr Cys
            115                 120                 125
Gly Met Asp Val Trp Gly Gln Gly Thr Thr Val Thr Val Ser Ser Ala
        130                 135                 140
Ser Thr Lys Gly Pro Ser Val Phe Pro Leu Ala Pro Cys Ser Arg Ser
145                 150                 155                 160
Thr Ser Glu Ser Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Asn Phe Gly Thr Gln Thr Tyr
    210                 215                 220
Thr Cys Asn Val Asp His Lys Pro Ser Asn Thr Lys Val Asp Lys Thr
225                 230                 235                 240
Val Glu Arg Lys Cys Cys Val Glu Cys Pro Pro Cys Pro Ala Pro Pro
                245                 250                 255
Val Ala Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Gln Phe Asn Trp Tyr Val Asp Gly Val
    290                 295                 300
Glu Val His Asn Ala Lys Thr Lys Pro Arg Glu Glu Gln Phe Asn Ser
305                 310                 315                 320
Thr Phe Arg Val Val Ser Val Leu Thr Val His Gln Asp Trp Leu
                325                 330                 335
Asn Gly Lys Glu Tyr Lys Cys Lys Val Ser Asn Lys Gly Leu Pro Ala
            340                 345                 350
Pro Ile Glu Lys Thr Ile Ser Lys Thr Lys Gly Gln Pro Arg Glu Pro
        355                 360                 365
Gln Val Tyr Thr Leu Pro Pro Ser Arg Glu Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Met Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 55
<211> LENGTH: 720
<212> TYPE: DNA
<213> ORGANISM: Homo sapiens

<400> SEQUENCE: 55
atgaggctcc ctgctcagct ccctggggctg ctaatgctct gggtctctgg atccagtggg    60
```

```
gatattgtga tgactcagtc tccactctcc ctgcccgtca cccctggaga gccggcctcc    120
atctcctgca ggtctagtca gagcctcctg tatagtaatg gatataacta tttggattgg    180
tacctgcaga agccagggca gtctccacac ctcctgatct atttgggttc taatcgggcc    240
tccggggtcc ctgacaggtt cagtggcagt ggttcaggca ctgattttac actgaaaatc    300
agcagagtgg aggctgagga tgttggggtt tattactgca tgcaagctct acaaactcct    360
cggacgttcg gccaagggac caaggtggaa atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccy tgacgctgag caaagcagac tacgagaaac acaaagtcta cgcctgcgaa    660
gtcacccatc agggcctgag ctcgcccgtc acaaagagct tcaacagggg agagtgttag    720
```

<210> SEQ ID NO 56  
<211> LENGTH: 239  
<212> TYPE: PRT  
<213> ORGANISM: Homo sapiens

<400> SEQUENCE: 56

```
Met Arg Leu Pro Ala Gln Leu Leu Gly Leu Leu Met Leu Trp Val Ser
 1               5                  10                  15

Gly Ser Ser Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Leu Tyr Ser Asn Gly Tyr Asn Tyr Leu Asp Trp Tyr Leu Gln Lys
     50                  55                  60

Pro Gly Gln Ser Pro His Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Met Gln Ala Leu Gln Thr Pro Arg Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 57  
<211> LENGTH: 376

-continued

<212> TYPE: DNA
<213> ORGANISM: Homo sapiens

<400> SEQUENCE: 57

```
caggtgcagc tggtggagtc tgggggaggc gtggtccagc ctgggaggtc cctgagactc    60
tcctgtgtag cctctggatt caccttcagt aactatggca tgcactgggt ccgccaggct   120
ccaggcaagg gctggagtg gtggcaatt atatcatatg atggaagtaa taaatactat    180
gcagactccg tgaagggccg attcaccatc tccagagaca attccaagaa cacgctgtat   240
gtgcaaatga acagcctgag agctgaggac acggctgtgt attactgtgc gagacgcggt   300
cactacggga gggattacta ctcctactac ggtttggacg tctggggcca agggaccacg   360
gtcaccgtct cctcag                                                   376
```

<210> SEQ ID NO 58
<211> LENGTH: 125
<212> TYPE: PRT
<213> ORGANISM: Homo sapiens

<400> SEQUENCE: 58

```
Gln Val Gln Leu Val Glu Ser Gly Gly Gly Val Val Gln Pro Gly Arg
 1               5                  10                  15
Ser Leu Arg Leu Ser Cys Val Ala Ser Gly Phe Thr Phe Ser Asn Tyr
             20                  25                  30
Gly Met His Trp Val Arg Gln Ala Pro Gly Lys Gly Leu Glu Trp Val
         35                  40                  45
Ala Ile Ile Ser Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Val Gln Met Asn Ser Leu Arg Ala Glu Asp Thr Ala Val Tyr Tyr Cys
                 85                  90                  95
Ala Arg Arg Gly His Tyr Gly Arg Asp Tyr Tyr Ser Tyr Tyr Gly Leu
            100                 105                 110
Asp Val Trp Gly Gln Gly Thr Thr Val Thr Val Ser Ser
        115                 120                 125
```

<210> SEQ ID NO 59
<211> LENGTH: 337
<212> TYPE: DNA
<213> ORGANISM: Homo sapiens

<400> SEQUENCE: 59

```
gatattgtga tgactcagtc tccactctcc ctgcccgtca cccctggaga gccggcctcc    60
atctcctgca ggtctagtca gagcctcctg cctggtaatg gatacaacta tttgattgg   120
tacctgcaga agccagggca gtctccacag ctcctgatct atttggttc taatcgggcc   180
tccggggtcc ctgacaggtt cagtggcagt ggatcaggca cagattttac actgaaaatc   240
agcagagtgg aggctgagga tgttgggtt tattactgca tgcaagctct acaaactcct   300
cggacgttcg gccaagggac caaggtggaa atcaaac                            337
```

<210> SEQ ID NO 60
<211> LENGTH: 112
<212> TYPE: PRT
<213> ORGANISM: Homo sapiens

<400> SEQUENCE: 60

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Pro Gly
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
             100                 105                 110
```

<210> SEQ ID NO 61
<211> LENGTH: 1413
<212> TYPE: DNA
<213> ORGANISM: Homo sapiens

<400> SEQUENCE: 61

| | | | | |
|---|---|---|---|---|
| atggagtttg | ggctgagctg | ggttttcctc | gttgctcttt | taagaggtgt ccagtgtcag | 60 |
| gtgcagctgg | tggagtctgg | gggaggcgtg | gtccagcctg | gaggtccct gagactctcc | 120 |
| tgtgtagcct | ctggattcac | cttcagtaac | tatggcatgc | actgggtccg ccaggctcca | 180 |
| ggcaagggc | tggagtgggt | ggcaattata | tcatatgatg | gaagtaataa atactatgca | 240 |
| gactccgtga | agggccgatt | caccatctcc | agagacaatt | ccaagaacac gctgtatgtg | 300 |
| caaatgaaca | gcctgagagc | tgaggacacg | gctgtgtatt | actgtgcgag acgcggtcac | 360 |
| tacgggaggg | attactactc | ctactacggt | ttggacgtct | ggggccaagg gaccacggtc | 420 |
| accgtctcct | cagcctccac | caagggccca | tcggtcttcc | cctggcgcc ctgctccagg | 480 |
| agcacctccg | agagcacagc | ggccctgggc | tgcctggtca | aggactactt ccccgaaccg | 540 |
| gtgacggtgt | cgtggaactc | aggcgctctg | accagcggcg | tgcacacctt cccagctgtc | 600 |
| ctacagtcct | caggactcta | ctccctcagc | agcgtggtga | ccgtgccctc agcaacttc | 660 |
| ggcacccaga | cctacacctg | caacgtagat | cacaagccca | gcaacaccaa ggtggacaag | 720 |
| acagttgagc | gcaaatgttg | tgtcgagtgc | ccaccgtgcc | cagcaccacc tgtggcagga | 780 |
| ccgtcagtct | tcctcttccc | cccaaaaccc | aaggacaccc | tcatgatctc ccggacccct | 840 |
| gaggtcacgt | gcgtggtggt | ggacgtgagc | cacgaagacc | ccgaggtcca gttcaactgg | 900 |
| tacgtggacg | gcgtggaggt | gcataatgcc | aagacaaagc | cacgggagga gcagttcaac | 960 |
| agcacgttcc | gtgtggtcag | cgtcctcacc | gttgtgcacc | aggactggct gaacggcaag | 1020 |
| gagtacaagt | gcaaggtctc | caacaaaggc | ctcccagccc | ccatcgagaa aaccatctcc | 1080 |
| aaaaccaaag | ggcagccccg | agaaccacag | gtgtacaccc | tgcccccatc ccgggaggag | 1140 |
| atgaccaaga | accaggtcag | cctgacctgc | ctggtcaaag | gcttctaccc cagcgacatc | 1200 |
| gccgtggagt | gggagagcaa | tgggcagccg | gagaacaact | acaagaccac acctcccatg | 1260 |
| ctggactccg | acggctcctt | cttcctctac | agcaagctca | ccgtggacaa gagcaggtgg | 1320 |
| cagcagggga | acgtcttctc | atgctccgtg | atgcatgagg | ctctgcacaa ccactacacg | 1380 |
| cagaagagcc | tctccctgtc | tccgggtaaa | tga | | 1413 |

<210> SEQ ID NO 62

-continued

```
<211> LENGTH: 470
<212> TYPE: PRT
<213> ORGANISM: Homo sapiens

<400> SEQUENCE: 62

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Val Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Ile Ile Ser Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Val Gln Met Asn Ser Leu Arg Ala Glu Asp Thr Ala Val
            100                 105                 110

Tyr Tyr Cys Ala Arg Arg Gly His Tyr Gly Arg Asp Tyr Tyr Ser Tyr
        115                 120                 125

Tyr Gly Leu Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
```

```
385                 390                 395                 400
Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 63
<211> LENGTH: 720
<212> TYPE: DNA
<213> ORGANISM: Homo sapiens

<400> SEQUENCE: 63
atgaggctcc ctgctcagct cctggggctg ctaatgctct gggtctctgg atccagtggg      60
gatattgtga tgactcagtc tccactctcc ctgcccgtca cccctggaga gccggcctcc     120
atctcctgca ggtctagtca gagcctcctg cctggtaatg gatacaacta tttggattgg     180
tacctgcaga agccagggca gtctccacag ctcctgatct atttggttc taatcgggcc      240 tccggggtcc ctgacaggtt cagtggcagt ggatcaggca cagattttac actgaaaatc     300
agcagagtgg aggctgagga tgttggggtt tattactgca tgcaagctct acaaactcct     360
cggacgttcg gccaagggac caaggtggaa atcaaacgaa ctgtggctgc accatctgtc     420
ttcatcttcc cgccatctga tgagcagttg aaatctggaa ctgcctstgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccy tgacgctgag caaagcagac tacgagaaac acaaagtcta cgcctgcgaa     660
gtcacccatc agggcctgag ctcgcccgtc acaaagagct tcaacagggg agagtgttaa     720

<210> SEQ ID NO 64
<211> LENGTH: 239
<212> TYPE: PRT
<213> ORGANISM: Homo sapiens
<220> FEATURE:
<221> NAME/KEY: MOD_RES
<222> LOCATION: (156)
<223> OTHER INFORMATION: Variable amino acid

<400> SEQUENCE: 64

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu Pro Gly Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95
```

```
Thr Leu Lys Ile Ser Arg Val Glu Ala Glu Asp Val Gly Val Tyr Tyr
            100                 105                 110

Cys Met Gln Ala Leu Gln Thr Pro Arg Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Xaa Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 65
<211> LENGTH: 364
<212> TYPE: DNA
<213> ORGANISM: Homo sapiens

<400> SEQUENCE: 65
caggtgcagc tgcaggagtc gggcccagga ctggtgaagc cttcggacac cctgtccctc        60
acctgcactg tctctggtgg ctccatcaga ggttactact ggagctggat ccggcagccc       120
cctgggaagg gactggagtg gattgggtat atctattaca gtgggagcac caactacaac       180
ccctccctca agagtcgagt caccatatca gtagacacgt ccaagaacca gttctccctg       240
aagctgaact ctgtgaccgc tgcggacacg gccgtgtatt attgtgcgag aaagggggc        300 ctctacggtg actacggctg gttcgccccc tggggccagg gaaccctggt caccgtctcc       360
tcag                                                                    364

<210> SEQ ID NO 66
<211> LENGTH: 121
<212> TYPE: PRT
<213> ORGANISM: Homo sapiens

<400> SEQUENCE: 66

Gln Val Gln Leu Gln Glu Ser Gly Pro Gly Leu Val Lys Pro Ser Asp
 1               5                  10                  15

Thr Leu Ser Leu Thr Cys Thr Val Ser Gly Gly Ser Ile Arg Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Lys Gly Gly Leu Tyr Gly Asp Tyr Gly Trp Phe Ala Pro Trp Gly
            100                 105                 110

Gln Gly Thr Leu Val Thr Val Ser Ser
```

<210> SEQ ID NO 67
<211> LENGTH: 322
<212> TYPE: DNA
<213> ORGANISM: Homo sapiens

<400> SEQUENCE: 67

```
gaaattgtgt tgacgcagtc tccaggcacc ctgtctttgt ctccagggga aagagccacc      60
ctctcctgca gggccagtca gagtgttagc agcagcgact tagcctggca ccagcagaaa     120
cctggccagg ctcccagact cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cactgtcgta gcttattcac tttcggccct     300
gggaccaaag tggatatcaa ac                                              322
```

<210> SEQ ID NO 68
<211> LENGTH: 107
<212> TYPE: PRT
<213> ORGANISM: Homo sapiens

<400> SEQUENCE: 68

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
            20                  25                  30

Asp Leu Ala Trp His Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Cys Arg Ser Leu Phe
                85                  90                  95

Thr Phe Gly Pro Gly Thr Lys Val Asp Ile Lys
            100                 105
```

<210> SEQ ID NO 69
<211> LENGTH: 1401
<212> TYPE: DNA
<213> ORGANISM: Homo sapiens

<400> SEQUENCE: 69

```
atgaaacatc tgtggttctt ccttctcctg gtggcagctc ccagatgggt cctgtcccag      60
gtgcagctgc aggagtcggg cccaggactg gtgaagcctt cggagaccct gtccctcacc     120
tgcactgtct ctggtggctc catcagaggt tactactgga gctggatccg cagccccct     180
gggaagggac tggagtggat tgggtatatc tattacagtg ggagcaccaa ctacaacccc     240
tccctcaaga gtcgagtcac catatcagta gacacgtcca agaaccagtt ctccctgaag     300
ctgaactctg tgaccgctgc ggacacggcc gtgtattatt gtgcgagaaa ggggggcctc     360
tacggtgact acggctggtt cgcccccctgg ggccagggaa ccctggtcac cgtctcctca     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
```

-continued

```
ggactctact ccctcagcag cgtggtgacc gtgccctcca gcaacttcgg cacccagacc      660
tacacctgca acgtagatca caagcccagc aacaccaagg tggacaagac agttgagcgc      720
aaatgttgtg tcgagtgccc accgtgccca gcaccacctg tggcaggacc gtcagtcttc      780
ctcttccccc caaaacccaa ggacaccctc atgatctccc ggacccctga ggtcacgtgc      840
gtggtggtgg acgtgagcca cgaagacccc gaggtccagt tcaactggta cgtggacggc      900
gtggaggtgc ataatgccaa gacaaagcca cgggaggagc agttcaacag cacgttccgt      960
gtggtcagcg tcctcaccgt tgtgcaccag gactggctga acggcaagga gtacaagtgc     1020
aaggtctcca acaaaggcct cccagccccc atcgagaaaa ccatctccaa aaccaaaggg     1080
cagccccgag aaccacaggt gtacaccctg cccccatccc gggaggagat gaccaagaac     1140
caggtcagcc tgacctgcct ggtcaaaggc ttctacccca gcgacatcgc cgtggagtgg     1200
gagagcaatg ggcagccgga gaacaactac aagaccacac tcccatgctg gactccgac      1260 ggctccttct cctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaatg a                                                1401
```

<210> SEQ ID NO 70
<211> LENGTH: 466
<212> TYPE: PRT
<213> ORGANISM: Homo sapiens

<400> SEQUENCE: 70

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Thr Val Ser Gly Gly Ser Ile
         35                  40                  45

Arg Gly Tyr Tyr Trp Ser Trp Ile Arg Gln Pro Pro Gly Lys Gly Leu
     50                  55                  60

Glu Trp Ile Gly Tyr Ile Tyr Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Asn Ser Val Thr Ala Ala Asp Thr Ala Val Tyr
            100                 105                 110

Tyr Cys Ala Arg Lys Gly Gly Leu Tyr Gly Asp Tyr Gly Trp Phe Ala
        115                 120                 125

Pro Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
```

```
                225                 230                 235                 240
Lys Cys Cys Val Glu Cys Pro Pro Cys Pro Ala Pro Val Ala Gly
                    245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
            275                 280                 285
Asp Pro Glu Val Gln Phe Asn Trp Tyr Val Asp Gly Val Glu Val His
        290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
                340                 345                 350
Lys Thr Ile Ser Lys Thr Lys Gly Gln Pro Arg Glu Pro Gln Val Tyr
                355                 360                 365
Thr Leu Pro Pro Ser Arg Glu Glu Met Thr Lys Asn Gln Val Ser Leu
            370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
                435                 440                 445
Glu Ala Leu His Asn His Tyr Thr Gln Lys Ser Leu Ser Leu Ser Pro
            450                 455                 460
Gly Lys
465

<210> SEQ ID NO 71
<211> LENGTH: 705
<212> TYPE: DNA
<213> ORGANISM: Homo sapiens

<400> SEQUENCE: 71
atggaaaccc cagcgcagct tctcttcctc ctgctactct ggctcccaga atccaccgga      60
gaaattgtgt tgacgcagtc tccaggcacc ctgtctttgt ctccagggga agagccacc     120 ctctcctgca gggccagtca gagtgttagc agcagcgact tagcctggca ccagcagaaa    180
cctggccagg ctcccagact cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cactgtcgta gcttattcac tttcggccct    360
gggaccaaag tggatatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac agggagagt gttag                    705
```

<210> SEQ ID NO 72
<211> LENGTH: 234
<212> TYPE: PRT
<213> ORGANISM: Homo sapiens

<400> SEQUENCE: 72

```
Met Glu Thr Pro Ala Gln Leu Leu Phe Leu Leu Leu Trp Leu Pro
 1               5                  10                  15

Glu Ser Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
                35                  40                  45

Val Ser Ser Asp Leu Ala Trp His Gln Gln Lys Pro Gly Gln Ala
        50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln His Cys
                100                 105                 110

Arg Ser Leu Phe Thr Phe Gly Pro Gly Thr Lys Val Asp Ile Lys Arg
                115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 73
<211> LENGTH: 376
<212> TYPE: DNA
<213> ORGANISM: Homo sapiens

<400> SEQUENCE: 73

| | | | | | |
|---|---|---|---|---|---|
| caggtgcagc | tggtggagtc | tgggggaggc | gtggtccagc | ctggagggtc | cctgagactc | 60 |
| tcctgtgcag | cctctggatt | caccttcagt | agctatgcca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tacagagaca | attccaagaa | cacgctgtat | 240 |
| ctgcaaatga | acagcctgag | agctgaggac | acggctgtgt | attactgtgc | gagacgcggt | 300 |
| cactacggga | ataattacta | ctcctattac | ggtttggacg | tctggggcca | agggaccacg | 360 |
| gtcaccgtct | cctcag | | | | | 376 |

<210> SEQ ID NO 74
<211> LENGTH: 125
<212> TYPE: PRT

-continued

<213> ORGANISM: Homo sapiens

<400> SEQUENCE: 74

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Tyr Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly His Tyr Gly Asn Asn Tyr Tyr Ser Tyr Tyr Gly Leu
            100                 105                 110

Asp Val Trp Gly Gln Gly Thr Thr Val Thr Val Ser Ser
        115                 120                 125
```

<210> SEQ ID NO 75
<211> LENGTH: 337
<212> TYPE: DNA
<213> ORGANISM: Homo sapiens

<400> SEQUENCE: 75

```
gatattgtga tgactcagtc tccactctcc ctgcccgtca cccctggaga gccggcctcc      60
atctcctgca ggtctagtca gagcctcctg cctggtaatg gatacaacta tttggattgg    120
tacctgcaga agccagggca gtctccacag ctcctgatct atttgggttc taatcgggcc    180
tccggggtcc ctgacaggtt cagtggcagt ggctcaggca cagattttac actgaaaatc    240
agcagagtgg aggctgagga tgttggaatt tattactgca tgcaagctct acaaactcct    300
cggacgttcg gccaagggac caaggtggaa atcaaac                              337
```

<210> SEQ ID NO 76
<211> LENGTH: 112
<212> TYPE: PRT
<213> ORGANISM: Homo sapiens

<400> SEQUENCE: 76

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Pro Gly
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ala
                 85                  90                  95

Leu Gln Thr Pro Arg Thr Phe Gly Gln Gly Thr Lys Val Glu Ile Lys
            100                 105                 110
```

<210> SEQ ID NO 77

```
<211> LENGTH: 1413
<212> TYPE: DNA
<213> ORGANISM: Homo sapiens

<400> SEQUENCE: 77
atggagtttg ggctgagctg ggttttcctc gttgctcttt taagaggtgt ccagtgtcag       60
gtgcaactgg tggagtctgg gggaggcgtg gtccagcctg gaggtccct gagactctcc      120 tgtgcagcct ctggattcac cttcagtagc tatgccatgc actgggtccg ccaggctcca      180 ggcaagggc tggagtgggt ggcagttata tcatatgatg gaagtaataa atactatgca      240
gactccgtga agggccgatt caccatctac agagacaatt ccaagaacac gctgtatctg      300
caaatgaaca gcctgagagc tgaggacacg gctgtgtatt actgtgcgag acgcggtcac      360
tacgggaata attactactc ctattacggt ttggacgtct ggggccaagg gaccacggtc      420
accgtctcct cagcctccac caagggccca tcggtcttcc ccctggcgcc ctgctccagg      480
agcacctccg agagcacagc ggccctgggc tgcctggtca aggactactt ccccgaaccg      540
gtgacggtgt cgtggaactc aggcgctctg accagcggcg tgcacacctt cccagctgtc      600
ctacagtcct caggactcta ctccctcagc agcgtggtga ccgtgccctc cagcaacttc      660
ggcacccaga cctacacctg caacgtagat cacaagccca gcaacaccaa ggtggacaag      720
acagttgagc gcaaatgttg tgtcgagtgc ccaccgtgcc cagcaccacc tgtggcagga      780
ccgtcagtct tcctcttccc cccaaaaccc aaggacaccc tcatgatctc ccggacccct      840
gaggtcacgt gcgtggtggt ggacgtgagc acgaagacc ccgaggtcca gttcaactgg      900
tacgtggacg gcgtggaggt gcataatgcc aagacaaagc cacgggagga gcagttcaac      960
agcacgttcc gtgtggtcag cgtcctcacc gttgtgcacc aggactggct gaacggcaag     1020
gagtacaagt gcaaggtctc caacaaaggc ctcccagccc ccatcgagaa aaccatctcc     1080
aaaaccaaag ggcagccccg agaaccacag gtgtacaccc tgcccccatc ccgggaggag     1140
atgaccaaga accaggtcag cctgacctgc ctggtcaaag gcttctaccc cagcgacatc     1200
gccgtggagt gggagagcaa tgggcagccg gagaacaact acaagaccac acctcccatg     1260
ctggactccg acggctcctt cttcctctac agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa tga                                 1413

<210> SEQ ID NO 78
<211> LENGTH: 470
<212> TYPE: PRT
<213> ORGANISM: Homo sapiens

<400> SEQUENCE: 78
```

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Ala Met His Trp Val Arg Gln Ala Pro Gly Lys Gly Leu
        50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Tyr Arg Asp Asn Ser Lys Asn
                85                  90                  95

```
Thr Leu Tyr Leu Gln Met Asn Ser Leu Arg Ala Glu Asp Thr Ala Val
            100                 105                 110
Tyr Tyr Cys Ala Arg Arg Gly His Tyr Gly Asn Asn Tyr Tyr Ser Tyr
            115                 120                 125
Tyr Gly Leu Asp Val Trp Gly Gln Gly Thr Thr Val Thr Val Ser Ser
        130                 135                 140
Ala Ser Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
            195                 200                 205
Leu Ser Ser Val Val Thr Val Pro Ser Ser Asn Phe Gly Thr Gln Thr
        210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
            275                 280                 285
Val Ser His Glu Asp Pro Glu Val Gln Phe Asn Trp Tyr Val Asp Gly
        290                 295                 300
Val Glu Val His Asn Ala Lys Thr Lys Pro Arg Glu Glu Gln Phe Asn
305                 310                 315                 320
Ser Thr Phe Arg Val Val Ser Val Leu Thr Val Val His Gln Asp Trp
                325                 330                 335
Leu Asn Gly Lys Glu Tyr Lys Cys Lys Val Ser Asn Lys Gly Leu Pro
            340                 345                 350
Ala Pro Ile Glu Lys Thr Ile Ser Lys Thr Lys Gly Gln Pro Arg Glu
            355                 360                 365
Pro Gln Val Tyr Thr Leu Pro Pro Ser Arg Glu Glu Met Thr Lys Asn
        370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Met Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
        450                 455                 460
Ser Leu Ser Pro Gly Lys
465                 470

<210> SEQ ID NO 79
<211> LENGTH: 720
<212> TYPE: DNA
<213> ORGANISM: Homo sapiens
```

```
<400> SEQUENCE: 79
atgaggctcc ctgctcagct cctggggctg ctaatgctct gggtctctgg atccagtggg      60
gatattgtga tgactcagtc tccactctcc ctgcccgtca ccctggaga gccggcctcc      120 atctcctgca ggtctagtca gagcctcctg cctggtaatg gatacaacta tttggattgg    180
tacctgcaga agccagggca gtctccacag ctcctgatct atttgggttc taatcgggcc    240
tccggggtcc ctgacaggtt cagtggcagt ggctcaggca cagattttac actgaaaatc    300
agcagagtgg aggctgagga tgttgggatt tattactgca tgcaagctct acaaactcct    360
cggacgttcg gccaagggac caaggtggaa atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gttcagtgga gggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720

<210> SEQ ID NO 80
<211> LENGTH: 239
<212> TYPE: PRT
<213> ORGANISM: Homo sapiens

<400> SEQUENCE: 80

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu Pro Gly Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Tyr
            100                 105                 110

Cys Met Gln Ala Leu Gln Thr Pro Arg Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Arg Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 81
<211> LENGTH: 364
<212> TYPE: DNA
<213> ORGANISM: Homo sapiens

<400> SEQUENCE: 81

```
caggtgcagc tgcaggagtc gggcccagga ctggtgaagc cttcggagac cctgtccctc      60
acctgcactg tctctggtgg ctccatcaga ggttactact ggagctggat ccggcagccc     120
ccagggaagg gactggagtg gattgggtat atctattaca gtgggagcac caactacaac     180
ccctccctca gagtcgagt caccatatca gtagacacgt ccaagaacca gttctccctg      240
aagctgagtt ctgtgaccgc tgcggacacg gccgtgtatt actgtgcgag aaggggggc      300
ctctacggtg actacggctg gttcgccccc tggggccagg gaaccctggt caccgtctcc     360
tcag                                                                  364
```

<210> SEQ ID NO 82
<211> LENGTH: 121
<212> TYPE: PRT
<213> ORGANISM: Homo sapiens

<400> SEQUENCE: 82

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Arg Gly Tyr
                 20                  25                  30
Tyr Trp Ser Trp Ile Arg Gln Pro Pro Gly Lys Gly Leu Glu Trp Ile
             35                  40                  45
Gly Tyr Ile Tyr Tyr Ser Gly Ser Thr Asn Tyr Asn Pro Ser Leu Lys
         50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Arg Gly Gly Leu Tyr Gly Asp Tyr Gly Trp Phe Ala Pro Trp Gly
            100                 105                 110
Gln Gly Thr Leu Val Thr Val Ser Ser
            115                 120
```

<210> SEQ ID NO 83
<211> LENGTH: 322
<212> TYPE: DNA
<213> ORGANISM: Homo sapiens

<400> SEQUENCE: 83

```
gaaattgtgt tgacgcagtc tccaggcacc ctgtctttgt ctccagggga aagagccacc      60
ctctcctgca gggccagtca gagtgttagc agcaccact  tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatagta gcttattcac tttcggccct     300
gggaccaaag tggatatcaa ac                                              322
```

<210> SEQ ID NO 84
<211> LENGTH: 107
<212> TYPE: PRT
<213> ORGANISM: Homo sapiens

<400> SEQUENCE: 84

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Leu Phe
                85                  90                  95

Thr Phe Gly Pro Gly Thr Lys Val Asp Ile Lys
            100                 105
```

<210> SEQ ID NO 85
<211> LENGTH: 1401
<212> TYPE: DNA
<213> ORGANISM: Homo sapiens

<400> SEQUENCE: 85

| | |
|---|---:|
| atgaaacatc tgtggttctt ccttctcctg gtggcagctc ccagatgggt cctgtcccag | 60 |
| gtgcagctgc aggagtcggg cccaggactg gtgaagcctt cggagaccct gtccctcacc | 120 |
| tgcactgtct ctggtggctc catcagaggt tactactgga gctggatccg gcagccccca | 180 |
| gggaagggac tggagtggat tgggtatatc tattacagtg ggagcaccaa ctacaacccc | 240 |
| tccctcaaga gtcgagtcac catatcagta gacacgtcca agaaccagtt ctccctgaag | 300 |
| ctgagttctg tgaccgctgc ggacacggcc gtgtattact gtgcgagaag gggggggcctc | 360 |
| tacggtgact acggctggtt cgccccctgg ggccagggaa ccctggtcac cgtctcctca | 420 |
| gcctccacca aggccccatc ggtcttccc ctggcgccct gctccaggag cacctccgag | 480 |
| agcacagcgg ccctgggctg cctggtcaag gactacttcc ccgaaccggt gacggtgtcg | 540 |
| tggaactcag gcgctctgac cagcggcgtg cacaccttcc cagctgtcct acagtcctca | 600 |
| ggactctact ccctcagcag cgtggtgacc gtgccctcca gcaacttcgg cacccagacc | 660 |
| tacacctgca acgtagatca caagcccagc aacaccaagg tggacaagac agttgagcgc | 720 |
| aaatgttgtg tcgagtgccc accgtgccca gcaccacctg tggcaggacc gtcagtcttc | 780 |
| ctcttccccc caaaacccaa ggacaccctc atgatctccc ggaccccctga ggtcacgtgc | 840 |
| gtggtggtgg acgtgagcca cgaagacccc gaggtccagt tcaactggta cgtggacggc | 900 |
| gtggaggtgc ataatgccaa gacaaagcca cgggaggagc agttcaacag cacgttccgt | 960 |
| gtggtcagcg tcctcaccgt tgtgcaccag gactggctga acggcaagga gtacaagtgc | 1020 |
| aaggtctcca acaaaggcct cccagccccc atcgagaaaa ccatctccaa aaccaaaggg | 1080 |
| cagccccgag aaccacaggt gtacaccctg cccccatccc gggaggagat gaccaagaac | 1140 |
| caggtcagcc tgacctgcct ggtcaaaggc ttctacccca gcgacatcgc cgtggagtgg | 1200 |
| gagagcaatg ggcagccgga gaacaactac aagaccacac ctcccatgct ggactccgac | 1260 |
| ggctccttct tcctctacag caagctcacc gtggacaaga gcaggtggca gcagggggaac | 1320 |
| gtcttctcat gctccgtgat gcatgaggct ctgcacaacc actacacgca gaagagcctc | 1380 |
| tccctgtctc cgggtaaatg a | 1401 |

<210> SEQ ID NO 86
<211> LENGTH: 466
<212> TYPE: PRT
<213> ORGANISM: Homo sapiens

<400> SEQUENCE: 86

```
Met Lys His Leu Trp Phe Phe Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Arg Gly Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Arg Gly Gly Leu Tyr Gly Asp Tyr Gly Trp Phe Ala
        115                 120                 125

Pro Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
```

-continued

```
                370                 375                 380
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465
```

<210> SEQ ID NO 87
<211> LENGTH: 705
<212> TYPE: DNA
<213> ORGANISM: Homo sapiens

<400> SEQUENCE: 87

```
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcacctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatagta gcttattcac tttcggccct   360
gggaccaaag tggatatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttag              705
```

<210> SEQ ID NO 88
<211> LENGTH: 234
<212> TYPE: PRT
<213> ORGANISM: Homo sapiens

<400> SEQUENCE: 88

```
Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Thr Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
```

```
                100                 105                 110
Ser Ser Leu Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 89
<211> LENGTH: 378
<212> TYPE: DNA
<213> ORGANISM: Homo sapiens

<400> SEQUENCE: 89

```
caggtgcagc tggtggagtc tgggggaggc gtggtccagc ctgggaggtc cctgagactc    60
tcctgtgcag cctctggatt caccttcagt agttatggca tgcactgggt ccgccaggct   120
ccaggcaagg ggctggagtg ggtggcagtt atatcaaagg atggaggtaa taaataccat   180
gcagactccg tgaagggccg attcaccatc tccagagaca attccaagaa tacgctgtat   240
ctgcaaatga atagcctgag agttgaagac acggctgtgt attactgtgt gagaagaggg   300
catcagctgg ttctgggata ctactactac aacggtctgg acgtctgggg ccaagggacc   360
acggtcaccg tctcctca                                                  378
```

<210> SEQ ID NO 90
<211> LENGTH: 126
<212> TYPE: PRT
<213> ORGANISM: Homo sapiens

<400> SEQUENCE: 90

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Lys Asp Gly Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Arg Arg Gly His Gln Leu Val Leu Gly Tyr Tyr Tyr Asn Gly
            100                 105                 110

Leu Asp Val Trp Gly Gln Gly Thr Thr Val Thr Val Ser Ser
        115                 120                 125
```

<210> SEQ ID NO 91
<211> LENGTH: 378
<212> TYPE: DNA
<213> ORGANISM: Homo sapiens

<400> SEQUENCE: 91

```
caggtgcagc tggtggagtc tgggggaggc gtggtccagc ctgggaggtc cctgagactc      60
tcctgtgcag cctctggatt caccttcagt agttatggca tgcactgggt ccgccaggct     120
ccaggcaagg ggctggagtg ggtggcagtt atatcaaagg atggaggtaa taaataccat     180
gcagactccg tgaagggccg attcaccatc tccagagaca attccaagaa tacgctgtat     240
ctgcaaatga atagcctgag agctgaagac acggctgtgt attactgtgc gagaagaggg     300
catcagctgg ttctgggata ctactactac aacggtctgg acgtctgggg ccaagggacc     360
acggtcaccg tctcctca                                                   378
```

<210> SEQ ID NO 92
<211> LENGTH: 126
<212> TYPE: PRT
<213> ORGANISM: Homo sapiens

<400> SEQUENCE: 92

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Lys Asp Gly Gly Asn Lys Tyr His Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Arg Gly His Gln Leu Val Leu Gly Tyr Tyr Tyr Tyr Asn Gly
            100                 105                 110

Leu Asp Val Trp Gly Gln Gly Thr Thr Val Thr Val Ser Ser
        115                 120                 125
```

<210> SEQ ID NO 93
<211> LENGTH: 336
<212> TYPE: DNA
<213> ORGANISM: Homo sapiens

<400> SEQUENCE: 93

```
gatattgtga tgactcagtc tccactctcc ctgcccgtca cccctggaga gccggcctcc      60
atctcctgca ggtctagtca gagcctcttg tatagtaatg gatacaactt tttggattgg     120
tacctgcaga agccagggca gtctccacag ctcctgatct atttggttc taatcgggcc      180
tccggggtcc ctgacaggtt cagtggcagt ggatcaggca cagattttac actgaaaatc     240
agcagagtgg aggctgagga tgttggggtt tattactgca tgcaagctct acaaactcct     300
cggacgttcg gccaagggac caaggtggaa atcaaa                               336
```

<210> SEQ ID NO 94
<211> LENGTH: 112
<212> TYPE: PRT

<213> ORGANISM: Homo sapiens

<400> SEQUENCE: 94

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110
```

<210> SEQ ID NO 95
<211> LENGTH: 373
<212> TYPE: DNA
<213> ORGANISM: Homo sapiens

<400> SEQUENCE: 95

```
caggtgcaac tggtggagtc tgggggaggc gtggtccagc ctggggaggtc cctgagactc    60 tcctgtgcag cctctggatt caccttcagt cgctatggca tgcactgggt ccgccaggct   120
ccaggcaagg ggctggagtg ggtggcagtt atatcatctg atggaggtaa taaatactat   180
gcagactccg tgaagggccg attcaccatc tccagagaca attccaagaa cacgctgtat   240
ctgcaaatga acagcctgag agctgaggac acggctgtgt attactgtac gagaagaggg   300
actggaaaga cttactacca ctacgccggt atggacgtct ggggccaagg gaccacggtc   360
accgtctcct cag                                                      373
```

<210> SEQ ID NO 96
<211> LENGTH: 124
<212> TYPE: PRT
<213> ORGANISM: Homo sapiens

<400> SEQUENCE: 96

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Ser Asp Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Thr Arg Arg Gly Thr Gly Lys Thr Tyr Tyr His Tyr Ala Gly Met Asp
            100                 105                 110

Val Trp Gly Gln Gly Thr Thr Val Thr Val Ser Ser
        115                 120
```

<210> SEQ ID NO 97
<211> LENGTH: 364
<212> TYPE: DNA
<213> ORGANISM: Homo sapiens

<400> SEQUENCE: 97

```
caggtgcagc tgcaggagtc gggcccagga ctggtgaagc cttcggagac cctgtccctc      60
acctgcactg tctctggtgg ctccatcaga ggttactact ggagctggat ccggcagccc     120
cctgggaagg gactggagtg gattgggtat atctattaca gtgggagcac caactacaac     180
ccctccctca agagtcgagt caccatatca gtagacacgt ccaagaacca gttctccctg     240
aagctgaact ctgtgaccgc tgcggacacg gccgtgtatt attgtgcgag aaagggggc     300
ctctacggtg actacggctg gttcgccccc tggggccagg gaaccctggt caccgtctcc     360
tcag                                                                 364
```

<210> SEQ ID NO 98
<211> LENGTH: 121
<212> TYPE: PRT
<213> ORGANISM: Homo sapiens

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Lys Gly Gly Leu Tyr Gly Asp Tyr Gly Trp Phe Ala Pro Trp Gly
            100                 105                 110

Gln Gly Thr Leu Val Thr Val Ser Ser
        115                 120

<210> SEQ ID NO 99
<211> LENGTH: 322
<212> TYPE: DNA
<213> ORGANISM: Homo sapiens

<400> SEQUENCE: 99

```
gaaattgtgt tgacgcagtc tccaggcacc ctgtctttgt ctccagggga aagagccacc      60
ctctcctgca gggccagtca gagtgttagc agcagcgact tagcctggca ccagcagaaa     120
cctggccagg ctcccagact cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cacgcccgta gcttattcac tttcggccct     300
gggaccaaag tggatatcaa ac                                             322
```

<210> SEQ ID NO 100
<211> LENGTH: 107
<212> TYPE: PRT
<213> ORGANISM: Homo sapiens -continued

<400> SEQUENCE: 100

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asp Leu Ala Trp His Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Ala Arg Ser Leu Phe
                85                  90                  95

Thr Phe Gly Pro Gly Thr Lys Val Asp Ile Lys
            100                 105

<210> SEQ ID NO 101
<211> LENGTH: 720
<212> TYPE: DNA
<213> ORGANISM: Homo sapiens

<400> SEQUENCE: 101
atgaggctcc ctgctcagct cctggggctg ctaatgctct gggtctctgg atccagtggg     60
gatattgtga tgactcagtc tccactctcc ctgcccgtca cccctggaga gccggcctcc    120
atctcctgca ggtctagtca gagcctcctg cctggtaatg gatacaacta tttggattgg    180
tacctgcaga agccagggca gtctccacag ctcctgatct atttgggttc taatcgggcc    240
tccggggtcc ctgacaggtt cagtggcagt ggctcaggca cagattttac actgaaaatc    300
agcagagtgg aggctgagga tgttggggatt tattactgca tgcaagctct acaaactcct    360
cggacgttcg gccaagggac caaggtggaa atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gttcagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720

<210> SEQ ID NO 102
<211> LENGTH: 239
<212> TYPE: PRT
<213> ORGANISM: Homo sapiens

<400> SEQUENCE: 102

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu Pro Gly Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

```
Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Ile Tyr Tyr
            100                 105                 110

Cys Met Gln Ala Leu Gln Thr Pro Arg Thr Phe Gly Gln Gly Thr Lys
            115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 103
<211> LENGTH: 112
<212> TYPE: PRT
<213> ORGANISM: Homo sapiens

<400> SEQUENCE: 103

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Trp Thr Phe Gly Gln Gly Thr Lys Val Glu Ile Lys
            100                 105                 110

<210> SEQ ID NO 104
<211> LENGTH: 112
<212> TYPE: PRT
<213> ORGANISM: Homo sapiens

<400> SEQUENCE: 104

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
             85                  90                  95

Leu Gln Thr Pro Tyr Thr Phe Gly Gln Gly Thr Lys Leu Glu Ile Lys
        100                 105                 110
```

<210> SEQ ID NO 105
<211> LENGTH: 107
<212> TYPE: PRT
<213> ORGANISM: Homo sapiens

<400> SEQUENCE: 105

```
Asp Ile Gln Met Thr Gln Ser Pro Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
             85                  90                  95

Thr Phe Gly Gly Gly Thr Lys Val Glu Ile Lys
        100                 105
```

<210> SEQ ID NO 106
<211> LENGTH: 124
<212> TYPE: PRT
<213> ORGANISM: Homo sapiens

<400> SEQUENCE: 106

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Gly His Gln Leu Leu Gly Tyr Tyr Tyr Tyr Gly Met Asp
        100                 105                 110

Val Trp Gly Gln Gly Thr Thr Val Thr Val Ser Ser
        115                 120
```

<210> SEQ ID NO 107
<211> LENGTH: 125
<212> TYPE: PRT
<213> ORGANISM: Homo sapiens

<400> SEQUENCE: 107

```
Gln Val Gln Leu Val Glu Ser Gly Gly Gly Val Val Gln Pro Gly Arg
  1               5                  10                  15
```

```
                1               5                    10                   15
Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                    85                  90                  95

Ala Arg Met Gly Ser Ser Gly Ser Asp Tyr Tyr Tyr Tyr Gly Met
                100                 105                 110

Asp Val Trp Gly Gln Gly Thr Thr Val Thr Val Ser Ser
            115                 120                 125

<210> SEQ ID NO 108
<211> LENGTH: 120
<212> TYPE: PRT
<213> ORGANISM: Homo sapiens

<400> SEQUENCE: 108

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
 65                 70                  75                  80

Lys Leu Ser Ser Val Thr Ala Ala Asp Thr Ala Val Tyr Tyr Cys Ala
                85                  90                  95

Arg Tyr Cys Gly Tyr Tyr Tyr Tyr Gly Met Asp Val Trp Gly Gln
                100                 105                 110

Gly Thr Thr Val Thr Val Ser Ser
            115                 120

<210> SEQ ID NO 109
<211> LENGTH: 118
<212> TYPE: PRT
<213> ORGANISM: Homo sapiens

<400> SEQUENCE: 109

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                 70                  75                  80

Lys Leu Ser Ser Val Thr Ala Ala Asp Thr Ala Val Tyr Tyr Cys Ala
```

```
                    85                  90                  95
Arg Asp Tyr Gly Gly Asn Ser Tyr Phe Asp Tyr Trp Gly Gln Gly Thr
                100                 105                 110

Leu Val Thr Val Ser Ser
            115

<210> SEQ ID NO 110
<211> LENGTH: 122
<212> TYPE: PRT
<213> ORGANISM: Homo sapiens

<400> SEQUENCE: 110

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Tyr Cys Thr Asn Gly Val Cys Tyr Tyr Phe Asp Tyr Trp
                100                 105                 110

Gly Gln Gly Thr Leu Val Thr Val Ser Ser
            115                 120

<210> SEQ ID NO 111
<211> LENGTH: 112
<212> TYPE: PRT
<213> ORGANISM: Homo sapiens

<400> SEQUENCE: 111

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
                100                 105                 110

<210> SEQ ID NO 112
<211> LENGTH: 112
<212> TYPE: PRT
<213> ORGANISM: Homo sapiens

<400> SEQUENCE: 112

Asp Ile Val Met Thr Gln Ser Pro Leu Ser Leu Pro Val Thr Pro Gly
  1               5                  10                  15
```

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 113
<211> LENGTH: 108
<212> TYPE: PRT
<213> ORGANISM: Homo sapiens

<400> SEQUENCE: 113

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 114
<211> LENGTH: 122
<212> TYPE: PRT
<213> ORGANISM: Homo sapiens

<400> SEQUENCE: 114

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Cys Gly Gly Asp Cys Tyr Gly Ile Ala Val Ala Gly Trp
            100                 105                 110

Gly Gln Gly Thr Leu Val Thr Val Ser Ser
            115                 120

<210> SEQ ID NO 115
<211> LENGTH: 123
<212> TYPE: PRT
<213> ORGANISM: Homo sapiens

<400> SEQUENCE: 115

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Thr Gly Thr Tyr Tyr Tyr Tyr Tyr Gly Met Asp Val
            100                 105                 110

Trp Gly Gln Gly Thr Thr Val Thr Val Ser Ser
        115                 120

<210> SEQ ID NO 116
<211> LENGTH: 123
<212> TYPE: PRT
<213> ORGANISM: Homo sapiens

<400> SEQUENCE: 116

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Asp Tyr Tyr Tyr Tyr Tyr Tyr Gly Met Asp Val
            100                 105                 110

Trp Gly Gln Gly Thr Thr Val Thr Val Ser Ser
        115                 120

<210> SEQ ID NO 117
<211> LENGTH: 123
<212> TYPE: PRT
<213> ORGANISM: Homo sapiens

<400> SEQUENCE: 117

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Gly Asp Tyr Tyr Tyr Tyr Gly Met Asp Val
             100                 105                 110

Trp Gly Gln Gly Thr Thr Val Thr Val Ser Ser
        115                 120
```

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)
<223> OTHER INFORMATION: i

<400> SEQUENCE: 118
caggtgcagc tggagcagtc ngg                                          23

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 119
gctgagggag tagagtcctg agga                                         24

<210> SEQ ID NO 120
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 120
tatctaagct tctagactcg accgccacca tggagtttgg gctgagctg              49

<210> SEQ ID NO 121
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 121
tatctaagct tctagactcg accgccacca tggagtttgg gctgagctg              49

<210> SEQ ID NO 122
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 122

```
tatctaagct tctagactcg agcgccacca tgaaacacct gtggttcttc c            51

<210> SEQ ID NO 123
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 123
tatctaagct tctagactcg agcgccacca tgaaacatct gtggttcttc c            51

<210> SEQ ID NO 124
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 124
tatctaagct tctagactcg agcgccacca tggactggac ctggaggatc c            51

<210> SEQ ID NO 125
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 125
ttctctgatc agaattccta tcatttaccc ggagacaggg agag                    44

<210> SEQ ID NO 126
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 126
cttcaagctt acccgggcca ccatgaggct ccctgctcag c                       41

<210> SEQ ID NO 127
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 127
ttctttgatc agaattctca ctaacactct ccctgttga agc                      43

<210> SEQ ID NO 128
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 128
tatctaagct tctagactcg accgccacca tggagtttgg gctgagctg               49

<210> SEQ ID NO 129
<211> LENGTH: 49
<212> TYPE: DNA
```

```
<213> ORGANISM: Artificial Sequence
<220> FEATURE:
<223> OTHER INFORMATION: Description of Artificial Sequence: Primer

<400> SEQUENCE: 129
tatctaagct tctagactcg accgccacca tggagtttgg gctgagctg           49

<210> SEQ ID NO 130
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 130
tatctaagct tctagactcg accgccacca tggagtttgg gctgagctg           49

<210> SEQ ID NO 131
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 131
tatctaagct tctagactcg agcgccacca tgaaacatct gtggttcttc c        51

<210> SEQ ID NO 132
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 132
tatctaagct tctagactcg accgccacca tggagtttgg gctgagctg           49

<210> SEQ ID NO 133
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 133
tatctaagct tctagactcg agcgccacca tgaaacatct gtggttcttc c        51

<210> SEQ ID NO 134
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 134
tcttcaagct tgcccgggcc cgccaccatg gaaaccccag cgcag               45

<210> SEQ ID NO 135
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 135
gcaagcttca ccaatggttc gtctgcctct gcagtg                         36
```

<210> SEQ ID NO 136
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 136
tcagtgatgg tgatggtgat gtctcagccg atcctgggga cca                    43

<210> SEQ ID NO 137
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 137
tcagtgatgg tgatggtgat gtgggcaggg ctcgcgatgg tat                    43

<210> SEQ ID NO 138
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 138
tcagtgatgg tgatggtgat gacaggtgca gatggtgtct gtt                    43

<210> SEQ ID NO 139
<211> LENGTH: 197
<212> TYPE: PRT
<213> ORGANISM: Homo sapiens

<400> SEQUENCE: 139

Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg His

```
                    180                 185                 190

His His His His His
            195

<210> SEQ ID NO 140
<211> LENGTH: 153
<212> TYPE: PRT
<213> ORGANISM: Homo sapiens

<400> SEQUENCE: 140

Met Val Arg Leu Pro Leu Gln Cys Val Leu Trp Gly Cys Leu Leu Thr
  1               5                  10                  15

Ala Val His Pro Glu Pro Pro Thr Ala Cys Arg Glu Lys Gln Tyr Leu
             20                  25                  30

Ile Asn Ser Gln Cys Cys Ser Leu Cys Gln Pro Gly Gln Lys Leu Val
         35                  40                  45

Ser Asp Cys Thr Glu Phe Thr Glu Thr Glu Cys Leu Pro Cys Gly Glu
     50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro His His His His His His
145                 150

<210> SEQ ID NO 141
<211> LENGTH: 111
<212> TYPE: PRT
<213> ORGANISM: Homo sapiens

<400> SEQUENCE: 141

Met Val Arg Leu Pro Leu Gln Cys Val Leu Trp Gly Cys Leu Leu Thr
  1               5                  10                  15

Ala Val His Pro Glu Pro Pro Thr Ala Cys Arg Glu Lys Gln Tyr Leu
             20                  25                  30

Ile Asn Ser Gln Cys Cys Ser Leu Cys Gln Pro Gly Gln Lys Leu Val
         35                  40                  45

Ser Asp Cys Thr Glu Phe Thr Glu Thr Glu Cys Leu Pro Cys Gly Glu
     50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys His His His His His His
            100                 105                 110

<210> SEQ ID NO 142
<211> LENGTH: 118
<212> TYPE: PRT
<213> ORGANISM: Homo sapiens

<400> SEQUENCE: 142
```

Gln Val Gln Leu Gln Glu Ser Gly Pro Gly Leu Val Lys Pro Ser Glu
 1               5                  10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Asp Tyr Asn Trp Phe Asp Pro Trp Gly Gln Gly Thr
            100                 105                 110

Leu Val Thr Val Ser Ser
            115

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 143

Gly Gly Gly Gly Ser Gly Gly Gly Gly Ser Gly Gly Gly Gly Ser
 1               5                  10                  15

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tttttttttt tttttttt                                                        18

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 145

His His His His His His
 1               5

<210> SEQ ID NO 146
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 146
tgcaagcttc accatggtgt ctttgcctcg gctgtg                                    36

<210> SEQ ID NO 147

-continued

```
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 147
gtcctcgagt cagtgatggt gatggtgatg tgggcaggga tgacagac            48
```

ANTIBODIES TO CD40

This application claims the benefit of U.S. Provisional Application 60/348,980, filed Nov. 9, 2001.

BACKGROUND OF THE INVENTION

The CD40 antigen is a 50 kDa cell surface glycoprotein which belongs to the Tumor Necrosis Factor Receptor (TNF-R) family. (Stamenkovic et al., *EMBO J.* 8: 1403-10 (1989).) CD40 is expressed in many normal and tumor cell types, including B lymphocytes, dendritic cells, monocytes, macrophages, thymic epithelium, endothelial cells, fibroblasts, and smooth muscle cells. (Paulie S. et al., *Cancer Immunol. Immunother.* 20:23-8 (1985); Banchereau J. et al., *Adv. Exp. Med. & Biol.* 378:79-83 (1995); Alderson M. R. et al., *J. of Exp. Med.* 178:669-74 (1993); Ruggiero G. et al., *J. of Immunol.* 156:3737-46 (1996); Hollenbaugh D. et al., *J. of Exp. Med.* 182:33-40 (1995); Yellin M. J. et al., *J. of Leukocyte Biol.* 58:209-16 (1995); and Lazaar A. L. et al., *J. of Immunol.* 161:3120-7 (1998).) CD40 is expressed in all B-lymphomas and in 70% of all solid tumors. Although constitutively expressed, CD40 is up-regulated in antigen presenting cells by maturation signals, such as LPS, IL-1βp, IFN-γ and GM-CSF.

CD40 activation plays a critical role in regulating humoral and cellular immune responses. Antigen presentation without CD40 activation can lead to tolerance, while CD40 signaling can reverse such tolerance, enhance antigen presentation by all antigen presenting cells (APCs), lead to secretion of helper cytokines and chemokines, increase co-stimulatory molecule expression and signaling, and stimulate cytolytic activity of immune cells.

CD40 plays a critical role in B cell proliferation, maturation and class switching. (Foy T. M. et al., *Ann. Rev. of Immunol.* 14:591-617 (1996).) Disruption of the CD40 signaling pathway leads to abnormal serum immunoglobulin isotype distribution, lack of CD4+ T cell priming, and defects in secondary humoral responses. For example, the X-linked hyper-IgM syndrome is a disease associated with a mutation in the human CD40L gene, and it is characterized by the inability of affected individuals to produce antibodies other than those of the IgM isotype, indicating that the productive interaction between CD40 and CD40L is required for an effective immune response.

CD40 engagement by CD40L leads to the association of the CD40 cytoplasmic domain with TRAFs (TNF-R associated factors). (Lee H. H. et al., *Proc. Natl. Acad. Sci. USA* 96:1421-6 (1999); Pullen S. S. et al., *Biochemistry* 37:11836-45 (1998); Grammar A. C. et al., *J. of Immunol.* 161:1183-93 (1998); Ishida T. K. et al., *Proc. Natl. Acad. Sci. USA* 93:9437-42 (1996); Pullen S. S. et al., *J. of Biol. Chem.* 274:14246-54 (1999)). The interaction with TRAFs can culminate in the activation of both NFκB and Jun/AP1 pathways. (Tsukamoto N. et al., *Proc. Natl. Acad. Sci. USA* 96:1234-9 (1999); Sutherland C. L. et al., *J. of Immunol.* 162:4720-30 (1999).) Depending on cell type, this signaling leads to enhanced secretion of cytokines such as IL-6 (Jeppson J. D. et al., *J. of Immunol.* 161:1738-42 (1998); Uejima Y. et al., *Int. Arch. of Allergy & Immunol.* 110:225-32, (1996), IL-8 (Gruss H. J. et al., *Blood* 84:2305-14 (1994); von Leoprechting A. et al., *Cancer Res.* 59:1287-94 (1999); Denfeld R. W. et al., *Europ. J. of Immunol.* 26:2329-34 (1996)), IL-12 (Cella M. et al., *J. of Exp. Med.* 184:747-52 (1996); Ferlin W. G. et al., *Europ. J. of Immunol.* 28:525-31 (1998); Armant M. et al., *Europ. J. of Immunol.* 26:1430-4 (1996); Koch F. et al., *J. of Exp. Med.* 184:741-6 (1996); Seguin R. and L. H. Kasper, *J. of Infect. Diseases* 179:467-74 (1999); Chaussabel D. et al., *Infection & Immunity* 67:1929-34 (1999)), IL-15 (Kuniyoshi J. S. et al., *Cellular Immunol.* 193:48-58 (1999)) and chemokines (MIP1α, MIP1β, RANTES, and others) (McDyer J. F. et al., *J. of Immunol.* 162:3711-7 (1999); Schaniel C. et al., *J. of Exp. Med.* 188:451-63 (1998); Altenburg A. et al., *J. of Immunol.* 162:4140-7 (1999); Deckers J. G. et al., *J. of the Am. Society of Nephrology* 9:1187-93 (1998)), increased expression of MHC class I and II (Santos-Argumedo L. et al., *Cellular Immunol.* 156:272-85 (1994)), and increased expression of adhesion molecules (e.g., ICAM) (Lee H. H. et al., *Proc. Natl. Acad. Sci. USA.* 96:1421-6 (1999); Grousson J. et al., *Archives of Dermatol. Res.* 290:325-30 (1998); Katada Y. et al., *Europ. J. of Immunol.* 26:192-200 (1996); Mayumi M. et al., *J. of Allergy & Clin. Immunol.* 96:1136-44 (1995); Flores-Romo L. et al., *Immunol.* 79:445-51 (1993)) and costimulatory molecules (e.g., B7) (Roy M. et al., *Europ. J. of Immunol.* 25:596-603 (1995); Jones K. W. and C. J. Hackett, *Cellular Immunol.* 174:42-53 (1996); Caux C. et al., *Journal of Exp. Med.* 180:1263-72 (1994); Kiener P. A. et al., *J. of Immunol.* 155:4917-25 (1995)). Cytokines induced by CD40 engagement enhance T cell survival and activation.

In addition to enhancement of cellular and immune function, the effects of CD40 activation include: cell recruitment and differentiation by chemokines and cytokines; activation of monocytes; increased cytolytic activity of cytolytic T lymphocyte (CTL) and natural killer (NK) cells; induction of apoptosis in CD40 positive tumors; enhancement of immunogenicity of CD40 positive tumors; and tumor-specific antibody production. The role of CD40 activation in cell-mediated immune responses is also well established, and it is reviewed in: Grewal et al., *Ann. Rev. of Immunol.* 16:111-35 (1998); Mackey et al., *J. of Leukocyte Biol.* 63:418-28 (1998); and Noelle R. J., *Agents & Actions-Suppl.* 49:17-22 (1998). Studies using a cross-priming model system showed that CD40 activation of APCs can replace helper T cell requirement for the generation of cytolytic T lymphocyte (CTL). (Bennett et al., *Nature* 393:478-480 (1998).) Evidence from CD40L deficient mice indicates a clear requirement for CD40 signaling in helper T cell priming. (Grewal I. S. et al., *Science* 273:1864-7 (1996); Grewal I. S. et al., *Nature* 378:617-20 (1995).) CD40 activation converts otherwise tolerogenic, antigen bearing B cells into competent APCs. (Buhlmann J. E. et al., *Immunity* 2:645-53 (1995).) CD40 activation induces maturation and differentiation of cord blood progenitors into dendritic cells. (Flores-Romo L. et al., *J. of Exp. Med.* 185:341-9 (1997); Mackey M. F. et al., *J. of Immunol.* 161:2094-8 (1998).) CD40 activation also induces differentiation of monocytes into functional dendritic cells. (Brossart P. et al., *Blood* 92:4238-47 (1998).) Further, CD40 activation enhances cytolytic activity of NK cells through APC-CD40 induced cytokines. (Carbone E. et al., *J. of Exp. Med.* 185:2053-60 (1997); Martin-Fontecha A. et al., *J. of Immunol.* 162:5910-6 (1999).) These observations indicate that CD40 plays an essential role in the initiation and enhancement of immune responses by inducing maturation of APCs, secretion of helper cytokines, upregulation of costimulatory molecules, and enhancement of effector functions.

The critical role of CD40 signaling in the initiation and maturation of humoral and cytotoxic immune responses makes this system an ideal target for immune enhancement. Such enhancement can be particularly important for mounting effective immune responses to tumor antigens, which are generally presented to the immune system through cross-priming of activated APCs. (Huang A. Y. et al., *Ciba Foundation Symp.* 187:229-44 (1994); Toes R. E. M. et al., *Seminars in Immunol.* 10:443-8 (1998); Albert M. L. et al., *Nature* 392:86-9 (1998); Bennett S. R. et al., *J. of Exp. Med.* 186:65-70 (1997).)

Several groups have demonstrated the effectiveness of CD40 activation for antitumor responses in vitro and in vivo. (Toes R. E. M. et al., *Seminars in Immunol.* 10:443-8 (1998).) Two groups, using lung metastatic model of renal cell carcinoma and subcutaneous tumors by virally transformed cells, have independently demonstrated that CD40 activation can reverse tolerance to tumor-specific antigens, resulting in efficient antitumor priming of T cells. (Sotomayor E. M. et al., *Nature Medicine* 5:780-787 (1999); Diehl L. et al., *Nature Medicine* 5:774-9 (1999).) Antitumor activity in the absence of immune cells was also reported by CD40L and anti-CD40 antibody treatment in a human breast cancer line model in SCID mice. (Hirano A. et al., *Blood* 93:2999-3007 (1999).) CD40 activation by anti-CD40 antibody was recently shown to eradicate CD40+ and CD40− lymphoma in mouse models. (French R. R. et al., *Nature Medicine* 5:548-53 (1999).) Furthermore, previous studies by Glennie and co-workers conclude that signaling activity by anti-CD40 antibodies is more effective for inducing in vivo tumor clearance than other anti-surface marker antibodies capable of recruiting effectors. (Tutt A. L. et al., *J. of Immunol.* 161:3176-85 (1998).) Consistent with these observations, when anti-CD40 antibodies were tested for activity against CD40+ tumor cells in vivo, most but not all of the tumoricidal activity was associated with CD40 signaling rather than ADCC. (Funakoshi S. et al., *J. of Immunotherapy with Emphasis on Tumor Immunol.* 19:93-101 (1996).) In another study, bone marrow dendritic cells were treated ex vivo with a variety of agents, and tested for in vivo antitumor activity. These studies demonstrated that CD40L stimulated DCs were the most mature and most effective cells that mounting an antitumor response.

The essential role of CD40 in antitumor immunity has also been demonstrated by comparing responses of wild-type and CD40−/− mice to tumor vaccines. These studies show that CD40−/− mice are incapable of achieving the tumor immunity observed in normal mice. (Mackey M. F. et al., *Cancer Research* 57:2569-74 (1997).) In another study, splenocytes from tumor bearing mice were stimulated with tumor cells and treated with activating anti-CD40 antibodies ex vivo, and were shown to have enhanced tumor specific CTL activity. (Donepudi M. et al., *Cancer Immunol. Immunother.* 48:153-164 (1999).) These studies demonstrate that CD40 occupies a critical position in antitumor immunity, in both CD40 positive and negative tumors. Since CD40 is expressed in lymphomas, leukemias, multiple myeloma, a majority of carcinomas of nasopharynx, bladder, ovary, and liver, and some breast and colorectal cancers, activation of CD40 can have a broad range of clinical applications.

Anti-CD40 activating monoclonal antibodies can contribute to tumor eradication via several important mechanisms. Foremost among these is activation of host dendritic cells for enhanced tumor antigen processing and presentation, as well as enhanced antigen presentation or immunogenicity of CD40 positive tumor cells themselves, leading to activation of tumor specific CD4+ and CD8+ lymphocytes. Additional antitumor activity can be mediated by other immune-enhancing effects of CD40 signaling (production of chemokines and cytokines, recruitment and activation monocytes, and enhanced CTL and NK cytolytic activity), as well as direct killing of CD40+ tumors by induction of apoptosis or by stimulating a humoral response leading to ADCC. Apoptotic and dying tumor cells can also become an important source of tumor-specific antigens that are processed and presented by CD40 activated APCs.

Accordingly, there is a critical need for therapeutic, clinically relevant anti-CD40 agonist antibodies.

SUMMARY OF THE INVENTION

The present invention provides an isolated antibody or antigen-binding portion thereof that binds CD40 and acts as a CD40 agonist.

The invention provides a composition comprising the anti-CD40 antibody, or antigen binding portion thereof, and a pharmaceutically acceptable carrier. The composition may further comprise another component, such as an anti-tumor agent or an imaging agent. Diagnostic and therapeutic methods are also provided by the invention.

The invention provides an isolated cell line, such as a hybridoma, that produces an anti-CD40 antibody or antigen binding portion thereof.

The invention also provides nucleic acid molecules encoding the heavy and/or light chain, or antigen-binding portions thereof, of an anti-CD40 antibody.

The invention provides vectors and host cells comprising the nucleic acid molecules, as well as methods of recombinantly producing the polypeptides encoded by nucleic acid molecules.

Non-human transgenic animals that express the heavy and/or light chain, or antigen-binding portions thereof, of an anti-CD40 antibody are also provided.

The invention also provides a method for treating a subject in need thereof with an effective amount of a nucleic acid molecule encoding the heavy and/or light chain, or antigen-binding portions thereof, of an anti-CD40 antibody.

BRIEF DESCRIPTION OF THE DRAWINGS

FIGS. 1A-1H are sequence alignments of predicted amino acid sequences of isolated anti-CD40 monoclonal antibody light and heavy chain variable domains with the germline amino acid sequences of the corresponding light and heavy chain genes.). Differences between the clones and the germline sequence are indicated by shading. The germline CDR1, CDR2, and CDR3 sequences are underlined. In alignments of heavy chain sequences, apparent insertions to the CDR3 region are indicated by a dash (−) in the germline sequence and apparent deletions in the CDR3 region are indicated by a dash (−) in the clone sequence.

FIG. 1A: the predicted kappa light chain variable region amino acid sequences of mAbs 3.1.1 (SEQ ID NO: 4) and 7.1.2 (SEQ ID NO: 12) with the Vκ-=A3/A19 and Jκ1 gene germline (SEQ ID NO: 103) amino acid sequences.

FIG. 1B: the predicted kappa light chain variable region amino acid sequence from clone 15.1.1 (SEQ ID NO: 28) and the germline amino acid sequence (Vκ=A3/A19 and J=Jκ2) (SEQ ID NO: 104);

FIG. 1C: the predicted kappa light chain variable region amino acid sequences from mAbs 10.8.3 (SEQ ID NO: 20) and 21.4.1 (SEQ ID NO: 44) and the germline amino acid sequence (Vκ=L5 (DP5) and J=Jκ4) (SEQ ID NO: 105);

FIG. 1D: the predicted heavy chain variable region amino acid sequence from mAb 3.1.1 (SEQ ID NO: 2) and the germline amino acid sequence ($V_H$=3-30+(DP-49), D=D4+DIR3 and J=$J_H$6) (SEQ ID NO: 106);

FIG. 1E: the predicted heavy chain variable region amino acid sequence from mAb 7.1.2 (SEQ ID NO: 10) and the germline amino acid sequence ($V_H$=3-30+ (DP-49), D=DIR5+D1-26 and J=$J_H$6) (SEQ ID NO: 107);

FIG. 1F: the predicted heavy chain amino acid sequences from mAb 10.8.3 (SEQ ID NO: 18): and the germline amino acid sequence ($V_H$=4.35 (VIV-4), D=DIR3 and J=$J_H$6) (SEQ ID NO: 108);

FIG. 1G: the predicted heavy chain variable region amino acid sequences from mAb 15.1.1 (SEQ ID NO: 26) and the germline amino acid sequence ($V_H$=4-59 (DP-71), D=D4-23 and J=$J_H$4) (SEQ ID NO: 109); and FIG. 1H: the predicted heavy variable region chain amino acid sequences from mAb 21.4.1 (SEQ ID NO: 42) and the germline amino acid sequence ($V_H$=1-02 (DP-75), D=DLR1 and J=$J_H$4) (SEQ ID NO: 110).

FIGS. 2A-2H are sequence alignments of predicted amino acid sequences of isolated anti-CD40 monoclonal antibody light and heavy chain variable domains with the germline amino acid sequences of the corresponding light and heavy chain genes.). Differences between the clones and the germline sequence are indicated in bold. The germline CDR1, CDR2, and CDR3 sequences are underlined. In alignments of heavy chain sequences, apparent insertions to the CDR3 region are indicated by a dash (–) in the germline sequence and apparent deletions in the CDR3 region are indicated by a dash (–) in the clone sequence.

FIG. 2A: the predicted kappa light chain amino acid sequences from mabs 22.1.1 (SEQ ID NO: 52), 23.5.1 (SEQ ID NO: 60) and 23.29.1 (SEQ ID NO: 76) and the germline amino acid sequence (Vκ=A3/A19 and J=Jκ1) (SEQ ID NO: 111);

FIG. 2B: the predicted kappa light chain amino acid sequence from mAb 21.2.1 (SEQ ID NO: 36) and the germline amino acid sequence (Vκ=A3/A19 and J=Jκ3) (SEQ ID NO: 112);

FIG. 2C: the predicted kappa light chain amino acid sequences from mAbs 23.28.1 (SEQ ID NO: 68), 23.28.1L-C92A (SEQ ID NO: 100) and 24.2.1 (SEQ ID NO: 84) and the germline amino acid sequence (Vκ=A27 and J=Jκ3); (SEQ ID NO: 113);

FIG. 2D: the predicted heavy chain amino acid sequence from mAb 21.2.1 (SEQ ID NO: 34) and the germline amino acid sequence ($V_H$=3-30+, D=DIR3+D6-19 and J=$J_H$4) (SEQ ID NO: 114);

FIG. 2E: the predicted heavy chain amino acid sequence from mAbs 22.1.1 (SEQ ID NO: 50), 22.1.1H-C109A (SEQ ID NO: 96) and the germline amino acid sequence ($V_H$=3-30-30+, D=D1-1 and J=$J_H$6) (SEQ ID NO: 115);

FIG. 2F: the predicted heavy chain amino acid sequence from mAb 23.5.1 (SEQ ID NO: 58) and the germline amino acid sequence ($V_H$=3-30+, D=D4-17 and J=$J_H$6) (SEQ ID NO: 116);

FIG. 2G: the predicted heavy chain amino acid sequence from mAb 23.29.1 (SEQ ID NO: 74) and the germline amino acid sequence ($V_H$=3-30.3, D=D4-17 and J=$J_H$6) (SEQ ID NO: 117); and FIG. 2H: the predicted heavy chain amino acid sequences from mAb 23.28.1 (SEQ ID NO: 66), 23.28.1H-D16E (SEQ ID NO: 98) and 24.2.1 (SEQ ID 30 NO: 82) and the germline amino acid sequence ($V_H$=4-59, D=DIR1+D4-17 and J=$J_H$5) (SEQ ID NO: 142).

FIG. 16 is an alignment of the D1-D4 domains of mouse and human CD40.

FIG. 17 is an alignment of the mouse and human CD40 amino acid sequences showing the location of the fusion sites of the chimeras.

DETAILED DESCRIPTION OF THE INVENTION

Definitions and General Techniques

Figure 3:
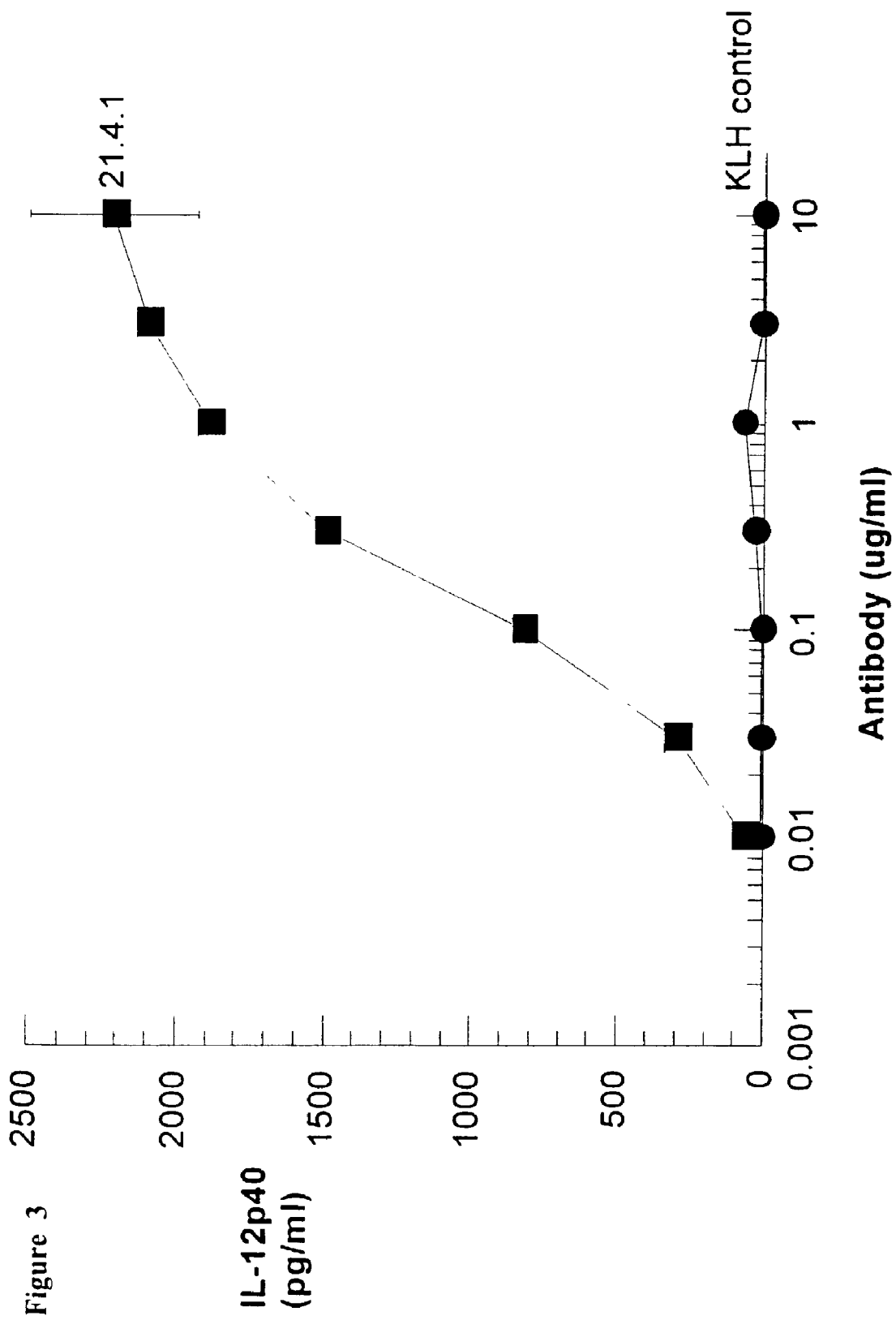
FIG. 3 is a dose-response curve that illustrates the ability of an anti-CD40 antibody of the invention (21.4.1) to enhance IL-12p40 production by human dendritic cells.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989) and Ausubel et al.,

*Current Protocols in Molecular Biology*, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include an anti-CD40 antibody that has been affinity purified using CD40, an anti-CD40 antibody that has been synthesized by a hybridoma or other cell line in vitro, and a human anti-CD40 antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "polypeptide analog" as used herein refers to a polypeptide that comprises a segment that has substantial identity to a portion of an amino acid sequence and that has at least one of the following properties: (1) specific binding to CD40 under suitable binding conditions, (2) ability to activate CD40, (3) the ability to upregulate the expression of cell surface molecules such as ICAM, MHC-II, B7-1, B7-2, CD71, CD23 and CD83, or (4) the ability to enhance the secretion of cytokines such as IFN-β1, IL-2, IL-8, IL-12, IL-15, IL-18 and IL-23. Typically, polypeptide analogs comprise a conservative amino acid substitution (or insertion or deletion) with respect to the naturally-occurring sequence. Analogs typically are at least 20 or 25 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), which are each incorporated herein by reference.

Non-peptide analogs are commonly used in the pharmaceutical industry as drugs with properties analogous to those of the template peptide. These types of non-peptide compound are termed "peptide mimetics" or "peptidomimetics." Fauchere, *J. Adv. Drug Res.* 15:29 (1986); Veber and Freidinger, TINS p. 392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH═CH— (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

An "antibody" refers to a complete antibody or to an antigen-binding portion thereof, that competes with the intact antibody for specific binding. See generally, *Fundamental Immunology*, Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. Antigen-binding portions include, inter alia, Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide.

From N-terminus to C-terminus, both light and heavy chain variable domains comprise the regions FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

As used herein, an antibody that is referred to by number is a monoclonal antibody that is obtained from the hybridoma of the same number. For example, monoclonal antibody 3.1.1 is obtained from hybridoma 3.1.1.

As used herein, a Fd fragment means an antibody fragment that consists of the $V_H$ and $C_H$ 1 domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which a $V_L$ and $V_H$ domains are paired to form a monovalent molecules via a synthetic linker that enables them to be made as a single protein chain. (Bird et al., *Science* 242:423-426 (1988) and Huston et al., *Proc. Natl. Acad. Sci. USA* 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90:6444-6448 (1993), and Poljak R. J. et al., *Structure* 2:1121-1123 (1994).) In some embodiments, one or more CDRs from an antibody of the invention may be incorporated into a molecule either covalently or noncovalently to make it an immunoadhesin that specifically binds to CD40. In such embodiments, the CDR(s) may be incorporated as part of a larger polypeptide chain, may be covalently linked to another polypeptide chain, or may be incorporated noncovalently.

In embodiments having one or more binding sites, the binding sites may be identical to one another or may be different.

As used herein, the term "human antibody" means any antibody in which all of the variable and constant domain sequences are human sequences. These antibodies may be prepared in a variety of ways, as described below.

The term "chimeric antibody" as used herein means an antibody that comprises regions from two or more different antibodies. In one embodiment, one or more of the CDRs are derived from a human anti-CD40 antibody. In another embodiment, all of the CDRs are derived from a human anti-CD40 antibody. In another embodiment, the CDRs from more than one human anti-CD40 antibodies are combined in a chimeric antibody. For instance, a chimeric antibody may comprise a CDR1 from the light chain of a first human anti-CD40 antibody, a CDR2 from the light chain of a second human anti-CD40 antibody and a CDR3 and CDR3 from the light chain of a third human anti-CD40 antibody, and the CDRs from the heavy chain may be derived from one or more other anti-CD40 antibodies. Further, the framework regions may be derived from one of the same anti-CD40 antibodies or from one or more different human.

An "activating antibody" (also referred to herein as an "agonist antibody" as used herein means an antibody that increases one or more CD40 activities by at least about 20% when added to a cell, tissue or organism expressing CD40. In some embodiments, the antibody activates CD40 activity by at least 40%, 50%, 60%, 70%, 80%, 85%. In some embodiments, the activating antibody is added in the presence of CD40L. In some embodiments, the activity of the activating antibody is measured using a whole blood surface molecule upregulation assay. See Example VII. In another embodiment, the activity of the activating antibody is measured using a dendritic cell assay to measure IL-12 release. See Example VIII. In another embodiment the activity of the activating antibody is measured using an in vivo tumor model. See Example X.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIAcore™ system (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "$K_D$" refers to the equilibrium dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the equilibrium dissociation constant is $\leq 1$ µM, preferably $\leq 100$ nM and most preferably $\leq 10$ nM.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "oligonucleotide" as used herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or to 40 bases in length. Oligonucleotides are usually single stranded, e.g. for primers and probes; although oligonucleotides may be double stranded, e.g. for use in the construction of a gene mutant. Oligonucleotides of the invention can be either sense or antisense oligonucleotides.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded DNA loop into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleotide sequence encompasses its complement unless otherwise specified. Thus, a reference to a nucleic acid having a particular sequence should be understood to encompass its complementary strand, with its complementary sequence.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, share at least 70, 75 or 80 percent sequence identity, preferably at least 90 or 95 percent sequence identity, and more preferably at least 97, 98 or 99 percent sequence identity. Preferably, residue positions that are not identical differ by conservative amino acid substitutions. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthamide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term patient includes human and veterinary subjects.

Throughout this specification and claims, the word "comprise," or variations such as "comprises" or "comprising," will be understood to imply the inclusion of a stated integer or group of integers but not the exclusion of any other integer or group of integers.

Human Anti-CD40 Antibodies and Characterization Thereof

Human antibodies avoid certain of the problems associated with antibodies that possess non-human (e.g., rodent) variable and/or constant regions. Such problems include the rapid clearance of the antibodies or immune response against the antibody. Therefore, in one embodiment, the invention provides humanized anti-CD40 antibodies. In another embodiment, the invention provides human anti-CD40 antibodies. In some embodiments, human anti-CD40 antibodies are produced by immunizing a rodent whose genome comprises human immunoglobulin genes so that the rodent produces human antibodies. Human anti-CD40 antibodies are expected to minimize the immunogenic and allergic responses intrinsic to non-human or non-human-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations.

The invention provides eleven activating human anti-CD40 monoclonal antibodies (mAbs) and the hybridoma cell lines that produce them. Table A lists the sequence identifiers (SEQ ID NOS:) of the nucleic acids encoding the full-length heavy and light chains (including leader sequence), the corresponding full-length deduced amino acid sequences, and the nucleotide and deduced amino acid sequence of the heavy and light chain variable regions.

changed to alanines. The invention also provides a variant light chain of mAb 3.1.1 in which the leucine at residue 4 and the leucine at residue 83 are changed to methionine and valine, respectively. Combination with a variant heavy or light chain with a wild type light or heavy chain, respectively is designated by the mutant chain. Thus, an antibody containing a wild type light chain and a heavy chain comprising the alanine to threonine mutation at residue 78 is designated as 3.1.1H-A78T. However, in other embodiments of the invention, antibodies containing any combination of a variant heavy chain and the variant light chain of 3.1.1 are included.

Further, the invention provides a variant of the heavy chain of mAb 22.1.1 in which the cysteine at residue 109 is changed to an alanine. A monoclonal antibody comprising the variant heavy chain and the 22.1.1 light chain is designated mAb 22.1.1H-C109A. The invention further provides two variant heavy chains and a variant light chain of mAb 23.28.1. In one heavy chain variant, the aspartic acid at residue 16 is changed to glutamic acid. A mAb comprising the variant heavy chain variant and the 23.28.1 light chain is designated 23.28.1H-D16E. The invention also includes a 23.28.1 light chain variant in which the cysteine at residue 92 is changed to an alanine. A mAb comprising the 23.28.1 heavy chain and the variant light chain is designated 23.28.1 L C92A. The invention also provides mAbs comprising either of the 23.28.1 heavy chain variants with the 23.28.1 light chain variant.

The light chain produced by hybridoma 23.29.1 contains a mutation in the constant region at residue 174. The light chain produced by the hybridoma has arginine at this position instead of the canonical lysine. Accordingly, the invention also provides a 23.29.1 light chain with the canonical

TABLE A

HUMAN ANTI-CD40 ANTIBODIES

SEQUENCE IDENTIFIER (SEQ ID NO:)

| | Variable Region | | | | Full Length | | | |
|---|---|---|---|---|---|---|---|---|
| | Heavy | | Light | | Heavy | | Light | |
| MAb | DNA | Protein | DNA | Protein | DNA | Protein | DNA | Protein |
| 3.1.1 | 1 | 2 | 3 | 4 | 5 | 6 | 7 | 8 |
| 7.1.2 | 9 | 10 | 11 | 12 | 13 | 14 | 15 | 16 |
| 10.8.3 | 17 | 18 | 19 | 20 | 21 | 22 | 23 | 24 |
| 15.1.1 | 25 | 26 | 27 | 28 | 29 | 30 | 31 | 32 |
| 21.2.1 | 33 | 34 | 35 | 36 | 37 | 38 | 39 | 40 |
| 21.4.1 | 41 | 42 | 43 | 44 | 45 | 46 | 47 | 48 |
| 22.1.1 | 49 | 50 | 51 | 52 | 53 | 54 | 55 | 56 |
| 23.5.1 | 57 | 58 | 59 | 60 | 61 | 62 | 63 | 64 |
| 23.28.1 | 65 | 66 | 67 | 68 | 69 | 70 | 71 | 72 |
| 23.29.1 | 73 | 74 | 75 | 76 | 77 | 78 | 79 | 80 |
| 24.2.1 | 81 | 82 | 83 | 84 | 85 | 86 | 87 | 88 |

The invention further provides human anti-CD40 mAb 23.25.1 and the hybridoma cell line that produces it.

The invention further provides heavy and/or light chain variants of certain of the above-listed human anti-CD40 mAbs, comprising one or more amino acid substitutions. The invention provides two variant heavy chains of mAb 3.1.1. In one, the alanine at residue 78 is changed to threonine. In the second, the alanine at residue 78 is changed to threonine, and the valines at residues 88 and 97 are lysine at residue 174 and a mAb, designated 23.29.1L-R174K, comprising the 23.29.1 heavy chain and the variant light chain.

In a preferred embodiment, the anti-CD40 antibody is 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K and 24.2.1. In some embodiments, the anti-CD40 antibody comprises a light chain comprising an amino acid sequence selected from SEQ ID NO: 8, 16, 24, 32, 40, 48, 56, 64, 72, 80, 88, 94, 100 or 102 or the variable region therefrom, or encoded by a nucleic acid sequence selected from SEQ ID NO: 7, 15, 23, 31, 39, 47, 55, 63, 71, 79, 87, 93, 99 or 101. In some embodiments, the anti-CD40 antibody comprises a light chain comprising at least the CDR2 from one of listed antibodies, one of the above-identified amino acid sequences (as shown in FIGS. 1A-1C and 2A-2C) or encoded by one of the above-identified nucleic acid sequences. In another embodiment, the light chain further comprises a CDR1 and CDR3 independently selected from a light chain variable region that comprises no more than ten amino acids from the amino acid sequence encoded by a germline Vκ A3/A19, L5 or A27 gene, or comprises a CDR1 and CDR3 independently selected from one of a CDR 1 and CDR3 of (1) an antibody selected from 3.1.1, 3.1.1L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1, 23.29.1L-R174K or 24.2.1; (2) the amino acid sequence of SEQ ID NO: 4, 12, 20, 28, 36, 44, 52, 60, 68, 76, 84, 94, 100 or 102 or (3) encoded by the nucleic acid sequence of SEQ ID NO: 3, 11, 19, 27, 35, 43, 51, 59, 67, 75, 83, 93, 99 or 101.

In another preferred embodiment, the anti-CD40 antibody comprises a heavy chain comprising an amino acid sequence selected from SEQ ID NOS: 6, 14, 22, 30, 38, 46, 54, 62, 70, 78 or 86 or the variable region therefrom or encoded by a nucleic acid sequence selected from SEQ ID NOS: 5, 13, 21, 29, 37, 45, 53, 61, 69, 77 or 85. In some embodiments, the anti-CD40 antibody comprises a heavy chain comprising at least the CDR3 from one of listed antibodies, one of the above-identified amino acid sequences (as shown in FIGS. 1A-1C and 2A-2C) or encoded by one of the above-identified nucleic acid sequences. In another embodiment, the heavy chain further comprises a CDR1 and CDR2 independently selected from a heavy chain variable region that comprises no more than eighteen amino acids from the amino acid sequence encoded by a germline $V_H$ 3-30+, 4-59, 1-02, 4.35 or 3-30.3 gene, or comprises a CDR1 and CDR2 independently selected from one of a CDR1 and CDR2 of (1) an antibody selected from 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 and 24.2.1; (2) the amino acid sequence of SEQ ID NO: 2, 10, 18, 26, 34, 42, 50, 58, 66, 74, 82, 90, 92, 96 or 98 or (3) encoded by the nucleic acid sequence of SEQ ID NO: 1, 9, 17, 25, 33, 41, 49, 57, 65, 73, 81, 89, 91, 95 or 97. In another embodiment, the anti-CD40 antibody comprises a heavy chain and a light chain as defined above.

As used herein, antibody 3.1.1H-A78T is identical to that of 3.1.1 except that residue 78 of the heavy chain is threonine instead of alanine. Similarly, in antibody 3.1.1H-A78T-V88A-V97A, residue 78 is changed to A, and residues 88 and 97 are changed from valine to alanine in the heavy chain. Antibody 3.1.1 L-L4M-L83V is identical to that of 3.1.1 except that residue 4 is methionine instead of leucine and residue 83 is valine instead of leucine in the light chain. Antibody 22.1.1H-C109A is identical to that of 22.1.1 except that residue 109 of the heavy chain is changed from a cysteine to an alanine. Antibodies 23.28.1H-D16E and 23.28.1 L-C92A are identical to that of 23.28.1 except that residue 16 of the heavy chain is changed from aspartate to glutamate, and residue 92 of the light chain is changed from cysteine to alanine, respectively. Antibody 23.29.1L-R174K is identical to that of 23.29.1 except that residue 174 of the light chain is changed from arginine to lysine.

Class and Subclass of Anti-CD40 Antibodies

The class and subclass of anti-CD40 antibodies may be determined by any method known in the art. In general, the class and subclass of an antibody may be determined using antibodies that are specific for a particular class and subclass of antibody. Such antibodies are available commercially. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-CD40 antibody is a monoclonal antibody. The anti-CD40 antibody can be an IgG, an IgM, an IgE, an IgA or an IgD molecule. In a preferred embodiment, the anti-CD40 antibody is an IgG and is an IgG1, IgG2, IgG3 or IgG4 subclass. In another preferred embodiment, the anti-CD40 antibodies are subclass IgG2.

Species and Molecule Selectivity

In another aspect of the invention, the anti-CD40 antibodies demonstrate both species and molecule selectivity. In some embodiments, the anti-CD40 antibody binds to primate and human CD40. In some embodiments, the anti-CD40 antibody binds to human, cynomolgus or rhesus CD40. In other embodiments, the anti-CD40 antibody does not bind to mouse, rat, dog or rabbit CD40. Following the teachings of the specification, one can determine the species selectivity for the anti-CD40 antibody using methods well known in the art. For instance, one can determine species selectivity using Western blot, FACS, ELISA or RIA. (See, e.g., Example IV.)

In some embodiments, the anti-CD40 antibody has a selectivity for CD40 that is more than 100 times greater than its selectivity for RANK (receptor activator of nuclear factor-kappa B), 4-1BB (CD137), TNFR-1 (Tumor Necrosis Factor Receptor-1) and TNFR-2 (Tumor Necrosis Factor Receptor-2). In some embodiments, the anti-CD40 antibody does not exhibit any appreciable specific binding to any other protein other than CD40. One can determine the selectivity of the anti-CD40 antibody for CD40 using methods well known in the art following the teachings of the specification. For instance, one can determine the selectivity using Western blot, FACS, ELISA or RIA. (See, e.g., Example V.)

Identification of CD40 Epitopes Recognized by Anti-CD40 Antibody

Further, the invention provides a human anti-CD40 monoclonal antibody that binds CD40 and cross-competes with and/or binds the same epitope and/or binds to CD40 with the same $K_D$ as a human anti-CD40 antibody selected from an antibody 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K or 24.2.1; or a human anti-CD40 antibody that comprises a heavy chain variable region having an amino acid sequence of SEQ ID NO: 2, 10, 18, 26, 34, 42, 50, 58, 66, 74, 82, 90, 92, 96 or 98 or a human anti-CD40 antibody that comprises a light chain variable region having an amino acid sequence of SEQ ID NO: 4, 12, 20, 28, 36, 44, 52, 60, 68, 76, 84, 94, 100 or 102.

One can determine whether an antibody binds to the same epitope as or cross competes for binding with an anti-CD40 antibody by using any method known in the art. In one embodiment, one can allow the anti-CD40 antibody of the invention to bind to CD40 under saturating conditions and then measure the ability of the test antibody to bind to CD40. If the test antibody is able to bind to the CD40 at the same time as the anti-CD40 antibody, then the test antibody binds to a different epitope as the anti-CD40 antibody. However, if the test antibody is not able to bind to the CD40 at the same time, then the test antibody binds to the same epitope, an overlapping epitope, or an epitope that is in close proximity to the epitope bound by the human anti-CD40 antibody. This experiment can be performed using ELISA, RIA, FACS or surface plasmon resonance. (See, e.g., Example VI.) In a preferred embodiment, the experiment is performed using surface plasmon resonance. In a more preferred embodiment, BIAcore is used.

Binding Affinity of Anti-CD40 Antibodies to CD40

In some embodiments of the invention, the anti-CD40 antibody binds to CD40 with high affinity. In some embodiments, the anti-CD40 antibody binds to CD40 with a $K^D$ of $2\times10^{-8}$ M or less. In another preferred embodiments, the antibody binds to CD40 with a $K_D$ of $2\times10^{-9}$, $2\times10^{-10}$, $4.0\times10^{-11}$ M or less. In an even more preferred embodiment, the antibody binds to CD40 with a $K_D$ of $2.5\times10^{-12}$ M or less. In some embodiments, the antibody binds to CD40 with substantially the same $K_D$ as an antibody selected from 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K or 24.2.1. In another preferred embodiment, the antibody binds to CD40 with substantially the same $K_D$ as an antibody that comprises a CDR2 of a light chain, and/or a CDR3 of a heavy chain from an antibody selected from 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K and 24.2.1. In still another preferred embodiment, the antibody binds to CD40 with substantially the same $K_D$ as an antibody that comprises a heavy chain variable region having an amino acid sequence of SEQ ID NO: 2, 10, 18, 26, 34, 42, 50, 58, 66, 74, 82, 90, 92, 96 or 98 or that comprises a light chain having an amino acid sequence of SEQ ID NO: 4, 12, 20, 28, 36, 44, 52, 60, 68, 76, 84, 94, 100 or 102. In another preferred embodiment, the antibody binds to CD40 with substantially the same $K_D$ as an antibody that comprises a CDR2 of a light chain variable region having an amino acid sequence of SEQ ID NO: 4, 12, 20, 28, 36, 44, 52, 60, 68, 76, 84, 94, 100 or 102 or a CDR3 of a heavy chain variable region having an amino acid sequence of SEQ ID NO: 2, 10, 18, 26, 34, 42, 50, 58, 66, 74, 82, 90, 92, 96 or 98.

In some embodiments, the anti-CD40 antibody has a low dissociation rate. In some embodiments, the anti-CD40 antibody has an $K_{off}$ of $2.0\times10^{-4}$ or lower. In some embodiments, the $k_{off}$ is $2.0\times10^{-7}$ or lower. In some embodiments, the $K_{off}$ is substantially the same as an antibody described herein, including an antibody selected from 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K and 24.2.1. In some embodiments, the antibody binds to CD40 with substantially the same $K_{off}$ as an antibody that comprises a CDR3 of a heavy chain or a CDR2 of a light chain from an antibody selected from 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.H-C109A, 23.5.1, 23.25.1, 23.28.1, 23.28.1H-D16E, 23.28.1L-C92A, 23.29.1, 23.29.1L-R174K and 24.2.1. In some embodiments, the antibody binds to CD40 with substantially the same $K_{off}$ as an antibody that comprises a heavy chain variable region having an amino acid sequence of SEQ ID NO: 2, 10, 18, 26, 34, 42, 50, 58, 66, 74, 82, 90, 92, 96 or 98 or that comprises a light chain variable region having an amino acid sequence of SEQ ID NO: 4, 12, 20, 28, 36, 44, 52, 60, 68, 76, 84, 94, 100 or 102. In another preferred embodiment, the antibody binds to CD40 with substantially the same $K_{off}$ as an antibody that comprises a CDR2 of a light chain variable region having an amino acid sequence of SEQ ID NO: 4, 12, 20, 28, 36, 44, 52, 60, 68, 76, 84, 94, 100 or 102 or a CDR3 of a heavy chain variable region having an amino acid sequence of SEQ ID NO: 6, 14, 22, 30, 38, 46, 54, 62, 70, 78, 86, 90, 92, 96 or 98.

The binding affinity and dissociation rate of an anti-CD40 antibody to CD40 can be determined by any method known in the art. The binding affinity can be measured by competitive ELISAs, RIAs or surface plasmon resonance, such as BIAcore. The dissociation rate also can be measured by surface plasmon resonance. Preferably, the binding affinity and dissociation rate is measured by surface plasmon resonance. More preferably, the binding affinity and dissociation rate are measured using a BIAcore™. See, e.g., Example XIV.

Light and Heavy Chain Gene Usage

An anti-CD40 antibody of the invention can comprise a human kappa or a human lambda light chain or an amino acid sequence derived therefrom. In some embodiments comprising a kappa light chain, the light chain variable domain ($V_L$) is encoded in part by a human A3/A19 (DPK-15), L5 (DP5), or A27 (DPK-22) Vκ gene.

In some embodiments, the $V_L$ of the anti-CD40 antibody contains one or more amino acid substitutions relative to the germline amino acid sequence. In some embodiments, the $V_L$ of the anti-CD40 antibody comprises 1, 2, 3, 4, 5, 6, 7, 8, 9, or 10 amino acid substitutions relative to the germline amino acid sequence. In some embodiments, one or more of those substitutions from germline is in the CDR regions of the light chain. In some embodiments, the amino acid substitutions relative to germline are at one or more of the same positions as the substitutions relative to germline in any one or more of the $V_L$ of antibodies 3.1.1, 3.1.1L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1, 23.29.1L-R174K and 24.2.1. For example, the $V_L$ of the anti-CD40 antibody may contain one or more amino acid substitutions compared to germline found in antibody 21.4.1, and other amino acid substitutions compared to germine found in antibody 10.8.3 which utilizes the same Vκ gene as antibody 21.4.1. In some embodiments, the amino acid changes are at one or more of the same positions but involve a different mutation than in the reference antibody.

In some embodiments, amino acid changes relative to germline occur at one or more of the same positions as in any of the $V_L$ of antibodies 3.1.1, 3.1.1 L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1, 23.29.1L-R174K and 24.2.1, but the changes may represent conservative amino acid substitutions at such position(s) relative to the amino acid in the reference antibody. For example, if a particular position in one of these antibodies is changed relative to germline and is glutamate, one may conservatively substitute aspartate at that position. Similarly, if an amino acid substitution compared to germline is serine, one may conservatively substitute threonine for serine at that position. Conservative amino acid substitutions are discussed supra.

In some embodiments, the light chain of the human anti-CD40 antibody comprises the amino acid sequence that is the same as the amino acid sequence of the $V_L$ of antibody 3.1.1 (SEQ. ID NO: 4), 3.1.1 L-L4M-L83V (SEQ ID NO: 94), 7.1.2 (SEQ. ID NO: 12), 10.8.3 (SEQ. ID NO: 20), 15.1.1 (SEQ. ID NO: 28), 21.4.1(SEQ. ID NO:), 21.2.1 (SEQ. ID NO: 36), 21.4.1 (SEQ ID NO: 44), 22.1.1 (SEQ. ID NO: 52), 23.5.1 (SEQ. ID NO: 60), 23.28.1 (SEQ. ID NO: 68), 23.28.1L-C92A (SEQ. ID NO: 100), 23.29.1 (SEQ. ID NO: 76), 23.29.1L-R174K (SEQ ID NO: 102) or 24.2.1 (SEQ. ID NO: 84), or said amino acid sequence having up to 1, 2, 3, 4, 6, 8 or 10 conservative amino acid substitutions and/or a total of up to 3 non-conservative amino acid substitutions.

In some embodiments, the light chain of the anti-CD40 antibody comprises at least the light chain CDR2, and may also comprise the CDR1 and CDR3 regions of a germline sequence, as described herein. In another embodiment, the light chain may comprise a CDR1 and CDR2 of an antibody independently selected from 3.1.1, 3.1.1L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1 and 24.2.1, or CDR regions each having less than 8, less than 6, less than 4 or less than 3 conservative amino acid substitutions and/or a total of three or fewer non-conservative amino acid substitutions. In other embodiments, the light chain of the anti-CD40 antibody comprises at least the light chain CDR2, and may also comprise the CDR1 and CDR3 regions, each of which are independently selected from the CDR1 and CDR3 regions of an antibody having a light chain variable region comprising the amino acid sequence selected from SEQ ID NOS: 4, 12, 20, 28, 36, 44, 52, 60, 68, 76, 84, 94 or 100, or encoded by a nucleic acid molecule selected from SEQ ID NOS: 3, 11, 19, 27, 35, 43, 51, 59, 67, 75, 83, 93 or 99.

With regard to the heavy chain, in some embodiments, the variable region of the heavy chain amino acid sequence is encoded in part by a human $V_H$3-30$^+$, $V_H$4-59, $V_H$1-02, $V_H$4.35 or $V_H$3-30.3 gene. In some embodiments, the $V_H$ of the anti-CD40 antibody contains one or more amino acid substitutions, deletions or insertions (additions) relative to the germline amino acid sequence. In some embodiments, the variable domain of the heavy chain comprises 1, 2, 3, 4, 5, 6, 7, 8, 9, 10, 11, 12, 13, 14, 15, 16, 17 or 18 mutations from the germline amino acid sequence. In some embodiments, the mutation(s) are non-conservative substitutions compared to the germline amino acid sequence. In some embodiments, the mutations are in the CDR regions of the heavy chain. In some embodiments, the amino acid changes are made at one or more of the same positions as the mutations from germline in any one or more of the $V_H$ of antibodies 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 and 24.2.1. In other embodiments, the amino acid changes are at one or more of the same positions but involve a different mutation than in the reference antibody.

In some embodiments, the heavy chain comprises an amino acid sequence of the variable domain ($V_H$) of antibody 3.1.1 (SEQ ID NO: 2), 3.1.1H-A78T (SEQ ID NO: 90), 3.1.1H-A78T-V88A-V97A (SEQ ID NO: 92), 7.1.2 (SEQ ID NO: 10), 10.8.3 (SEQ ID NO: 18), 15.1.1 (SEQ ID NO: 26), 21.2.1 (SEQ ID NO: 34), 21.4.1 (SEQ ID NO: 42), 22.1.1 (SEQ ID NO: 50), 22.1.1H-C109A (SEQ ID NO: 96), 23.5.1 (SEQ ID NO: 58), 23.28.1 (SEQ ID NO: 66), 23.28.1H-D16E (SEQ ID NO: 98), 23.29.1 (SEQ ID NO: 74) and 24.2.1(SEQ ID NO: 82), or said amino acid sequence having up to 1, 2, 3, 4, 6, 8 or 10 conservative amino acid substitutions and/or a total of up to 3 non-conservative amino acid substitutions.

In some embodiments, the heavy chain comprises the heavy chain CDR1, CDR2 and CDR3 regions of antibody 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 and 24.2.1 (as shown in FIGS. 1D-1H or 2D-2H), or said CDR regions each having less than 8, less than 6, less than 4, or less than 3 conservative amino acid substitutions and/or a total of three or fewer non-conservative amino acid substitutions.

In some embodiments, the heavy chain comprises a CDR3, and may also comprise the CDR1 and CDR2 regions of a germline sequence, as described above, or may comprise a CDR1 and CDR2 of an antibody, each of which are independently selected from an antibody comprising a heavy chain of an antibody selected from 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 and 24.2.1. In another embodiment, the heavy chain comprises a CDR3, and may also comprise the CDR1 and CDR2 regions, each of which are independently selected from a CDR1 and CDR2 region of a heavy chain variable region comprising an amino acid sequence selected from SEQ ID NOS: 2, 10, 18, 26, 34, 42, 50, 58, 66, 74, 82, 90, 92, 96 or 98 (as shown in FIGS. 1D-1H or FIGS. 2D-2H)or encoded by a nucleic acid sequence selected from SEQ ID NOS: 1, 9, 17, 25, 33, 41, 49, 57, 65, 73, 81, 89, 91, 95 or 97. In another embodiment, the antibody comprises a heavy chain as disclosed above and a light chain as disclosed above.

One type of amino acid substitution that may be made is to change one or more cysteines in the antibody, which may be chemically reactive, to another residue, such as, without limitation, alanine or serine. In one embodiment, the cysteine substitution is made in a framework region of a variable domain or in the constant domain of an antibody. In another embodiment, the cysteine is in a non-canonical region of the antibody. Another type of amino acid substitution that may be made is to change any potential proteolytic sites in the antibody, particularly those that are in a framework region of a variable domain, in the constant domain of an antibody, or in a non-canonical region of the antibody Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues. This is preferably done in framework regions, the constant domain or non-canonical regions of the antibody.

Activation of CD40 by Anti-CD40 Antibody

Another aspect of the present invention involves an anti-CD40 antibody that is an activating antibody, i.e., a CD40 agonist. An activating antibody amplifies or substitutes for the effects of CD40L on CD40. In some embodiments, the activating antibody is essentially a mimic of CD40L, and competes with CD40L for binding to CD40. In some embodiments, the antibody does not compete with CD40L for binding to CD40, but amplifies the effect of CD40L binding to CD40. In some embodiments, the anti-CD40 antibody activates CD40 in the presence or absence of CD40L.

Inhibition of Tumor Growth In Vivo by Anti-CD40 Antibodies

According to some embodiments, the invention provides an anti-CD40 antibody that inhibits the proliferation of tumor cells in vitro or tumor growth in vivo.

In some embodiments, the antibody inhibits tumor growth by at least 50%, 55%, 60%, 65%, 70%, 75%. In some embodiments, the antibody inhibits tumor growth by 75%. In one embodiment, the inhibition of tumor growth is detectable 14 days after initial treatment with the antibody. In other embodiments, the inhibition of tumor growth is detectable 7 days after initial treatment with the antibody. In some embodiments, another antineoplastic agent is administered to the animal with the anti-CD40 antibody. In some embodiments, the antineoplastic agent further inhibits tumor growth. In some embodiments, the antineoplastic agent is adriamycin or taxol. In some embodiments, the co-administration of an antineoplastic agent and the anti-CD40 antibody inhibits tumor growth by at least 50%, after a period of 22-24 days from initiation of treatment compared to tumor growth on an untreated animal.

Induction of Apoptosis by Anti-CD40 Antibodies

Another aspect of the invention provides an anti-CD40 antibody that induces cell death of CD40 positive cells. In some embodiments, the antibody causes apoptosis of CD40 positive cells either in vivo or in vitro.

Enhancement of Expression of Cell Surface Molecules

In some embodiments, the anti-CD40 antibody enhances the expression of B cell surface molecules, including but not limited to ICAM, MHC-II, B7-2, CD71, CD23 and CD83. In some embodiments, 1 µg/ml of the antibody enhances ICAM expression in a whole blood B-cell surface molecule up-regulation assay by at least 2 fold, or more preferably by at least 4 fold. In some embodiments, 1 µg/ml of the antibody enhances MHC-II expression in a whole blood B-cell surface molecule upregulation assay by at least 2 fold, or more preferably by at least 3 fold. In some embodiments, 1 µg/ml of the antibody enhances CD23 expression in whole blood B-cell surface molecule up-regulation assay by at least 2 fold, or more preferably by at least 5 fold. See, e.g., Example VII, Table 25.

In some embodiments, the anti-CD40 antibody enhances the expression of dendritic cell surface molecules including but not limited to MHC-II, ICAM, B7-2, CD83 and B7-1. In some embodiments the range of upregulation is similar to the range of upregulation observed in B cells. See, e.g., Tables 25 and 26, infra. In some embodiments, the antibody preferentially upregulates the expression of dendritic cell surface molecules, such as B7-2 and MHC-II, compared to B cell expression of these molecules. See, e.g., Table 27.

Enhancement of Secretion of Cellular Cytokines

In some embodiments the antibody enhances cellular secretion of cytokines including but not limited to IL-8, IL-12, IL-15, IL-18 and IL-23.

In some embodiments the antibody enhances cytokine secretion by dendritic cells and adherent monocytes. In some embodiments cytokine production is further enhanced by co-stimulation with one or more of LPS, IFN-γ or IL-1β. In yet another aspect of the invention, the antibody with LPS co-stimulation enhances IL-12p70 production in a dendritic cell assay with an $EC_{50}$ of about 0.48 µg/ml. In some embodiments, the antibody enhances IL-12p40 production in dendritic cells with an $EC_{50}$ of about 0.21 µg/ml. (See, e.g., Example VIII.)

In some embodiments, the antibody enhances secretion of IFN-gamma by T cells in an allogenic T cell/dendritic cell assay, as described in Example VIII. In some embodiments, the antibody enhances IFN-gamma secretion in an allogenic T cell/dendritic cell assay with an $EC_{50}$ of about 0.3 µg/ml. In some embodiments, the antibody enhances IFN-gamma secretion in an allogenic T cell/dendritic cell assay with an $EC_{50}$ of about 0.2 µg/ml. In one embodiment, the antibody enhances IFN-gamma secretion in an allogenic T cell/dendritic cell assay with an $EC_{50}$ Of about 0.03 µg/ml.

Methods of Producing Antibodies and Antibody-Producing Cell Lines

Immunization

In some embodiments, human antibodies are produced by immunizing a non-human animal comprising in its genome some or all of human immunoglobulin heavy chain and light chain loci with a CD40 antigen. In a preferred embodiment, the non-human animal is a XenoMouse™ animal.

XenoMouse™ mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-CD40 antibodies from non-human, non-mouse animals by immunizing non-human transgenic animals that comprise human immunoglobulin loci with a CD40 antigen. One can produce such animals using the methods described in the above-cited documents. The methods disclosed in these documents can be modified as described in U.S. Pat. No. 5,994,619. In preferred embodiments, the non-human animals are rats, sheep, pigs, goats, cattle or horses.

XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration yeast artificial chromosome (YAC) fragments of the human heavy chain loci and kappa light chain loci. See Mendez et al., Nature Genetics 15:146-156 (1997), Green and Jakobovits, J. Exp. Med. 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

An advantage of the minilocus approach is the rapidity with which constructs including portions of the Ig locus can be generated and introduced into animals. However, a potential disadvantage of the minilocus approach is that there may not be sufficient immunoglobulin diversity to support full B-cell development, such that there may be lower antibody production.

In another aspect, the invention provides a method for making humanized anti-CD40 antibodies. In some embodiments, non-human animals are immunized with a CD40 antigen as described below under conditions that permit antibody production. Antibody-producing cells are isolated from the animals, fused with myelomas to produce hybridomas, and nucleic acids encoding the heavy and light chains of an anti-CD40 antibody of interest are isolated. These nucleic acids are subsequently engineered using techniques known to those of skill in the art and as described further below to reduce the amount of non-human sequence, i.e., to humanize the antibody to reduce the immune response in humans In some embodiments, the CD40 antigen is isolated and/or purified CD40. In a preferred embodiment, the CD40 antigen is human CD40. In some embodiments, the CD40 antigen is a fragment of CD40. In some embodiments, the CD40 fragment is the extracellular domain of CD40. In some embodiments, the CD40 fragment comprises at least one epitope of CD40. In other embodiments, the CD40 antigen is a cell that expresses or overexpresses CD40 or an immunogenic fragment thereof on its surface. In some embodiments, the CD40 antigen is a CD40 fusion protein.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In a preferred embodiment, the CD40 antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotacetic for macrophages and other components of the immune system. Preferably, if a polypeptide is being administered, the immunization schedule will involve two or more administrations of the polypeptide, spread out over several weeks.

Example I describes the production of anti-CD40 monoclonal antibodies.

Production of Antibodies and Antibody-Producing Cell Lines

After immunization of an animal with a CD40 antigen, antibodies and/or antibody-producing cells can be obtained from the animal. In some embodiments, anti-CD40 antibody-containing serum is obtained from the animal by bleeding or sacrificing the animal. The serum may be used as it is obtained from the animal, an immunoglobulin fraction may be obtained from the serum, or the anti-CD40 antibodies may be purified from the serum. It is well known to one of ordinary skill in the art that serum or immunoglobulins obtained in this manner will be polyclonal. The disadvantage is using polyclonal antibodies prepared from serum is that the amount of antibodies that can be obtained is limited and the polyclonal antibody has a heterogeneous array of properties.

In some embodiments, antibody-producing immortalized cell lines are prepared from cells isolated from the immunized animal. After immunization, the animal is sacrificed and lymph node and/or splenic B cells are immortalized. Methods of immortalizing cells include, but are not limited to, transferring them with oncogenes, inflecting them with the oncogenic virus cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using CD40, a portion thereof, or a cell expressing CD40. In a preferred embodiment, the initial screening is performed using an enzyme-linked immunoassay (ELISA) or a radioimmunoassay. An example of ELISA screening is provided in WO 00/37504, herein incorporated by reference.

Anti-CD40 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE animal and the myeloma cell line is a non-secretory mouse myeloma. In an even more preferred embodiment, the myeloma cell line is P3-X63-AG8.653. See, e.g., Example I.

In another aspect, the invention provides hybridomas that produce an human anti-CD40 antibody. In a preferred embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

Nucleic Acids, Vectors, Host Cells and Recombinant Methods of Making Antibodies

Nucleic Acids

The present invention also encompasses nucleic acid molecules encoding anti-CD40 antibodies. In some embodiments, different nucleic acid molecules encode a heavy chain and a light chain of an anti-CD40 immunoglobulin. In other embodiments, the same nucleic acid molecule encodes a heavy chain and a light chain of an anti-CD40 immunoglobulin.

In some embodiments, the nucleic acid molecule encoding the variable domain of the light chain comprises a human A3/A19 (DPK-15), L5 (DP5) or A27 (DPK-22) Vκ gene sequence or a sequence derived therefrom. In some embodiments, the nucleic acid molecule comprises a nucleotide sequence of a A3/A19 Vκ gene and a Jκ1, Jκ2 or Jκ3 gene or sequences derived therefrom. In some embodiments, the nucleic acid molecule comprises a nucleotide sequence of an L5 Vκ gene and a Jκ4 gene. In some embodiments, the nucleic acid molecule comprises a nucleotide sequence of a A27 Vκ gene and a Jκ3 gene.

In some embodiments, the nucleic acid molecule encoding the light chain, encodes an amino acid sequence comprising 1, 2, 3, 4, 5, 6, 7, 8, 9 or 10 mutations from the germline amino acid sequence. In some embodiments, the nucleic acid molecule comprises a nucleotide sequence that encodes a $V_L$ amino acid sequence comprising 1, 2, 3, 4, 5, 6, 7, 8, 9 or 10 non-conservative amino acid substitutions and/or 1, 2 or 3 non-conservative substitutions compared to the germline sequence. Substitutions may be in the CDR regions, the framework regions or in the constant domain.

In some embodiments, the nucleic acid molecule encoding the variable domain of the light chain ($V_L$) encodes a $V_L$ amino acid sequence comprising one or more mutations compared to the germline sequence that are identical to the mutations found in the $V_L$ of one of the antibodies 3.1.1, 3.1. IL-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1 and 24.2.1. In some embodiments, the nucleic acid molecule encodes at least three amino acid mutations compared to the germline sequence found in the $V_L$ of one of the antibodies 3.1.1, 3.1.1 L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1 and 24.2.1.

In some embodiments, the nucleic acid molecule comprises a nucleotide sequence that encodes the $V_L$ amino acid sequence of monoclonal antibody 3.1.1 (SEQ ID NO: 4), 3.1.1L-L4M-L83V (SEQ ID NO: 94), 7.1.2 (SEQ ID NO: 12), 10.8.3 (SEQ ID NO: 20), 15.1.1 (SEQ ID NO: 28), 21.2.1 (SEQ ID NO: 36), 2.1.4.1 (SEQ ID NO: 44), 22.1.1 (SEQ ID NO: 52), 23.5.1 (SEQ ID NO: 60), 23.28.1 (SEQ ID NO: 68), 23.28.1L-C92A (SEQ ID NO: 100), 23.29.1 (SEQ ID NO: 76) or 24.2.1 (SEQ ID NO: 84), or a portion thereof. In some embodiments, said portion comprises at least the CDR3 region. In some embodiments, the nucleic acid encodes the amino acid sequence of the light chain CDRs of said antibody. In some embodiments, said portion is a contiguous portion comprising CDR1-CDR3.

In some embodiments, the nucleic acid molecule comprises a nucleotide sequence that encodes the amino acid sequence of one of SEQ ID NOS: 4, 12, 20, 28, 36, 44, 52, 60, 68, 76, 84, 94 or 100, or said sequence lacking the signal sequence. In some preferred embodiments, the nucleic acid molecule comprises the nucleotide sequence of SEQ ID NOS: 3, 11, 19, 27, 35, 43, 51, 59, 67, 75, 83, 93 or 99, or a portion thereof, said sequences optionally lacking the signal sequence.

In some embodiments, said portion encodes a $V_L$ region. In some embodiments, said portion encodes at least the CDR2 region. In some embodiments, the nucleic acid encodes the amino acid sequence of the light chain CDRs of said antibody. In some embodiments, said portion encodes a contiguous region from CDR1-CDR3.

In some embodiments, the nucleic acid molecule encodes a $V_L$ amino acid sequence that is at least 70%, 75%, 80%, 85%, 90%, 95%, 97%, 98% or 99% identical to a $V_L$ amino acid sequence of any one of antibodies 3.1.1, 3.1. IL-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1 or 24.2.1, or a $V_L$ amino acid sequence of any one of SEQ ID NOS: 4, 12, 20, 28, 36, 44, 52, 60, 68, 76, 84, 94 or 100. Nucleic acid molecules of the invention include nucleic acids that hybridize under highly stringent conditions, such as those described above, to a nucleic acid sequence encoding the amino acid sequence of SEQ ID NOS: 4, 12, 20, 28, 36, 44, 52, 60, 68, 76, 84, 94 or 100, or that has the nucleic acid sequence of SEQ ID NOS: 3, 11, 19, 27, 35, 43, 51, 59, 67, 75, 83, 93 or 99.

In another embodiment, the nucleic acid encodes a full-length light chain of an antibody selected from 3.1.1, 3.1.1L-L4M-L83V, 7.1.2, 10.8.3, 15.1.1, 21.4.1, 21.2.1, 22.1.1, 23.5.1, 23.25.1, 23.28.1, 23.28.1L-C92A, 23.29.1, 23.29.1L-R174K or 24.2.1, or a light chain comprising the amino acid sequence of SEQ ID NOS: 8, 16, 24, 32, 40, 48, 56, 64, 72, 80, 88, 94, 100 or 102, or a light chain comprising a mutation, such as one disclosed herein. Further, the nucleic acid may comprise the nucleotide sequence of SEQ ID NOS: 7, 15, 23, 31, 39, 47, 55, 63, 71, 79 or 87, or a nucleic acid molecule encoding a light chain comprise a mutation, such as one disclosed herein.

In another preferred embodiment, the nucleic acid molecule encodes the variable domain of the heavy chain ($V_H$) that comprises a human 3-30+, 4-59, 1-02, 4.35 or 3-30.3 $V_H$ gene sequence or a sequence derived therefrom. In various embodiments, the nucleic acid molecule comprises a human 3-30+$V_H$ gene, a D4 (DIR3) gene and a human $J_H6$ gene; a human 3-30+$V_H$ gene, a human D1-26 (DIR5) gene and a human $J_H6$ gene; a human 4.35 $V_H$ gene, a human DIR3 gene and a human $J_H6$ gene; a human 4-59 $V_H$ gene, a human D4-23 gene and a human $J_H4$ gene; a human 1-02 $V_H$ gene, a human DLR1 gene and a human $J_H^4$ gene; a human 3-30+$V_H$ gene, a human D6-19 (DIR3) gene and a human $J_H^4$ gene; a human 3-30+$V_H$ gene, a human D1-1 gene and a human $J_H6$ gene; a human 3-30+$V_H$ gene, a human D4-17 gene and a human $J_H6$ gene; a human 3-30.3 $V_H$ gene, a human D4-17 gene and a human $J_H6$ gene; a human 4-59 $V_H$ gene, a human D4-17 (DIR1) gene and a human $J_H5$ gene, or sequence derived from the human genes.

In some embodiments, the nucleic acid molecule encodes an amino acid sequence comprising 1, 2, 3, 4, 5, 6, 7, 8, 9, 10, 11, 12, 13, 14, 15, 16, 17 or 18 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes one or more amino acid mutations compared to the germline sequence that are identical to amino acid mutations found in the $V_H$ of monoclonal antibody 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 or 24.2.1. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of antibody 3.1.1 (SEQ ID NO: 2), 3.1.1H-A78T (SEQ ID NO: 90), 3.1.1H-A78T-V88A-V97A (SEQ ID NO: 92), 7.1.2 (SEQ ID NO: 10), 10.8.3 (SEQ ID NO: 18), 15.1.1 (SEQ ID NO: 26), 21.2.1 (SEQ ID NO: 34), 21.4.1 (SEQ ID NO: 42), 22.1.1 (SEQ ID NO: 50), 22.1.1H-C109A (SEQ ID NO: 96), 23.5.1 (SEQ ID NO: 58), 23.28.1 (SEQ ID NO: 66), 23.28.1H-D16E (SEQ ID NO: 98), 23.29.1 (SEQ ID NO: 74) or 24.2.1 (SEQ ID NO: 82), or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region, with or without a signal sequence.

In some embodiments, the nucleic acid molecule comprises a nucleotide sequence that encodes the amino acid sequence of one of SEQ ID NOS: 2, 10, 18, 26, 34, 42, 50, 58, 66, 74, 82, 90, 92, 96 or 98, or said sequence lacking the signal sequence. In some preferred embodiments, the nucleic acid molecule comprises at least a portion of the nucleotide sequence of SEQ ID NO: 1, 9, 17, 25, 33, 41, 49, 57, 65, 73, 81, 89, 91, 95 or 97, or said sequence lacking the signal sequence. In some embodiments, said portion encodes the $V_H$ region (with or without a signal sequence), a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequences shown in FIGS. 1A-1C or 2A-2C or to a $V_H$ amino acid sequence of any one of SEQ ID NOS: 2, 10, 18, 26, 34, 42, 50, 58, 66, 74, 82, 90, 92, 96 or 98. Nucleic acid molecules of the invention include nucleic acids that hybridize under highly stringent conditions, such as those described above, to a nucleic acid sequence encoding the amino acid sequence of SEQ ID NOS: 2, 10, 18, 26, 34, 42, 50, 58, 66, 74, 82, 90, 92, 96 or 98, or that has the nucleic acid sequence of SEQ ID NOS: 1, 9, 17, 25, 33, 41, 49, 57, 65, 73, 81, 89, 91, 95 or 97. Nucleic acid molecule of the invention include nucleic acid molecule that hybridize under highly stringent conditions, such as those described above, to a nucleic acid sequence encoding a $V_H$ described immediately above.

In another embodiment, the nucleic acid encodes a full-length heavy chain of an antibody selected from 3.1.1, 3.1.1H-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 and 24.2.1, or a heavy chain having the amino acid sequence of SEQ ID NOS: 6, 14, 22, 30, 38, 46, 54, 62, 70, 78 or 86, or a heavy chain comprising a mutation, such as one of the mutations discussed herein Further, the nucleic acid may comprise the nucleotide sequence of SEQ ID NOS: 5, 13, 21, 29, 37, 45, 53, 61, 69, 77, 85 or 89, or a nucleic acid molecule encoding a heavy chain comprising a mutation, such as one of the mutations discussed herein.

A nucleic acid molecule encoding the heavy or entire light chain of an anti-CD40 antibody or portions thereof can be isolated from any source that produces such antibody. In various embodiments, the nucleic acid molecules are isolated from a B cell isolated from an animal immunized with CD40 or from an immortalized cell derived from such a B cell that expresses an anti-CD40 antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin-producing cell from a non-human transgenic animal. In an even more preferred embodiment, the human immunoglobulin producing cell is isolated from a XenoMouse™ animal. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies.

In some embodiments, a nucleic acid encoding a heavy chain of an anti-CD40 antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-CD40 antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant or light chain constant domains, respectively, such that the $V_H$ segment is operatively linked to the $C_H$ segment(s) within the vector, and the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., *Sequences of Proteins of Immunological Interest*, 5th Ed., NIH Publ. No. 91-3242, 1991. Nucleic acid molecules encoding the full-length heavy and/or light chains may then be expressed from a cell into which they have been introduced and the anti-CD40 antibody isolated.

The nucleic acid molecules may be used to recombinantly express large quantities of anti-CD40 antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-CD40 antibodies. In some embodiments, the nucleic acid molecules are oligonucleotides. In some embodiments, the oligonucleotides are from highly variable regions of the heavy and light chains of the antibody of interest. In some embodiments, the oligonucleotides encode all or a part of one or more of the CDRs of antibody 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D116E, 23.28.1L-C92A, 23.29.1 or 24.2.1.

Vectors

The invention provides vectors comprising nucleic acid molecules that encode the heavy chain of an anti-CD40 antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-CD40 antibodies, or antigen-binding portions of the invention are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, herein incorporated by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding anti-CD40 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-CD40 antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-CD40 antibodies can be produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized with CD40 or an immunogenic portion thereof, as described above. Methods for making antibodies in plants are described, e.g., in U.S. Pat. No. 6,046,037 and U.S. Pat. No. 5,959,177.

In some embodiments, non-human transgenic animals or plants are produced by introducing one or more nucleic acid molecules encoding an anti-CD40 antibody of the invention into the animal or plant by standard transgenic techniques. See Hogan and U.S. Pat. No. 6,417,429, supra. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to CD40, preferably human CD40. In some embodiments, the transgenic animals comprise nucleic acid molecules encoding a modified antibody such as a single-chain antibody, a chimeric antibody or a humanized antibody. The anti-CD40 antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-CD40 antibody or antigen-binding portion thereof comprising the steps of synthesizing a library of human antibodies on phage, screening the library with CD40 or a portion thereof, isolating phage that bind CD40, and obtaining the antibody from the phage. By way of example, one method for preparing the library of antibodies for use in phage display techniques comprises the steps of immunizing a non-human animal comprising human immunoglobulin loci with CD40 or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant anti-CD40 antibodies of the invention may be obtained in this way.

Recombinant anti-CD40 human antibodies of the invention can be isolated by screening a recombinant combinatorial antibody library. Preferably the library is a scFv phage display library, generated using human $V_L$ and $V_H$ cDNAs prepared from mRNA isolated from B cells. Methodologies for preparing and screening such libraries are known in the art. There are commercially available kits for generating phage display libraries (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991).

In one embodiment, to isolate a human anti-CD40 antibodies with the desired characteristics, a human anti-CD40 antibody as described herein is first used to select human heavy and light chain sequences having similar binding activity toward CD40, using the epitope imprinting methods described in PCT Publication No. WO 93/06213. The antibody libraries used in this method are preferably scFv libraries prepared and screened as described in PCT Publication No. WO 92/01047, McCafferty et al., *Nature* 348: 552-554 (1990); and Griffiths et al., *EMBO J.* 12:725-734 (1993). The scFv antibody libraries preferably are screened using human CD40 as the antigen.

Once initial human $V_L$ and $V_H$ domains are selected, "mix and match" experiments are performed, in which different pairs of the initially selected $V_L$ and $V_H$ segments are screened for CD40 binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be rescreened for binding to CD40.

Following screening and isolation of an anti-CD40 antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the invention provides a method for converting the class or subclass of an anti-CD40 antibody to another class or subclass. In some embodiments, a nucleic acid molecule encoding a $V_L$ or $V_H$ that does not include any nucleic acid sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an anti-CD40 antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-CD40 antibody and a nucleic acid encoding a light chain of an anti-CD40 antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-CD40 antibody with the desired isotype.

Deimmunized Antibodies

Another way of producing antibodies with reduced immunogenicity is the deimmunization of antibodies. In another aspect of the invention, the antibody may be deimmunized using the techniques described in, e.g., PCT Publication Nos. WO98/52976 and WO00/34317 (which incorporated herein by reference in their entirety).

Mutated Antibodies

In another embodiment, the nucleic acid molecules, vectors and host cells may be used to make mutated anti-CD40 antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for CD40, to increase or decrease $K_{off}$, or to alter the binding specificity of the antibody. Techniques in site-directed mutagenesis are well-known in the art. See, e.g., Sambrook et al. and Ausubel et al., supra. In a preferred embodiment, mutations are made at an amino acid residue that is known to be changed compared to germline in a variable domain of an anti-CD40 antibody. In another embodiment, one or more mutations are made at an amino acid residue that is known to be changed compared to the germline in a CDR region or framework region of a variable domain, or in a constant domain of a monoclonal antibody 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K and 24.2.1. In another embodiment, one or more mutations are made at an amino acid residue that is known to be changed compared to the germline in a CDR region or framework region of a variable domain of an amino acid sequence selected from SEQ ID NOS: 4, 12, 20, 28, 36, 44, 52, 60, 68, 76, 84, 94, 100, 102, 2, 10, 18, 26, 34, 42, 50, 58, 66, 74, 82, 90, 92, 96, 98, 100 or 102, or whose nucleic acid sequence is presented in SEQ ID NOS: 3, 11, 19, 27, 35, 43, 51, 59, 67, 75, 83, 93, 99, 101, 1, 9, 17, 25, 33, 41, 49, 57, 65, 73, 81, 89, 91, 95, 97, 99 or 101.

In one embodiment, the framework region is mutated so that the resulting framework region(s) have the amino acid sequence of the corresponding germline gene. A mutation may be made in a framework region or constant domain to increase the half-life of the anti-CD40 antibody. See, e.g., PCT Publication No. WO 00/09560, herein incorporated by reference. A mutation in a framework region or constant domain also can be made to alter the immunogenicity of the antibody, to provide a site for covalent or non-covalent binding to another molecule, or to alter such properties as complement fixation, FcR binding and ADCC. According to the invention, a single antibody may have mutations in any one or more of the framework regions, the constant domain and in the variable regions.

In some embodiments, there are from 1 to 18, including any number in between, amino acid mutations in either the $V_H$ or $V_L$ domains of the mutated anti-CD40 antibody compared to the anti-CD40 antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-CD40 antibody of the invention linked to another polypeptide. In a preferred embodiment, only the variable domains of the anti-CD40 antibody are linked to the polypeptide. In another preferred embodiment, the $V_H$ domain of an anti-CD40 antibody is linked to a first polypeptide, while the $V_L$ domain of an anti-CD40 antibody is linked to a second polypeptide that associates with the first polypeptide in a manner such that the $V_H$ and $V_L$ domains can interact with one another to form an antibody binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to a CD40–expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence (Gly$_4$-Ser)$_3$ (SEQ ID NO: 143), such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to CD40 and to another molecule.

In other embodiments, other modified antibodies may be prepared using anti-CD40 antibody-encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). In addition, bispecific antibodies may be formed as "diabodies" or "Janusins." In some embodiments, the bispecific antibody binds to two different epitopes of CD40. In some embodiments, the bispecific antibody has a first heavy chain and a first light chain from monoclonal antibody 3.1.1, 3.1.1H-A78T, 3.1.1H-A78T-V88A-V97A, 3.1.1L-L4M-L83V, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.28.1L-C92A, 23.29.1, 23.29.1L-R174K and 24.2.1, and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-CD40 monoclonal antibody provided herein, from an amino acid sequence of said monoclonal antibody, or from a heavy chain or light chain encoded by a nucleic acid sequence encoding said monoclonal antibody.

Derivatized and Labeled Antibodies

An anti-CD40 antibody or antigen-binding portion of the invention can be derivatized or linked to another molecule (e.g., another peptide or protein). In general, the antibodies or portion thereof is derivatized such that the CD40 binding is not affected adversely by the derivatization or labeling. Accordingly, the antibodies and antibody portions of the invention are intended to include both intact and modified forms of the human anti-CD40 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycoerythrin, lanthamide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-CD40 antibody can also be labeled with a radiolabeled amino acid. The radiolabel can be used for both diagnostic and therapeutic purposes. For instance, the radiolabel can be used to detect CD40-expressing tumors by x-ray or other diagnostic techniques. Further, the radiolabel can be used therapeutically as a toxin for cancerous cells or tumors. Examples of labels for polypeptides include, but are not limited to, the following radioisotopes or radionuclides— $^3$H, $^{14}$C, $^{15}$N, $^{35}$S, $^{90}$Y, $^{99}$Tc, $^{111}$In, $^{125}$I, $^{131}$I.

An anti-CD40 antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

Pharmaceutical Compositions and Kits

The invention also relates to compositions comprising a human anti-CD40 agonist antibody for the treatment of subjects in need of immunostimulation. Such compositions are useful to treat, prevent, reduce the frequency of or severity of infection, including viral and bacterial infection, for treating a hyperproliferative disorder, including cancerous and pre-cancerous conditions, for treating genetic immunodeficiency conditions, such as hyper-IgM syndrome and for treating primary or combined immunodeficiency conditions, including conditions characterized by neutropenia, in a mammal, including humans. Subjects for treatment with agonist anti-CD40 antibody therapy include any subject in need of immune enhancement, including but not limited to the elderly and individuals who are immunosuppressed, for example due to chemotherapy.

Hyperproliferative disorders that may be treated by an agonist anti-CD40 antibody of the invention can involve any tissue or organ and include but are not limited to brain, lung, squamous cell, bladder, gastric, pancreatic, breast, head, neck, liver, renal, ovarian, prostate, colorectal, esophageal, gynecological, nasopharynx, or thyroid cancers, melanomas, lymphomas, leukemias or multiple myelomas. In particular, human agonist anti-CD40 antibodies of the invention are useful to treat carcinomas of the breast, prostate, colon and lung.

Treatment may involve administration of one or more agonist anti-CD40 monoclonal antibodies of the invention, or antigen-binding fragments thereof, alone or with a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Agonist anti-CD40 antibodies of the invention and compositions comprising them, can be administered in combination with one or more other therapeutic, diagnostic or prophylactic agents. Additional therapeutic agents include other anti-neoplastic, anti-tumor, anti-angiogenic or chemotherapeutic agents. Such additional agents may be included in the same composition or administered separately. In some embodiments, one or more agonist anti-CD40 antibodies of the invention can be used as a vaccine or as adjuvants to a vaccine.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-CD40 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

In certain embodiments, an anti-CD40 antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-CD40 antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an anti-CD40 antibody of the invention is co-formulated with and/or co-administered with one or more additional therapeutic agents. These agents include, without limitation, antibodies that bind other targets (e.g., antibodies that bind one or more growth factors or cytokines or their cell surface receptors, such as anti-CTL4-antibody), antineoplastic agents, antitumor agents, chemotherapeutic agents, peptide analogues that activate CD40, soluble CD40L, one or more chemical agents that activates CD40, and/or other agents known in the art that can enhance an immune response against tumor cells, e.g., IFN-β1, IL-2, IL-8, IL-12, IL-15, IL-18, IL-23, IFN-γ, and GM-CSF. Such combination therapies may require lower dosages of the anti-CD40 antibody as well as the co-administered agents, thus avoiding possible toxicities or complications associated with the various monotherapies.

Agonist anti-CD40 antibodies of the invention and compositions comprising them also may be administered in combination with other therapeutic regimens, in particular in combination with radiation treatment.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-CD40 antibody or portion and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-CD40 antibody or antibody portion of the invention or a composition comprising such an antibody. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

This invention also relates to compositions for inhibiting abnormal cell growth in a mammal comprising an amount of an antibody of the invention in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens, and anti-angiogenesis agents.

Anti-angiogenic agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with an anti-CD40 antibody of the invention. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-prop ionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

A compound of the invention can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN® (Genentech, Inc.). EGF-R inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WH1-P97 (Parker Hughes Cancer Center), GW-282974 (Glaxo), KT-8391 (Kyowa Hakko) and EGF-R Vaccine (York Medical/Centro de Immunologia Molecular (CIM)). These and other EGF-R-inhibiting agents can be used in the present invention.

VEGF inhibitors, for example SU-5416 and SU-6668 (Sugen Inc.), SH-268 (Schering), and NX-1838 (NeXstar) can also be combined with the compound of the present invention. VEGF inhibitors are described in, for example in WO 99/24440 (published May 20, 1999), PCT International Application PCT/EB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc.); anti-VEGF monoclonal antibody of Genentech, Inc.; and angiozyme, a synthetic ribozyme from Ribozyme and Chiron. These and other VEGF inhibitors can be used in the present invention as described herein. ErbB2 receptor inhibitors, such as GW-282974 (Glaxo Wellcome plc), and the monoclonal antibodies AR-209 (Aronex Pharmaceuticals Inc.) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

Anti-survival agents include anti-IGF-IR antibodies and anti-integrin agents, such as anti-integrin antibodies.

Diagnostic Methods of Use

In another aspect, the invention provides diagnostic methods. The anti-CD40 antibodies can be used to detect CD40 in a biological sample in vitro or in vivo. In one embodiment, the invention provides a method for diagnosing the presence or location of an CD40-expressing tumor in a subject in need thereof, comprising the steps of injecting the antibody into the subject, determining the expression of CD40 in the subject by localizing where the antibody has bound, comparing the expression in the subject with that of a normal reference subject or standard, and diagnosing the presence or location of the tumor.

The anti-CD40 antibodies can be used in a conventional immunoassay, including, without limitation, an ELISA, an RIA, FACS, tissue immunohistochemistry, Western blot or immunoprecipitation. The anti-CD40 antibodies of the invention can be used to detect CD40 from humans. In another embodiment, the anti-CD40 antibodies can be used to detect CD40 from Old World primates such as cynomolgus and rhesus monkeys, chimpanzees and apes. The invention provides a method for detecting CD40 in a biological sample comprising contacting a biological sample with an anti-CD40 antibody of the invention and detecting the bound antibody. In one embodiment, the anti-CD40 antibody is directly labeled with a detectable label. In another embodiment, the anti-CD40 antibody (the first antibody) is unlabeled and a second antibody or other molecule that can bind the anti-CD40 antibody is labeled. As is well known to one of skill in the art, a second antibody is chosen that is able to specifically bind the particular species and class of the first antibody. For example, if the anti-CD40 antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

In other embodiments, CD40 can be assayed in a biological sample by a competition immunoassay utilizing CD40 standards labeled with a detectable substance and an unlabeled anti-CD40 antibody. In this assay, the biological sample, the labeled CD40 standards and the anti-CD40 antibody are combined and the amount of labeled CD40 standard bound to the unlabeled antibody is determined. The amount of CD40 in the biological sample is inversely proportional to the amount of labeled CD40 standard bound to the anti-CD40 antibody.

One can use the immunoassays disclosed above for a number of purposes. For example, the anti-CD40 antibodies can be used to detect CD40 in cells in cell culture. In a preferred embodiment, the anti-CD40 antibodies are used to determine the amount of CD40 on the surface of cells that have been treated with various compounds. This method can be used to identify compounds that are useful to activate or inhibit CD40. According to this method, one sample of cells is treated with a test compound for a period of time while another sample is left untreated. If the total level of CD40 is to be measured, the cells are lysed and the total CD40 level is measured using one of the immunoassays described above. The total level of CD40 in the treated versus the untreated cells is compared to determine the effect of the test compound.

A preferred immunoassay for measuring total CD40 levels is an ELISA or Western blot. If the cell surface level of CD40 is to be measured, the cells are not lysed, and the cell surface levels of CD40 are measured using one of the immunoassays described above. A preferred immunoassay for determining cell surface levels of CD40 includes the steps of labeling the cell surface proteins with a detectable label, such as biotin or $^{125}$I, immunoprecipitating the CD40 with an anti-CD40 antibody and then detecting the labeled CD40. Another preferred immunoassay for determining the localization of CD40, e.g., cell surface levels, is by using immunohistochemistry. Methods such as ELISA, RIA, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of CD40.

The anti-CD40 antibodies of the invention can also be used to determine the levels of CD40 in a tissue or in cells derived from the tissue. In some embodiments, the tissue is a diseased tissue. In some embodiments, the tissue is a tumor or a biopsy thereof. In some embodiments of the method, a tissue or a biopsy thereof is excised from a patient. The tissue or biopsy is then used in an immunoassay to determine, e.g., total CD40 levels, cell surface levels of CD40 or localization of CD40 by the methods discussed above.

The above-described diagnostic method can be used to determine whether a tumor expresses high levels of CD40, which could be indicative that the tumor is a target for treatment with anti-CD40 antibody. Further, the same method can also be used to monitor the effect of the treatment with anti-CD40 antibody by detecting cell death in the tumor. The diagnostic method can also be used to determine whether a tissue or cell expresses insufficient levels of CD40 or activated CD40, and thus is a candidate for treatment with activating anti-CD40 antibodies, CD40L and/or other therapeutic agents for increasing CD40 levels or activity.

The antibodies of the present invention can also be used in vivo to identify tissues and organs that express CD40. In some embodiments, the anti-CD40 antibodies are used to identify CD40-expressing tumors. One advantage of using the human anti-CD40 antibodies of the present invention is that they may safely be used in vivo without eliciting an immune response to the antibody upon administration, unlike antibodies of non-human origin or with humanized antibodies.

The method comprises the steps of administering a detectably labeled an anti-CD40 antibody or a composition comprising them to a patient in need of such a diagnostic test and subjecting the patient to imaging analysis to determine the location of the CD40-expressing tissues. Imaging analysis is well known in the medical art, and includes, without limitation, x-ray analysis, magnetic resonance imaging (MRI) or computed tomography (CE). The antibody can be labeled with any agent suitable for in vivo imaging, for example a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-CD40 antibody will be unlabeled and will be imaged by administering a second antibody or other molecule that is detectable and that can bind the anti-CD40 antibody. In embodiment, a biopsy is obtained from the patient to determine whether the tissue of interest expresses CD40.

Therapeutic Methods of use

In another aspect, invention provides therapeutic methods of using an anti-CD40 antibody of the invention.

A human agonist anti-CD40 antibody of the invention can be administered to a human or to a non-human mammal that expresses a cross-reacting CD40. The antibody can be administered to such a non-human mammal (i.e., a primate, cynomolgus or rhesus monkey) for veterinary purposes or as an animal model of human disease. Such animal models are useful for evaluating the therapeutic efficacy of antibodies of this invention.

In some embodiments, the anti-CD40 antibody is administered to a subject who suffers from primary and/or combined immunodeficiencies, including CD40– dependent immunodeficiency with Hyper-IgM syndrome, Common Variable Immunodeficiency, Bruton's Agammaglobulinemia, IgG subclass deficiencies, and X-linked SCID (common gamma chain mutations). In some embodiments, the anti-CD40 antibody is administered to treat a subject who is immunosuppressed, for example due to chemotherapy, or has an immune-debilitating disease, including any acquired immune deficiency disease, such as HIV. In some embodiments, the anti-CD40 antibody is administered to enhance the immunity of an elderly subject. In some embodiments, the anti-CD40 antibody is administered to treat a subject who has a bacterial, viral, fungal or parasitic infection. In some embodiments, a human agonist anti-CD40 antibody of the invention may be administered prophylactically to a subject who, because of age, illness or general poor health is susceptible to infection to prevent or to reduce the number or severity of infections.

In some embodiments, the anti-CD40 antibody is administered to a subject who has a hyperproliferative disorder.

In some embodiments, the anti-CD40 antibody is administered to treat a subject who has a tumor. In some embodiments, the tumor is CD40 positive. In some embodiments, the tumor is a CD40 negative. The tumor can be a solid tumor or a non-solid tumor such as lymphoma. In some embodiments, an anti-CD40 antibody is administered to a patient who has a tumor that is cancerous. In some embodiments, the antibody inhibits cancer cell proliferation, inhibits or prevents an increase in tumor weight or volume, and/or causes a decrease in tumor weight or volume.

Patients that can be treated with anti-CD40 antibodies or antibody portions of the invention include, but are not limited to, patients that have been diagnosed as having brain cancer, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, gastric cancer, colorectal cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), cancer of the esophagus, cancer of the small intestine, cancer of the endocrine system (e.g., cancer of the thyroid, parathyroid or adrenal glands), sarcomas of soft tissues, leukemia, myeloma, multiple myeloma, cancer of the urethra, cancer of the penis, prostate cancer, chronic or acute leukemia, solid tumors of childhood, Hodgkin's disease, lymphocytic lymphomas, non-Hodgkin lymphoma, cancer of the bladder, liver cancer, renal cancer, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas), glioma or fibrosarcoma.

The antibody may be administered from three times daily to once every six months, and preferably may be administered via an oral, mucosal, buccal, intranasal, inhalable, intravenous, subcutaneous, intramuscular, parenteral, intratumor, transdermal or topical route. The antibody can also be administered continuously via a minipump. The antibody generally will be administered for as long as the tumor is present provided that the antibody causes the tumor or cancer to stop growing or to decrease in weight or volume. The dosage of antibody generally will be in the range of 0.025 to 50 mg/kg, more preferably 0.1 to 50 mg/kg, more preferably 0.1-20 mg/kg, 0.1-10 mg/kg, 0.1-5 mg/kg or even more preferable 0.1-2 mg/kg. The antibody can also be administered prophylactically.

In some embodiments, the anti-CD40 antibody is administered as part of a therapeutic regimen that includes one or more additional antineoplastic drugs or molecules to a patient who has a hyperproliferative disorder, such as cancer or a tumor. Exemplary antitumor agents include, but are not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and antiandrogens. In more preferred embodiments, the anti-CD40 antibody is administered with an antineoplastic agent, such as adriamycin or taxol. In some preferred embodiments, the anti-CD40 therapy is performed along with radiotherapy, chemotherapy, photodynamic therapy, surgery or other immunotherapy. In some embodiments, the anti-CD40 antibody is administered with one or more additional antibodies. For example, the anti-CD40 antibody can be administered with antibodies that are known to inhibit tumor or cancer cell proliferation. Such antibodies include, but are not limited to, an antibody that inhibits CTLA4, erbB2 receptor, EGF-R, IGF-1R, CD20 or VEGF.

In some embodiments, the anti-CD40 antibody is labeled with a radiolabel, an immunotoxin or a toxin, or is a fusion protein comprising a toxic peptide. The anti-CD40 antibody or anti-CD40 antibody fusion protein directs the radiolabel, immunotoxin, toxin or toxic peptide to the tumor or cancer cell. In a preferred embodiment, the radiolabel, immunotoxin, toxin or toxic peptide is internalized by the tumor or cancer cell after the anti-CD40 antibody binds to the CD40 on the surface of the cell.

In another aspect, the anti-CD40 antibody can be used therapeutically to induce apoptosis of specific cells in a patient. In many cases, the cells targeted for apoptosis are cancerous or tumor cells. Thus, the invention provides a method of inducing apoptosis by administering an anti-CD40 antibody to a patient in need thereof.

In another aspect, the invention provides a method of administering an activating anti-CD40 antibody to a patient to increase CD40 activity. An anti-CD40 antibody is administered with one or more other factors that increase CD40 activity. Such factors include CD40L, and/or analogues of CD40L that activate CD40.

In some embodiments, the anti-CD40 antibody is administered with one or more additional immune enhancing agents, including, without limitation IFN-β1, IL-2, IL-8, IL-12, IL-15, IL-18, IL-23, IFN-γ, and GM-CSF.

In some embodiments, a human agonist anti-CD40 antibody of the invention is used as an adjuvant to enhance the efficacy of a vaccine. When used in this way, the anti-CD-40 antibody activates CD40 on antigen presenting cells, including B cells, dendritic cells and monocytes as well as enhancing the production of immunomodulatory molecules, such as cytokines and chemokines. The immunostimulatory effect of the antibody enhances the immune response of the vaccinated subject to the vaccine antigen.

In another aspect, the invention provides a method for generating a dendritic cell vaccine for cancer or for dendritic cell immunotherapy. According to the method dendritic cells from a cancer patient are cultured for 1-5 days with tumor lysate or homogenate, tumor cells killed by irradiation or other means, or tumor specific antigens (e.g., peptides, idiotypes) and 1-10 µg/ml of an anti-CD40 antibody. The tumor antigen-pulsed dendritic cells are re-injected into the patient to stimulate anti-tumor immune responses, particularly anti-tumor CTL responses. Monocyte-derived dendritic cells for use in the method can be obtained from a peripheral blood sample by culture in IL-4 and GM-CSF. Dendritic cells also can be derived from the bone marrow of a patient by magnetic purification or sorting of CD34 positive cells, followed by culture in IL-4 and GM-CSF.

Gene Therapy

The nucleic acid molecules of the instant invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-CD40 antibody and expressing the nucleic acid molecule. In another embodiment, the gene therapy method comprises the steps of administering an isolated nucleic acid molecule encoding the light chain or an antigen-binding portion thereof of an anti-CD40 antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-CD40 antibody of the invention and expressing the nucleic acid molecules. The gene therapy method may also comprise the step of administering another anti-cancer agent, such as taxol or adriamycin.

In order that this invention may be better understood, the following examples are set forth. These examples are for purposes of illustration only and are not to be construed as limiting the scope of the invention in any manner.

EXAMPLE I

Generation of Hybridomas Producing Anti-CD40 Antibody

Antibodies of the invention were prepared, selected, and assayed as follows:

Immunization and Hybridoma Generation

We immunized eight to ten week old XenoMice™ intraperitoneally or in their hind footpads with either a CD40-IgG fusion protein (10 μg/dose/mouse) or with 300.19-CD40 cells which is a transfected cell line that express human CD40 on its plasma membrane ($10 \times 10^6$ cells/dose/mouse). We repeated this dose five to seven times over a three to eight week period. Four days before fusion, we gave the mice a final injection of the extracellular domain of human CD40 in PBS. We fused the spleen and lymph node lymphocytes from immunized mice with the non-secretory myeloma P3-X63-Ag8.653 cell line, and subjected the fused cells to HAT selection as previously described (Galfre and Milstein, *Methods Enzymol.* 73:3-46, 1981). We recovered a panel of hybridomas all secreting CD40 specific human IgG2κ antibodies. We selected eleven hybridomas for further study and designated them 3.1.1, 7.1.2, 10.8.3, 15.1.1, 21.4.1, 21.2.1, 22.1.1, 23.5.1, 23.25.1, 23.29.1 and 24.2.1.

We deposited hybridomas 3.1.1, 7.1.2, 10.8.3, 15.1.1 and 21.4.1 in the American Type Culture Collection (ATCC) in accordance with the Budapest Treaty, 10801 University Boulevard, Manassas, Va. 20110-2209, on Aug. 6, 2001. We deposited hybridomas 21.2.1, 22.1.1, 23.5.1, 23.25.1, 23.28.1, 23.29.1 and 24.2.1 in the ATCC on Jul. 16, 2002. The hybridomas have been assigned the following deposit numbers:

| Hybridoma | Deposit No. |
|---|---|
| 3.1.1 (LN 15848) | PTA-3600 |
| 7.1.2 (LN 15849) | PTA-3601 |
| 10.8.3 (LN 15850) | PTA-3602 |
| 15.1.1 (LN 15851) | PTA-3603 |
| 21.4.1 (LN 15853) | PTA-3605 |
| 21.2.1 (LN 15874) | PTA-4549 |
| 22.1.1 (LN 15875) | PTA-4550 |
| 23.5.1 (LN 15855) | PTA-4548 |
| 23.25.1 (LN 15876) | PTA-4551 |

-continued

| Hybridoma | Deposit No. |
|---|---|
| 23.28.1 (LN 15877) | PTA-4552 |
| 23.29.1 (LN 15878) | PTA-4553 |
| 24.2.1 (LN 15879) | PTA-4554 |

EXAMPLE II

Sequences of Anti-CD40-Antibodies Prepared in Accordance with the Invention

To analyze the structure of antibodies produced in accordance with the invention, we cloned nucleic acids encoding heavy and light chain fragments from hybridomas producing anti-CD40 monoclonal antibodies. Cloning and sequencing was accomplished as follows.

We isolated Poly(A)$^+$ mRNA from approximately $2 \times 10^5$ hybridoma cells derived from XenoMouse™ mice immunized with human CD40 as described in Example I using a Fast-Track kit (Invitrogen). We followed by PCR the generation of random primed cDNA. We used human $V_H$ or human Vκ family specific variable region primers (Marks et al., "Oligonucleotide primers for polymerase chain reaction amplification of human immunoglobulin variable genes and design of family-specific oligonucleotide probes." *Eur. J. Immunol.* 21:985-991 (1991)) or a universal human $V_H$ primer, MG-30, CAGGTGCAGCTGGAGCAGTCIGG (SEQ ID NO: 118), in conjunction with primers specific for the human Cj2 constant region, MG-40d, 5'-GCTGAGG-GAGTAGAGTCCTGAGGA-3' (SEQ ID NO: 119) or CK constant region (hκP2; as previously described in Green et al., 1994). We obtained nucleic acid molecules encoding human heavy and kappa light chain transcripts from the anti-CD40 producing hybridomas by direct sequencing of PCR products generated from poly(A$^+$) RNA using the primers described above. We also cloned PCR products into pCRII using a TA cloning kit (Invitrogen) and sequenced both strands using Prism dye-terminator sequencing kits and an ABI 377 sequencing machine. We analyzed all sequences by alignments to the "V BASE sequence directory" (Tomlinson et al., MRC Centre for Protein Engineering, Cambridge, UK) using MacVector and Geneworks software programs.

Further, we subjected monoclonal antibodies 3.1.1, 7.1.2, 10.8.3, 15.1.1, 21.4.1, 21.2.1, 22.1.1, 23.5.1, 23.28.1, 23.29.1 and 24.2.1 to full length DNA cloning and sequencing. For such sequencing, we isolated RNA from approximately $4 \times 10^6$ hybridoma cells using QIAGEN RNeasy® RNA isolation kit (QIAGEN). We reverse transcribed the mRNA using oligo-dT(18) (SEQ ID NO: 144) and the Advantage® RT/PCR kit (Clontech). We used V Base to design forward amplification primers that included restriction sites, optimal Kozak sequence, the ATG start site and part of the signal sequence of the heavy chain. Table 1 lists the forward amplification primers used to sequence the antibody clones.

TABLE 1

| Clone | Forward Primer Heavy Chain |
|---|---|
| 3.1.1 | 5'-TATCTAAGCTTCTAGACTCGACCGCCACCATGGAGTTT GGGCTGAGCTG-3' (SEQ ID NO: 120) |

TABLE 1-continued

| Clone | Forward Primer Heavy Chain |
|---|---|
| 7.1.2 | 5'-TATCTAAGCTTCTAGACTCGACCGCCACCATGGAGTTT GGGCTGAGCTG-3' (SEQ ID NO: 121) |
| 10.8.3 | 5'-TATCTAAGCTTCTAGACTCGAGCGCCACCATGAAACAC CTGTGGTTCTTCC-3' (SEQ ID NO: 122) |
| 15.1.1 | 5'-TATCTAAGCTTCTAGACTCGAGCGCCACCATGAAACAT CTGTGGTTCTTCC 3' (SEQ ID NO: 123) |
| 21.4.1 | 5'-TATCTAAGCTTCTAGACTCGAGCGCCACCATGGACTGG ACCTGGAGGATCC-3' (SEQ ID NO: 124) |
| 21.2.1 | 5'-TATCTAAGCTTCTAGACTCGACCGCCACCATGGA GTTTGGGCTGAGCTG-3' (SEQ ID NO:128) |
| 22.1.1 | 5'-TATCTAAGCTTCTAGACTCGACCGCCACCATGGAG TTTGGGCTGAGCTG-3' (SEQ ID NO:129) |
| 23.5.1 | 5'-TATCTAAGCTTCTAGACTCGACCGCCACCATGGAG TTTGGGCTGAGCTG-3' (SEQ ID NO:130) |
| 23.28.1 | 5'-TATCTAAGCTTCTAGACTCGAGCGCCACCATGAAA CATCTGTGGTTCTTCC-3' (SEQ ID NO:131) |
| 23.29.1 | 5'-TATCTAAGCTTCTAGACTCGACCGCCACCATGGAG TTTGGGCTGAGCTG-3' (SEQ ID NO:132) |
| 24.2.1 | 5'-TATCTAAGCTTCTAGACTCGAGCGCCACCATGAA ACATCTGTGGTTCTTCC-3' (SEQ ID NO:133) |

We used the same method to design a primer to include the 3' coding sequences, the stop codon of the IgG2 constant region, (5'-TTCTCTGATCAGAATTCC TATCATTTAC-CCGGAGACAGGGAGAG-3') (SEQ ID NO:125) and restriction sites.

We also used the same method to design a primer around the ATG start site of the kappa chain: (5'-CTTCAAGCT-TACCCGGGCCACCATGAGGCTCC CTGCTCAGC-3') (SEQ ID NO:126). An optimal Kozak sequence (CCGC-CACC) was added 5' to the ATG start site. This primer was used to PCR clone the light chains of following antibody clones: 3.1.1, 7.1.2, 10.8.3, 15.1.1, 21.4.1, 21.2.1, 22.1.1, 23.5.1 and 23.29.1. We used a second forward primer 5'-TCTTC AAGCTTGCCCGGGCCCGCCACCATG-GAAACCCCAGCGCAG-3' (SEQ ID NO. 134) to clone the light chains of clones 23.28.1 and 24.2.1. We also used the same method to design a primer around the stop codon of the kappa constant region (5'-TTCTTTGATCAGAATTCT-CACTAACACTCTCCCCTGTTGAAGC-3') (SEQ ID NO: 127). We used the primer pairs to amplify the cDNAs using Advantage® High Fidelity PCR Kit (Clontech). We obtained the sequence of the PCR product by direct sequencing using standard techniques (e.g., primer walking) using dye-terminator sequencing kits and an ABI sequencing machine. We cloned the PCR product into a mammalian expression vector and we sequenced clones to confirm somatic mutations. For each clone, we verified the sequence on both strands in at least three reactions.

Gene Utilization Analysis

Table 2 sets forth the gene utilization evidenced by selected hybridoma clones of antibodies in accordance with the invention:

TABLE 2

Heavy and Light Chain Gene Utilization

| | Heavy Chain | | | Kappa Light Chain | |
|---|---|---|---|---|---|
| Clone | VH | D | JH | VK | JK |
| 3.1.1 | (3-30+) DP-49 | D4+ DIR3 | JH6 | A3/A19 (DPK-15) | JK1 |
| 7.1.2 | (3-30+) DP-49 | DIR5+ D1-26 | JH6 | A3/A19 (DPK-15) | JK1 |
| 10.8.3 | (4.35) VIV-4 | DIR3 | JH6 | L5 (DP5) | JK4 |
| 15.1.1 | (4-59) DP-71 | D4-23 | JH4 | A3/A19 (DPK-15) | JK2 |
| 21.4.1 | (1-02) DP-75 | DLR1 | JH4 | L5 (DP5) | JK4 |
| 21.2.1 | (3-30+) DP-49 | DIR3+ D6-19 | JH4 | A3/A19 (DPK-15) | JK3 |
| 22.1.1 | (3-30+) DP-49 | D1-1 | JH6 | A3/A19 (DPK-15) | JK1 |
| 23.5.1 | (3-30+) DP-49 | D4-17 | JH6 | A3/A19 (DPK-15) | JK1 |
| 23.28.1 | (4-59) DP-71 | DIR1+ D4-17 | JH5 | A27 (DPK-22) | JK3 |
| 23.29.1 | (3-30.3) DP-46 | D4-17 | JH6 | A3/A19 (DPK-15) | JK1 |
| 24.2.1 | (4-59) DP-71 | DIR1+ D4-17 | JH5 | A27 (DPK-22) | JK3 |

Sequence And Mutation Analysis

As will be appreciated, gene utilization analysis provides only a limited overview of antibody structure. As the B-cells in XenoMouse™ animals stochastically generate V-D-J heavy or V-J kappa light chain transcripts, there are a number of secondary processes that occur, including, without limitation, somatic hypermutation, deletions, N-additions, and CDR3 extensions. See, for example, Mendez et al., *Nature Genetics* 15:146-156 (1997) and International Patent Publication WO 98/24893. Accordingly, to further examine antibody structure, we generated predicted amino acid sequences of the antibodies from the cDNAs obtained from the clones. Table A provides the sequence identifiers for each of the nucleotide and predicted amino acid sequences of the sequenced antibodies.

Tables 3-7 provide the nucleotide and predicted amino acid sequences of the heavy and kappa light chains of antibodies 3.1.1 (Table 3), 7.1.2 (Table 4), 10.8.3 (Table 5), 15.1.1 (Table 6) and 21.4.1 (Table 7).

Tables 8-13 provide the nucleotide and predicted amino acid sequences of the variable domain of the heavy chain and kappa light chain of antibodies 21.2.1 (Table 8), 22.1.1 (Table 9), 23.5.1 (Table 10), 23.28.1 (Table 11), 23.29.1 (Table 12) and 24.2.1 (Table 13).

The DNA sequence from the full-length sequencing of monoclonal antibody 23.28.1 differs from DNA sequences obtained from sequencing the $V_H$ region of the initial PCR product by one base pair (C to G), resulting in a change of residue 16 of the natural heavy chain from D to E.

Tables 14-19 provide the nucleotide and predicted amino acid sequences of the heavy and kappa light chains of antibodies 21.2.1 (Table 14), 22.1.1 (Table 15), 23.5.1 (Table 16), 23.28.1 (Table 17), 23.29.1 (Table 18) and 24.2.1 (Table 19). In the Tables, the signal peptide sequence (or the bases encoding the same) are underlined.

We generated two mutated antibodies, 22.1.1 and 23.28.1. The heavy chain of antibody 22.1.1 was mutated to change a cysteine residue at position 109 to an alanine residue. We designated the mutated clone 22.1.1H-$C_{019}$A. The light chain of antibody 23.28.1 at position 92 was mutated also to change a cysteine residue to an alanine residue. We designated the mutated clone 23.28.1L-C92A.

Mutagenesis of specific residues was carried out by designing primers and using the Quikchange® Site-Directed Mutagenesis Kit from Stratagene, according to the manufacturer's instructions. Mutations were confirmed by automated sequencing, and mutagenized inserts were subcloned into expression vectors.

Table 20 provides the nucleotide and amino acid sequences of the mutated heavy chain of antibody 22.1.1H-C109A. Table 21 provides the nucleotide and amino acid sequences of the mutated light chain of antibody 23.28.1. The mutated DNA codons are shown in italics. The mutated amino acid residue is in bold.

TABLE 3

DNA and protein sequences of antibody 3.1.1

| DESCRIPTION: | SEQUENCE (signal sequence underlined): |
|---|---|
| Heavy Chain DNA Sequence (SEQ ID NO: 5) | <u>ATGGAGTTTGGGCTGAGCTGGGTTTTCCTCGTTGC</u> |
| | <u>TCTTTTAAGAGGTGTCCAGTGT</u>CAGGTGCAGCTG |
| | GTGGAGTCTGGGGGAGGCGTGGTCCAGCCTGGG |
| | AGGTCCCTGAGACTCTCCTGTGCAGCCTCTGGAT |
| | TCACCTTCAGTAGTTATGGCATGCACTGGGTCCG |
| | CCAGGCTCCAGGCAAGGGGCTGGAGTGGGTGGC |
| | AGTTATATCAAAGGATGGAGGTAATAAATACCAT |
| | GCAGACTCCGTGAAGGGCCGATTCACCATCTCCA |
| | GAGACAATTCCAAGAATGCGCTGTATCTGCAAAT |
| | GAATAGCCTGAGAGTTGAAGACACGGCTGTGTAT |
| | TACTGTGTGAGAAGAGGGCATCAGCTGGTTCTGG |
| | GATACTACTACTACAACGGTCTGGACGTCTGGGG |
| | CCAAGGGACCACGGTCACCGTCTCCTCAGCCTCC |
| | ACCAAGGGCCCATCGGTCTTCCCCCTGGCGCCCT |
| | GCTCCAGGAGCACCTCCGAGAGCACAGCGGCCCT |
| | GGGCTGCCTGGTCAAGGACTACTTCCCCGAACCG |
| | GTGACGGTGTCGTGGAACTCAGGCGCTCTGACCA |
| | GCGGCGTGCACACCTTCCCAGCTGTCCTACAGTC |
| | CTCAGGACTCTACTCCCTCAGCAGCGTGGTGACC |
| | GTGCCCTCCAGCAACTTCGGCACCCAGACCTACA |
| | CCTGCAACGTAGATCACAAGCCCAGCAACACCAA |
| | GGTGGACAAGACAGTTGAGCGCAAATGTTGTGTC |
| | GAGTGCCCACCGTGCCCAGCACCACCTGTGGCAG |
| | GACCGTCAGTCTTCCTCTTCCCCCCAAAACCCAA |
| | GGACACCCTCATGATCTCCCGGACCCCTGAGGTC |
| | ACGTGCGTGGTGGTGGACGTGAGCCACGAAGAC |
| | CCCGAGGTCCAGTTCAACTGGTACGTGGACGGCG |
| | TGGAGGTGCATAATGCCAAGACAAAGCCACGGG |
| | AGGAGCAGTTCAACAGCACGTTCCGTGTGGTCAG |
| | CGTCCTCACCGTTGTGCACCAGGACTGGCTGAAC |
| | GGCAAGGAGTACAAGTGCAAGGTCTCCAACAAA |
| | GGCCTCCCAGCCCCCATCGAGAAAACCATCTCCA |

TABLE 3-continued

DNA and protein sequences of antibody 3.1.1

| DESCRIPTION: | SEQUENCE (signal sequence underlined): |
|---|---|
| | AAACCAAAGGGCAGCCCCGAGAACCACAGGTGT |
| | ACACCCTGCCCCCATCCCGGGAGGAGATGACCAA |
| | GAACCAGGTCAGCCTGACCTGCCTGGTCAAAGGC |
| | TTCTACCCCAGCGACATCGCCGTGGAGTGGGAGA |
| | GCAATGGGCAGCCGGAGAACAACTACAAGACCA |
| | CACCTCCCATGCTGGACTCCGACGGCTCCTTCTTC |
| | CTCTACAGCAAGCTCACCGTGGACAAGAGCAGGT |
| | GGCAGCAGGGGAACGTCTTCTCATGCTCCGTGAT |
| | GCATGAGGCTCTGCACAACCACTACACGCAGAAG |
| | AGCCTCTCCCTGTCTCCGGGTAAATGA |
| Heavy Chain Protein Sequence (SEQ ID NO: 6) | <u>MEFGLSWVFLVALLRGVQC</u>QVQLVESGGGVVQPG |
| | RSLRLSCAASGFTFSSYGMHWVRQAPGKGLEWVA |
| | VISKDGGNKYHADSVKGRFTISRDNSKNALYLQMN |
| | SLRVEDTAVYYCVRRGHQLVLGYYYYNGLDVWG |
| | QGTTVTVSSASTKGPSVFPLAPCSRSTSESTAALGCL |
| | VKDYFPEPVTVSWNSGALTSGVHTFPAVLQSSGLY |
| | SLSSVVTVPSSNFGTQTYTCNVDHKPSNTKVDKTV |
| | ERKCCVECPPCPAPPVAGPSVFLFPPKPKDTLMISRT |
| | PEVTCVVVDVSHEDPEVQFNWYVDGVEVHNAKTK |
| | PREEQFNSTFRVVSVLTVVHQDWLNGKEYKCKVS |
| | NKGLPAPIEKTISKTKGQPREPQVYTLPPSREEMTK |
| | NQVSLTCLVKGFYPSDIAVEWESNGQPENNYKTTP |
| | PMLDSDGSFFLYSKLTVDKSRWQQGNVFSCSVMHE |
| | ALHNHYTQKSLSLSPGK |
| Light Chain DNA Sequence (SEQ ID NO: 7) | <u>ATGAGGCTCCCTGCTCAGCTCCTGGGGCTGCTAA</u> |
| | <u>TGCTCTGGGTCTCTGGATCCAGTGGG</u>GATATTGT |
| | GCTGACTCAGTCTCCACTCTCCCTGCCCGTCACCC |
| | CTGGAGAGCCGGCCTCCATCTCCTGCAGGTCTAG |
| | TCAGAGCCTCTTGTATAGTAATGGATACAACTTTT |
| | TGGATTGGTACCTGCAGAAGCCAGGGCAGTCTCC |
| | ACAGCTCCTGATCTATTTGGGTTCTAATCGGGCCT |
| | CCGGGGTCCCTGACAGGTTCAGTGGCAGTGGATC |
| | AGGCACAGATTTTACACTGAAAATCAGCAGATTG |
| | GAGGCTGAGGATGTTGGGGTTTATTACTGCATGC |
| | AAGCTCTACAAACTCCTCGGACGTTCGGCCAAGG |
| | GACCAAGGTGGAAATCAAACGAACTGTGGCTGC |
| | ACCATCTGTCTTCATCTTCCCGCCATCTGATGAGC |
| | AGTTGAAATCTGGAACTGCCTCTGTTGTGTGCCT |

TABLE 3-continued

DNA and protein sequences of antibody 3.1.1

| DESCRIPTION: | SEQUENCE (signal sequence underlined): |
|---|---|
| | GCTGAATAACTTCTATCCCAGAGAGGCCAAAGTA |
| | CAGTGGAAGGTGGATAACGCCCTCCAATCGGGTA |
| | ACTCCCAGGAGAGTGTCACAGAGCAGGACAGCA |
| | AGGACAGCACCTACAGCCTCAGCAGCACCCTGAC |
| | GCTGAGCAAAGCAGACTACGAGAAACACAAAGT |
| | CTACGCCTGCGAAGTCACCCATCAGGGCCTGAGC |
| | TCGCCCGTCACAAAGAGCTTCAACAGGGGAGAGT |
| | GTTAG |
| Light Chain Protein Sequence (SEQ ID NO: 8) | MRLPAQLLGLLMLWVSGSSGDIVLTQSPLSLPVTPG |
| | EPASISCRSSQSLLYSNGYNFLDWYLQKPGQSPQLLI |
| | YLGSNRASGVPDRFSGSGSGTDFTLKISRLEAEDVG |
| | VYYCMQALQTPRTFGQGTKVEIKRTVAAPSVFIFPP |
| | SDEQLKSGTASVVCLLNNFYPREAKVQWKVDNAL |
| | QSGNSQESVTEQDSKDSTYSLSSTLTLSKADYEKHK |
| | VYACEVTHQGLSSPVTKSFNRGEC |
| Mature Variable Domain of Heavy Chain DNA Sequence (SEQ ID NO: 1) | CAGGTGCAGCTGGTGGAGTCTGGGGGAGGCGTG |
| | GTCCAGCCTGGGAGGTCCCTGAGACTCTCCTGTG |
| | CAGCCTCTGGATTCACCTTCAGTAGTTATGGCAT |
| | GCACTGGGTCCGCCAGGCTCCAGGCAAGGGGCTG |
| | GAGTGGGTGGCAGTTATATCAAAGGATGGAGGT |
| | AATAAATACCATGCAGACTCCGTGAAGGGCCGAT |
| | TCACCATCTCCAGAGACAATTCCAAGAATGCGCT |
| | GTATCTGCAAATGAATAGCCTGAGAGTTGAAGAC |
| | ACGGCTGTGTATTACTGTGTGAGAAGAGGGCATC |
| | AGCTGGTTCTGGGATACTACTACTACAACGGTCT |
| | GGACGTCTGGGGCCAAGGGACCACGGTCACCGTC |
| | TCCTCA |
| Mature Variable Domain of Heavy Chain Protein Sequence (SEQ ID NO: 2) | QVQLVESGGGVVQPGRSLRLSCAASGFTFSSYGMH |
| | WVRQAPGKGLEWVAVISKDGGNKYHADSVKGRFT |
| | ISRDNSKNALYLQMNSLRVEDTAVYYCVRRGHQL |
| | VLGYYYYNGLDVWGQGTTVTVSS |
| Mature Variable Domain of Light Chain DNA Sequence (SEQ ID NO: 3) | GATATTGTGCTGACTCAGTCTCCACTCTCCCTGCC |
| | CGTCACCCCTGGAGAGCCGGCCTCCATCTCCTGC |
| | AGGTCTAGTCAGAGCCTCTTGTATAGTAATGGAT |
| | ACAACTTTTTGGATTGGTACCTGCAGAAGCCAGG |
| | GCAGTCTCCACAGCTCCTGATCTATTTGGGTTCTA |
| | ATCGGGCCTCCGGGGTCCCTGACAGGTTCAGTGG |

TABLE 3-continued

DNA and protein sequences of antibody 3.1.1

| DESCRIPTION: | SEQUENCE (signal sequence underlined): |
|---|---|
| | CAGTGGATCAGGCACAGATTTTACACTGAAAATC |
| | AGCAGATTGGAGGCTGAGGATGTTGGGGTTTATT |
| | ACTGCATGCAAGCTCTACAAACTCCTCGGACGTT |
| | CGGCCAAGGGACCAAGGTGGAAATCAAA |
| Mature Variable Domain of Light Chain Protein Sequence (SEQ ID NO: 4) | DIVLTQSPLSLPVTPGEPAAISCRSSQSLLYSNGYNFL DWYLQKPGQSPQLLIYLGSNRASGVPDPYSGSGSGT DFTLKISRLEAEDVGVYYCMQALQTPRTFGQGTKV EIK |
| Heavy chain DNA (variable domain) (3.1.1H-A78T) SEQ ID NO: 89 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTTATGGCAT GCACTGGGTCCGCCAGGCTCCAGGCAAGGGGCTG GAGTGGGTGGCAGTTATATCAAAGGATGGAGGT AATAAATACCATGCAGACTCCGTGAAGGGCCGAT TCACCATCTCCAGAGACAATTCCAAGAATaCGCT GTATCTGCAAATGAATAGCCTGAGAGTTGAAGAC ACGGCTGTGTATTACTGTGTGAGAAGAGGGCATC AGCTGGTTCTGGGATACTACTACTACAACGGTCT GGACGTCTGGGGCCAAGGGACCACGGTCACCGTC TCCTCA |
| Heavy chain protein (variable domain) (3.1.1H-A78T) SEQ ID NO: 90 | QVQLVESGGGVVQPGRSLRLSCAASGFTFSSYGMH WVRQAPGKGLEWVAVISKDGGNKYHADSVKGRFT ISRDNSKNTLYLQMNSLRVEDTAVYYCVRRGHQLV LGYYYYNGLDVWGQGTTVTVSS |
| Heavy chain DNA (variable domain) (3.1.1H-A78T-V88A-V97A) SEQ ID NO: 91 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTTATGGCAT GCACTGGGTCCGCCAGGCTCCAGGCAAGGGGCTG GAGTGGGTGGCAGTTATATCAAAGGATGGAGGT AATAAATACCATGCAGACTCCGTGAAGGGCCGAT TCACCATCTCCAGAGACAATTCCAAGAATaCGCT GTATCTGCAAATGAATAGCCTGAGAGcTGAAGAC ACGGCTGTGTATTACTGTGcGAGAAGAGGGCATC AGCTGGTTCTGGGATACTACTACTACAACGGTCT GGACGTCTGGGGCCAAGGGACCACGGTCACCGTC TCCTCA |

TABLE 3-continued

DNA and protein sequences of antibody 3.1.1

| DESCRIPTION: | SEQUENCE (signal sequence underlined): |
|---|---|
| Heavy chain protein (variable domain) (3.1.1H-A78T-V88A-V97A) SEQ ID NO: 92 | QVQLVESGGGVVQPGRSLRLSCAASGFTFSSYGMH WVRQAPGKGLEWVAVISKDGGNKYHADSVKGRFT ISRDNSK*N*T*L*YLQMNSLRAEDTAVYYCARRGHQLV LGYYYYNGLDVWGQGTTVTVSS |
| Light chain DNA (variable domain) (3.1.1L-L4M-L83V) SEQ ID NO: 93 | GATATTGTGaTGACTCAGTCTCCACTCTCCCTGCC CGTCACCCCTGGAGAGCCGGCCTCCATCTCCTGC AGGTCTAGTCAGAGCCTCTTGTATAGTAATGGAT ACAACTTTTTGGATTGGTACCTGCAGAAGCCAGG GCAGTCTCCACAGCTCCTGATCTATTTGGGTTCTA ATCGGGCCTCCGGGGTCCCTGACAGGTTCAGTGG CAGTGGATCAGGCACAGATTTTACACTGAAAATC AGCAGAgTGGAGGCTGAGGATGTTGGGGTTTATT ACTGCATGCAAGCTCTACAAACTCCTCGGACGTT CGGCCAAGGGACCAAGGTGGAAATCAAA |
| Light chain protein (variable domain) (3.1.1L-L4M-L83V) SEQ ID NO: 94 | DIV*M*TQSPLSLPVTPGEPASISCRSSQSLLYSNGYNF LDWYLQKPGQSPQLLIYLGSNRASGVPDRFSGSGSG TDFTLKISRVEAEDVGVYYCMQALQTPRTFGQGTK VEIK |

TABLE 4

DNA and protein sequences of antibody 7.1.2

| DESCRIPTION: | SEQUENCE (signal sequence underlined): |
|---|---|
| Heavy Chain DNA Sequence (SEQ ID NO: 13) | <u>ATGGAGTTTGGGCTGAGCTGGGTTTTCCTCGTTGC</u> <u>TCTTTTAAGAGGTGTCCAGTGT</u>CAGGTGCAGCTG GTGGAGTCTGGGGGAGGCGTGGTCCAGCCTGGG AGGTCCCTGAGACTCTCCTGTGCAGCCTCTGGAT TCACCTTCAGTAGCTATGGCATGCACTGGGTCCG CCAGGCTCCAGGCAAGGGGCTGGAGTGGGTGGC AGTTATATCAAATGATGGAGATAATAAATACCAT GCAGACTCCGTGTGGGGCCGATTCACCATCTCCA GAGACAATTCCAGGAGCACGCTTTATCTGCAAAT GAACAGCCTGAGAGCTGAGGACACGGCTGTATAT TACTGTGCGAGAAGAGGCATGGGGTCTAGTGGG AGCCGTGGGGATTACTACTACTACTACGGTTTGG ACGTCTGGGGCCAAGGGACCACGGTCACCGTCTC CTCAGCCTCCACCAAGGGCCCATCGGTCTTCCCC CTGGCGCCCTGCTCCAGGAGCACCTCCGAGAGCA |

TABLE 4-continued

DNA and protein sequences of antibody 7.1.2

| DESCRIPTION: | SEQUENCE (signal sequence underlined): |
|---|---|
| | CAGCGGCCCTGGGCTGCCTGGTCAAGGACTACTT |
| | CCCCGAACCGGTGACGGTGTCGTGGAACTCAGGC |
| | GCTCTGACCAGCGGCGTGCACACCTTCCCAGCTG |
| | TCCTACAGTCCTCAGGACTCTACTCCCTCAGCAG |
| | CGTGGTGACCGTGCCCTCCAGCAACTTCGGCACC |
| | CAGACCTACACCTGCAACGTAGATCACAAGCCCA |
| | GCAACACCAAGGTGGACAAGACAGTTGAGCGCA |
| | AATGTTGTGTCGAGTGCCCACCGTGCCCAGCACC |
| | ACCTGTGGCAGGACCGTCAGTCTTCCTCTTCCCCC |
| | CAAAACCCAAGGACACCCTCATGATCTCCCGGAC |
| | CCCTGAGGTCACGTGCGTGGTGGTGGACGTGAGC |
| | CACGAAGACCCCGAGGTCCAGTTCAACTGGTACG |
| | TGGACGGCGTGGAGGTGCATAATGCCAAGACAA |
| | AGCCACGGGAGGAGCAGTTCAACAGCACGTTCC |
| | GTGTGGTCAGCGTCCTCACCGTTGTGCACCAGGA |
| | CTGGCTGAACGGCAAGGAGTACAAGTGCAAGGT |
| | CTCCAACAAAGGCCTCCCAGCCCCCATCGAGAAA |
| | ACCATCTCCAAAACCAAAGGGCAGCCCCGAGAA |
| | CCACAGGTGTACACCCTGCCCCCATCCCGGGAGG |
| | AGATGACCAAGAACCAGGTCAGCCTGACCTGCCT |
| | GGTCAAAGGCTTCTACCCCAGCGACATCGCCGTG |
| | GAGTGGGAGAGCAATGGGCAGCCGGAGAACAAC |
| | TACAAGACCACACCTCCCATGCTGGACTCCGACG |
| | GCTCCTTCTTCCTCTACAGCAAGCTCACCGTGGAC |
| | AAGAGCAGGTGGCAGCAGGGGAACGTCTTCTCAT |
| | GCTCCGTGATGCATGAGGCTCTGCACAACCACTA |
| | CACGCAGAAGAGCCTCTCCCTGTCTCCGGGTAAA |
| | TGA |
| Heavy Chain Protein Sequence (SEQ ID NO: 14) | MEFGLSWVFLVALLRGVQCQVQLVESGGGVVQPG |
| | RSLRLSCAASGFTFSSYGMHWVRQAPGKGLEWVA |
| | VISNDGDNKYHADSVWGRFTISRDNSRSTLYLQMN |
| | SLRAEDTAVYYCARRGMGSSGSRGDYYYYYGLDV |
| | WGQGTTVTVSSASTKGPSVFPLAPCSRSTSESTAAL |
| | GCLVKDYFPEPVTVSWNSGALTSGVHTFPAVLQSS |
| | GLYSLSSVVTVPSSNFGTQTYTCNVDHKPSNTKVD |
| | KTVERKCCVECPPCPAPPVAGPSVFLFPPKPKDTLM |
| | ISRTPEVTCVVVDVSHEDPEVQFNWYVDGVEVHNA |

TABLE 4-continued

DNA and protein sequences of antibody 7.1.2

| DESCRIPTION: | SEQUENCE (signal sequence underlined): |
|---|---|
| | KTKPREEQFNSTFRVVSVLTVVHQDWLNGKEYKC |
| | KVSNKGLPAPIEKTISKTKGQPREPQVYTLPPSREEM |
| | TKNQVSLTCLVKGFYPSDIAVEWESNGQPENNYKT |
| | TPPMLDSDGSFFLYSKLTVDKSRWQQGNVFSCSVM |
| | HEALHNHYTQKSLSLSPGK |
| Light Chain DNA Sequence (SEQ ID NO: 15) | <u>ATGAGGCTCCCTGCTCAGCTCCTGGGGCTGCTAA</u> <u>TGCTCTGGGTCTCTGGATCCAGTGGG</u>GATATTGT GATGACTCAGTCTCCACTCTCCCTGCCCGTCACCC CTGGAGAGCCGGCCTCCATCTCCTGCAGGTCTAG TCAGAGCCTCTTGTATAGTAATGGATACAACTTTT TGGATTGGTACCTGCAGAAGCCAGGGCAGTCTCC ACAGCTCCTGATCTATTTGGGTTCTAATCGGGCCT CCGGGGTCCCTGACAGGTTCAGTGGCAGTGGATC AGGCACAGATTTTACACTGAAAATCAGCAGAGTG GAGGCTGAGGATGTTGGGGTTTATTACTGCATGC AAGCTCTACAAACTCCTCGGACGTTCGGCCAAGG GACCAAGGTGGAAATCAAACGAACTGTGGCTGC ACCATCTGTCTTCATCTTCCCGCCATCTGATGAGC AGTTGAAATCTGGAACTGCCTCTGTTGTGTGCCT GCTGAATAACTTCTATCCCAGAGAGGCCAAAGTA CAGTGGAAGGTGGATAACGCCCTCCAATCGGGTA ACTCCCAGGAGAGTGTCACAGAGCAGGACAGCA AGGACAGCACCTACAGCCTCAGCAGCACCCTGAC GCTGAGCAAAGCAGACTACGAGAAACACAAAGT CTACGCCTGCGAAGTCACCCATCAGGGCCTGAGC TCGCCCGTCACAAAGAGCTTCAACAGGGGAGAGT GTTAG |
| Light Chain Protein Sequence (SEQ ID NO: 16) | <u>MRLPAQLLGLLMLWVSGSSG</u>DIVMTQSPLSLPVTP GEPASISCRSSQSLLYSNGYNFLDWYLQKPGQSPQL LIYLGSNRASGVPDRFSGSGSGTDFTKISRVEAEDV GVYYCMQALQTPRTFGQGTKVEIKRTVAAPSVFIFP PSDEQLKSGTASVVCLLNNFYPREAKVQWKVDNA LQSGNSQESVTEQDSKDSTYSLSSTLTLSKADYEKH KVYACEVTHQGLSSPVTKSFNRGEC |
| Mature Variable Domain of Heavy Chain DNA Sequence (SEQ ID NO: 9) | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCTG |

TABLE 4-continued

DNA and protein sequences of antibody 7.1.2

| DESCRIPTION: | SEQUENCE (signal sequence underlined): |
|---|---|
| | GAGTGGGTGGCAGTTATATCAAATGATGGAGATA |
| | ATAAATACCATGCAGACTCCGTGTGGGCCGATT |
| | CACCATCTCCAGAGACAATTCCAGGAGCACGCTT |
| | TATCTGCAAATGAACAGCCTGAGAGCTGAGGACA |
| | CGGCTGTATATTACTGTGCGAGAAGAGGCATGGG |
| | GTCTAGTGGGAGCCGTGGGATTACTACTACTAC |
| | TACGGTTTGGACGTCTGGGGCCAAGGGACCACGG |
| | TCACCGTCTCCTCA |
| Mature Variable Domain of Heavy Chain Protein Sequence (SEQ ID NO: 10) | QVQLVESGGGVVQPGRSLRLSCAASGFTFSSYGMH WVRQAPGKGLEWVAVISNDGDNKYHADSVWGRF TISRDNSRSTLYLQMNSLRAEDTAVYYCARRGMGS SGSRGDYYYYGLDVWGQGTTVTVSS |
| Mature Variable Domain of Light Chain DNA Sequence (SEQ ID NO: 11) | GATATTGTGATGACTCAGTCTCCACTCTCCCTGCC CGTCACCCCTGGAGAGCCGGCCTCCATCTCCTGC AGGTCTAGTCAGAGCCTCTTGTATAGTAATGGAT ACAACTTTTTGGATTGGTACCTGCAGAAGCCAGG GCAGTCTCCACAGCTCCTGATCTATTTGGGTTCTA ATCGGGCCTCCGGGGTCCCTGACAGGTTCAGTGG CAGTGGATCAGGCACAGATTTTACACTGAAAATC AGCAGAGTGGAGGCTGAGGATGTTGGGGTTTATT ACTGCATGCAAGCTCTACAAACTCCTCGGACGTT CGGCCAAGGGACCAAGGTGGAAATCAAA |
| Mature Variable Domain of Light Chain Protein Sequence (SEQ ID NO: 12) | DIVMTQSPLSLPVTPGEPASISCRSSQSLLYSNGYNF LDWYLQKPGQSPQLLIYLGSNRASGVPDRFSGSGSG TDFTLKISRVEAEDVGVYYCMQALQTPRTFGQGTK VEIK |

TABLE 5

DNA and protein sequences of antibody 10.8.3

| DESCRIPTION: | SEQUENCE (signal sequence underlined): |
|---|---|
| Heavy Chain DNA Sequence (SEQ ID NO: 21) | <u>ATGAAACACCTGTGGTTCTTCCTCCTGCTGGTGGC</u> <u>AGCTCCCAGATGGGTCCTGTCCC</u>AGGTGCAGCTG CAGGAGTCGGGCCCAGGACTGGTGAAGCCTTCGG AGACCCTGTCCCTCACCTGCACTGTCTCTGGTGGC TCCATCAGTAGTTACTACTGGATCTGGATCCGGC AGCCCGCCGGGAAGGGACTGGAATGGATTGGGC GTGTCTATACCAGTGGGAGCACCAACTACAACCC |

TABLE 5-continued

DNA and protein sequences of antibody 10.8.3

| DESCRIPTION: | SEQUENCE (signal sequence underlined): |
|---|---|

CTCCCTCAAGAGTCGAGTCACCATGTCAGTAGAC

ACGTCCAAGAACCAGTTCTCCCTGAAGCTGAGCT

CTGTGACCGCCGCGGACACGGCCGTGTATTACTG

TGCGAGAGATGGTCTTTACAGGGGGTACGGTATG

GACGTCTGGGGCCAAGGGACCACGGTCACCGTCT

CCTCAGCCTCCACCAAGGGCCCATCGGTCTTCCC

CCTGGCGCCCTGCTCCAGGAGCACCTCCGAGAGC

ACAGCGGCCCTGGGCTGCCTGGTCAAGGACTACT

TCCCCGAACCGGTGACGGTGTCGTGGAACTCAGG

CGCTCTGACCAGCGGCGTGCACACCTTCCCAGCT

GTCCTACAGTCCTCAGGACTCTACTCCCTCAGCA

GCGTGGTGACCGTGCCCTCCAGCAACTTCGGCAC

CCAGACCTACACCTGCAACGTAGATCACAAGCCC

AGCAACACCAAGGTGGACAAGACAGTTGAGCGC

AAATGTTGTGTCGAGTGCCCACCGTGCCCAGCAC

CACCTGTGGCAGGACCGTCAGTCTTCCTCTTCCCC

CCAAAACCCAAGGACACCCTCATGATCTCCCGGA

CCCCTGAGGTCACGTGCGTGGTGGTGGACGTGAG

CCACGAAGACCCCGAGGTCCAGTTCAACTGGTAC

GTGGACGGCGTGGAGGTGCATAATGCCAAGACA

AAGCCACGGGAGGAGCAGTTCAACAGCACGTTC

CGTGTGGTCAGCGTCCTCACCGTTGTGCACCAGG

ACTGGCTGAACGGCAAGGAGTACAAGTGCAAGG

TCTCCAACAAAGGCCTCCCAGCCCCCATCGAGAA

AACCATCTCCAAAACCAAAGGGCAGCCCCGAGA

ACCACAGGTGTACACCCTGCCCCCATCCCGGGAG

GAGATGACCAAGAACCAGGTCAGCCTGACCTGCC

TGGTCAAAGGCTTCTACCCCAGCGACATCGCCGT

GGAGTGGGAGAGCAATGGGCAGCCGGAGAACAA

CTACAAGACCACACCTCCCATGCTGGACTCCGAC

GGCTCCTTCTTCCTCTACAGCAAGCTCACCGTGG

ACAAGAGCAGGTGGCAGCAGGGGAACGTCTTCT

CATGCTCCGTGATGCATGAGGCTCTGCACAACCA

CTACACGCAGAAGAGCCTCTCCCTGTCTCCGGGT

AAATGA

TABLE 5-continued

DNA and protein sequences of antibody 10.8.3

| DESCRIPTION: | SEQUENCE (signal sequence underlined): |
|---|---|
| Heavy Chain Protein Sequence (SEQ ID NO: 22) | MKHLWFFLLLVAAPRWVLSQVQLQESGPGLVKPSE TLSLTCTVSGGSISSYYWIWIRQPAGKGLEWIGRVY TSGSTNYNPSLKSRVTMSVDTSKNQFSLKLSSVTAA DTAVYYCARDGLYRGYGMDVWGQGTTVTVSSAS TKGPSVFPLAPCSRSTSESTAALGCLVKDYFPEPVT VSWNSGALTSGVHTFPAVLQSSGLYSLSSVVTVPSS NFGTQTYTCNVDHKPSNTKVDKTVERKCCVECPPC PAPPVAGPSVFLFPPKPKDTLMISRTPEVTCVVVDV SHEDPEVQFNWYVDGVEVHNAKTKPREEQFNSTFR VVSVLTVVHQDWLNGKEYKCKVSNKGLPAPIEKTI SKTKGQPREPQVYTLPPSREEMTKNQVSLTCLVKG FYPSDIAVEWESNGQPENNYKTTPPMLDSDGSFFLY SKLTVDKSRWQQGNVFSCSVMHEALHNHYTQKSL SLSPGK |
| Light Chain DNA Sequence (SEQ ID NO: 23) | ATGAGGCTCCCTGCTCAGCTCCTGGGGCTCCTGC TGCTCTGGTTCCCAGGTTCCAGATGCGACATCCA GATGACCCAGTCTCCATCTTCCGTGTCTGCATCTG TAGGAGACAGAGTCACCATCACTTGTCGGGCGAG TCAGCCTATTAGCAGCTGGTTAGCCTGGTATCAG CAGAAACCAGGGAAAGCCCCTAAACTCCTGATTT ATTCTGCCTCCGGTTTGCAAAGTGGGGTCCCATC AAGGTTCAGCGGCAGTGGATCTGGGACAGATTTC ACTCTCACCATCAGCAGCCTGCAGCCTGAAGATT TTGCAACTTACTATTGTCAACAGACTGACAGTTTC CCGCTCACTTTCGGCGGCGGGACCAAGGTGGAGA TCAAACGAACTGTGGCTGCACCATCTGTCTTCAT CTTCCCGCCATCTGATGAGCAGTTGAAATCTGGA ACTGCCTCTGTTGTGTGCCTGCTGAATAACTTCTA TCCCAGAGAGGCCAAAGTACAGTGGAAGGTGGA TAACGCCCTCCAATCGGGTAACTCCCAGGAGAGT GTCACAGAGCAGGACAGCAAGGACAGCACCTAC AGCCTCAGCAGCACCCTGACGCTGAGCAAAGCA GACTACGAGAAACACAAAGTCTACGCCTGCGAA GTCACCCATCAGGGCCTGAGCTCGCCCGTCACAA AGAGCTTCAACAGGGGAGAGTGTTAG |

TABLE 5-continued

DNA and protein sequences of antibody 10.8.3

| DESCRIPTION: | SEQUENCE (signal sequence underlined): |
|---|---|
| Light Chain Protein Sequence (SEQ ID NO: 24) | <u>MRLPAQLLGLLLLWFPGSRC</u>DIQMTQSPSSVSASVG DRVTITCRASQPISSWLAWYQQKPGKAPKLLIYSAS GLQSGVPSRFSGSGSGTDFTLTISSLQPEDFATYYCQ QTDSFPLTFGGGTKVEIKRTVAAPSVFIFPPSDEQLK SGTASVVCLLNNFYPREAKVQWKVDNALQSGNSQ ESVTEQDSKDSTYSLSSTLTLSKADYEKHKVYACE VTHQGLSSPVTKSFNRGEC |
| Mature Variable Domain of Heavy Chain DNA Sequence (SEQ ID NO: 17) | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTACTGG ATCTGGATCCGGCAGCCCGCCGGGAAGGGACTG GAATGGATTGGGCGTGTCTATACCAGTGGGAGCA CCAACTACAACCCCTCCCTCAAGAGTCGAGTCAC CATGTCAGTAGACACGTCCAAGAACCAGTTCTCC CTGAAGCTGAGCTCTGTGACCGCCGCGGACACGG CCGTGTATTACTGTGCGAGAGATGGTCTTTACAG GGGGTACGGTATGGACGTCTGGGGCCAAGGGAC CACGGTCACCGTCTCCTCA |
| Mature Variable Domain of Heavy Chain Protein Sequence (SEQ ID NO: 18) | QVQLQESGPGLVKPSETLSLTCTVSGGSISSYYWIWI RQPAGKGLEWIGRVYTSGSTNYNPSLKSRVTMSVD TSKNQFSLKLSSVTAADTAVYYCARDGLYRGYGM DVWGQGTTVTVSS |
| Mature Variable Domain of Light Chain DNA Sequence (SEQ ID NO: 19) | GACATCCAGATGACCCAGTCTCCATCTTCCGTGT CTGCATCTGTAGGAGACAGAGTCACCATCACTTG TCGGGCGAGTCAGCCTATTAGCAGCTGGTTAGCC TGGTATCAGCAGAAACCAGGGAAAGCCCCTAAA CTCCTGATTTATTCTGCCTCCGGTTTGCAAAGTGG GGTCCCATCAAGGTTCAGCGGCAGTGGATCTGGG ACAGATTTCACTCTCACCATCAGCAGCCTGCAGC CTGAAGATTTTGCAACTTACTATTGTCAACAGAC TGACAGTTTCCCGCTCACTTTCGGCGGCGGGACC AAGGTGGAGATCAAA |
| Mature Variable Domain of Light Chain Protein Sequence (SEQ ID NO: 20) | DIQMTQSPSSVSASVGDRVTITCRASQPISSWLAWY QQKPGKAPKLLIYSASGLQSGVPSRFSGSGSGTDFT LTISSLQPEDFATYYCQQTDSFPLTFGGGTKVEIK |

TABLE 6

DNA and protein sequences of antibody 15.1.1

| DESCRIPTION: | SEQUENCE (signal sequence underlined): |
| --- | --- |
| Heavy Chain DNA Sequence (SEQ ID NO: 29) | <u>ATGAAACATCTGTGGTTCTTCCTTCTCCTGGTGGC</u> |
| | <u>AGCTCCCAGATGGGTCCTGTCCC</u>AGGTGCAGCTG |
| | CAGGAGTCGGGCCCAGGACTGGTGAAGCCTTCGG |
| | AGACCCTGTCCCTCACCTGCACTGTCTCTGGTGGC |
| | TCCATCAGAAGTTACTACTGGACCTGGATCCGGC |
| | AGCCCCCAGGGAAGGGACTGGAGTGGATTGGAT |
| | ATATCTATTACAGTGGGAGCACCAACTACAATCC |
| | CTCCCTCAAGAGTCGAGTCACCATATCAGTAGAC |
| | ATGTCCAAGAACCAGTTCTCCCTGAAGCTGAGTT |
| | CTGTGACCGCTGCGGACACGGCCGTTTATTACTG |
| | TGCGAGAAAGGGTGACTACGGTGGTAATTTTAAC |
| | TACTTTCACCAGTGGGGCCAGGGAACCCTGGTCA |
| | CCGTCTCCTCAGCCTCCACCAAGGGCCCATCGGT |
| | CTTCCCCCTGGCGCCCTGCTCCAGGAGCACCTCC |
| | GAGAGCACAGCGGCCCTGGGCTGCCTGGTCAAG |
| | GACTACTTCCCCGAACCGGTGACGGTGTCGTGGA |
| | ACTCAGGCGCTCTGACCAGCGGCGTGCACACCTT |
| | CCCAGCTGTCCTACAGTCCTCAGGACTCTACTCCC |
| | TCAGCAGCGTGGTGACCGTGCCCTCCAGCAACTT |
| | CGGCACCCAGACCTACACCTGCAACGTAGATCAC |
| | AAGCCCAGCAACACCAAGGTGGACAAGACAGTT |
| | GAGCGCAAATGTTGTGTCGAGTGCCCACCGTGCC |
| | CAGCACCACCTGTGGCAGGACCGTCAGTCTTCCT |
| | CTTCCCCCCAAAACCCAAGGACACCCTCATGATC |
| | TCCCGGACCCCTGAGGTCACGTGCGTGGTGGTGG |
| | ACGTGAGTCACGAAGACCCCGAGGTCCAGTTCAA |
| | CTGGTACGTGGACGGCGTGGAGGTGCATAATGCC |
| | AAGACAAAGCCACGGGAGGAGCAGTTCAACAGC |
| | ACGTTCCGTGTGGTCAGCGTCCTCACCGTTGTGC |
| | ACCAGGACTGGCTGAACGGCAAGGAGTACAAGT |
| | GCAAGGTCTCCAACAAAGGCCTCCCAGCCCCCAT |
| | CGAGAAAACCATCTCCAAAACCAAAGGGCAGCC |
| | CCGAGAACCACAGGTGTACACCCTGCCCCCATCC |
| | CGGGAGGAGATGACCAAGAACCAGGTCAGCCTG |
| | ACCTGCCTGGTCAAAGGCTTCTACCCCAGCGACA |
| | TCGCCGTGGAGTGGGAGAGCAATGGGCAGCCGG |
| | AGAACAACTACAAGACCACACCTCCCATGCTGGA |
| | CTCCGACGGCTCCTTCTTCCTCTACAGCAAGCTCA |

TABLE 6-continued

DNA and protein sequences of antibody 15.1.1

| DESCRIPTION: | SEQUENCE (signal sequence underlined): |
|---|---|
| | CCGTGGACAAGAGCAGGTGGCAGCAGGGGAACG |
| | TCTTCTCATGCTCCGTGATGCATGAGGCTCTGCAC |
| | AACCACTACACGCAGAAGAGCCTCTCCCTGTCTC |
| | CGGGTAAATGA |
| Heavy Chain Protein Sequence (SEQ ID NO: 30) | MKHLWFFLLLVAAPRWVLSQVQLQESGPGLVKPSE TLSLTCTVSGGSIRSYYWTWIRQPPGKGLEWIGYIY YSGSTNYNPSLKSRVTISVDMSKNQFSLKLSSVTAA DTAVYYCARKGDYGGNFNYFHQWGQGTLVTVSS ASTKGPSVFPLAPCSRSTSESTAALGCLVKDYFPEPV TVSWNSGALTSGVHTFPAVLQSSGLYSLSSVVTVPS SNFGTQTYTCNVDHKPSNTKVDKTVERKCCVECPP CPAPPVAGPSVFLFPPKPKDTLMISRTPEVTCVVVD VSHEDPEVQFNWYVDGVEVHNAKTKPREEQFNSTF RVVSVLTVVHQDWLNGKEYKCKVSNKGLPAPIEK TISKTKGQPREPQVYTLPPSREEMTKNQVSLTCLVK GFYPSDIAVEWESNGQPENNYKTTPPMLDSDGSFFL YSKLTVDKSRWQQGNVFSCSVMHEALHNHYTQKS LSLSPGK |
| Light Chain DNA Sequence (SEQ ID NO: 31) | ATGAGGCTCCCTGCTCAGCTCCTGGGGCTGCTAA TGCTCTGGGTCTCTGGATCCAGTGGGGATATTGT GATGACTCAGTCTCCACTCTCCCTGCCCGTCACCC CTGGAGAGCCGGCCTCCATCTCCTGCAGGTCTAG TCAGAGCCTCCTACATACTAATGGATACAACTAT TTCGATTGGTACCTGCAGAAGCCAGGGCAGTCTC CACAACTCCTGATCTATTTGGGTTCTAATCGGGCC TCCGGGGTCCCTGACAGGTTCAGTGGCAGTGGAT CAGGCACAGATTTTACACTGAAAATCAGCAGAGT GGAGGCTGAGGATGTTGGGGTTTATTACTGCATG CAAGCTCTACAAACTCCGTACAGTTTTGGCCAGG GGACCAAGCTGGAGATCAAACGAACTGTGGCTG CACCATCTGTCTTCATCTTCCCGCCATCTGATGAG CAGTTGAAATCTGGAACTGCCTCTGTTGTGTGCCT GCTGAATAACTTCTATCCCAGAGAGGCCAAAGTA CAGTGGAAGGTGGATAACGCCCTCCAATCGGGTA ACTCCCAGGAGAGTGTCACAGAGCAGGACAGCA AGGACAGCACCTACAGCCTCAGCAGCACCCTGAC GCTGAGCAAAGCAGACTACGAGAAACACAAAGT |

TABLE 6-continued

DNA and protein sequences of antibody 15.1.1

| DESCRIPTION: | SEQUENCE (signal sequence underlined): |
|---|---|
| | CTACGCCTGCGAAGTCACCCATCAGGGCCTGAGC |
| | TCGCCCGTCACAAAGAGCTTCAACAGGGGAGAGT |
| | GTTAG |
| Light Chain Protein Sequence (SEQ ID NO: 32) | MRLPAQLLGLLMLWVSGSSGDIVMTQSPLSLPVTP GEPASISCRSSQSLLHTNGYNYFDWYLQKPGQSPQL LIYLGSNRASGVPDRFSGSGSGTDFTLKISRVEAEDV GVYYCMQALQTPYSFGQGTKLEIKRTVAAPSVFIFP PSDEQLKSGTASVVCLLNNFYPREAKVQWKVDNA LQSGNSQESVTEQDSKDSTYSLSSTLTLSKADYEKH KVYACEVTHQGLSSPVTKSFNRGEC |
| Mature Variable Domain of Heavy Chain DNA Sequence (SEQ ID NO: 25) | CAGGTGCAGCTGCAGGAGTCGGGCCCAGGACTG GTGAAGCCTTCGGAGACCCTGTCCCTCACCTGCA CTGTCTCTGGTGGCTCCATCAGAAGTTACTACTG GACCTGGATCCGGCAGCCCCCAGGGAAGGGACT GGAGTGGATTGGATATATCTATTACAGTGGGAGC ACCAACTACAATCCCTCCCTCAAGAGTCGAGTCA CCATATCAGTAGACATGTCCAAGAACCAGTTCTC CCTGAAGCTGAGTTCTGTGACCGCTGCGGACACG GCCGTTTATTACTGTGCGAGAAAGGGTGACTACG GTGGTAATTTTAACTACTTTCACCAGTGGGGCCA GGGAACCCTGGTCACCGTCTCCTCA |
| Mature Variable Domain of Heavy Chain Protein Sequence (SEQ ID NO: 26) | QVQLQESGPGLVKPSETLSLTCTVSGGSIRSYYWTW IRQPPGKGLEWIGYIYYSGSTNYNPSLKSRVTISVD MSKNQFSLKLSSVTAADTAVYYCARKGDYGGNFN YFHQWGQGTLVTVSS |
| Mature Variable Domain of Light Chain DNA Sequence (SEQ ID NO: 27) | GATATTGTGATGACTCAGTCTCCACTCTCCCTGCC CGTCACCCCTGGAGAGCCGGCCTCCATCTCCTGC AGGTCTAGTCAGAGCCTCCTACATACTAATGGAT ACAACTATTTCGATTGGTACCTGCAGAAGCCAGG GCAGTCTCCACAACTCCTGATCTATTTGGGTTCTA ATCGGGCCTCCGGGGTCCCTGACAGGTTCAGTGG CAGTGGATCAGGCACAGATTTTACACTGAAAATC AGCAGAGTGGAGGCTGAGGATGTTGGGGTTTATT ACTGCATGCAAGCTCTACAAACTCCGTACAGTTT TGGCCAGGGGACCAAGCTGGAGATCAAA |

TABLE 6-continued

DNA and protein sequences of antibody 15.1.1

| DESCRIPTION: | SEQUENCE (signal sequence underlined): |
|---|---|
| Mature Variable Domain of Light Chain Protein Sequence (SEQ ID NO: 28) | DIVMTQSPLSLPVTPGEPASISCRSSQSLLHTNGYNY FDWYLQKPGQSPQLLIYLGSNRASGVPDRFSGSGSG TDFTLKISRVEAEDVGVYYCMQALQTPYSFGQGTK LEIK |

TABLE 7

DNA and protein sequences of antibody 21.4.1

| DESCRIPTION: | SEQUENCE (signal sequence underlined): |
|---|---|
| Heavy Chain DNA Sequence (SEQ ID NO: 45) | <u>ATGGACTGGACCTGGAGGATCCTCTTCTTGGTGG</u> <u>CAGCAGCCACAGGAGCCCACTCCC</u>AGGTGCAGCT GGTGCAGTCTGGGGCTGAGGTGAAGAAGCCTGG GGCCTCAGTGAAGGTCTCCTGCAAGGCTTCTGGA TACACCTTCACCGGCTACTATATGCACTGGGTGC GACAGGCCCCTGGACAAGGGCTTGAGTGGATGG GATGGATCAACCCTGACAGTGGTGGCACAAACTA TGCACAGAAGTTTCAGGGCAGGGTCACCATGACC AGGGACACGTCCATCAGCACAGCCTACATGGAGC TGAACAGGCTGAGATCTGACGACACGGCCGTGTA TTACTGTGCGAGAGATCAGCCCCTAGGATATTGT ACTAATGGTGTATGCTCCTACTTTGACTACTGGG GCCAGGGAACCCTGGTCACCGTCTCCTCAGCCTC CACCAAGGGCCCATCGGTCTTCCCCCTGGCGCCC TGCTCCAGGAGCACCTCCGAGAGCACAGCGGCCC TGGGCTGCCTGGTCAAGGACTACTTCCCCGAACC GGTGACGGTGTCGTGGAACTCAGGCGCTCTGACC AGCGGCGTGCACACCTTCCCAGCTGTCCTACAGT CCTCAGGACTCTACTCCCTCAGCAGCGTGGTGAC CGTGCCCTCCAGCAACTTCGGCACCCAGACCTAC ACCTGCAACGTAGATCACAAGCCCAGCAACACCA AGGTGGACAAGACAGTTGAGCGCAAATGTTGTGT CGAGTGCCCACCGTGCCCAGCACCACCTGTGGCA GGACCGTCAGTCTTCCTCTTCCCCCCAAAACCCA AGGACACCCTCATGATCTCCCGGACCCCTGAGGT CACGTGCGTGGTGGTGGACGTGAGCCACGAAGA CCCCGAGGTCCAGTTCAACTGGTACGTGGACGGC GTGGAGGTGCATAATGCCAAGACAAAGCCACGG GAGGAGCAGTTCAACAGCACGTTCCGTGTGGTCA |

TABLE 7-continued

DNA and protein sequences of antibody 21.4.1

| DESCRIPTION: | SEQUENCE (signal sequence underlined): |
|---|---|
| | GCGTCCTCACCGTTGTGCACCAGGACTGGCTGAA |
| | CGGCAAGGAGTACAAGTGCAAGGTCTCCAACAA |
| | AGGCCTCCCAGCCCCCATCGAGAAAACCATCTCC |
| | AAAACCAAAGGGCAGCCCCGAGAACCACAGGTG |
| | TACACCCTGCCCCCATCCCGGGAGGAGATGACCA |
| | AGAACCAGGTCAGCCTGACCTGCCTGGTCAAAGG |
| | CTTCTACCCCAGCGACATCGCCGTGGAGTGGGAG |
| | AGCAATGGGCAGCCGGAGAACAACTACAAGACC |
| | ACACCTCCCATGCTGGACTCCGACGGCTCCTTCTT |
| | CCTCTACAGCAAGCTCACCGTGGACAAGAGCAGG |
| | TGGCAGCAGGGGAACGTCTTCTCATGCTCCGTGA |
| | TGCATGAGGCTCTGCACAACCACTACACGCAGAA |
| | GAGCCTCTCCCTGTCTCCGGGTAAATGA |
| Heavy Chain Protein Sequence (SEQ ID NO: 46) | <u>MDWTWRILFLVAAATGAHS</u>QVQLVQSGAEVKKPG |
| | ASVKVSCKASGYTFTGYYMHWVRQAPGQGLEWM |
| | GWINPDSGGTNYAQKFQGRVTMTRDTSISTAYMEL |
| | NRLRSDDTAVYYCARDQPLGYCTNGVCSYFDYWG |
| | QGTLVTVSSASTKGPSVFPLAPCSRSTSESTAALGCL |
| | VKDYFPEPVTVSWNSGALTSGVHTFPAVLQSSGLY |
| | SLSSVVTVPSSNFGTQTYTCNVDHKPSNTKVDKTV |
| | ERKCCVECPPCPAPPVAGPSVFLFPPKPKDTLMISRT |
| | PEVTCVVVDVSHEDPEVQFNWYVDGVEVHNAKTK |
| | PREEQFNSTFRVVSVLTVVHQDWLNGKEYKCKVS |
| | NKGLPAPIEKTISKTKGQPREPQVYTLPPSREEMTK |
| | NQVSLTCLVKGFYPSDIAVEWESNGQPENNYKTTP |
| | PMLDSDGSFFLYSKLTVDKSRWQQGNVFSCSVMHE |
| | ALHNHYTQKSLSLSPGK |
| Light Chain DNA Sequence (SEQ ID NO: 47) | <u>ATGAGGCTCCCTGCTCAGCTCCTGGGGCTCCTGC</u> |
| | <u>TGCTCTGGTTCCCAGGTTCCAGATGC</u>GACATCCA |
| | GATGACCCAGTCTCCATCTTCCGTGTCTGCATCTG |
| | TAGGAGACAGAGTCACCATCACTTGTCGGGCGAG |
| | TCAGGGTATTTACAGCTGGTTAGCCTGGTATCAG |
| | CAGAAACCAGGGAAAGCCCCTAACCTCCTGATCT |
| | ATACTGCATCCACTTTACAAAGTGGGGTCCCATC |
| | AAGGTTCAGCGGCAGTGGATCTGGGACAGATTTC |
| | ACTCTCACCATCAGCAGCCTGCAACCTGAAGATT |
| | TTGCAACTTACTATTGTCAACAGGCTAACATTTTC |

TABLE 7-continued

DNA and protein sequences of antibody 21.4.1

| DESCRIPTION: | SEQUENCE (signal sequence underlined): |
|---|---|
| | CCGCTCACTTTCGGCGGAGGGACCAAGGTGGAGA |
| | TCAAACGAACTGTGGCTGCACCATCTGTCTTCAT |
| | CTTCCCGCCATCTGATGAGCAGTTGAAATCTGGA |
| | ACTGCCTCTGTTGTGTGCCTGCTGAATAACTTCTA |
| | TCCCAGAGAGGCCAAAGTACAGTGGAAGGTGGA |
| | TAACGCCCTCCAATCGGGTAACTCCCAGGAGAGT |
| | GTCACAGAGCAGGACAGCAAGGACAGCACCTAC |
| | AGCCTCAGCAGCACCCTGACGCTGAGCAAAGCA |
| | GACTACGAGAAACACAAAGTCTACGCCTGCGAA |
| | GTCACCCATCAGGGCCTGAGCTCGCCCGTCACAA |
| | AGAGCTTCAACAGGGGAGAGTGTTAG |
| Light Chain Protein Sequence (SEQ ID NO: 48) | <u>MRLPAQLLGLLLLWFPGSRC</u>DIQMTQSPSSVSASVG DRVTITCRASQGIYSWLAWYQQKPGKAPNLLIYTA STLQSGVPSRFSGSGSGTDFTLTISSLQPEDFATYYC QQANIFPLTFGGGTKVEIKRTVAAPSVFIFPPSDEQL KSGTASVVCLLNNFYPREAKVQWKVDNALQSGNS QESVTEQDSKDSTYSLSSTLTLSKADYEKHKVYAC EVTHQGLSSPVTKSFNRGEC |
| Mature Variable Domain of Heavy Chain DNA Sequence (SEQ ID NO: 41) | CAGGTGCAGCTGGTGCAGTCTGGGGCTGAGGTGA AGAAGCCTGGGGCCTCAGTGAAGGTCTCCTGCAA GGCTTCTGGATACACCTTCACCGGCTACTATATG CACTGGGTGCGACAGGCCCCTGGACAAGGGCTTG AGTGGATGGGATGGATCAACCCTGACAGTGGTGG CACAAACTATGCACAGAAGTTTCAGGGCAGGGTC ACCATGACCAGGGACACGTCCATCAGCACAGCCT ACATGGAGCTGAACAGGCTGAGATCTGACGACA CGGCCGTGTATTACTGTGCGAGAGATCAGCCCCT AGGATATTGTACTAATGGTGTATGCTCCTACTTTG ACTACTGGGGCCAGGGAACCCTGGTCACCGTCTC CTCA |
| Mature Variable Domain of Heavy Chain Protein Sequence (SEQ ID NO: 42) | QVQLVQSGAEVKKPGASVKVSCKASGYTFTGYYM HWVRQAPGQGLEWMGWINPDSGGTNYAQKFQGR VTMTRDTSISTAYMELNRLRSDDTAVYYCARDQPL GYCTNGVCSYFDYWGQGTLVTVSS |
| Mature Variable Domain of Light Chain DNA Sequence (SEQ ID NO: 43) | GACATCCAGATGACCCAGTCTCCATCTTCCGTGT CTGCATCTGTAGGAGACAGAGTCACCATCACTTG TCGGGCGAGTCAGGGTATTTACAGCTGGTTAGCC TGGTATCAGCAGAAACCAGGGAAAGCCCCTAAC |

TABLE 7-continued

DNA and protein sequences of antibody 21.4.1

| DESCRIPTION: | SEQUENCE (signal sequence underlined): |
|---|---|
| | CTCCTGATCTATACTGCATCCACTTTACAAAGTGG |
| | GGTCCCATCAAGGTTCAGCGGCAGTGGATCTGGG |
| | ACAGATTTCACTCTCACCATCAGCAGCCTGCAAC |
| | CTGAAGATTTTGCAACTTACTATTGTCAACAGGC |
| | TAACATTTTCCCGCTCACTTTCGGCGGAGGGACC |
| | AAGGTGGAGATCAAA |
| Mature Variable Domain of Light Chain Protein Sequence (SEQ ID NO: 44) | DIQMTQSPSSVSASVGDRVTITCRASQGIYSWLAWY QQKPGKAPNLLIYTASTLQSGVPSRFSGSGSGTDFT LTISSLQPEDFATYYCQQANIFPLTFGGGTKVEIK |

TABLE 8

DNA and protein sequences of mature variable domains of 21.2.1 antibody

| DESCRIPTION: | SEQUENCE: |
|---|---|
| Heavy Chain DNA (SEQ ID NO: 33) | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGTCAT GCACTGGGTCCGCCAGGCTCCAGGCAAGGGGCTG GAGTGGGTGGCAGTTATGTCATATGATGGAAGTA GTAAATACTATGCAAACTCCGTGAAGGGCCGATT CACCATCTCCAGAGACAATTCCAAGAACACGCTG TATCTGCAAATAAACAGCCTGAGAGCTGAGGACA CGGCTGTGTATTACTGTGCGAGAGATGGGGTAA AGCAGTGCCTGGTCCTGACTACTGGGGCCAGGGA ATCCTGGTCACCGTCTCCTCAG |
| Heavy Chain Protein (SEQ ID NO: 34) | QVQLVESGGGVVQPGRSLRLSCAASGFTFSSYVM HWVRQAPGKGLEWVAVMSYDGSSKYYANSVKGRF TISRDNSKNTLYLQINSLRAEDTAVYYCARDGGK AVPGPDYWGQGILVTVSS |
| Light Chain DNA (SEQ ID NO: 35) | GATATTGTGATGACTCAGTCTCCACTCTCCCTGC CCGTCACCCCTGGAGAGCCGGCCTCCATCTCCTG CAGGTCTAGTCAGAGTGTTCTGTATAGTAATGGA TACAACTATTTGGATTGGTACCTGCAGAAGCCAG GGCAGTCTCCACAGCTCCTGATCTATTTGGGTTC TAATCGGGCCTCCGGGGTCCCTGACAGGTTCAGT GGCAGTGGATCAGGCACAGATTTTACACTGAAAA TCAGCAGAGTGGAGGCTGAGGATGTTGGGGTTTA TTACTGCATGCAAGTTTTACAAACTCCATTCACT TTCGGCCCTGGGACCAAAGTGGATATCAAAC |
| Light Chain Protein (SEQ ID NO: 36) | DIVMTQSPLSLPVTPGEPASISCRSSQSVLYSNG YNYLDWYLQKPGQSPQLLIYLGSNRASGVPDRFS GSGSGTDFTLKISRVEAEDVGVYYCMQVLQTPFT FGPGTKVDIK |

TABLE 9

DNA and protein sequences of mature variable domains of 22.1.1 antibody

| DESCRIPTION: | SEQUENCE: |
|---|---|
| Heavy Chain DNA (SEQ ID NO: 49) | CAGGTGCAGCTGGTGGAGTCTGGGGGAGGCGTG GTCCAGCCTGGGAGGTCCCTGAGACTCTCCTGTG CAGCCTCTGGATTCACCTTCAGTCGCTATGGCAT GCACTGGGTCCGCCAGGCTCCAGGCAAGGGGCTG GAGTGGGTGGCAGTTATATCATCTGATGAGGTA ATAAATACTATGCAGACTCCGTGAAGGGCCGATT CACCATCTCCAGAGACAATTCCAAGAACACGCTG TATCTGCAAATGAACAGCCTGAGAGCTGAGGACA CGGCTGTGTATTACTGTACGAGAAGAGGGACTGG AAAGACTTACTACCACTACTGTGGTATGGACGTC TGGGGCCAAGGGACCACGGTCACCGTCTCCTCAG |
| Heavy Chain Protein (SEQ ID | QVQLVESGGGVVQPGRSLRLSCAASGFTFSRYGM HWVRQAPGKGLEWVAVISSDGGNKYYADSVKGRF |

TABLE 9-continued

DNA and protein sequences of mature variable domains of 22.1.1 antibody

| DESCRIPTION: | SEQUENCE: |
|---|---|
| NO: 50) | TISRDNSKNTLYLQMNSLRAEDTAVYYCTRRGTG KTYYHYCGMDVWGQGTTVTVSS |
| Light Chain DNA (SEQ ID NO: 51) | GATATTGTGATGACTCAGTCTCCACTCTCCCTGC CCGTCACCCCTGGAGAGCCGGCCTCCATCTCCTG CAGGTCTAGTCAGAGCCTCCTGTATAGTAATGGA TATAACTATTTGGATTGGTACCTGCAGAAGCCAG GGCAGTCTCCACACCTCCTGATCTATTTGGGTTC TAATCGGGCCTCCGGGGTCCCTGACAGGTTCAGT GGCAGTGGTTCAGGCACTGATTTTACACTGAAAA TCAGCAGAGTGGAGGCTGAGGATGTTGGGGTTTA TTACTGCATGCAAGCTCTACAAACTCCTCGGACG TTCGGCCAAGGGACCAAGGTGGAAATCAAAC |
| Light Chain Protein (SEQ ID NO: 52) | DIVMTQSPLSLPVTPGEPASISCRSSQSLLYSNG YNYLDWYLQKPGQSPHLLIYLGSNRASGVPDRFS GSGSGTDFTLKISRVEAEDVGVYYCMQALQTPRT FGQGTKVEIK |

TABLE 10

DNA and protein sequences of mature variable domains of 23.5.1 antibody

| DESCRIPTION: | SEQUENCE: |
|---|---|
| Heavy Chain DNA (SEQ ID NO: 57) | CAGGTGCAGCTGGTGGAGTCTGGGGGAGGCGTG GTCCAGCCTGGGAGGTCCCTGAGACTCTCCTGTG ) TAGCCTCTGGATTCACCTTCAGTAACTATGGCAT GCACTGGGTCCGCCAGGCTCCAGGCAAGGGGCTG GAGTGGGTGGCAATTATATCATATGATGGAAGTA ATAAATACTATGCAGACTCCGTGAAGGGCCGATT CACCATCTCCAGAGACAATTCCAAGAACACGCTG TATGTGCAAATGAACAGCCTGAGAGCTGAGGAC ACGGCTGTGTATTACTGTGCGAGACGCGGTCACT ACGGGAGGGATTACTACTCCTACTACGGTTTGGA CGTCTGGGGCCAAGGGACCACGGTCACCGTCTCC TCAG |
| Heavy Chain Protein (SEQ ID | QVQLVESGGGVVQPGRSLRLSCVASGFTFSNYGM HWVRQAPGKGLEWVAIISYDGSNKYYADSVKGRF |

TABLE 10-continued

DNA and protein sequences of mature variable domains of 23.5.1 antibody

| DESCRIPTION: | SEQUENCE: |
|---|---|
| NO: 58) | TISRDNSKNTLYVQMNSLRAEDTAVYYCARRGHY GRDYYSYYGLDVWGQGTTVTVSS |
| Light Chain DNA (SEQ ID NO: 59) | GATATTGTGATGACTCAGTCTCCACTCTCCCTGC CCGTCACCCCTGGAGAGCCGGCCTCCATCTCCTG CAGGTCTAGTCAGAGCCTCCTGCCTGGTAATGGA TACAACTATTTGGATTGGTACCTGCAGAAGCCAG GGCAGTCTCCACAGCTCCTGATCTATTTGGGTTC TAATCGGGCCTCCGGGGTCCCTGACAGGTTCAGT GGCAGTGGATCAGGCACAGATTTTACACTGAAAA TCAGCAGAGTGGAGGCTGAGGATGTTGGGGTTTA TTACTGCATGCAAGCTCTACAAACTCCTCGGACG TTCGGCCAAGGGACCAAGGTGGAAATCAAAC |
| Light Chain Protein (SEQ ID NO: 60) | DIVMTQSPLSLPVTPGEPASISCRSSQSLLPGNG YNYLDWYLQKPGQSPQLLIYLGSNRASGVPDRFS GSGSGTDFTLKISRVEAEDVGVYYCMQALQTPRT FGQGTKVEIK |

TABLE 11

DNA and protein sequences of mature variable domains of 23.28.1 antibody

| DESCRIPTION: | SEQUENCE: |
|---|---|
| Heavy Chain DNA (SEQ ID NO: 65) | CAGGTGCAGCTGCAGGAGTCGGGCCCAGGACTG GTGAAGCCTTCGGACACCCTGTCCCTCACCTGCA CTGTCTCTGGTGGCTCCATCAGAGGTTACTACTG GAGCTGGATCCGGCAGCCCCCTGGGAAGGGACT GGAGTGGATTGGGTATATCTATTACAGTGGGAGC ACCAACTACAACCCCTCCCTCAAGAGTCGAGTCA CCATATCAGTAGACACGTCCAAGAACCAGTTCTC CCTGAAGCTGAACTCTGTGACCGCTGCGGACACG GCCGTGTATTATTGTGCGAGAAAGGGGGGCCTCT ACGGTGACTACGGCTGGTTCGCCCCCTGGGGCCA GGGAACCCTGGTCACCGTCTCCTCAG |
| Heavy Chain Protein (SEQ ID NO: 66) | QVQLQESGPGLVKPSDTLSLTCTVSGGSIRGYYWS WIIRQPPGKGLEWIGYIYYSGSTNYNPSLKSRVTISV DTSKNQFSLKLNSVTAADTAVYYCARKGGLYGDY GWFAPWGQGTLVTVSS |

TABLE 11-continued

DNA and protein sequences of mature variable domains of 23.28.1 antibody

| DESCRIPTION: | SEQUENCE: |
|---|---|
| Light Chain DNA (SEQ ID NO: 67) | GAAATTGTGTTGACGCAGTCTCCAGGCACCCTGT CTTTGTCTCCAGGGGAAAGAGCCACCCTCTCCTG CAGGGCCAGTCAGAGTGTTAGCAGCAGCGACTTA GCCTGGCACCAGCAGAAACCTGGCCAGGCTCCCA GACTCCTCATCTATGGTGCATCCAGCAGGGCCAC TGGCATCCCAGACAGGTTCAGTGGCAGTGGGTCT GGGACAGACTTCACTCTCACCATCAGCAGACTGG AGCCTGAAGATTTTGCAGTGTATTACTGTCAGCA CTGTCGTAGCTTATTCACTTTCGGCCCTGGGACCA AAGTGGATATCAAAC |
| Light Chain Protein (SEQ ID NO: 68) | EIVLTQSPGTLSLSPGERATLSCRASQSVSSSDLAWH QQKPGQAPRLLIYGASSRATGIPDRFSGSGSGTDFTL TISRLEPEDFAVYYCQHCRSLFTFGPGTKVDIK |
| Heavy Chain DNA (variable domain) (23.28.1H-D16E) (SEQ ID NO: 97) | CAGGTGCAGCTGCAGGAGTCGGGCCCAGGACTG GTGAAGCCTTCGGAGACCCTGTCCCTCACCTGCA CTGTCTCTGGTGGCTCCATCAGAGGTTACTACTG GAGCTGGATCCGGCAGCCCCCTGGGAAGGGACT GGAGTGGATTGGGTATATCTATTACAGTGGGAGC ACCAACTACAACCCCTCCCTCAAGAGTCGAGTCA CCATATCAGTAGACACGTCCAAGAACCAGTTCTC CCTGAAGCTGAACTCTGTGACCGCTGCGGACACG GCCGTGTATTATTGTGCGAGAAAGGGGGGCCTCT ACGGTGACTACGGCTGGTTCGCCCCCTGGGGCCA GGGAACCCTGGTCACCGTCTCCTCAG |
| Heavy Chain Protein (variable domain) (23.28.1H-D16E) (SEQ ID NO: 98) | QVQLQESGPGLVKPSLTLSLTCTVSGGSIRGYYWS WIRQPPGKGLEWIGYIYYSGSTNYNPSLKSRVTISV DTSKNQFSLKLNSVTAADTAVYYCARKGGLYGDY GWFAPWGQGTLVTVSS. |

TABLE 12

DNA and protein sequences of mature variable domains of 23.29.1 antibody

| DESCRIPTION: | SEQUENCE: |
|---|---|
| Heavy Chain DNA (SEQ ID NO: 73) | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGCCAT GCACTGGGTCCGCCAGGCTCCAGGCAAGGGGCTG GAGTGGGTGGCAGTTATATCATATGATGGAAGTA ATAAATACTATGCAGACTCCGTGAAGGGCCGATT CACCATCTACAGAGACAATTCCAAGAACACGCTG TATCTGCAAATGAACAGCCTGAGAGCTGAGGACA CGGCTGTGTATTACTGTGCGAGACGCGGTCACTA CGGGAATAATTACTACTCCTATTACGGTTTGGAC GTCTGGGGCCAAGGGACCACGGTCACCGTCTCCT CAG |
| Heavy Chain Protein (SEQ ID NO: 74) | QVQLVESGGGVVQPGRSLRLSCAASGFTFSSYAMH WVRQAPGKGLEWVAVISYDGSNKYYADSVKGRFT IYRDNSKNTLYLQMNSLRAEDTAVYYCARRGHYG NNYYSYYGLDVWGQGTTVTVSS |
| Light Chain DNA (SEQ ID NO: 75) | GATATTGTGATGACTCAGTCTCCACTCTCCCTGCC CGTCACCCCTGGAGAGCCGGCCTCCATCTCCTGC AGGTCTAGTCAGAGCCTCCTGCCTGGTAATGGAT ACAACTATTTGGATTGGTACCTGCAGAAGCCAGG GCAGTCTCCACAGCTCCTGATCTATTTGGGTTCTA ATCGGGCCTCCGGGGTCCCTGACAGGTTCAGTGG CAGTGGCTCAGGCACAGATTTTACACTGAAAATC AGCAGAGTGGAGGCTGAGGATGTTGGGATTTATT ACTGCATGCAAGCTCTACAAACTCCTCGGACGTT CGGCCAAGGGACCAAGGTGGAAATCAAAC |
| Light Chain Protein (SEQ ID NO: 76) | DIVMTQSPLSLPVTPGEPASISCRSSQSLLPGNGYNY LDWYLQKPGQSPQLLIYLGSNRASGVPDRFSGSGSG TDFTLKISRVEAEDVGIYYCMQALQTPRTFGQGTK VEIK |

TABLE 13

DNA and protein sequences of mature variable domains of 24.2.1 antibody

| DESCRIPTION: | SEQUENCE |
|---|---|
| Heavy Chain DNA (SEQ ID NO: 81) | CAGGTGCAGCTGCAGGAGTCGGGCCCAGGACTG GTGAAGCCTTCGGAGACCCTGTCCCTCACCTGCA CTGTCTCTGGTGGCTCCATCAGAGGTTACTACTG GAGCTGGATCCGGCAGCCCCCAGGGAAGGGACT GGAGTGGATTGGGTATATCTATTACAGTGGGAGC ACCAACTACAACCCCTCCCTCAAGAGTCGAGTCA |

TABLE 13-continued

DNA and protein sequences of mature variable domains of 24.2.1 antibody

| DESCRIPTION: | SEQUENCE |
|---|---|
| | CCATATCAGTAGACACGTCCAAGAACCAGTTCTC |
| | CCTGAAGCTGAGTTCTGTGACCGCTGCGGACACG |
| | GCCGTGTATTACTGTGCGAGAAGGGGGGGCCTCT |
| | ACGGTGACTACGGCTGGTTCGCCCCCTGGGGCCA |
| | GGGAACCCTGGTCACCGTCTCCTCAG |
| Heavy Chain Protein (SEQ ID NO: 82) | QVQLQESGPGLVKPSETLSLTCTVSGGSIRGYYWS WIRQPPGKGLEWIGYIYYSGSTNYNPSLKSRVTISV DTSKNQFSLKLSSVTAADTAVYYCARRGGLYGDY GWFAPWGQGTLVTVSS |
| Light Chain DNA (SEQ ID NO: 83) | GAAATTGTGTTGACGCAGTCTCCAGGCACCCTGT CTTTGTCTCCAGGGGAAAGAGCCACCCTCTCCTG CAGGGCCAGTCAGAGTGTTAGCAGCACCTACTTA GCCTGGTACCAGCAGAAACCTGGCCAGGCTCCCA GGCTCCTCATCTATGGTGCATCCAGCAGGGCCAC TGGCATCCCAGACAGGTTCAGTGGCAGTGGGTCT GGGACAGACTTCACTCTCACCATCAGCAGACTGG AGCCTGAAGATTTTGCAGTGTATTACTGTCAGCA GTATAGTAGCCTTATTCACTTTCGGCCCTGGGACC AAAGTGGATATCAAAC |
| Light Chain Protein (SEQ ID NO: 84) | ETVLTQSPGTLSLSPGERATLSCRASQSVSSTYLAWY QQKPGQAPRLLIYGASSRATGIIPDRFSGSGSGTDFT LTISRLEPEDFAVYYCQQYSSLFTFGPGTKVDIK |

TABLE 14

DNA and protein sequences of antibody 21.2.1

| DESCRIPTION: | SEQUENCE (signal sequence underlined): |
|---|---|
| Heavy Chain DNA (SEQ ID NO: 37) | <u>ATGGAGTTTGGGCTGAGCTGGGTTTTCCTCGTTGC</u> <u>TCTTTTAAGAGGTGTCCAGTGT</u>CAGGTGCAGCTG GTGGAGTCTGGGGGAGGCGTGGTCCAGCCTGGG AGGTCCCTGAGACTCTCCTGTGCAGCCTCTGGAT TCACCTTCAGTAGCTATGTCATGCACTGGGTCCG CCAGGCTCCAGGCAAGGGGCTGGAGTGGGTGGC AGTTATGTCATATGATGGAAGTAGTAAATACTAT GCAAACTCCGTGAAGGGCCGATTCACCATCTCCA GAGACAATTCCAAGAACACGCTGTATCTGCAAAT AAACAGCCTGAGAGCTGAGGACACGGCTGTGTAT TACTGTGCGAGAGATGGGGGTAAAGCAGTGCCTG GTCCTGACTACTGGGGCCAGGGAATCCTGGTCAC CGTCTCCTCAGCCTCCACCAAGGGCCCATCGGTC TTCCCCCTGGCGCCCTGCTCCAGGAGCACCTCCG AGAGCACAGCGGCCCTGGGCTGCCTGGTCAAGG ACTACTTCCCCGAACCGGTGACGGTGTCGTGGAA CTCAGGCGCTCTGACCAGCGGCGTGCACACCTTC CCAGCTGTCCTACAGTCCTCAGGACTCTACTCCCT CAGCAGCGTGGTGACCGTGCCCTCCAGCAACTTC GGCACCCAGACCTACACCTGCAACGTAGATCACA AGCCCAGCAACACCAAGGTGGACAAGACAGTTG AGCGCAAATGTTGTGTCGAGTGCCCACCGTGCCC AGCACCACCTGTGGCAGGACCGTCAGTCTTCCTC TTCCCCCCAAAACCCAAGGACACCCTCATGATCT CCCGGACCCCTGAGGTCACGTGCGTGGTGGTGGA CGTGAGCCACGAAGACCCCGAGGTCCAGTTCAAC TGGTACGTGGACGGCGTGGAGGTGCATAATGCCA AGACAAAGCCACGGGAGGAGCAGTTCAACAGCA CGTTCCGTGTGGTCAGCGTCCTCACCGTTGTGCAC CAGGACTGGCTGAACGGCAAGGAGTACAAGTGC AAGGTCTCCAACAAAGGCCTCCCAGCCCCCATCG AGAAAACCATCTCCAAAACCAAAGGGCAGCCCC GAGAACCACAGGTGTACACCCTGCCCCCATCCCG GGAGGAGATGACCAAGAACCAGGTCAGCCTGAC CTGCCTGGTCAAAGGCTTCTACCCCAGCGACATC GCCGTGGAGTGGGAGAGCAATGGGCAGCCGGAG AACAACTACAAGACCACACCTCCCATGCTGGACT CCGACGGCTCCTTCTTCCTCTACAGCAAGCTCACC GTGGACAAGAGCAGGTGGCAGCAGGGGAACGTC TTCTCATGCTCCGTGATGCATGAGGCTCTGCACA ACCACTACACGCAGAAGAGCCTCTCCCTGTCTCC GGGTAAATGA |
| Heavy Chain Protein (SEQ ID NO: 38) | MEFGLSWVFLVALLRGVQCQVQLVESGGGVVQPG RSLRLSCAASGFTFSSYVMHWVRQAPGKGLEWVA VMSYDGSSKYYANSVKGRIFTISRDNSKNTLYLQINS LRAEDTAVYYCARDGGKAVPGPDYWGQILVTVS SASTKGPSVFPLAPCSRSTSESTAALGCLVKDYFPEP |

TABLE 14-continued

DNA and protein sequences of antibody 21.2.1

| DESCRIPTION: | SEQUENCE (signal sequence underlined): |
|---|---|
| | VTVSWNSGALTSGVHTFPAVLQSSGLYSLSSVVTVP |
| | SSNTGTQTYTCNVDHKPSNTKVDKTVERKCCVECP |
| | PCPAPPVAGPSVFLFPPKPKDTLMISRTPEVTCVVVD |
| | VSHEDPEVQFNWYVDGVEVHNAKTKPREEQFNSTF |
| | RVVSVLTVVHQDWLNGKEYKCKVSNKGLPAPIEK |
| | TISKTKGQPREPQVYTLPPSREEMTKNQVSLTCLVK |
| | GFYPSDIAVEWESNGQPENNYKTTPPMLDSDGSFFL |
| | YSKLTVDKSRWQQGNVFSCSVMHEALHNHYTQKS |
| | LSLSPGK |
| Light Chain DNA (SEQ ID NO: 39) | <u>ATGAGGCTCCCTGCTCAGCTCCTGGGGCTGCTAA</u> <u>TGCTCTGGGTCTCTGGATCCAGTGGG</u>GATATTGT GATGACTCAGTCTCCACTCTCCCTGCCCGTCACCC CTGGAGAGCCGGCCTCCATCTCCTGCAGGTCTAG TCAGAGTGTTCTGTATAGTAATGGATACAACTAT TTGGATTGGTACCTGCAGAAGCCAGGGCAGTCTC CACAGCTCCTGATCTATTTGGGTTCTAATCGGGCC TCCGGGGTCCCTGACAGGTTCAGTGGCAGTGGAT CAGGCACAGATTTTACACTGAAAATCAGCAGAGT GGAGGCTGAGGATGTTGGGGTTTATTACTGCATG CAAGTTTTACAAACTCCATTCACTTTCGGCCCTGG GACCAAAGTGGATATCAAACGAACTGTGGCTGCA CCATCTGTCTTCATCTTCCCGCCATCTGATGAGCA GTTGAAATCTGGAACTGCCTCTGTTGTGTGCCTGC TGAATAACTTCTATCCCAGAGAGGCCAAAGTACA GTGGAAGGTGGATAACGCCCTCCAATCGGGTAAC TCCCAGGAGAGTGTCACAGAGCAGGACAGCAAG GACAGCACCTACAGCCTCAGCAGCACCCTGACGC TGAGCAAAGCAGACTACGAGAAACACAAAGTCT ACGCCTGCGAAGTCACCCATCAGGGCCTGAGCTC GCCCGTCACAAAGAGCTTCAACAGGGGAGAGTG TTAG |
| Light Chain Protein (SEQ ID NO: 40) | <u>MRLPAQLLGLLMLWVSGSSG</u>DIVMTQSPLSLPVTP GEPASISCRSSQSVLYSNGYNYLDWYLQKPGQSPQL LIYLGSNRASGVPDRFSGSGSGTDFTLKISRVEAEDV GVYYCMQVLQTPFTFGPGTKVDWRTVAAPSVFIFP PSDEQLKSGTASVVCLLNNFYPREAKVQWKVDNA LQSGNSQESVTEQDSKDSTYSLSSTLTLSKADYEKH KVYACEVTHQGLSSPVTKSFNRGEC |

TABLE 15

DNA and protein sequences of antibody 22.1.1

| DESCRIPTION: | SEQUENCE (signal sequence underlined): |
|---|---|
| Heavy Chain DNA (SEQ ID NO: 53) | <u>ATGGAGTTTGGGCTGAGCTGGGTTTTCCTCGTTGC</u> <u>TCTTTTAAGAGGTGTCCAGTGC</u>AGGTGCAACTG GTGGAGTCTGGGGGAGGCGTGGTCCAGCCTGGG AGGTCCCTGAGACTCTCCTGTGCAGCCTCTGGAT TCACCTTCAGTCGCTATGGCATGCACTGGGTCCG CCAGGCTCCAGGCAAGGGGCTGGAGTGGGTGGC AGTTATATCATCTGATGGAGGTAATAAATACTAT GCAGACTCCGTGAAGGGCCGATTCACCATCTCCA GAGACAATTCCAAGAACACGCTGTATCTGCAAAT GAACAGCCTGAGAGCTGAGGACACGGCTGTGTAT TACTGTACGAGAAGAGGGACTGGAAAGACTTACT ACCACTACTGTGGTATGGACGTCTGGGGCCAAGG GACCACGGTCACCGTCTCCTCAGCCTCCACCAAG GGCCCATCGGTCTTCCCCCTGGCGCCCTGCTCCA GGAGCACCTCCGAGAGCACAGCGGCCCTGGGCT GCCTGGTCAAGGACTACTTCCCCGAACCGGTGAC GGTGTCGTGGAACTCAGGCGCTCTGACCAGCGGC GTGCACACCTTCCCAGCTGTCCTACAGTCCTCAG GACTCTACTCCCTCAGCAGCGTGGTGACCGTGCC CTCCAGCAACTTCGGCACCCAGACCTACACCTGC AACGTAGATCACAAGCCCAGCAACACCAAGGTG GACAAGACAGTTGAGCGCAAATGTTGTGTCGAGT GCCCACCGTGCCCAGCACCACCTGTGGCAGGACC GTCAGTCTTCCTCTTCCCCCCAAAACCCAAGGAC ACCCTCATGATCTCCCGGACCCCTGAGGTCACGT GCGTGGTGGTGGACGTGAGCCACGAAGACCCCG AGGTCCAGTTCAACTGGTACGTGGACGGCGTGGA GGTGCATAATGCCAAGACAAAGCCACGGGAGGA GCAGTTCAACAGCACGTTCCGTGTGGTCAGCGTC CTCACCGTTGTGCACCAGGACTGGCTGAACGGCA |

TABLE 15-continued

DNA and protein sequences of antibody 22.1.1

| DESCRIPTION: | SEQUENCE (signal sequence underlined): |
|---|---|
| | AGGAGTACAAGTGCAAGGTCTCCAACAAAGGCC |
| | TCCCAGCCCCCATCGAGAAAACCATCTCCAAAAC |
| | CAAAGGGCAGCCCCGAGAACCACAGGTGTACAC |
| | CCTGCCCCCATCCCGGGAGGAGATGACCAAGAAC |
| | CAGGTCAGCCTGACCTGCCTGGTCAAAGGCTTCT |
| | ACCCCAGCGACATCGCCGTGGAGTGGGAGAGCA |
| | ATGGGCAGCCGGAGAACAACTACAAGACCACAC |
| | CTCCCATGCTGGACTCCGACGGCTCCTTCTTCCTC |
| | TACAGCAAGCTCACCGTGGACAAGAGCAGGTGG |
| | CAGCAGGGGAACGTCTTCTCATGCTCCGTGATGC |
| | ATGAGGCTCTGCACAACCACTACACGCAGAAGA |
| | GCCTCTCCCTGTCTCCGGGTAAATGA |
| Heavy Chain Protein (SEQ ID NO: 54) | <u>MEFGLSWVFLVALLRGVQC</u>QVQLVESGGGVVQPG RSLRLSCAASGFTFSRYGMHWVRQAPGKGLEWVA VISSDGGNKYYADSVKGRFTISRDNSKNTLYLQMN SLRAEDTAVYYCTRRGTGKTYYHYCGMDVWGQG TTVTVSSASTKGPSVFPLAPCSRSTSESTAALGCLVK DYFPEPVTVSWNSGALTSGVHTFPAVLQSSGLYSLS SVVTVPSSNFGTQTYTCNVDHKPSNTKVDKTVERK CCVECPPCPAPPVAGPSVFLFPPKPKDTLMISRTPEV TCVVVDVSHEDPEVQFNWYVDGVEVTHNAKTKPRE EQFNSTFRVVSVLTVVHQDWLNGKEYKCKVSNKG LPAPTEKTISKTKGQPREPQVYTLPPSREEMTKNQVS LTCLVKGFYPSDIAVEWESNGQPENNYKTTPPMLD SDGSFFLYSKLTVDKSRWQQGNVFSCSVMHEALHN HYTQKSLSLSPGK |
| Light Chain DNA (SEQ ID NO: 55) | <u>ATGAGGCTCCCTGCTCAGCTCCTGGGGCTGCTAA TGCTCTGGGTCTCTGGATCCAGTGGG</u>GATATTGT GATGACTCAGTCTCCACTCTCCCTGCCCGTCACCC CTGGAGAGCCGGCCTCCATCTCCTGCAGGTCTAG TCAGAGCCTCCTGTATAGTAATGGATATAACTAT TTGGATTGGTACCTGCAGAAGCCAGGGCAGTCTC CACACCTCCTGATCTATTTGGGTTCTAATCGGGCC TCCGGGGTCCCTGACAGGTTCAGTGGCAGTGGTT CAGGCACTGATTTTACACTGAAAATCAGCAGAGT GGAGGCTGAGGATGTTGGGGTTTATTACTGCATG CAAGCTCTACAAACTCCTCGGACGTTCGGCCAAG GGACCAAGGTGGAAATCAAACGAACTGTGGCTG CACCATCTGTCTTCATCTTCCCGCCATCTGATGAG CAGTTGAAATCTGGAACTGCCTCTGTTGTGTGCCT GCTGAATAACTTCTATCCCAGAGAGGCCAAAGTA CAGTGGAAGGTGGATAACGCCCTCCAATCGGGTA ACTCCCAGGAGAGTGTCACAGAGCAGGACAGCA AGGACAGCACCTACAGCCTCAGCAGCACCYTGAC GCTGAGCAAAGCAGACTACGAGAAACACAAAGT CTACGCCTGCGAAGTCACCCATCAGGGCCTGAGC TCGCCCGTCACAAAGAGCTTCAACAGGGGAGAGT GTTAG |
| Light Chain Protein (SEQ ID NO: 56) | <u>MRLPAQLLGLLMLWVSGSSG</u>DIVMTQSPLSLPVTP GEPASISCRSSQSLLYSNGYNYLDWYLQKPGQSPHL LIYLGSNRASGVPDRFSGSGSGTDFTLKISRVEAEDV GVYYCMQALQTPRTFGQGTKVEIKRTVAAPSVFWP PSDEQLKSGTASVVCLLNNFYPREAKVQWKVDNA LQSGNSQESVTEQDSKDSTYSLSSTLTLSKADYEKH KVYACEVTHQGLSSPVTKSFNRGEC |

TABLE 16

DNA and protein sequences of antibody 23.5.1

| DESCRIPTION: | SEQUENCE (signal sequence underlined): |
|---|---|
| Heavy Chain DNA (SEQ ID NO: 61) | <u>ATGGAGTTTGGGCTGAGCTGGGTTTTCCTCGTTGC</u> |
| | <u>TCTTTTAAGAGGTGTCCAGTGT</u>CAGGTGCAGCTG |
| | GTGGAGTCTGGGGGAGGCGTGGTCCAGCCTGGG |
| | AGGTCCCTGAGACTCTCCTGTGTAGCCTCTGGATT |
| | CACCTTCAGTAACTATGGCATGCACTGGGTCCGC |
| | CAGGCTCCAGGCAAGGGGCTGGAGTGGGTGGCA |
| | ATTATATCATATGATGGAAGTAATAAATACTATG |
| | CAGACTCCGTGAAGGGCCGATTCACCATCTCCAG |
| | AGACAATTCCAAGAACACGCTGTATGTGCAAATG |
| | AACAGCCTGAGAGCTGAGGACACGGCTGTGTATT |
| | ACTGTGCGAGACGCGGTCACTACGGGAGGGATTA |
| | CTACTCCTACTACGGTTTGGACGTCTGGGGCCAA |
| | GGGACCACGGTCACCGTCTCCTCAGCCTCCACCA |
| | AGGGCCCATCGGTCTTCCCCCTGGCGCCCTGCTC |
| | CAGGAGCACCTCCGAGAGCACAGCGGCCCTGGG |
| | CTGCCTGGTCAAGGACTACTTCCCCGAACCGGTG |
| | ACGGTGTCGTGGAACTCAGGCGCTCTGACCAGCG |
| | GCGTGCACACCTTCCCAGCTGTCCTACAGTCCTC |
| | AGGACTCTACTCCCTCAGCAGCGTGGTGACCGTG |
| | CCCTCCAGCAACTTCGGCACCCAGACCTACACCT |
| | GCAACGTAGATCACAAGCCCAGCAACACCAAGG |
| | TGGACAAGACAGTTGAGCGCAAATGTTGTGTCGA |
| | GTGCCCACCGTGCCCAGCACCACCTGTGGCAGGA |
| | CCGTCAGTCTTCCTCTTCCCCCCAAAACCCAAGG |
| | ACACCCTCATGATCTCCCGGACCCCTGAGGTCAC |
| | GTGCGTGGTGGTGGACGTGAGCCACGAAGACCCC |
| | GAGGTCCAGTTCAACTGGTACGTGGACGGCGTGG |
| | AGGTGCATAATGCCAAGACAAAGCCACGGGAGG |
| | AGCAGTTCAACAGCACGTTCCGTGTGGTCAGCGT |
| | CCTCACCGTTGTGCACCAGGACTGGCTGAACGGC |
| | AAGGAGTACAAGTGCAAGGTCTCCAACAAAGGC |
| | CTCCCAGCCCCCATCGAGAAAACCATCTCCAAAA |
| | CCAAAGGGCAGCCCCGAGAACCACAGGTGTACA |
| | CCCTGCCCCCATCCCGGGAGGAGATGACCAAGAA |
| | CCAGGTCAGCCTGACCTGCCTGGTCAAAGGCTTC |
| | TACCCCAGCGACATCGCCGTGGAGTGGGAGAGC |
| | AATGGGCAGCCGGAGAACAACTACAAGACCACA |
| | CCTCCCATGCTGGACTCCGACGGCTCCTTCTTCCT |

TABLE 16-continued

DNA and protein sequences of antibody 23.5.1

| DESCRIPTION: | SEQUENCE (signal sequence underlined): |
|---|---|
| | CTACAGCAAGCTCACCGTGGACAAGAGCAGGTG |
| | GCAGCAGGGGAACGTCTTCTCATGCTCCGTGATG |
| | CATGAGGCTCTGCACAACCACTACACGCAGAAGA |
| | GCCTCTCCCTGTCTCCGGGTAAATGA |
| Heavy Chain Protein (SEQ ID NO: 62) | MEFGLSWVFLVALLRGVQCQVQLVESGGGVVQPG RSLRLSCVASGFTFSNYGMHWVRQAPGKGLEWVA IISYDGSNKYYADSVKGRETISRDNSKNTLYVQMNS LRAEDTAVYYCARRGHYGRDYYSYYGLDVWGQG TTVTVSSASTKGPSVFPLAPCSRSTSESTAALGCLVK DYFPEPVTVSWNSGALTSGVHTFPAVLQSSGLYSLS SVVTVPSSNFGTQTYTCNVDHKPSNTKVDKTVERK CCVECPPCPAPPVAGPSVFLFPPKPKDTLMISRTPEV TCVVVDVSHEDPEVQFNWYVDGVEVHNAKTKPRE EQFNSTFRVVSVLTVVHQDWLNGKEYKCKVSNKG LPAPIEKTLSKTKGQPREPQVYTLPPSREEMTKNQVS LTCLVKGFYPSDIAVEWESNGQPENNYKTTPPMLD SDGSFFLYSKLTVDKSRWQQGNVFSCSVMHEALHN HYTQKSLSLSPGK |
| Light Chain DNA (SEQ ID NO: 63) | <u>ATGAGGCTCCCTGCTCAGCTCCTGGGGCTGCTAA TGCTCTGGGTCTCTGGATCCAGTGGG</u>GATATTGT GATGACTCAGTCTCCACTCTCCCTGCCCGTCACCC CTGGAGAGCCGGCCTCCATCTCCTGCAGGTCTAG TCAGAGCCTCCTGCCTGGTAATGGATACAACTAT TTGGATTGGTACCTGCAGAAGCCAGGGCAGTCTC CACAGCTCCTGATCTATTTGGGTTCTAATCGGGCC TCCGGGGTCCCTGACAGGTTCAGTGGCAGTGGAT CAGGCACAGATTTTACACTGAAAATCAGCAGAGT GGAGGCTGAGGATGTTGGGGTTTATTACTGCATG CAAGCTCTACAAACTCCTCGGACGTTCGGCCAAG GGACCAAGGTGGAAATCAAACGAACTGTGGCTG CACCATCTGTCTTCATCTTCCCGCCATCTGATGAG CAGTTGAAATCTGGAACTGCCTSTGTTGTGTGCCT GCTGAATAACTTCTATCCCAGAGAGGCCAAAGTA CAGTGGAAGGTGGATAACGCCCTCCAATCGGGTA ACTCCCAGGAGAGTGTCACAGAGCAGGACAGCA AGGACAGCACCTACAGCCTCAGCAGCACCYTGAC |

TABLE 16-continued

DNA and protein sequences of antibody 23.5.1

| DESCRIPTION: | SEQUENCE (signal sequence underlined): |
|---|---|
| | GCTGAGCAAAGCAGACTACGAGAAACACAAAGT |
| | CTACGCCTGCGAAGTCACCCATCAGGGCCTGAGC |
| | TCGCCCGTCACAAAGAGCTTCAACAGGGGAGAGT |
| | GTTAA |
| Light Chain Protein (SEQ ID NO: 64) | MRLPAQLLGLLMLWVSGSSGDIVMTQSPLSLPVTP |
| | GEPASISCRSSQSLLPGNGYNYLDWYLQKPGQSPQL |
| | LIYLGSNRASGVPDRFSGSGSGTDFTLKISRVEAEDV |
| | GVYYCMQALQTPRTFGQGTKVEIKRTVAAPSVFIFP |
| | PSDEQLKSGTAXVVCLLNNFYPREAKVQWKVDNA |
| | LQSGNSQESVTEQDSKDSTYSLSSTLTLSKADYEKH |
| | KVYACEVTHQGLSSPVTKSFNRGEC |

TABLE 17

DNA and protein sequences of antibody 23.28.1

| DESCRIPTION: | SEQUENCE (signal sequence underlined): |
|---|---|
| Heavy Chain DNA (SEQ ID NO: 69) | ATGAAACATCTGTGGTTCTTCCTTCTCCTGGTGGC |
| | AGCTCCCAGATGGGTCCTGTCCCAGGTGCAGCTG |
| | CAGGAGTCGGGCCCAGGACTGGTGAAGCCTTCGG |
| | AGACCCTGTCCCTCACCTGCACTGTCTCTGGTGGC |
| | TCCATCAGAGGTTACTACTGGAGCTGGATCCGGC |
| | AGCCCCCTGGGAAGGGACTGGAGTGGATTGGGT |
| | ATATCTATTACAGTGGGAGCACCAACTACAACCC |
| | CTCCCTCAAGAGTCGAGTCACCATATCAGTAGAC |
| | ACGTCCAAGAACCAGTTCTCCCTGAAGCTGAACT |
| | CTGTGACCGCTGCGGACACGGCCGTGTATTATTG |
| | TGCGAGAAAGGGGGCCTCTACGGTGACTACGG |
| | CTGGTTCGCCCCCTGGGGCCAGGGAACCCTGGTC |
| | ACCGTCTCCTCAGCCTCCACCAAGGGCCCATCGG |
| | TCTTCCCCCTGGCGCCCTGCTCCAGGAGCACCTCC |
| | GAGAGCACAGCGGCCCTGGGCTGCCTGGTCAAG |
| | GACTACTTCCCCGAACCGGTGACGGTGTCGTGGA |
| | ACTCAGGCGCTCTGACCAGCGGCGTGCACACCTT |
| | CCCAGCTGTCCTACAGTCCTCAGGACTCTACTCCC |
| | TCAGCAGCGTGGTGACCGTGCCCTCCAGCAACTT |
| | CGGCACCCAGACCTACACCTGCAACGTAGATCAC |
| | AAGCCCAGCAACACCAAGGTGGACAAGACAGTT |
| | GAGCGCAAATGTTGTGTCGAGTGCCCACCGTGCC |

TABLE 17-continued

DNA and protein sequences of antibody 23.28.1

| DESCRIPTION: | SEQUENCE (signal sequence underlined): |
|---|---|
| | CAGCACCACCTGTGGCAGGACCGTCAGTCTTCCT |
| | CTTCCCCCCAAAACCCAAGGACACCCTCATGATC |
| | TCCCGGACCCCTGAGGTCACGTGCGTGGTGGTGG |
| | ACGTGAGCCACGAAGACCCCGAGGTCCAGTTCAA |
| | CTGGTACGTGGACGGCGTGGAGGTGCATAATGCC |
| | AAGACAAAGCCACGGGAGGAGCAGTTCAACAGC |
| | ACGTTCCGTGTGGTCAGCGTCCTCACCGTTGTGC |
| | ACCAGGACTGGCTGAACGGCAAGGAGTACAAGT |
| | GCAAGGTCTCCAACAAAGGCCTCCCAGCCCCCAT |
| | CGAGAAAACCATCTCCAAAACCAAAGGGCAGCC |
| | CCGAGAACCACAGGTGTACACCCTGCCCCCATCC |
| | CGGGAGGAGATGACCAAGAACCAGGTCAGCCTG |
| | ACCTGCCTGGTCAAAGGCTTCTACCCCAGCGACA |
| | TCGCCGTGGAGTGGGAGAGCAATGGGCAGCCGG |
| | AGAACAACTACAAGACCACACCTCCCATGCTGGA |
| | CTCCGACGGCTCCTTCTTCCTCTACAGCAAGCTCA |
| | CCGTGGACAAGAGCAGGTGGCAGCAGGGGAACG |
| | TCTTCTCATGCTCCGTGATGCATGAGGCTCTGCAC |
| | AACCACTACACGCAGAAGAGCCTCTCCCTGTCTC |
| | CGGGTAAATGA |
| Heavy Chain Protein (SEQ ID NO: 70) | <u>MKIHLWFFLLLVAAPRWVLS</u>QVQLQESGPGLVKPSE |
| | TLSLTCTVSGGSIRGYYWSWRQPPGKGLEWIGYIY |
| | YSGSTNYNPSLKSRVTISVDTSKNQFSLKLNSVTAA |
| | DTAVYYCARKGGLYGDYGWFAPWGQGTLVTVSS |
| | ASTKGPSVFPLAPCSRSTSESTAALGCLVKDYFPEPV |
| | TVSWNSGALTSGVHTFPAVLQSSGLYSLSSVVTVPS |
| | SNFGTQTYTCNVDHKPSNTKVDKTVERKCCVECPP |
| | CPAPPVAGPSVFLFPPKPKDTLMISRTPEVTCVVVD |
| | VSHEDPEVQFNWYVDGVEVHNAKTKPREEQFNSTF |
| | RVVSVLTVVHQDWLNGKEYKCKVSNKGLPAPIIEK |
| | TISKTKGQPREPQVYTLPPSREEMTKNQVSLTCLVK |
| | GFYPSDIAVEWESNGQPENNYKTTPPMLDSDGSFFL |
| | YSKLTVDKSRWQQGNVFSCSVMHEALHNHYTQKS |
| | LSLSPGK |
| Light Chain DNA (SEQ ID NO: 71) | <u>ATGGAAACCCCAGCGCAGCTTCTCTTCCTCCTGCT</u> |
| | <u>ACTCTGGCTCCCAGAATCCACCGGA</u>GAAATTGTG |
| | TTGACGCAGTCTCCAGGCACCCTGTCTTTGTCTCC |

TABLE 17-continued

DNA and protein sequences of antibody 23.28.1

| DESCRIPTION: | SEQUENCE (signal sequence underlined): |
|---|---|
| | AGGGGAAAGAGCCACCCTCTCCTGCAGGGCCAGT |
| | CAGAGTGTTAGCAGCAGCGACTTAGCCTGGCACC |
| | AGCAGAAACCTGGCCAGGCTCCCAGACTCCTCAT |
| | CTATGGTGCATCCAGCAGGGCCACTGGCATCCCA |
| | GACAGGTTCAGTGGCAGTGGGTCTGGGACAGACT |
| | TCACTCTCACCATCAGCAGACTGGAGCCTGAAGA |
| | TTTTGCAGTGTATTACTGTCAGCACTGTCGTAGCT |
| | TATTCACTTTCGGCCCTGGGACCAAAGTGGATAT |
| | CAAACGAACTGTGGCTGCACCATCTGTCTTCATC |
| | TTCCCGCCATCTGATGAGCAGTTGAAATCTGGAA |
| | CTGCCTCTGTTGTGTGCCTGCTGAATAACTTCTAT |
| | CCCAGAGAGGCCAAAGTACAGTGGAAGGTGGAT |
| | AACGCCCTCCAATCGGGTAACTCCCAGGAGAGTG |
| | TCACAGAGCAGGACAGCAAGGACAGCACCTACA |
| | GCCTCAGCAGCACCCTGACGCTGAGCAAAGCAG |
| | ACTACGAGAAACACAAAGTCTACGCCTGCGAAGT |
| | CACCCATCAGGGCCTGAGCTCGCCCGTCACAAAG |
| | AGCTTCAACAGGGGAGAGTGTTAG |
| Light Chain Protein (SEQ ID NO: 72) | METPAQLLFLLLLWLPESTGEIVLTQSPGTLSLSPGE |
| | RATLSCRASQSVSSSDLAWHQQKPGQAPRLLIYGA |
| | SSRATGTPDRFSGSGSGTDFTLTISRLEPEDFAVYYC |
| | QHCRSLFTFGPGTKVDIKRTVAAPSVFIFPPSDEQLK |
| | SGTASVVCLLNNFYPREAKVQWKVDNALQSGNSQ |
| | ESVTEQDSKDSTYSLSSTLTLSKADYEKHKVYACE |
| | VTHQGLSSPVTKSFNRGEC |

TABLE 18

DNA and protein sequences of antibody 23.29.1

| DESCRIPTION: | SEQUENCE (signal sequence underlined): |
|---|---|
| Heavy Chain DNA (SEQ ID NO: 77) | ATGGAGTTTGGGCTGAGCTGGGTTTTCCTCGTTGC |
| | TCTTTTAAGAGGTGTCCAGTGTCAGGTGCAACTG |
| | GTGGAGTCTGGGGGAGGCGTGGTCCAGCCTGGG |
| | AGGTCCCTGAGACTCTCCTGTGCAGCCTCTGGAT |
| | TCACCTTCAGTAGCTATGCCATGCACTGGGTCCG |
| | CCAGGCTCCAGGCAAGGGGCTGGAGTGGGTGGC |
| | AGTTATATCATATGATGGAAGTAATAAATACTAT |
| | GCAGACTCCGTGAAGGGCCGATTCACCATCTACA |

TABLE 18-continued

DNA and protein sequences of antibody 23.29.1

| DESCRIPTION: | SEQUENCE (signal sequence underlined): |
|---|---|
| | GAGACAATTCCAAGAACACGCTGTATCTGCAAAT |
| | GAACAGCCTGAGAGCTGAGGACACGGCTGTGTAT |
| | TACTGTGCGAGACGCGGTCACTACGGGAATAATT |
| | ACTACTCCTATTACGGTTTGGACGTCTGGGGCCA |
| | AGGGACCACGGTCACCGTCTCCTCAGCCTCCACC |
| | AAGGGCCCATCGGTCTTCCCCCTGGCGCCCTGCT |
| | CCAGGAGCACCTCCGAGAGCACAGCGGCCCTGG |
| | GCTGCCTGGTCAAGGACTACTTCCCCGAACCGGT |
| | GACGGTGTCGTGGAACTCAGGCGCTCTGACCAGC |
| | GGCGTGCACACCTTCCCAGCTGTCCTACAGTCCT |
| | CAGGACTCTACTCCCTCAGCAGCGTGGTGACCGT |
| | GCCCTCCAGCAACTTCGGCACCCAGACCTACACC |
| | TGCAACGTAGATCACAAGCCCAGCAACACCAAG |
| | GTGGACAAGACAGTTGAGCGCAAATGTTGTGTCG |
| | AGTGCCCACCGTGCCCAGCACCACCTGTGGCAGG |
| | ACCGTCAGTCTTCCTCTTCCCCCCAAAACCCAAG |
| | GACACCCTCATGATCTCCCGGACCCCTGAGGTCA |
| | CGTGCGTGGTGGTGGACGTGAGCCACGAAGACCC |
| | CGAGGTCCAGTTCAACTGGTACGTGGACGGCGTG |
| | GAGGTGCATAATGCCAAGACAAAGCCACGGGAG |
| | GAGCAGTTCAACAGCACGTTCCGTGTGGTCAGCG |
| | TCCTCACCGTTGTGCACCAGGACTGGCTGAACGG |
| | CAAGGAGTACAAGTGCAAGGTCTCCAACAAAGG |
| | CCTCCCAGCCCCCATCGAGAAAACCATCTCCAAA |
| | ACCAAAGGGCAGCCCCGAGAACCACAGGTGTAC |
| | ACCCTGCCCCCATCCCGGGAGGAGATGACCAAGA |
| | ACCAGGTCAGCCTGACCTGCCTGGTCAAAGGCTT |
| | CTACCCCAGCGACATCGCCGTGGAGTGGGAGAGC |
| | AATGGGCAGCCGGAGAACAACTACAAGACCACA |
| | CCTCCCATGCTGGACTCCGACGGCTCCTTCTTCCT |
| | CTACAGCAAGCTCACCGTGGACAAGAGCAGGTG |
| | GCAGCAGGGGAACGTCTTCTCATGCTCCGTGATG |
| | CATGAGGCTCTGCACAACCACTACACGCAGAAGA |
| | GCCTCTCCCTGTCTCCGGGTAAATGA |
| Heavy Chain Protein (SEQ ID NO: 78) | <u>MEFGLSWVFLVALLRGVQC</u>QVQLVESGGGVVQPG |
| | RSLRLSCAASGFTFSSYAMHWVRQAPGKGLEWVA |
| | VISYDGSNKYYADSVKGRFTIYRDNSKNTLYLQMN |
| | SLRAEDTAVYYCARRGHYGNNYYSYYGLDVWGQ |

TABLE 18-continued

DNA and protein sequences of antibody 23.29.1

| DESCRIPTION: | SEQUENCE (signal sequence underlined): |
|---|---|
| | GTTVTVSSASTKGPSVFPLAPCSRSTSESTAALGCLV |
| | KDYFPEPVTVSWNSGALTSGVHTFPAVLQSSGLYSL |
| | SSVVTVPSSNEGTQTYTCNVDHKPSNTKVDKTVER |
| | KCCVECPPCPAPPVAGPSVFLFPPKPKDTLMISRTPE |
| | VTCVVVDVSHEDPEVQFNWYVDGVEVHNAKTKPR |
| | EEQFNSTFRVVSVLTVVHQDWLNGKEYKCKVSNK |
| | GLPAPIEKTISKTKGQPREPQVYTLPPSREEMTKNQ |
| | VSLTCLVKGFYPSDIAVEWESNGQPENNYKTTPPM |
| | LDSDGSFFLYSKLTVDKSRWQQGNVFSCSVMHEAL |
| | HNHYTQKSLSLSPGK |
| Light Chain DNA (SEQ ID NO: 79) | <u>ATGAGGCTCCCTGCTCAGCTCCTGGGGCTGCTAA</u> |
| | <u>TGCTCTGGGTCTCTGGATCCAGTGGG</u>GATATTGT |
| | GATGACTCAGTCTCCACTCTCCCTGCCCGTCACCC |
| | CTGGAGAGCCGGCCTCCATCTCCTGCAGGTCTAG |
| | TCAGAGCCTCCTGCCTGGTAATGGATACAACTAT |
| | TTGGATTGGTACCTGCAGAAGCCAGGGCAGTCTC |
| | CACAGCTCCTGATCTATTTGGGTTCTAATCGGGCC |
| | TCCGGGGTCCCTGACAGGTTCAGTGGCAGTGGCT |
| | CAGGCACAGATTTTACACTGAAAATCAGCAGAGT |
| | GGAGGCTGAGGATGTTGGGATTTATTACTGCATG |
| | CAAGCTCTACAAACTCCTCGGACGTTCGGCCAAG |
| | GGACCAAGGTGGAAATCAAACGAACTGTGGCTG |
| | CACCATCTGTCTTCATCTTCCCGCCATCTGATGAG |
| | CAGTTGAAATCTGGAACTGCCTCTGTTGTGTGCCT |
| | GCTGAATAACTTCTATCCCAGAGAGGCCAAAGTT |
| | CAGTGGAGGGTGGATAACGCCCTCCAATCGGGTA |
| | ACTCCCAGGAGAGTGTCACAGAGCAGGACAGCA |
| | AGGACAGCACCTACAGCCTCAGCAGCACCCTGAC |
| | GCTGAGCAAAGCAGACTACGAGAAACACAAAGT |
| | CTACGCCTGCGAAGTCACCCATCAGGGCCTGAGC |
| | TCGCCCGTCACAAAGAGCTTCAACAGGGGAGAGT |
| | GTTAG |
| Light Chain Protein (SEQ ID NO: 80) | <u>MRLPAQLLGLLMLWVSGSSG</u>DIVMTQSPLSLPVTP |
| | GEPASISCRSSQSLLPGNGYNYLDWYLQKPGQSPQL |
| | LIYLGSNRASGVPDRFSGSGSGTDFTLKISRVEAEDV |
| | GIYYCMQALQTPRTFGQGTKVEIKRTVAAPSVFIFP |
| | PSDEQLKSGTASVVCLLNNFYPREAKVQWRVDNA |

TABLE 18-continued

DNA and protein sequences of antibody 23.29.1

| DESCRIPTION: | SEQUENCE (signal sequence underlined): |
|---|---|
| | LQSGNSQESVTEQDSKDSTYSLSSTLTLSKADYEKH |
| | KVYACEVTHQGLSSPVTKSFNRGEC |
| Light Chain DNA (23.29.1LR174K) (SEQ ID NO:101) | <u>ATGAGGCTCCCTGCTCAGCTCCTGGGGCTGCTAA</u> |
| | <u>TGCTCTGGGTCTCTGGATCCAGTGGGG</u>ATATTGT |
| | GATGACTCAGTCTCCACTCTCCCTGCCCGTCACCC |
| | CTGGAGAGCCGGCCTCCATCTCCTGCAGGTCTAG |
| | TCAGAGCCTCCTGCCTGGTAATGGATACAACTAT |
| | TTGGATTGGTACCTGCAGAAGCCAGGGCAGTCTC |
| | CACAGCTCCTGATCTATTTGGGTTCTAATCGGGCC |
| | TCCGGGGTCCCTGACAGGTTCAGTGGCAGTGGCT |
| | CAGGCACAGATTTTACACTGAAAATCAGCAGAGT |
| | GGAGGCTGAGGATGTTGGGATTTATTACTGCATG |
| | CAAGCTCTACAAACTCCTCGGACGTTCGGCCAAG |
| | GGACCAAGGTGGAAATCAAACGAACTGTGGCTG |
| | CACCATCTGTCTTCATCTTCCCGCCATCTGATGAG |
| | CAGTTGAAATCTGGAACTGCCTCTGTTGTGTGCCT |
| | GCTGAATAACTTCTATCCCAGAGAGGCCAAAGTT |
| | CAGTGGAAGGTGGATAACGCCCTCCAATCGGGTA |
| | ACTCCCAGGAGAGTGTCACAGAGCAGGACAGCA |
| | AGGACAGCACCTACAGCCTCAGCAGCACCCTGAC |
| | GCTGAGCAAAGCAGACTACGAGAAACACAAAGT |
| | CTACGCCTGCGAAGTCACCCATCAGGGCCTGAGC |
| | TCGCCCGTCACAAAGAGCTTCAACAGGGGAGAGT |
| | GTTAG |
| Light Chain Protein (23.29.1LR174K) (SEQ ID NO:101) | <u>MRLPAQLLGLLMLWVSGSSG</u>DIVMTQSPLSLPVTP |
| | GEPASISCRSSQSLLPGNGYNYLDWYLQKPGQSPQL |
| | LIYLGSNRASGVPDRFSGSGSGTDFTLKISRVEAEDV |
| | GIYYCMQALQTPRTFGQGTKVEIKRTVAAPSVFIIFP |
| | PSDEQLKSGTASVVCLLNMYPREAKVQWKVDNA |
| | LQSGNSQESVTEQDSKDSTYSLSSTLTLSKADYEKH |
| | KVYACEVTHQGLSSPVTKSFNRGEC |

TABLE 19

DNA and protein sequences of antibody 24.2.1

| DESCRIPTION: | SEQUENCE (signal sequence underlined): |
|---|---|
| Heavy Chain DNA (SEQ ID NO: 85) | <u>ATGAAACATCTGTGGTTCTTCCTTCTCCTGGTGGC</u> <u>AGCTCCCAGATGGGTCCTGTCC</u>CAGGTGCAGCTG CAGGAGTCGGGCCCAGGACTGGTGAAGCCTTCGG AGACCCTGTCCCTCACCTGCACTGTCTCTGGTGGC TCCATCAGAGGTTACTACTGGAGCTGGATCCGGC AGCCCCCAGGGAAGGGACTGGAGTGGATTGGGT ATATCTATTACAGTGGGAGCACCAACTACAACCC CTCCCTCAAGAGTCGAGTCACCATATCAGTAGAC ACGTCCAAGAACCAGTTCTCCCTGAAGCTGAGTT CTGTGACCGCTGCGGACACGGCCGTGTATTACTG TGCGAGAAGGGGGGCCTCTACGGTGACTACGG CTGGTTCGCCCCCTGGGGCCAGGGAACCCTGGTC ACCGTCTCCTCAGCCTCCACCAAGGGCCCATCGG TCTTCCCCCTGGCGCCCTGCTCCAGGAGCACCTCC GAGAGCACAGCGGCCCTGGGCTGCCTGGTCAAG GACTACTTCCCCGAACCGGTGACGGTGTCGTGGA ACTCAGGCGCTCTGACCAGCGGCGTGCACACCTT CCCAGCTGTCCTACAGTCCTCAGGACTCTACTCCC TCAGCAGCGTGGTGACCGTGCCCTCCAGCAACTT CGGCACCCAGACCTACACCTGCAACGTAGATCAC AAGCCCAGCAACACCAAGGTGGACAAGACAGTT GAGCGCAAATGTTGTGTCGAGTGCCCACCGTGCC CAGCACCACCTGTGGCAGGACCGTCAGTCTTCCT CTTCCCCCCAAAACCCAAGGACACCCTCATGATC TCCCGGACCCCTGAGGTCACGTGCGTGGTGGTGG ACGTGAGCCACGAAGACCCCGAGGTCCAGTTCAA CTGGTACGTGGACGGCGTGGAGGTGCATAATGCC AAGACAAAGCCACGGGAGGAGCAGTTCAACAGC ACGTTCCGTGTGGTCAGCGTCCTCACCGTTGTGC ACCAGGACTGGCTGAACGGCAAGGAGTACAAGT GCAAGGTCTCCAACAAAGGCCTCCCAGCCCCCAT CGAGAAAACCATCTCCAAAACCAAAGGGCAGCC CCGAGAACCACAGGTGTACACCCTGCCCCCATCC CGGGAGGAGATGACCAAGAACCAGGTCAGCCTG ACCTGCCTGGTCAAAGGCTTCTACCCCAGCGACA TCGCCGTGGAGTGGGAGAGCAATGGGCAGCCGG AGAACAACTACAAGACCACACCTCCCATGCTGGA CTCCGACGGCTCCTTCTTCCTCTACAGCAAGCTCA |

TABLE 19-continued

DNA and protein sequences of antibody 24.2.1

| DESCRIPTION: | SEQUENCE (signal sequence underlined): |
|---|---|
| | CCGTGGACAAGAGCAGGTGGCAGCAGGGGAACG |
| | TCTTCTCATGCTCCGTGATGCATGAGGCTCTGCAC |
| | AACCACTACACGCAGAAGAGCCTCTCCCTGTCTC |
| | CGGGTAAATGA |
| Heavy Chain Protein (SEQ ID NO: 86) | <u>MKHLWFFLLLVAAPRWVLS</u>QVQLQESGPGLVKPSE |
| | TLSLTCTVSGGSIRGYYWSWIRQPPGKGLEWIGYW |
| | YSGSTNYNIPSLKSRVTJSVDTSKNQFSLKISSVTAA |
| | DTAVYYCARRGGLYGDYGWFAPWGQGTLVTVSS |
| | ASTKGPSVFPLAPCSRSTSESTAALGCLVKDYFPEPV |
| | TVSWNSGALTSGVHTFPAVLQSSGLYSLSSVVTVPS |
| | SNFGTQTYTCNVDHKPSNTKVDKTVERKCCVECPP |
| | CPAPPVAGPSVFLFPPKPKDTLMISRTPEVTCVVVD |
| | VSHEDPEVQFNWYVDGVEVHNAKTKPREEQFNSTF |
| | RVVSVLTVVHQDWLNGKEYKCKVSNKGLPAPIEK |
| | TISKTKGQPREPQVYTLPPSREEMTKNQVSLTCLVK |
| | GFYPSDJAVEWESNGQPENNYKTTPPMLDSDGSFFL |
| | YSKLTVDKSRWQQGNVFSCSVMHEALHNIIYTQKS |
| | LSLSPGK |
| Light Chain DNA (SEQ ID NO: 87) | <u>ATGGAAACCCCAGCGCAGCTTCTCTTCCTCCTGCT</u> |
| | <u>ACTCTGGCTCCCAGATACCACCGGA</u>GAAATTGTG |
| | TTGACGCAGTCTCCAGGCACCCTGTCTTTGTCTCC |
| | AGGGGAAAGAGCCACCCTCTCCTGCAGGGCCAGT |
| | CAGAGTGTTAGCAGCACCTACTTAGCCTGGTACC |
| | AGCAGAAACCTGGCCAGGCTCCCAGGCTCCTCAT |
| | CTATGGTGCATCCAGCAGGGCCACTGGCATCCCA |
| | GACAGGTTCAGTGGCAGTGGGTCTGGGACAGACT |
| | TCACTCTCACCATCAGCAGACTGGAGCCTGAAGA |
| | TTTTGCAGTGTATTACTGTCAGCAGTATAGTAGCT |
| | TATTCACTTTCGGCCCTGGGACCAAAGTGGATAT |
| | CAAACGAACTGTGGCTGCACCATCTGTCTTCATC |
| | TTCCCGCCATCTGATGAGCAGTTGAAATCTGGAA |
| | CTGCCTCTGTTGTGTGCCTGCTGAATAACTTCTAT |
| | CCCAGAGAGGCCAAAGTACAGTGGAAGGTGGAT |
| | AACGCCCTCCAATCGGGTAACTCCCAGGAGAGTG |
| | TCACAGAGCAGGACAGCAAGGACAGCACCTACA |
| | GCCTCAGCAGCACCCTGACGCTGAGCAAAGCAG |
| | ACTACGAGAAACACAAAGTCTACGCCTGCGAAGT |

TABLE 19-continued

DNA and protein sequences of antibody 24.2.1

| DESCRIPTION: | SEQUENCE (signal sequence underlined): |
|---|---|
| | CACCCATCAGGGCCTGAGCTCGCCCGTCACAAAG |
| | AGCTTCAACAGGGGAGAGTGTTAG |
| Light Chain Protein (SEQ ID NO: 88) | METPAQLLFLLLLWLPDTTGEIVLTQSPGTLSLSPGE RATLSCRASQSVSSTYLAWYQQKPGQAPRLLIYGA SSRATGTPDRFSGSGSGTDFTLTISRLEPEDFAVYYC QQYSSLFTFGPGTKVD1KRTVAAPSVFWPPSDEQLK SGTASVVCLLNNFYPREAKVQWKVDNALQSGNSQ ESVTEQDSKDSTYSLSSTLTLSKADYEKHKVYACE VTHQGLSSPVTKSFNRGEC |

TABLE 20

DNA and protein sequences of the mature variable domains of antibody 22.1.1 H-C109A

| DESCRIPTION: | SEQUENCE (signal sequence underlined): |
|---|---|
| Heavy Chain DNA (SEQ ID NO:95) | CAGGTGCAACTGGTGGAGTCTGGGGGAGGCGTG GTCCAGCCTGGGAGGTCCCTGAGACTCTCCTGTG CAGCCTCTGGATTCACCTTCAGTCGCTATGGCAT GCACTGGGTCCGCCAGGCTCCAGGCAAGGGGCTG GAGTGGGTGGCAGTTATATCATCTGATGGAGGTA ATAAATACTATGCAGACTCCGTGAAGGGCCGATT CACCATCTCCAGAGACAATTCCAAGAACACGCTG TATCTGCAAATGAACAGCCTGAGAGCTGAGGACA CGGCTGTGTATTACTGTACGAGAAGAGGGACTGG AAAGACTTACTACCACTACGCCGGTATGGACGTC TGGGGCCAAGGGACCACGGTCACCGTCTCCTCAG |
| Heavy Chain Protein (SEQ ID NO:96) | QVQLVESGGGVVQPGRSLRLSCAASGFTFSRYGM HWVRQAPGKGLEWVAVISSDGGNKYYADSVKGRF TISRDNSKNTLYLQMNSLRAEDTAVYYCTRRGTG KTYYHYAGMDVWGQGTTVTVSS |

TABLE 21

DNA and protein sequences of the mature variable domains of antibody 23.28.1 L-C92A

| DESCRIPTION: | SEQUENCE (signal sequence underlined): |
|---|---|
| Light Chain DNA (SEQ ID NO:99) | GAAATTGTGTTGACGCAGTCTCCAGGCACCCTGT CTTTGTCTCCAGGGGAAAGAGCCACCCTCTCCTG CAGGGCCAGTCAGAGTGTTAGCAGCAGCGACTTA GCCTGGCACCAGCAGAAACCTGGCCAGGCTCCCA GACTCCTCATCTATGGTGCATCCAGCAGGGCCAC TGGCATCCCAGACAGGTTCAGTGGCAGTGGGTCT GGGACAGACTTCACTCTCACCATCAGCAGACTGG AGCCTGAAGATTTTGCAGTGTATTACTGTCAGCA CGCCCGTAGCTTATTCACTTTCGGCCCTGGGACC AAAGTGGATATCAAAC |
| Light Chain Protein (SEQ ID NO:100) | EIVLTQSPGTLSLSPGERATLSCRASQSVSSSDL AWHQQKPGQAPRLLIYGASSRATGIPDRYSGSGS GTDFTLTISRLEPEDFAVYYCQHARSLFTFGPGT KVDIK |

EXAMPLE III

Analysis of Heavy and Light Chain Amino Acid Substitutions

FIGS. 1D-1H and 2D-2H provide sequence alignments between the predicted heavy chain variable domain amino acid sequences of monoclonal antibodies 3.1.1, 7.1.2, 10.8.3, 15.1.1, 21.4.1, 21.2.1, 22.1.1, 22.1.1H-C109A, 23.5.1, 23.28.1, 23.28.1H-D16E, 23.29.1 and 24.2.1 antibodies and the germline amino acid sequences of their respective genes. Most of the heavy chain CDR3 regions contain amino acid insertions.

The DLR1 gene used in the $V_H$ domain of antibody 21.4.1 codes for two cysteine (Cys) residues. Mass spectrometry analysis and homology modeling demonstrated that the two Cys residues are disulfide-linked, and that this disulfide link does not disrupt the structure of the antibody.

FIGS. 1A-1C and 2A-2C provide sequence alignments between the predicted light chain variable amino acid sequences of monoclonal antibodies 3.1.1, 7.1.2, 10.8.3, 15.1.1, 21.4.1, 21.2.1, 22.1.1, 23.5.1, 23.28.1, 23.28.1L-C92A, 23.29.1 and 24.2.1 clones and the germline amino acid sequences of their respective genes. The light chains of these antibodies are derived from three different Vκ genes. Seven of the eleven antibodies use the A3/A19 Vκ gene, six of which have two mutations in the CDR1 region. Further, five of the seven antibodies that use the A3/A19 Vκ gene, also use the Jκ1 gene; in all of these antibodies the first amino acid derived from the Jκ1 gene is consistently changed from a W to an R.

It will be appreciated that many of the above-identified amino acid substitutions or insertions exist in close proximity to or within a CDR. Such substitutions would appear to bear some effect upon the binding of the antibody to the CD40 molecule. Further, such substitutions could have significant effect upon the affinity of the antibodies.

EXAMPLE IV

Species Crossreactivity of the Antibodies of the Invention

We performed FACS analyses to determine the binding and affinity of the antibodies of the invention for CD40 from various species, particularly certain old world monkeys. We incubated aliquots of human and monkey whole blood for 1 hour on ice with increasing concentrations of anti-CD40 antibodies of the invention exemplified herein or with an anti-keyhole limpet hemocyanin (KLH) antibody as a negative control. We then incubated the samples for 30 minutes on ice with anti-human IgG2-conjugated RPE (phycoerythrin). We measured binding by flow cytometry of CD19/CD20 positive B cells and analyzed the histograms of fluorescence intensity (F12-H) versus cell number (Counts) using CellQuest software. We estimated binding ($K_D$) for each antibody from graphs of mean fluorescence intensity versus antibody concentration. We controlled for depletion of the antibody by measuring binding over a range of cell concentrations.

We tested antibodies 3.1.1, 7.1.2, 10.8.3, 15.1.1 and 21.4.1 for binding to human, rhesus and cynomolgus B cells. We also tested antibodies 21.2.1, 22.1.1, 23.5.1, 23.25.1, 23.28.1, 23.29.1 and 24.2.1 for binding to human and cynomolgus B cells.

We observed that the maximum signal and the concentration for half maximum binding to monkey cells, was within a factor of two to the corresponding parameters for human B cells. No binding was observed in similar experiments with mouse, rat, rabbit and dog blood.

EXAMPLE V

Selectivity of Antibodies for CD40

We conducted another in vitro assay to determine the selectivity of antibodies of the invention with respect to CD40.

CD40 Selectivity ELISA: Materials and Methods

We coated a 96-well FluoroNUNC plate (Nunc Cat No. 475515) with four antigens: CD40/Ig, CD44/Ig, RANK/Ig, 4-1BB/Ig, TNFR-1/Ig and TNFR-2/Ig (antigens generated in-house), overnight at +4° C. at 1 µg/ml of 100 µl/well in 0.1 M sodium bicarbonate buffer, pH 9.6. We then washed the plate with PBST (PBS+0.1% Tween-20) three times and blocked the plate with PBST+0.5% BSA at 150 µl/well. We incubated the plate at room temperature for 1 hour and then washed with PBST three times. Next, we diluted the anti-CD40 antibodies generated in Example I in block at 1 µg/ml and added the diluted antibodies to the plate. We incubated the plate at room temperature for 1 hour then washed with PBST three times. We then treated the wells that contained the antibodies generated in Example I with 100 ml/well anti-human IgG2-HRP (Southern Biotech Cat No.9070-05) at a 1:4000 dilution in block. Also, we treated one row with anti-human IgG (Jackson Cat No. 209-035-088) diluted to 1:5000 in block and added at 1001/well to normalize for plate coating. We also treated one row with anti-human CD40-HRP (Pharmingen Cat No. 345815/Custom HRP conjugated) at 0.05 µg/ml diluted in block as a positive control. We incubated the plate at room temperature for 1 hour and then washed with PBST three times. We added TMB substrate (K & P Labs) at 1001/well and incubated the plate for 5 to 10 minutes. We then read the plate using a SpectraMax™ plate reader. The results showed that the antibodies have a selectivity for CD40 that is at least 100 times greater than their selectivity for RANK, 4-1BB, TNFR-1 and TNFR-2 in that the CD4 specific signal (CD40 signal minus background) is at least 100× greater than the corresponding signal for the other molecules.

EXAMPLE VI

Epitope Classification Studies

Having demonstrated that the antibodies of the invention are selective for CD40, we performed competition binding analysis using BIAcore and FACS.

BIAcore Competition Studies

We conducted BIAcore competition studies to determine whether the human anti-CD40 antibodies of the invention bind to the same or distinct sites on the CD40 molecule.

In these experiments we used a BIAcore 2000 instrument, following the manufacturer's protocols. Protein-A was immobilized on the sensor chip surfaces of the BIAcore. A saturating concentration of CD40-Ig which comprises the extracellular domain of CD40 was bound to the sensorchip. We then bound a first human agonist anti-CD40 antibody of the invention, a commercial anti-CD40 antibody or CD40L to the sensorchip-bound CD40 under saturating conditions. We then measured the ability of a second human agonist anti-CD40 antibody of the invention to compete with the first antibody, commercial antibody or CD40L for binding to CD40. This technique enabled us to assign the antibodies to different binding groups. Binding to CD40 indicated recognition of an independent epitope. Lack of binding may indicate recognition of the same epitope or overlapping epitopes.

FACS Studies

We conducted FACS studies to determine whether the human anti-CD40 antibodies of the invention bind to the same or distinct sites on the CD40 molecule, and to determine whether they bind to the same or distinct site on the CD40 molecule as commercially available anti-CD40 antibodies EA5 (Alexis Cat. No. ANC-300-050), LOB7/6 (Serotec MCA/590PE) and 5C3 (Pharmingen # 555458 (unlabeled) and 555460 (PE labeled for FACS).

We counter-stained dendritic cells treated with anti-CD40 antibodies of the invention with PE labeled EA5 or PE labeled LOB7/6 antibody on ice for 30 minutes. After a wash, cell staining was analyzed on a B-D caliber cytometer. Reduced binding of the commercial antibodies was interpreted as an indication that the test antibody bound to the same or overlapping epitope.

Competition binding analysis by BIAcore and FACS showed that the epitopes recognized by mAb 21.4.1 antibodies overlaps with the epitope recognized by the EA5 antibody, did not overlap with the epitope recognized by the commercially available LOB7/6 antibody and does not overlap with the binding site for CD40L. The epitopes recognized by the remaining antibodies do overlap with the binding site for CD40L.

Table 22 summarizes the results of these epitope classification studies.

TABLE 22

BIAcore Competition Epitope Classification of Certain Anti-CD40 Antibodies Of The Invention

| | EA5 | 5C3 | LOB7/6 | 3.1.1, 21.2.1, 22.1.1, 23.5.1, 23.29.1 | 21.4.1 | 23.25.1, 23.28.1, 24.2.1 | CD40L |
|---|---|---|---|---|---|---|---|
| EA5 | X | X | | | X | | X |
| 5C3 | X | X | | | X | X | X |
| LOB7/6 | | | X | X | | X | X |
| 3.1.1, 21.2.1, 22.1.1, 23.5.1, 23.29.1 | | | X | X | | | X |
| 21.4.1 | X | X | | | X | | |
| 23.25.1, 23.28.1, 24.2.1 | | X | X | | | X | X |
| CD40L | X | X | X | X | | X | |

EXAMPLE VII

Upregulation of Surface Molecules by Anti-CD40 Antibodies

We conducted a whole blood assay to determine whether the human anti-CD40 antibodies of the invention upregulate the expression of surface molecules on B cells.

Human or primate whole blood was diluted 1:1 with RPMI medium and incubated 24 hours with various concentrations of CD40 agonist antibodies or controls. Cells were stained for 30 minutes (on ice, in the dark) for HLA-DR, ICAM, B7-1, B7-2, CD19/CD20, CD40, CD23 and CD71, using commercially available, fluorochrome labeled antibody reagents. The cells were then analyzed on a FACSCalibur™ (Becton-Dickinson). B-cells were identified by gating on CD19 or CD20 positive cells, and activation markers determined for this gate.

The maximum fold increase of median fluorescence (at $\leq 1$ µg/ml antibody), and mean $EC_{50}$ obtained using one of the anti-CD40 antibodies of the claimed invention (21.4.1) are shown in Table 23.

TABLE 23

Upregulation of B-Cell Surface Molecules by an Anti-CD40 Antibody of the Invention

| | Maximum Fold Increase Mean +/− St. Dev. | $EC_{50}$ (ng/ml) Mean +/− St. Dev. |
|---|---|---|
| MHC II | 4.50 +/− 0.52 | 3.85 +/− 0.35 |
| CD71 | 2.30 +/− 0.77 | 0.73 +/− 0.28 |
| ICAM | 4.52 +/− 2.42 | 15.3 +/− 7.3 |
| CD23 | 69.9 +/− 25.8 | 19.0 +/− 4.4 |
| B7-2 | 2.74 +/− 0.14 | 16.0 +/− 21.9 |

We also conducted experiments to determine whether the human anti-CD40 antibodies of the invention upregulate the expression of surface molecules of monocyte-derived dendritic cell.

Preparation of the Monocyte Derived Dendritic Cells

Peripheral blood was collected from normal human volunteers. Mononuclear cells were isolated using Sigma ACCUSPIN™ tubes (St. Louis, Mo.), washed with RPMI media (Gibco BRL, Rockville, Md.) and placed into tissue culture flasks at $5 \times 10^6$/ml in complete RPMI medium (containing 100 U/ml penicillin/streptomycin, 10 mM HEPES buffer, 2 mM glutamine, 0.1 mM non-essential amino acids; all from Gibco BRL); and 10% fetal calf serum (HyClone, Logan, Utah). After a 3 hours of incubation at 37° C. (5% $CO_2$), non-adherent cells were removed and the T cells were isolated using selection columns (R&D Systems, Minneapolis, Minn.). The adherent cells were washed with RPMI medium and incubated for 7 days in complete RPMI medium supplemented with 10 ng/ml IL-4 (R&D Systems) and 100 ng/ml GM-CSF (R&D systems). The non-adherent cells were then isolated, washed, and utilized as monocyte derived dendritic cells (mDCs) for all experiments. The remaining adherent cells were removed using trypsin/EDTA and utilized in experiments employing adherent monocytes.

To determine whether the anti-CD40 antibodies of the invention upregulate the expression of cell surface markers, the monocyte derived dendritic cells were cultured with various concentrations of agonist antibodies for 48-72 hours, followed by staining (30 minutes, on ice, in the dark) for HLA-DR, ICAM, B7-1, B7-2, CD40 and CD83, using commercially available fluorochrome labeled antibody reagents. The cells were then analyzed on a FACS-Caliber (Becton-Dickinson).

The maximum fold increase of median fluorescence (at $\leq 1$ μg/ml antibody), and mean $EC_{50}$ obtained using one of the anti-CD40 antibodies of the claimed invention (21.4.1) are shown in Table 24.

TABLE 24

Upregulation of Dendritic Cell Surface Molecules by an Anti-CD40 Antibody of the Invention

|  | Maximum Fold Increase Mean +/− St. Dev. | $EC_{50}$ (ng/ml) Mean +/− St. Dev. |
|---|---|---|
| MHC II | 7.7 +/− 5.6 | 252 +/− 353 |
| CD83 | 36.3 +/− 42.2 | 233 +/− 262 |

TABLE 24-continued

Upregulation of Dendritic Cell Surface Molecules by an Anti-CD40 Antibody of the Invention

|  | Maximum Fold Increase Mean +/− St. Dev. | $EC_{50}$ (ng/ml) Mean +/− St. Dev. |
|---|---|---|
| ICAM | 10.4 +/− 4.8 | 241 +/− 140 |
| B7-2 | 21.9 +/− 9.4 | 71.4 +/− 44.4 |

We conducted similar experiments with B cells and mDCs using various anti-CD40 antibodies of the invention and additional markers. We measured the expression of B cell surface molecules (MHC-II, ICAM, B7-1, B7-2 and CD23) as described above but using 1 μg/ml of the anti-CD40 antibody. The results of this experiment are presented in Table 25. We measured the expression of dendritic cell surface molecules (MHC-II, ICAM, B7-1, B7-2 and CD83) after 72 hours as indicated above but using 1 μg/ml of the anti-CD40 antibody. The results of this experiment are presented in Table 26. Tables 25-26 show the fold increase in median intensity +/− standard deviation.

TABLE 25

Upregulation of B-Cell Surface Molecules by Anti-CD40 Antibodies Of The Invention

|  | MHC Class II B cell | ICAM (CD54) B cell | B7-1 (CD 80) B cell | B7-2 (CD86) B cell | CD23 B cell |
|---|---|---|---|---|---|
| 3.1.1 | 3.2 +/− 2.6 | 1.3 +/− 0.2 | 1.7 +/− 0.2 | 1.2 +/− 0.4 | 5.6 +/− 4.8 |
| 21.2.1 | 1.2 +/− 0.2 | 1.3 +/− 0.9 | 0.9 +/− 0.5 | 1.0 +/− 0.04 | 1.0 +/− 0.1 |
| 21.4.1 | 3.6 +/− 3.0 | 5.0 +/− 3.0 | 1.9 +/− 0.8 | 1.8 +/− 0.7 | 21.5 +/− 34.8 |
| 22.1.1 | 1.4 +/− 0.5 | 1.1 +/− 0.2 | 1.2 +/− 0.3 | 1.0 +/− 0.1 | 1.3 +/− 0.2 |
| 23.5.1 | 1.4 +/− 0.5 | 1.1 +/− 0.2 | 1.4 +/− 0.6 | 1.0 +/− 0.1 | 1.1 +/− 0.2 |
| 23.25.1 | 2.5 +/− 1.1 | 2.5 +/− 0.9 | 1.6 +/− 0.4 | 1.3 +/− 0.2 | 4.3 +/− 2.3 |
| 23.28.1 | 1.1 +/− 0.2 | 1.1 +/− 0.2 | 1.8 +/− 0.6 | 1.0 +/− 0.1 | 1.1 +/− 0.4 |
| 23.29.1 | 1.2 +/− 0.2 | 1.0 +/− 0.2 | 1.3 +/− 0.6 | 0.9 +/− 0.2 | 1.1 +/− 0.1 |
| 24.2.1 | 1.8 +/− 1.0 | 1.6 +/− 0.8 | 1.1 +/− 0.4 | 1.1 +/− 0.2 | 0.9 +/− 0.6 |

TABLE 26

Upregulation of Dendritic Cell Surface Molecules by Anti-CD40 Antibodies Of The Invention

|  | MHC Class II DC | ICAM (CD54) DC | B7-1 (CD 80) DC | B7-2 (CD86) DC | CD83 DC |
|---|---|---|---|---|---|
| 3.1.1 | 4.4 +/− 2.4 | 1.5 +/− 0.7 | 1.8 +/− 0.9 | 23.7 +/− 33.5 | 15.2 +/− 18.2 |
| 21.2.1 | 1.8 +/− 1.3 | 1.5 +/− 0.9 | 0.9 +/− 0.4 | 7.4 +/− 10.5 | 10.8 +/− 16.5 |
| 21.4.1 | 5.0 +/− 3.8 | 3.7 +/− 1.4 | 1.5 +/− 1.1 | 12.9 +/− 13.3 | 48.6 +/− 49.5 |
| 22.1.1 | 2.3 +/− 1.2 | 1.6 +/− 0.7 | 1.4 +/− 1.0 | 16.3 +/− 25.5 | 12.0 +/− 17.0 |
| 23.5.1 | 2.3 +/− 1.8 | 1.2 +/− 0.5 | 1.1 +/− 0.6 | 10.7 +/− 17.5 | 9.2 +/− 11.1 |
| 23.25.1 | 2.1 +/− 1.8 | 2.4 +/− 1.0 | 1.1 +/− 0.5 | 3.3 +/− 4.2 | 13.6 +/− 28.9 |
| 23.28.1 | 2.4 +/− 1.7 | 2.7 +/− 2.1 | 1.3 +/− 0.6 | 10.6 +/− 17.5 | 18.3 +/− 22.6 |
| 23.29.1 | 2.0 +/− 1.5 | 1.2 +/− 0.4 | 0.9 +/− 0.5 | 8.4 +/− 10.6 | 10.6 +/− 13.1 |
| 24.2.1 | 4.7 +/− 3.0 | 2.1 +/− 1.2 | 3.8 +/− 3.8 | 56.6 +/− 95.8 | 31.2 +/− 28.4 |

Table 27 compares the upregulation of cell surface molecules in dendritic cells over B cells in terms of the ratio of the mean-fold increase on dendritic cells over the mean-fold increase on B cells.

TABLE 27

Upregulation of Cell Surface Molecules On Dendritic Cells Over B Cells

|         | B7-1 (CD80) | B7-2 (CD86) | MHC Class II | ICAM (CD54) |
|---------|-------------|-------------|--------------|-------------|
| 3.1.1   | 1.08        | 19.40       | 1.38         | 1.15        |
| 21.2.1  | 1.01        | 7.37        | 1.49         | 1.12        |
| 21.4.1  | 0.77        | 7.04        | 1.37         | 0.74        |
| 22.1.1  | 1.18        | 16.36       | 1.61         | 1.44        |
| 23.5.1  | 0.83        | 10.54       | 1.59         | 1.06        |
| 23.25.1 | 0.66        | 2.57        | 0.85         | 0.98        |
| 23.28.1 | 0.71        | 10.81       | 2.16         | 2.57        |
| 23.29.1 | 0.73        | 9.07        | 1.66         | 1.23        |
| 24.2.1  | 3.48        | 52.30       | 2.64         | 1.35        |

EXAMPLE VIII

Enhancement of Cytokine Secretion

We conducted a monocyte derived dendritic cell assay to determine whether the human anti-CD40 antibodies of the invention enhance the secretion of IL-12p40, IL-12p70 and IL-8.

The monocyte derived dendritic cells and the adherent monocytes were prepared as described above. Cells were cultured in the presence of an anti-CD40 antibody of the invention (21.4.1) or with a anti-keyhole limpet hemocyanin (KLH) antibody as a negative control. The cytokines were measured in the supernatants at 24 hours by ELISA (R&D Systems). In some studies (see Table 28), the monocyte derived dendritic cells treated with the antibody also were co-stimulated with either 100 ng/ml LPS (Sigma), 1000 U/ml IFNγ (R&D Systems) or 25 ng/ml IL-1β R&D systems.

Figure 4:
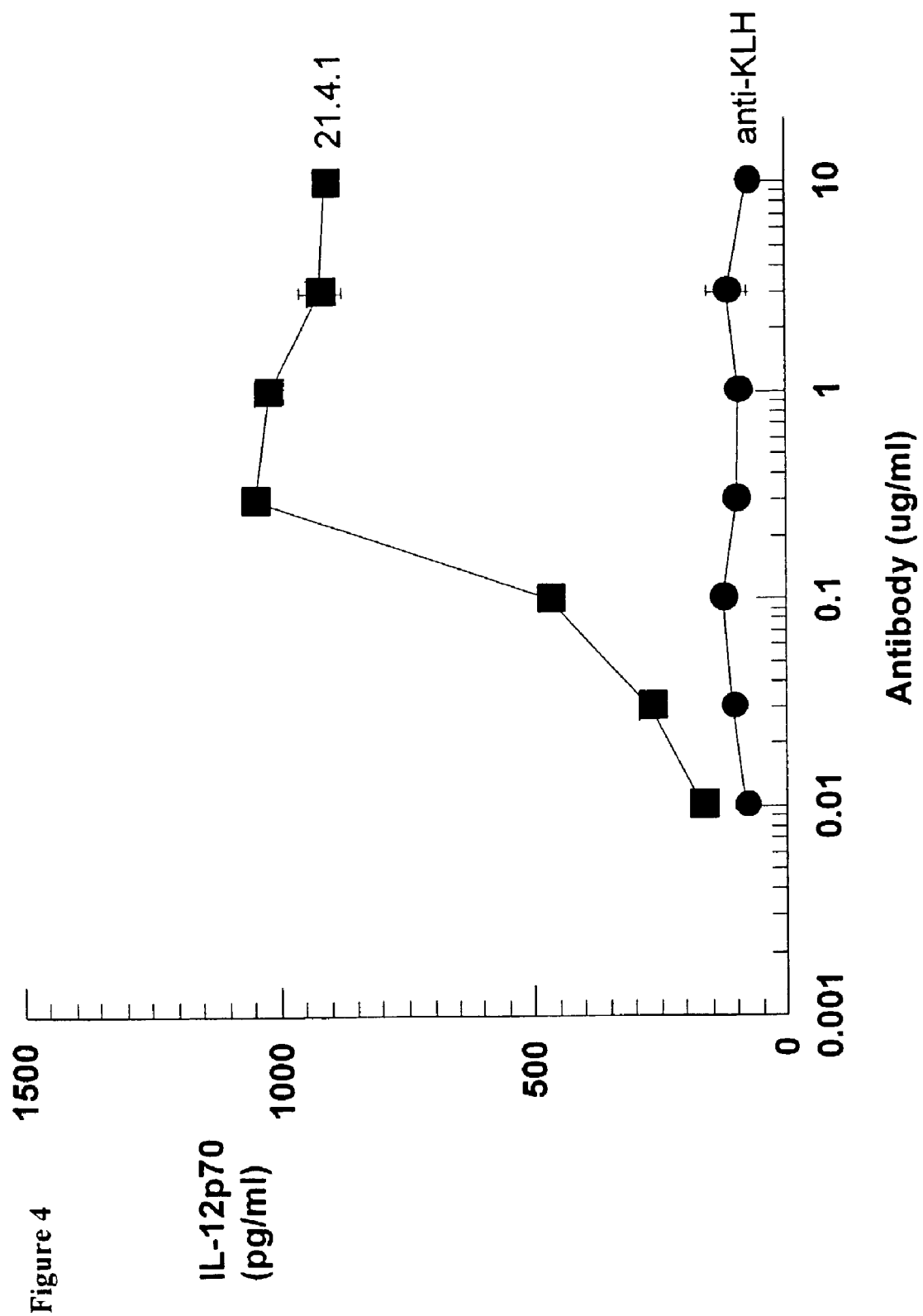
FIG. 4 is a dose-response curve that illustrates the ability of an anti-CD40 antibody of the invention (21.4.1) to enhance IL-12p70 production by human dendritic cells.

The anti-CD40 antibody enhanced IL-12p40, IL-12p70 and IL-8 production in both monocyte derived dendritic cells and adherent monocytes. The presence of LPS further enhanced the production of IL-12p40 and IL-12p70. Only minimal levels of cytokines were detected in the supernatants of dendritic cells incubated with the isotype control antibody, anti-KLH. Representative results are presented in Table 28 and in FIGS. 3 and 4. Table 28 summarizes the principle cytokines produced by dendritic cells or adherent monocytes by 1 µg/ml of an anti-CD40 antibody of the invention (21.4.1)+/−100 ng/ml LPS. As shown in FIG. 3, the anti-CD40 antibody enhanced IL-12p40 production by human dendritic cells. FIG. 4 illustrates enhanced IL-12p70 production by human dendritic cells in the presence of antibody and 100 ng/ml LPS.

TABLE 28

Enhancement of IL-12p40, IL-12p70 and IL-8 Secretion by an Anti-CD40 Antibody of the Invention

| Cell Type | Treatment Antibody 1 µg/ml | LPS 100 ng/ml | IL-12p40 pg/ml | IL-12p70 pg/ml | IL-8 pg/ml |
|-----------|---------------------------|---------------|----------------|----------------|------------|
| Dendritic cell | 21.4.1 | + | 32252 | 1000 | ND |
|  | 21.4.1 | − | 1200 | 76 | 1200 |
|  | anti-KLH | + | 14280 | 352 | ND |
|  | anti-KLH | − | 200 | 4 | 150 |
| Adherent monocyte | 21.4.1 | − | ND | ND | 7000 |
|  | 21.4.1 | + | ND | 425 | ND |
|  | anti-KLH | − | ND | ND | 400 |
|  | anti-KLH | + | ND | 30 | ND |

ND = not determined

Similar experiments were performed using multiple anti-CD40 antibodies of the invention. The monocyte derived dendritic cells were prepared as described above and cultured in the presence of various concentrations of the anti-CD40 antibodies and were co-stimulated with 100 ng/ml LPS (Sigma). The IL-12p70 in the supernatant was measured at 24 hours by ELISA (R&D Systems) and the for each antibody $EC_{50}$ was determined. The results of the experiments are presented in Table 29.

TABLE 29

Enhancement of IL-12p70 Secretion In Dendritic Cells

| Antibody Clone | DC IL-12p70 $EC_{50}$ µg/ml | Max pg/ml |
|----------------|------------------------------|-----------|
| 21.4.1  | 0.3  | 1796–7004 |
| 22.1.1  | 0.1  | 720–1040  |
| 23.25.1 | 0.2  | 540–960   |
| 23.5.1  | 0.1  | 676–1112  |
| 24.2.1  | 0.2  | 754–3680  |
| 3.1.1   | 0.2  | 668–960   |
| 23.28.1 | 0.2  | 1332–1404 |
| 23.29.1 | 0.1  | 852–900   |
| 21.2.1  | 0.03 | 656–872   |

We also tested the ability of the anti-CD40 antibodies of the invention to enhance the secretion of IFN-gamma from T cells in an allogenic T cell/dendritic cell assay. To perform this assay, T cells and monocytes were isolated from the peripheral blood of healthy volunteers. Monocytes were differentiated into dendritic cells using the above-described methods. $1 \times 10^5$ T cells obtained from an individual were cultured with $1 \times 10^5$ dendritic cells obtained from a different individual in the presence of an anti-CD40 antibody of the invention or a control antibody. After 4 days of culture, the supernatants were assayed for IFN-gamma secretion by ELISA. The results of this assay are shown in Table 30.

TABLE 30

Enhancement of IFN-gamma Secretion
by Anti-CD40 Antibodies Of The Invention

| Antibody Clone | Allo DC/T IFN$_\gamma$ | |
|---|---|---|
| | EC$_{50}$ µg/ml | Max pg/ml |
| 21.4.1 | 0.3 | 212 |
| 22.1.1 | 0.3 | 110–180 |
| 23.25.1 | 0.3 | 180–232 |
| 23.5.1 | 0.2 | 150–240 |
| 24.2.1 | 0.2 | 111–194 |
| 3.1.1 | 0.1 | 100–195 |
| 23.28.1 | 0.2 | 120–190 |
| 23.29.1 | 0.3 | 134–150 |
| 21.2.1 | 0.03 | 230–256 |

EXAMPLE IX

Induction of Inflammatory Cytokines by the Anti-CD40 Antibodies of the Invention Antibodies 10.8.3, 15.1.1, 21.4.1 and 3.1.1 were tested in a whole-blood cytokine release assay described by Wing et al., *Therapeutic. Immunol.* 2:183-90 (1995) to determine if inflammatory cytokines are induced by the antibodies at 1, and 100 µg/ml concentration. No significant release of TNF-α, IL-1β, IFN-γ, or IL-6 was observed with these antibodies at the indicated concentrations in blood from 10 normal donors.

EXAMPLE X

Enhancement of Immunogenicity of Cell Line Jy by Anti-CD40 Antibodies

CD40 positive JIYOYE cells (ATCC CCL 87) ("Jy cells") were cultured and maintained in RPMI medium. JIYOYE cells were incubated for 24 hours with an anti-CD40 antibody of the invention (21.4.1), or with an isotype matched antibody (anti-KLH), in complete RPMI medium. Cells were then washed and treated with 25 mg mitomycin C (Sigma)/7 ml media for 60 min. These cells were then incubated with isolated human T cells at a 1:100 ratio for 6 days at 37° C. (5% CO$_2$). T cells were then collected, washed, and the level of CTL activity determined against fresh chromium 51 (New England Nuclear, Boston, Mass.) labeled JIYOYE cells. Specific CTL activity was calculated as % specific cytolysis=(cytolysis Jy (cpm)−spontaneous cytolysis (cpm))/(total cytolysis (cpm)−spontaneous cytolysis (cpm)).

Figure 5:
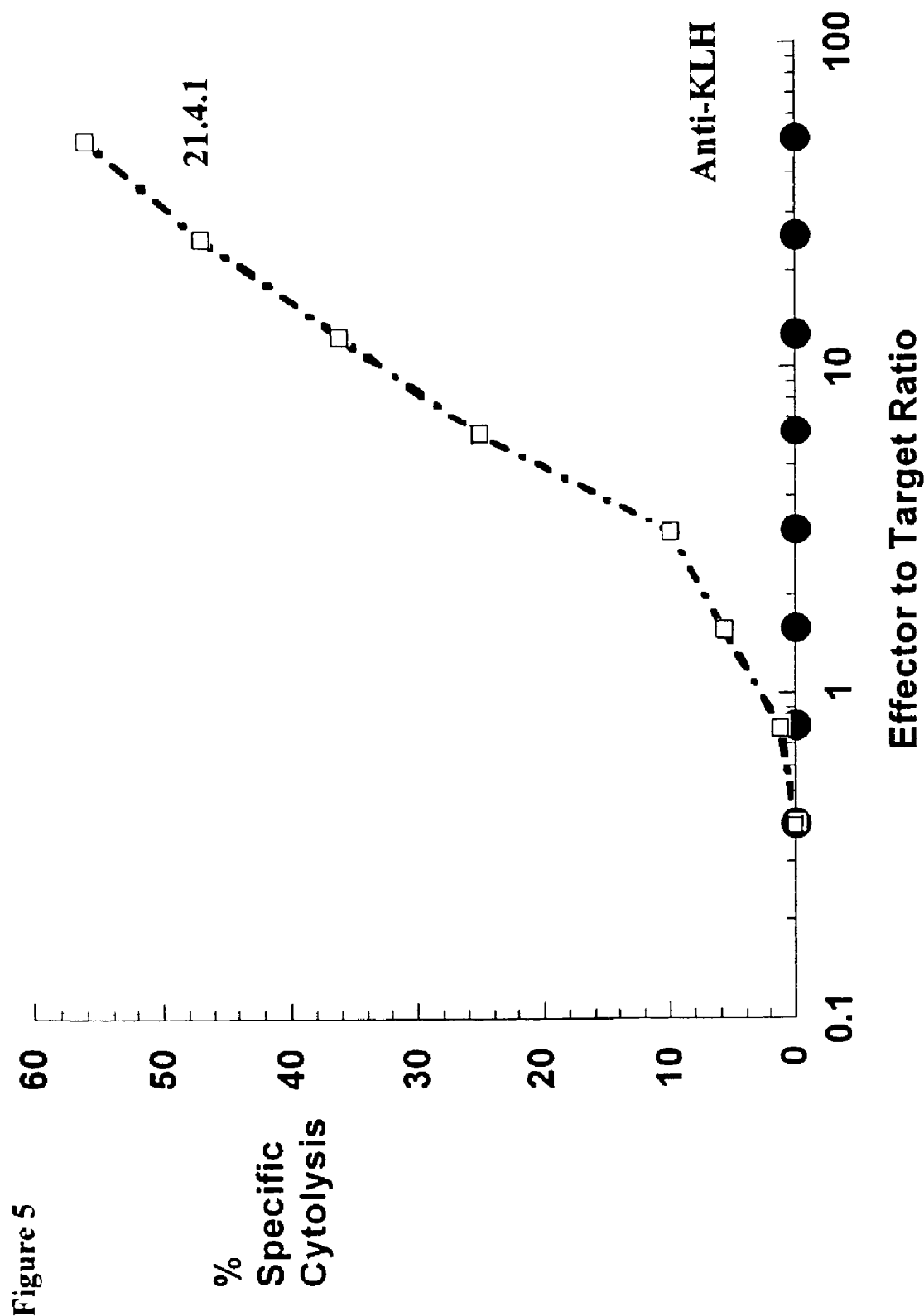
FIG. 5 is a graph that illustrates the ability of an anti-CD40 antibody of the invention (21.4.1) to increase immunogenicity of Jy stimulator cells and enhance CTL activity against Jy target cells.

As FIG. 5 illustrates, an anti-CD40 antibody of the invention (21.4.1) significantly enhanced the immunogenicity against Jy cells treated with the antibody.

EXAMPLE XI

Animal Tumor Model

To further investigate the anti-tumor activity of the anti-CD40 antibodies made in accordance with the invention, we designed a SCID-beige mouse model to test the in vivo effect of the antibody on tumor growth.

We obtained SCID-beige mice from Charles River and we allowed the mice to acclimate one week prior to use. We injected tumor cells (Daudi cells (ATCC CCL 213), CD40 (−) K$_{562}$ cells (ATCC CCL 243) and CD40(+) Raji cells (ATCC CCL 86), BT474 breast cancer cells (ATCC HTB 20) or PC-3 prostate cells (ATCC CRL 1435)) subcutaneously at a concentration of 1×10$^7$ cells/animal. In some cases, we injected T cells (5×10$^5$) and dendritic cells (1×10$^5$) from the same human donor along with the tumor cells. We also injected an anti-CD40 antibody of the invention, or an isotype matched control (anti-KLH), intraperitoneally, immediately prior to tumor injection (one injection only). We then measured tumor growth. Specific experiments are described below.

Figure 6:
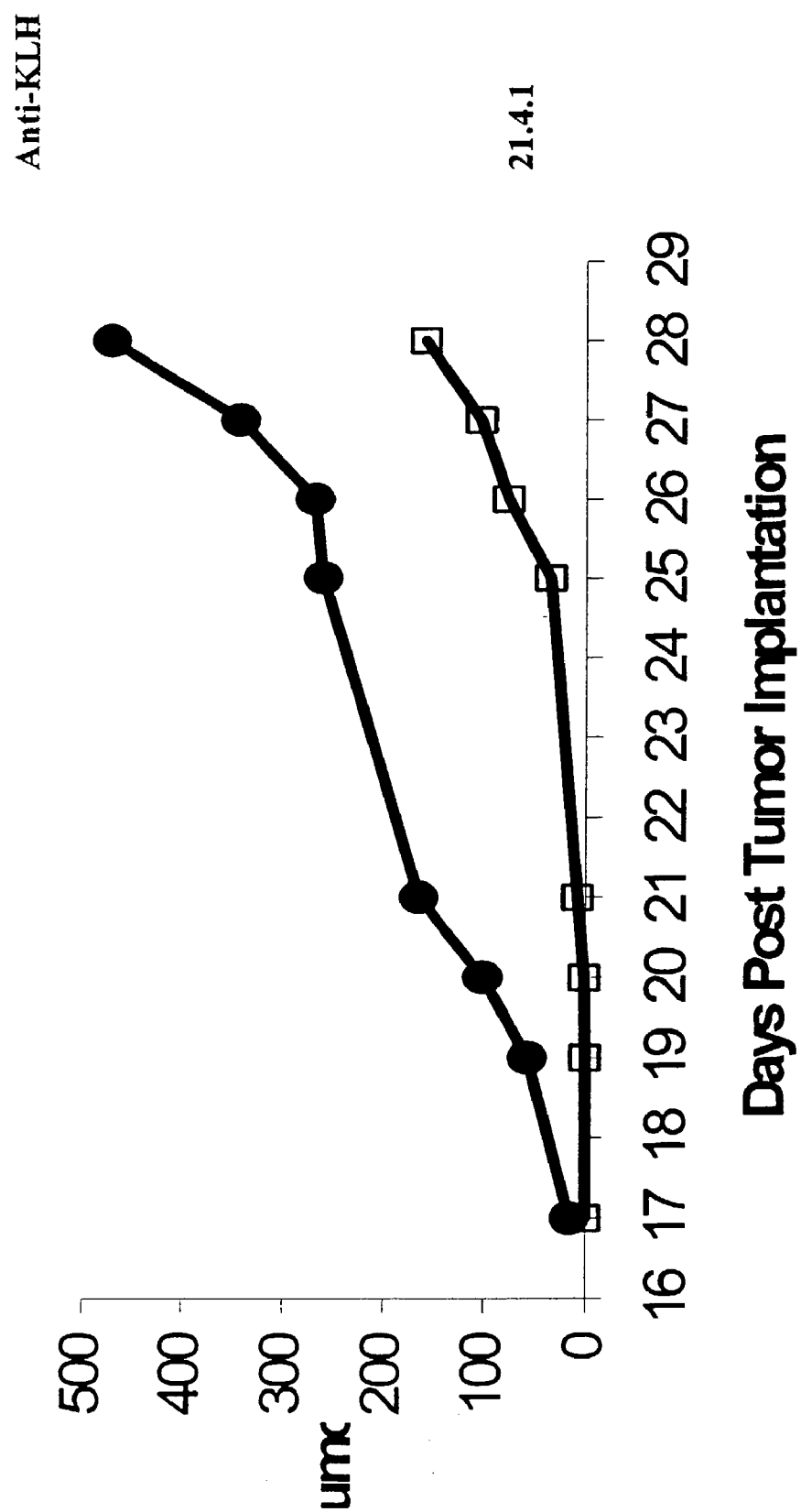
FIG. 6 is a tumor growth inhibition curve that illustrates the reduced growth of CD40 positive Daudi tumors in SCID-beige mice treated with an anti-CD40 antibody of the invention (21.4.1).

In one experiment, we injected an anti-CD40 antibody of the invention (21.4.1), or an isotype matched control (anti-KLH), intraperitoneally, at a dose of 10 mg/kg immediately prior to tumor injection (one injection only). The tumor cells (Daudi cells) were injected subcutaneously at a concentration of 1×10$^7$ cells/animal. We measured tumor growth with calipers at days 17, 19, 20, 21, 25, 26, 27 and 28 after implantation in the presence of human T cells and dendritic cells. As shown in FIG. 6, the anti-CD40 antibody inhibited tumor growth by about [60]%.

Figure 7:
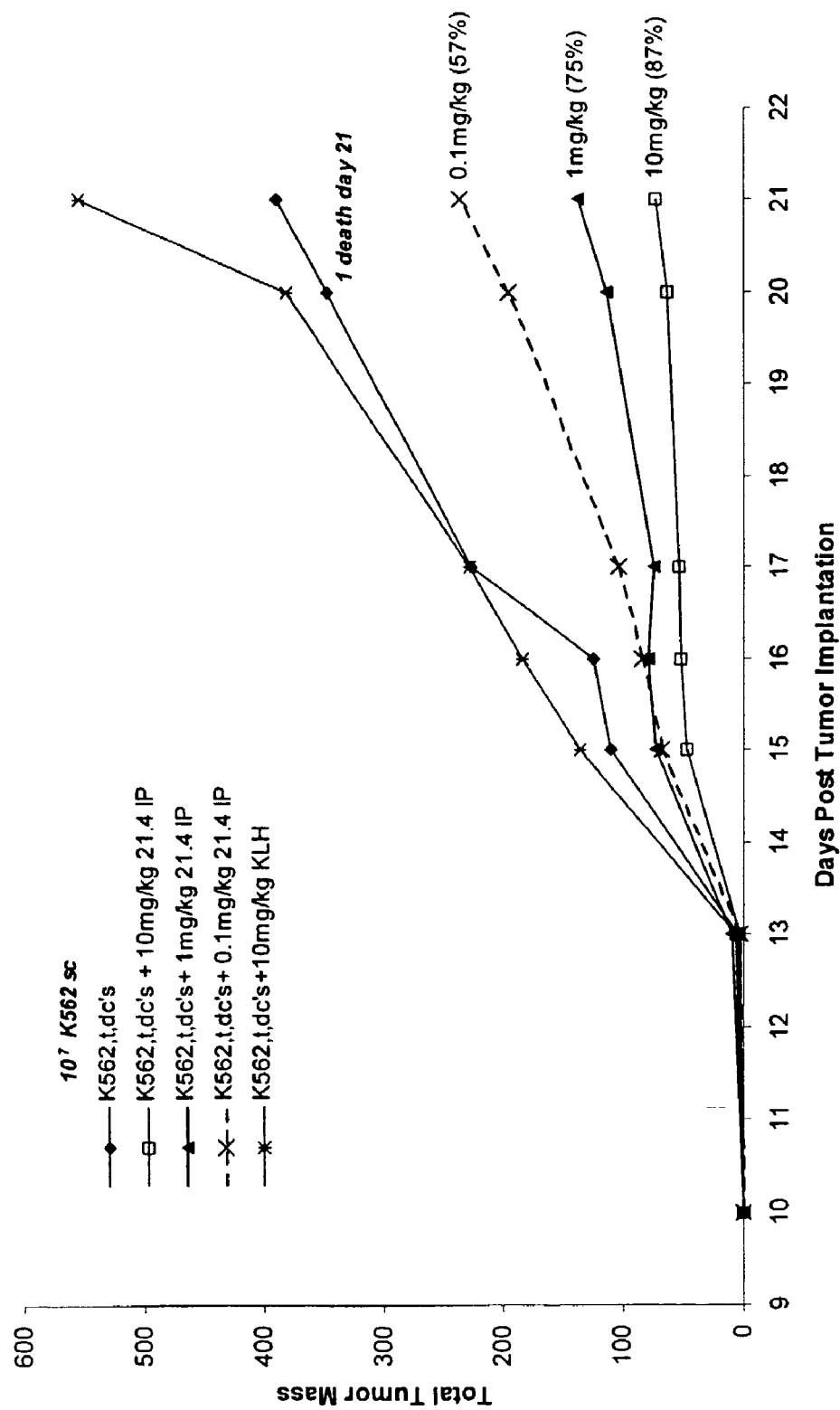
FIG. 7 is a tumor growth inhibition curve that illustrates the reduced growth of CD40 negative K562 tumors in SCID-beige mice treated with an anti-CD40 antibody of the invention (21.4.1) and human dendritic cells and T cells.

In another experiment, we injected an anti-CD40 antibody of the invention (21.4.1), or an isotype matched control (anti-KLH), intraperitoneally, at a dose of 0.1 mg/kg, 1 mg/kg or 10 mg/kg immediately prior to tumor injection (one injection only). The tumor cells (K562 cells) were injected subcutaneously at a concentration of 1×10$^7$ cells/animal. In this experiment we injected T cells (5×10$^5$) and dendritic cells (1×10$^5$) from the same human donor along with the tumor cells. We measured tumor growth with calipers at days 17, 19, 20, 21, 25, 26, 27 and 28 after implantation. As shown in FIG. 7, the anti-CD40 antibody inhibited tumor growth by 60-85%.

Figure 8:
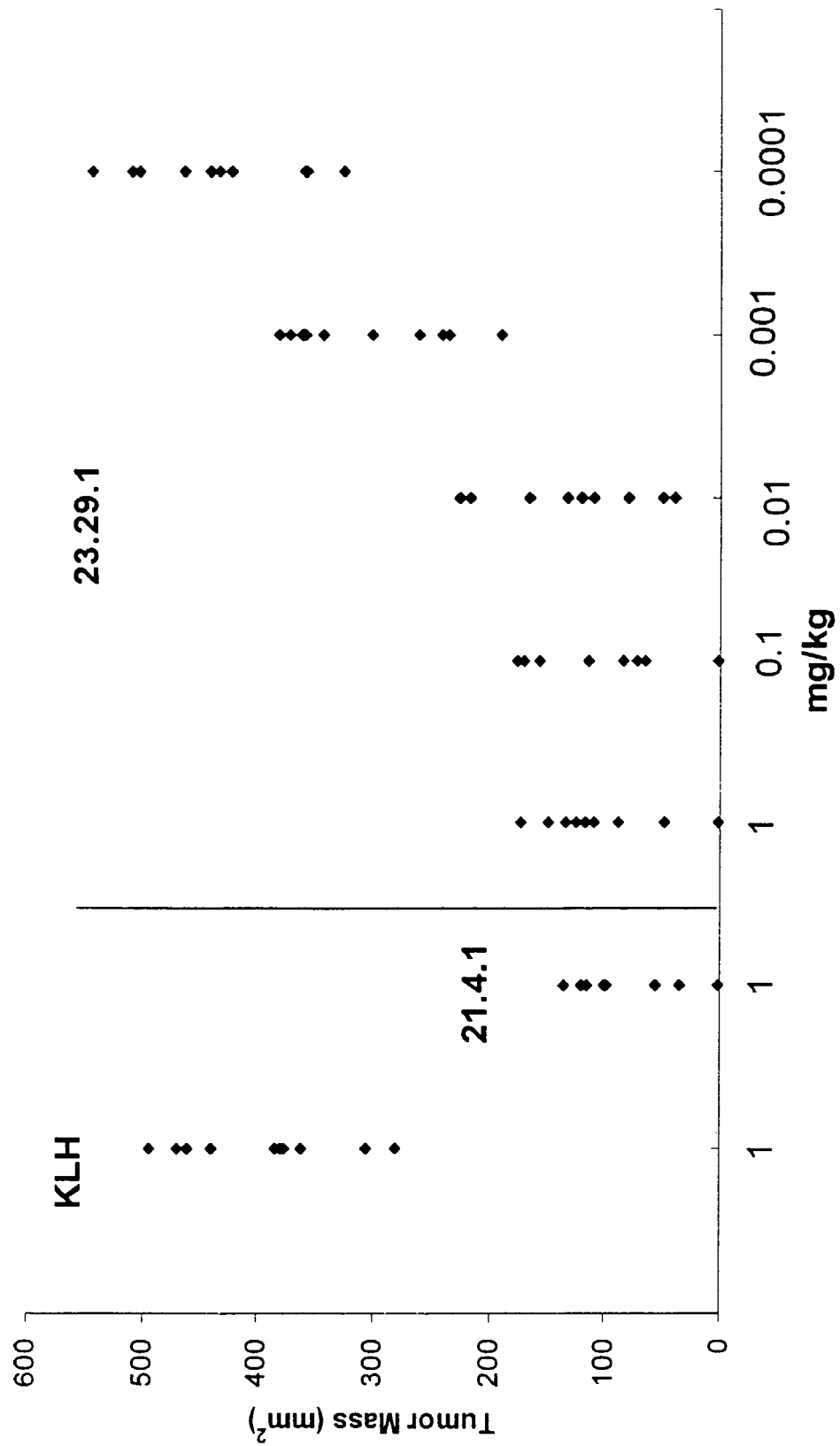
FIG. 8 shows inhibition in the growth of CD40 negative K562 tumors in SCID mice by different concentrations of anti-CD40 agonist mAb 23.29.1.
Figure 9:
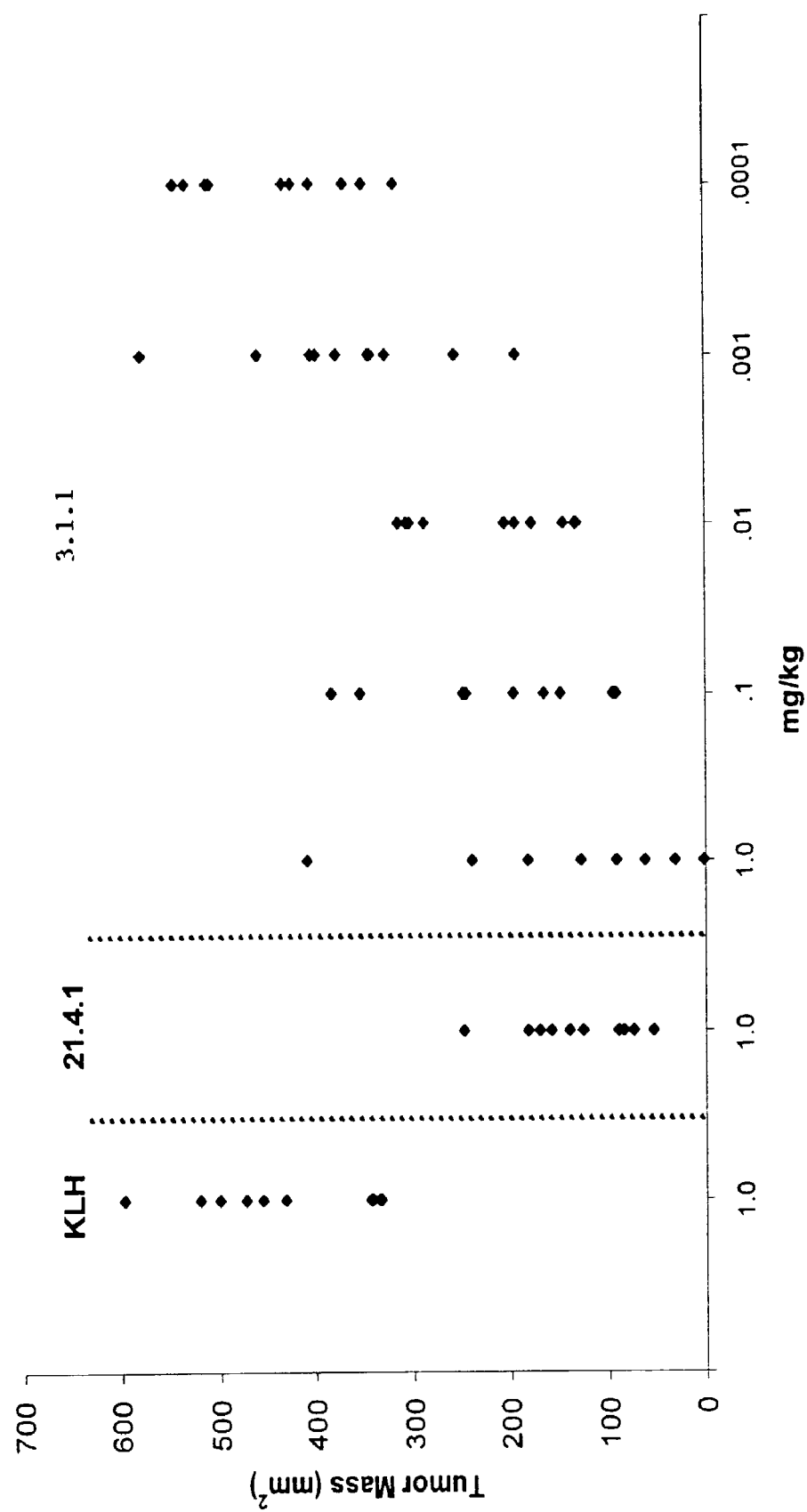
FIG. 9 shows inhibition in the growth of CD40 negative K562 tumors in SCID mice by different concentrations of anti-CD40 agonist mAb 3.1.1.

In another experiment, we injected an anti-CD40 antibody of the invention (21.4.1, 23.29.1 or 3.1.1), or an isotype matched control (anti-KLH), intraperitoneally, immediately prior to tumor injection (one injection only). The isotype matched control antibody and antibody 21.4.1 were injected at a dose of 1 mg/ml. Antibodies 23.29.1 and 3.1.1 were injected at a dose of 1, 0.1, 0.01, 0.001 or 0.0001 mg/kg. The tumor cells (K562 cells) were injected subcutaneously at a concentration of 1×10$^7$ cells/animal. In this experiment we injected T cells (5×10$^5$) and dendritic cells (1×10$^5$) from the same human donor along with the tumor cells. We then measured tumor growth with calipers at day 28 after implantation. The results of this experiment are shown in FIGS. 8 and 9. Each point in the figures represents a measurement from an individual animal.

Figure 10:
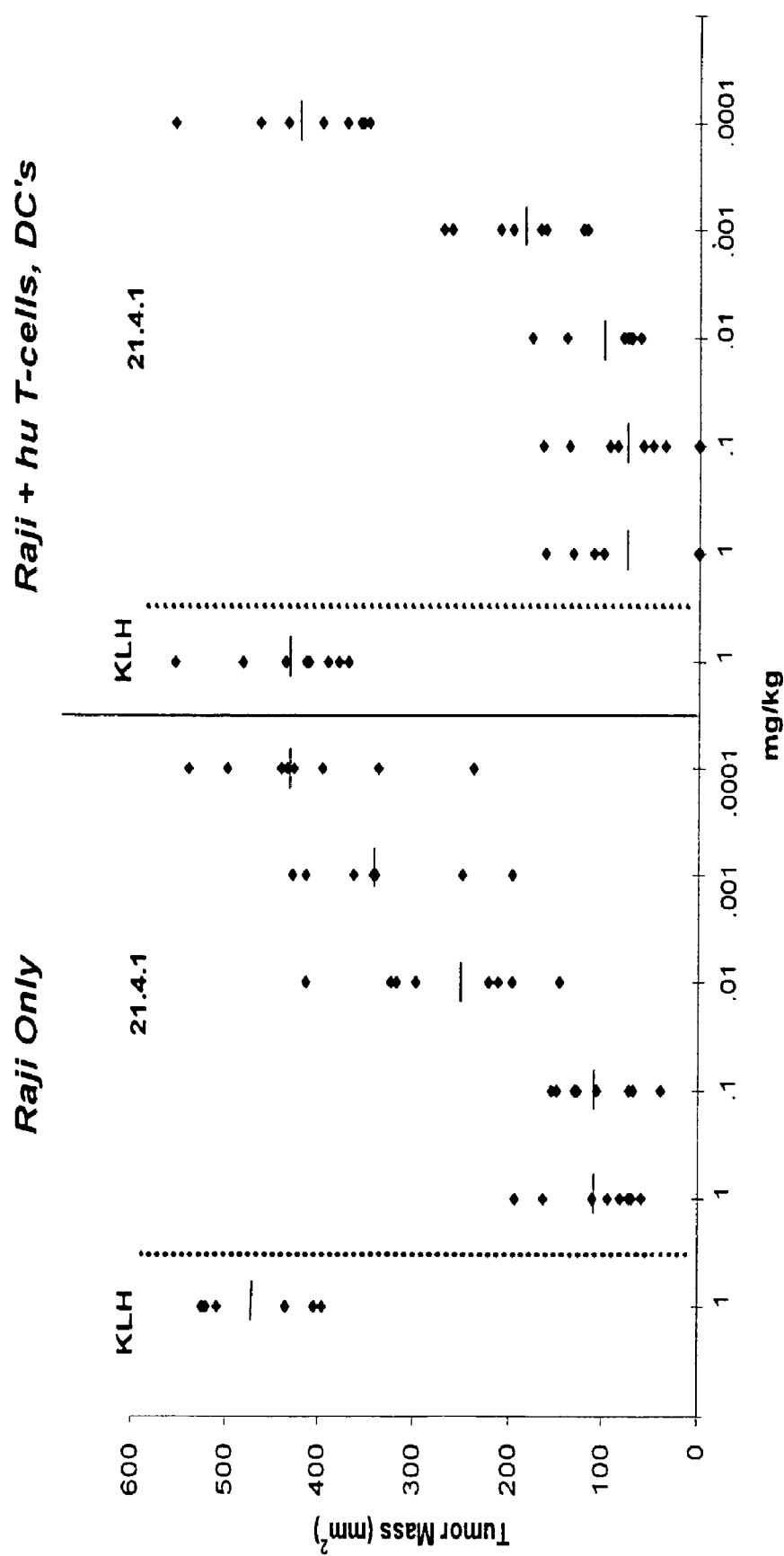
FIG. 10 shows inhibition in the growth of CD40 positive Raji tumors in the presence and absence of T cells and dendritic cells in SCID mice by an anti-CD40 agonist mAb.

In another experiment, we injected an anti-CD40 antibody of the invention (21.4.1), or an isotype matched control (anti-KLH), intraperitoneally, immediately prior to tumor injection (one injection only). The antibodies were injected at a dose of 1, 0.1, 0.01, 0.001 or 0.0001 mg/kg. The tumor cells (Raji cells) were injected subcutaneously at a concentration of 1×10$^7$ cells/animal. In some animals, we injected T cells (5×10$^5$) and dendritic cells (1×10$^5$) from the same human donor along with the tumor cells. We then measured tumor growth with calipers at day 28 after implantation. The results of this experiment are shown in FIG. 10. Each point in the figure represents a measurement from an individual animal.

Figure 11:
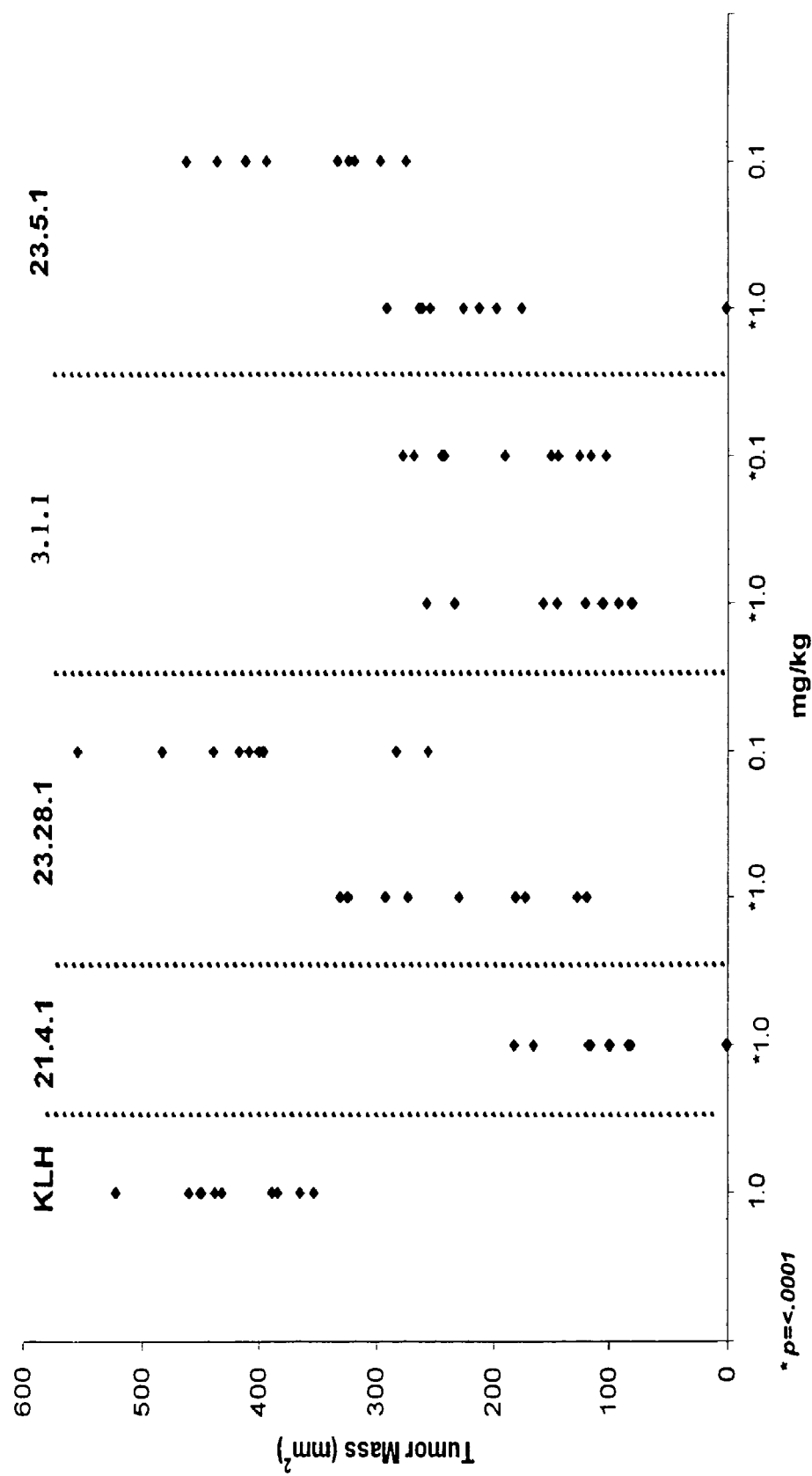
FIG. 11 shows inhibition in the growth of CD40 positive Raji tumors in SCID mice by anti-CD40 agonist antibodies.

In yet another experiment, we injected an anti-CD40 antibody of the invention (21.4.1, 23.28.1, 3.1.1 or 23.5.1), or an isotype matched control (anti-KLH), intraperitoneally, immediately prior to tumor injection (one injection only). The antibodies were injected at a dose of 1 or 0.1 mg/kg. The tumor cells (Raji cells) were injected subcutaneously at a concentration of $1 \times 10^7$ cells/animal. We then measured tumor growth with calipers at day 28 after implantation. The results of this experiment are shown in FIG. 11. Each point in the figure represents a measurement from an individual animal.

Figure 12:
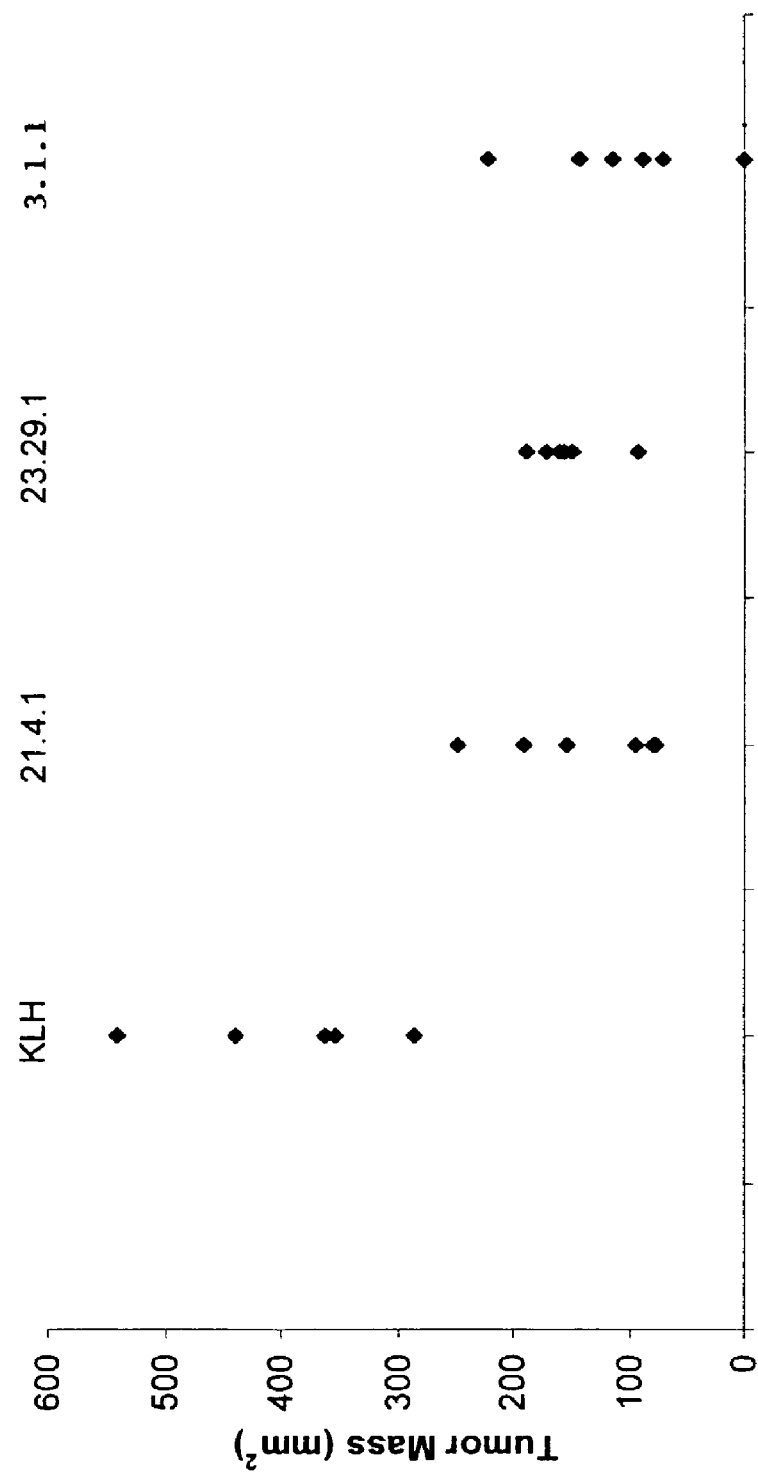
FIG. 12 shows inhibition in the growth of BT 474 breast cancer cells in SCID-beige mice by anti-CD40 agonist antibodies.

In yet another experiment, we injected an anti-CD40 antibody of the invention (21.4.1, 23.29.1, or 3.1.1), or an isotype matched control (anti-KLH), intraperitoneally, immediately prior to tumor injection (one injection only). The antibodies were injected at a dose of 1 mg/kg. The tumor cells (BT474 breast cancer cells) were injected subcutaneously at a concentration of $1 \times 10^7$ cells/animal. We injected T cells ($5 \times 10^5$) and dendritic cells ($1 \times 10^5$) from the same human donor along with the tumor cells. We then measured tumor growth with calipers at day 39 after implantation. As shown in FIG. 12, all of the antibodies inhibited breast cancer tumor growth. Each point in the figure represents a measurement from an individual animal.

Figure 13:
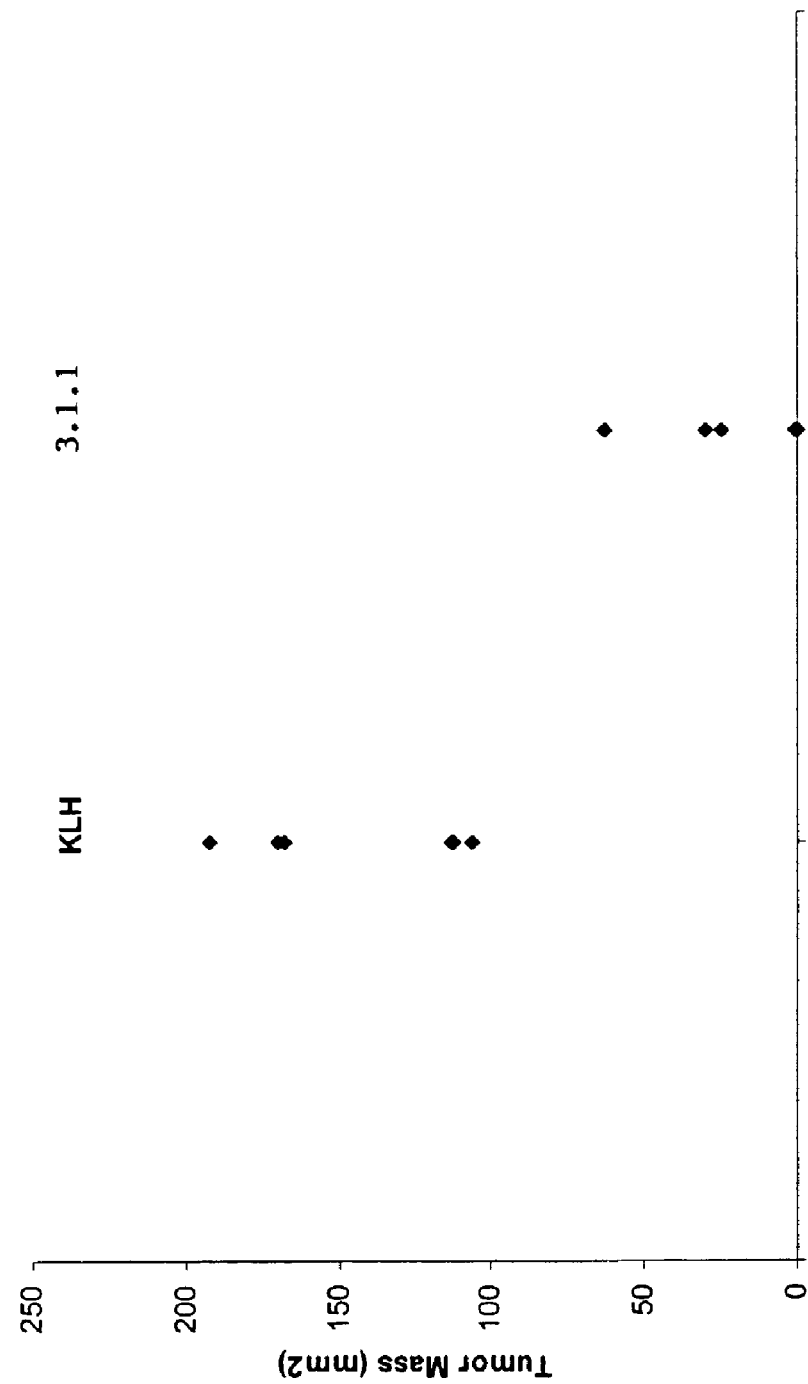
FIG. 13 shows inhibition in the growth of PC-3 prostate tumors in SCID-beige mice by anti-CD40 agonist antibodies.

In yet another experiment, we injected an anti-CD40 antibody of the invention (3.1.1), or an isotype matched control (anti-KLH), intraperitoneally, immediately prior to tumor injection (one injection only). The antibodies were injected at a dose of 1 mg/kg. The tumor cells (PC-3 prostate tumor cells) were injected subcutaneously at a concentration of $1 \times 10^7$ cells/animal. We then measured tumor growth with calipers at day 41 after implantation. As shown in FIG. 13, the anti-CD40 antibody inhibited prostate tumor growth by about 60%. Each point in the figure represents a measurement from an individual animal.

EXAMPLE XII

Figure 14:
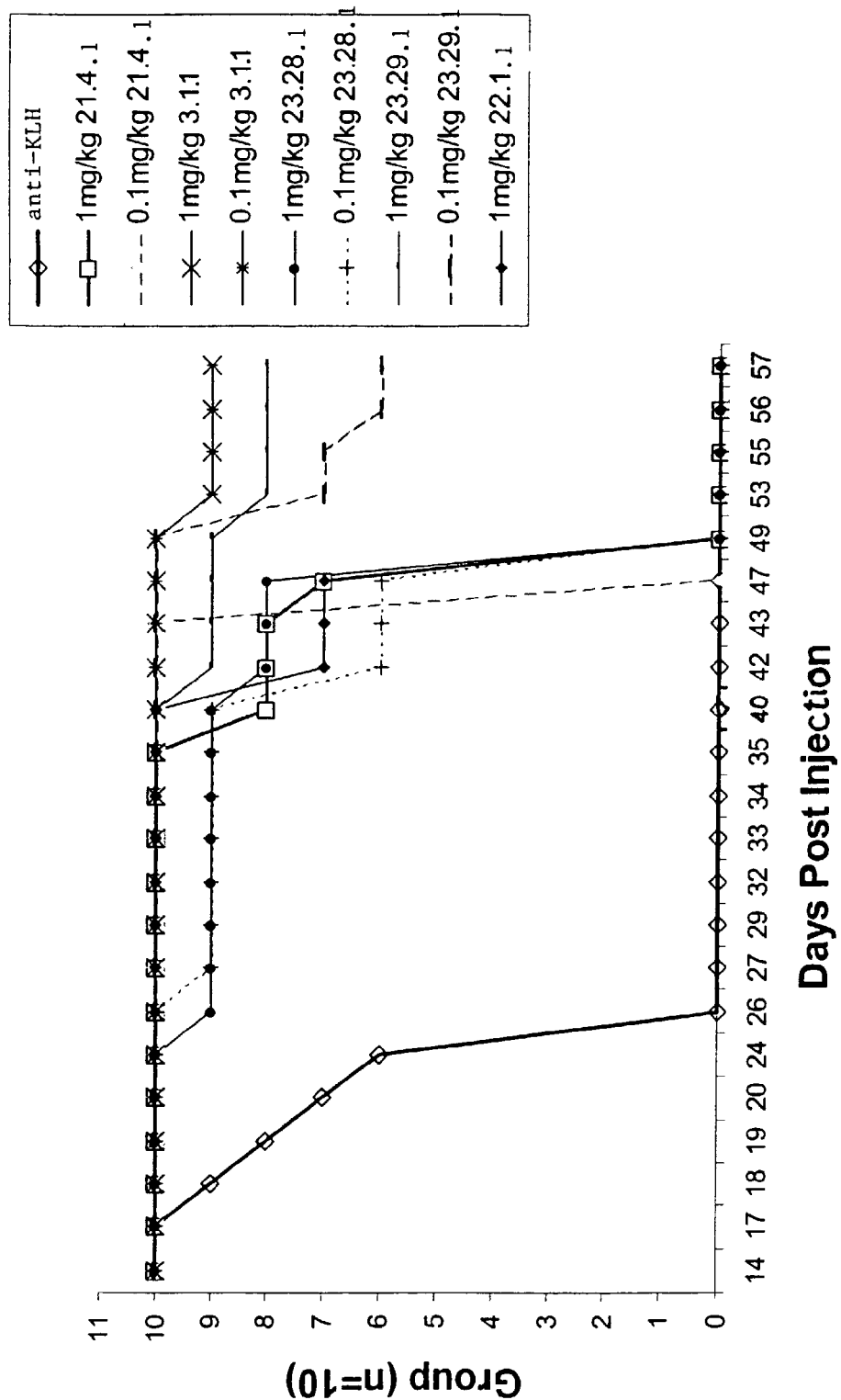
FIG. 14 is a survival curve for SCID-beige mice injected (iv) with Daudi tumor cells and treated with anti-CD40 agonist antibodies.

Survival of SCID-Beige Mice Injected with Daudi Tumor Cells and Treated with the Anti-CD40 Antibodies of the Invention In another experiment, we injected an anti-CD40 antibody of the invention, or an isotype matched (one injection) control, intraperitoneally, immediately prior to tumor injection. The antibodies were injected at a dose of 1 or 0.1 mg/kg. The tumor cells (Daudi cells) were injected intravenously at a dose of $5 \times 10^6$ cells/animal. We then monitor animal survival. As shown in FIG. 14, all of the anti-CD40 antibodies tested prolonged the survival of mice injected tumors by at least six days.

Table 31 lists the $ED_{50}$ of the anti-CD40 antibodies in the different solid tumor models described in Example XI. Table 31 summarizes the in vivo anti-tumor activity of some of the anti-CD40 antibodies of the invention in SCID mice. In addition, the table lists the $ED_{50}$ of the anti-CD40 antibodies in the Daudi systemic tumor model described above in Example XII.

TABLE 31

$ED_{50}$ Of Anti-CD40 Antibodies Of The Invention Using Different In Vivo Tumor Models in SCID mice

| Antibody | CD40(−) K562 & T/DC sub-cutaneous (mg/kg) | CD40(+) Raji & T/DC sub-cutaneous (mg/kg) | CD40(+) Raji sub-cutaneous (mg/kg) | CD40(+) Daudi intra-venous (mg/kg) |
|---|---|---|---|---|
| 21.4.1 | 0.005 | 0.0008 | 0.016 | 0.1 |
| 22.1.1 | 0.01 | ND | >1.0 | 0.1 |
| 23.25.1 | ≧1.0 | ND | >1.0 | ND |
| 23.5.1 | >1.0 | ND | ≧1.0 | ND |
| 24.2.1 | >1.0 | ND | >1.0 | ND |
| 3.1.1 | 0.02 | ND | ≧0.1 | ≦0.1 |
| 23.28.1 | >1.0 | ND | ≧1.0 | 0.1 |
| 23.29.1 | 0.009 | ND | >1.0 | ≦0.1 |
| 21.2.1 | ≦1.0 | ND | ND | ND |

ND = Not Done

EXAMPLE XIII

Determination of Affinity Constants ($K_D$) of Fully Human Anti-CD40 Antibodies by BIAcore We performed affinity measures of purified antibodies by surface plasmon resonance using the BIAcore 3000 instrument, following the manufacturer's protocols.

The Biosensor biospecific interaction analysis instrument (BIAcore) uses surface plasmon resonance to measure molecular interactions on a CM5 sensor chip. Changes in the refractive indices between two media, glass and carboxymethylated dextran, caused by the interaction of molecules to the dextran side of the sensor chip, is measured and reported as changes in arbitrary reflectance units (RU) as detailed in the manufacturer's application notes.

The carboxymethylated dextran surface of a flow cell on a sensor chip was activated by derivatization with 0.05 M N-hydroxysuccinimide mediated by 0.2 M N-ethyl-N'-(dimethylaminopropyl) carbodiimide for 7 min. CD40-Ig fusion protein (described in Example I) at a concentration of 5 µg/ml, in 10 mM Na acetate, pH 3.5, was manually injected into the flow cell at a rate of 5 µl/min and covalently immobilized to the flow cell surface with the desired amount of RU's. Deactivation of unreacted N-hydroxysuccinimide esters was performed using 1 M ethanolamine hydrochloride, pH 8.5. Following immobilization, the flow cells are cleaned of any unreacted or poorly bound material with 5 regeneration injections of 5 µl of 50 mM NaOH until a stable baseline is achieved. Flow cell 2, a high density surface, measured approximately 300 RU's following surface preparation and flow cell 3, a low density surface, measured approximately 150 RU's. For flow cell 1, the activated blank surface, 35 µl of 10 mM Na acetate buffer was injected during immobilization in place of antigen. Flow cell 4 contained approximately 450 RU's of immobilized CTLA4-Ig, an irrelevant antigen control.

A dilution series of each antibody was prepared in the concentration range of 100 µg/ml to 0.1 µg/ml by half logs. The flow rate was set at 5 µl/min and 25 µl of each concentration point sample was injected over the sensor chip with a regeneration injection of 5 µl of 50 mM NaOH between each concentration of antibody injected. The data was analyzed using BIAevaluation 3.0 software.

In reverse orientation kinetic experiments, the antibody 21.4.1 was immobilized to the sensor chip surface using the protocol described above. Anti-KLH was used as a control antibody surface. The antigen, CD40-Ig fusion protein, was injected in the concentration range of 100 µg/ml to 0.1 µg/ml.

Table 32 lists affinity measurements for representative anti-CD40 antibodies of the present invention:

TABLE 32

Affinity Measurements For Anti-CD40 Antibodies Of The Invention

| Antibody | $K_{on}$ (1/Ms) | $K_{off}$ (1/s) | $K_D$ (M) |
|---|---|---|---|
| 3.1.1 | $1.12 \times 10^{6}$ | $3.31 \times 10^{-5}$ | $3.95 \times 10^{-11}$ |
| 10.8.3 | $2.22 \times 10^{5}$ | $4.48 \times 10^{-7}$ | $2.23 \times 10^{-12}$ |
| 15.1.1 | $8.30 \times 10^{4}$ | $2.83 \times 10^{-7}$ | $4.05 \times 10^{-12}$ |
| 21.4.1 | $8.26 \times 10^{4}$ | $2.23 \times 10^{-5}$ | $3.48 \times 10^{-10}$ |
| 22.1.1 | $9.55 \times 10^{5}$ | $1.55 \times 10^{-4}$ | $2.79 \times 10^{-10}$ |
| 23.25.1 | $3.83 \times 10^{5}$ | $1.65 \times 10^{-7}$ | $7.78 \times 10^{-12}$ |
| 23.28.1 | $7.30 \times 10^{5}$ | $8.11 \times 10^{-5}$ | $1.61 \times 10^{-10}$ |
| 23.29.1 | $3.54 \times 10^{5}$ | $3.90 \times 10^{-5}$ | $7.04 \times 10^{-11}$ |

EXAMPLE XIV

Epitope Mapping of Anti-CD40 Antibodies

The binding assays were done using Protein A purified CD40-human IgG1 Fc fusion antigen. The human CD40-IgG1 Fc fusion protein was cloned at Pfizer. The human CD40-IgG1 fusion protein was expressed in a mammalian cell line and purified over Protein A column. The purity of the fusion antigen was assessed by SDS/PAGE.

CD40 has a structure of a typical type I transmembrane protein. The mature molecule is composed of 277 amino acids. The extracellular domain of CD40 consists of four TNFR-like cysteine rich domains. See, e.g., Neismith and Sprang, TIBS 23:74-79 (1998); van Kooten and Banchereau, J. Leukocyte Biol. 67:2-17 (2000); Stamenkovic et al., EMBO J. 8:1403-1410(1989).

Binding of Anti-CD40 Antibodies to Reduced and Non-Reduced Human CD40:

Because the extracellular domain of CD40 consists of four cysteine rich domains, disruption of the intramolecular bonds, by reducing agent, can change antibody reactivity. To determine whether disruption of the intramolecular bonds, by reducing agent, changed the reactivity of selected anti-CD40 antibodies of the invention, purified CD40-hIgG was loaded on SDS/PAGE (4-20% gel) under non-reducing (NR), or reducing (R), conditions. SDS/PAGE was performed by the method of Laemmli, using a mini-gel system. Separated proteins were transferred on to nitrocellulose membrane. Membranes were blocked using PBS containing 5% (w/v) non fat dried milk for at least 1 hour before developing, and probed for 1 hr with each antibody. Anti-CD40 antibodies were detected using HRP-conjugated goat anti-human immunoglobulins (1:8,000 dilution; Catalog No. A-8667 from Sigma). Membranes were developed by using enhanced Chemiluminescence (ECL®; Amersham Bioscience) according to the manufacturer's instructions.

Figure 15:
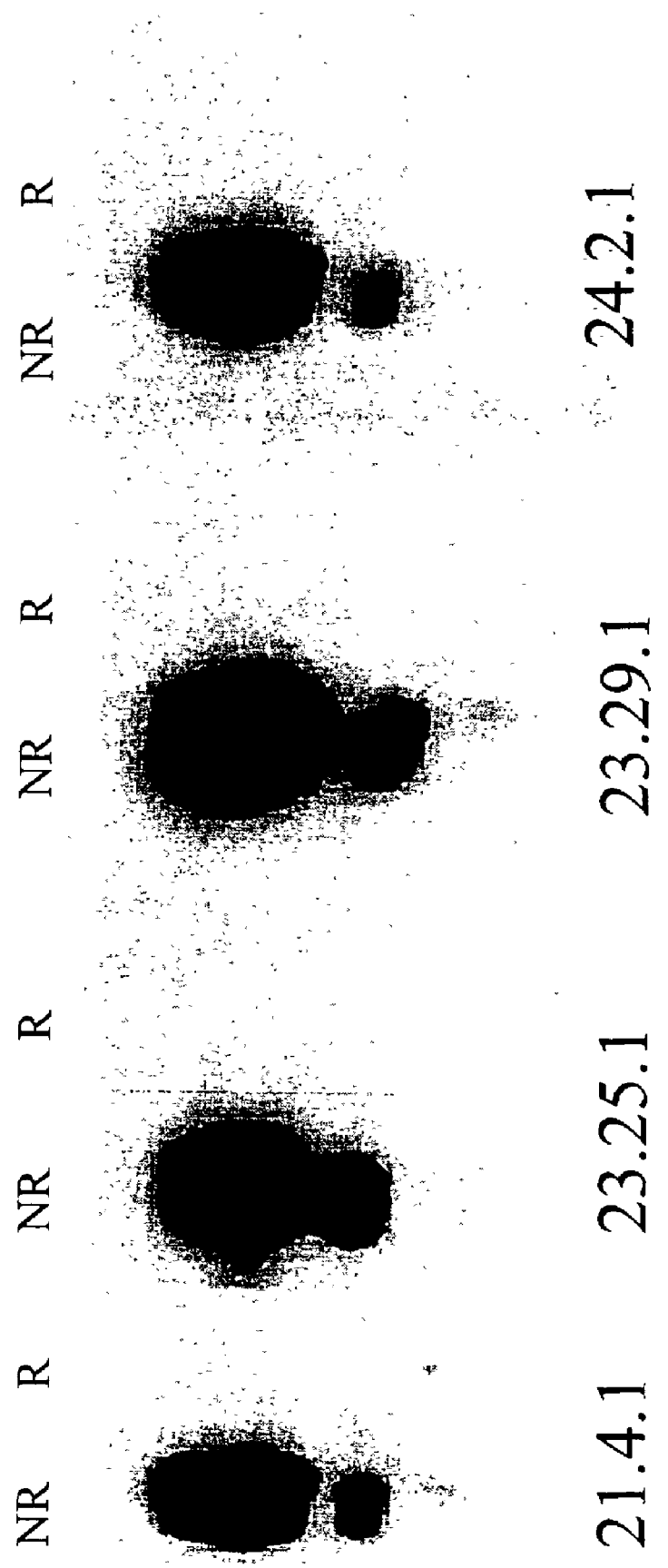
FIG. 15 is a Western blot analysis of anti-CD40 agonist antibodies to reduced (R) and non-reduced (NR) human CD40.

The Western Blot was then probed with four anti-CD40 antibodies of the invention: 21.4.1, 23.25.1, 23.29.1 and 24.2.1 (1 µg/ml,) followed by HRP conjugated goat anti-human IgG (1:8000 dilution). The results of this experiment are show in FIG. 15. The results indicate that antibodies 21.4.1, 23.25.1, 23.29.1 and 24.2.1 bind non-reduced but do not bind reduced CD40, the antibodies, thus, recognize a conformational epitope.

Binding of Anti-CD40 Antibodies to Human CD40 Domain Deleted Proteins:

The extracellular region of CD40 includes four TNFR-like repeat domains (referred to as D1-D4). See, e.g., Neismith and Sprang, TIBS 23:74-79 (1998); van Kooten and Banchereau, J. Leukocyte Biol. 67:2-17 (2000); Stamenkovic et al., EMBO J. 8:1403-1410(1989). FIG. 16 shows the amino acid sequences of the mouse and human CD40 domains D1-D4. To investigate the contribution of different regions of the CD40 molecule in the presentation of the epitope, a number of domain deleted mutants were constructed.

To make the human CD40 deletion constructs, the entire extracellular domain of human CD40 (amino acids 1-193) was amplified from human B cells (CD19+) cDNA (Multiple tissue cDNA panels, Catalog No. K1428-1, from Clontech) by PCR using sequence specific primers, and a 6×His-tag was added at the C-terminal. A human CD405' primer 5'-GCAAGCTTCACCAATGGT TCGTCTGCCTCTG-CAGTG-3' (SEQ ID NO: 135) was used with different combination of 3' primers for cloning of full length and truncated CD40 molecules. The 3' primer for cloning the full-length extracellular domain of human CD40 was: 5'-TCAGTGATGGTGATGGTGATGTCTCAGCCGAT CCTGGGGACCA-3' (SEQ ID NO: 136). The 3' primer used to clone the D1-D3 domains of human CD40 was: 5'-TCAGTGATGGTGATGGTGATGTGGGCA GGGCTCGCGATGGTAT-3' (SEQ ID NO: 137) The 3' primer used to clone the D1-D2 domains of CD40 was: 5'-TCAGTGATGGTGATGGTGATGA CAGGTGCA-GATGGTGTCTGTT-3' (SEQ ID NO: 138). After these constructs of truncated CD40 cDNA were generated, they were expressed in the 293F cell line using the pCR3.1 vector (Invitrogen). The CD40-6xH is fusion proteins (SEQ ID NOS 139-141) were purified by elution from a nickel column.

The amino acid sequences of these four deletion mutants are shown in Table 33.

TABLE 33

CD40 His-Tag Fusion Proteins

| Deletion Mutant: | Amino Acid Sequence (leader sequence underlined) | |
|---|---|---|
| Human CD40-6XHis (full length extra-cellular domain)- | MVRLPLQCVLWGCLLTAVHPEPPTACREKQYLNS QCCSLCQPGQKLVSDCTEFTETECLPC GESEFLDTWNRETHCHQHKYCDPNLGLRVQQKGT SETDTICTCEEGWHCTSEACESCVLHRS | (SEQ ID NO:139) |

TABLE 33-continued

CD40 His-Tag Fusion Proteins

| Deletion Mutant: | Amino Acid Sequence (leader sequence underlined) | |
|---|---|---|
| | CSPGFGVKQJATGVSDTICEPCPVGFFSNVSSAFEK | |
| | CHPWTSCETKDLVVQQAGTNKTDVVC | |
| | GPQDRHHHHHH | |
| Human CD40 (D1-D3)-6xHis | MVRLPLQCVLWGCLLTAVHPEPPTACREKQYLINS | (SEQ ID NO:140) |
| | QCCSLCQPGQKIVSDCTEFTETECLPC | |
| | GESEFLDTWNRETHCHQHKYCDPNLGLRVQQKGT | |
| | SETDTICTCEEGWHCTSEACESCVLHRS | |
| | CSPGFGVKQIATGVSDTICEPCPHHHHHH | |
| Human CD40 (D1-D2)-6Xhis | MVRLPLQCVLWGCLLTAVHPEPPTACREKQYLINS | (SEQ ID NO:141) |
| | QCCSLCQPGQKLVSDCTEFTETECLPC | |
| | GESEFLDTWNRETHCHQHKYCDPNLGLRVQQKGT | |
| | SETDTICTCHHHHHH | |

To express these human CD40 deletion constructs, the constructs were cloned into the pCR3.1 vector (Invitrogen) and expression was assessed in various stable and transiently transfected 293F cell lines. The supernatants from transiently transfected 293F cells were analyzed for binding to antibodies 21.4.1, 23.25.1, 23.29.1 and 24.2.1 by ELISA and Western Blot.

ELISA assays were preformed using supernatant from 293F cells transfected with different CD40 constructs. ELISA plates were coated goat anti-human CD40 polyclonal antibodies (R&D catalog No. AF 632) or goat anti-mouse CD40 polyclonal antibodies (R&D catalog No. AF 440) diluted to 1 µg/ml in ELISA plate coating buffer. Expression of CD40 constructs in 293F cells was confirmed by detection with biotinylated goat anti-human CD40 (R&D catalog No. BAF 632), goat anti-mouse CD40 (R&D catalog No. BAF 440), or HRP-conjugated anti-H is (C terminal) antibody (Invitrogen, Catalog No. 46-0707). Binding of anti-CD40 human antibodies were detected with HRP conjugated goat anti-human IgG (FC specific Caltag H10507), diluted 1:2,000. The results, as shown in Table 34, indicate that most if not all of the epitope recognized by mAbs 21.4.1, 23.28.1 and 23.29.1 is located in the D1-D2 region of CD40 while the epitope for mAb 24.2.1 is located at least partly in domain D3-D4. A human CD40-rabbit Fc fusion protein was used a control to confirm the specificity of the antibody binding.

TABLE 34

ELISA: Antibody Binding To CD40 Deletion Mutants

| | Human CD40 (D1-D2)-6Xhis | Human CD40 (D1-D3)-6XHis | Human CD40-6XHis |
|---|---|---|---|
| 21.4.1 | + | + | + |
| 23.25.1 | + | + | + |
| 23.29.1 | + | + | + |
| 24.2.1 | − | + | + |

TABLE 34-continued

ELISA: Antibody Binding To CD40 Deletion Mutants

| | Human CD40 (D1-D2)-6Xhis | Human CD40 (D1-D3)-6XHis | Human CD40-6XHis |
|---|---|---|---|
| anti-His | + | + | + |
| anti-RbIg | ND | ND | ND |

The CD40 deletion constructs also were analyzed by Western Blot analysis. The results are shown in Table 35. The ELISA results show that the binding site of antibodies 21.4.1, 23.25.1, 23.29.1 and 24.2.1 involves domains D1-D3. The results also show that the binding site for antibodies 21.4.1, 23.25.1 and 23.29.1 involve domains D1-D2, and that the binding site of antibody 24.2.1 involves domain D3.

TABLE 35

Western Blot: Antibody Binding To CD40 Deletion Mutant

| | Human CD40(D1-D3)-6Xhis | Human CD40-6Xhis |
|---|---|---|
| 21.4.1 | + | + |
| 23.25.1 | + | + |
| 23.29.1 | + | + |
| 24.2.1 | + | + |
| anti-His | + | + |
| Anti-RbIg | ND | ND |

Binding of Anti-CD40 Antibodies to Mouse CD40:

We set out to determine the ability of antibodies 21.4.1, 23.25.1, 23.29.1 and 24.2.1 to bind mouse CD40.

For this experiment, mouse CD40 was amplified from mouse B cells cDNA. Mouse CD40(D1-D3)-6xH is fusion protein was cloned into pCR3.1, which utilizes the CMV promoter, to drive transcription. The 5' primer used to clone the extracellular domain of the mouse CD40 was: 5'-TG- CAAGCTTCACCATGGTGTCTTTGCCTCGGCTGTG-3' (SEQ ID NO: 146). The 3' primer used to clone the D1-D3 domains of mouse CD40 was: 5'-GTCCTCGAGTCAGT-GATGGTGATGGTGATGTGGGCAGGGATGACAGAC-3' (SEQ ID NO: 147). Mouse and human cDNA constructs were transfected into 293F cells transiently. The expression of recombinant CD40 was detected by ELISA using polyclonal antibodies against mouse and human CD40, anti-H is antibodies, and anti-CD40 antibodies 21.4.1, 23.25.1, 23.29.1 and 24.2.1. The results of these experiments are shown in Table 36. This experiment shows that all antibodies are specific to human CD40 and do not cross react with mouse CD40.

TABLE 36

Cross-Reactivity of Mouse and Human CD40

| | Mouse CD40(D1-D3)-6Xhis | Human CD40(D1-D3)-6XHis |
|---|---|---|
| 21.4.1 | No | Yes |
| 23.25.1 | No | Yes |
| 23.29.1 | No | Yes |
| 24.2.1 | No | Yes |
| goat anti-human CD40 | No | Yes |
| goat anti-mouse CD40 | Yes | No |
| Anti-His | Yes | Yes |

Binding of Anti-CD40 Antibodies to of Human/Mouse Chimeric CD40:

Because antibodies 21.4.1, 23.25.1, 23.29.1 and 24.2.1 do not bind mouse CD40, we constructed human/mouse chimeric CD40 proteins to more definitively map the epitopes of those antibodies.

For the construction of in-frame fusions of the human and murine CD40 chimeric proteins, we used unique restriction sites at the borders of CD40 domains at identical positions in the cDNA of both human and mouse CD40. Various cDNA constructs of CD40 were generated using the EcoRI restriction site at the end of domain 1 (nucleotide 244, amino acid 64) and the BanI restriction site at the end of domain 2 (nucleotide 330, amino acid 94) (FIG. 17).

Figure 18:
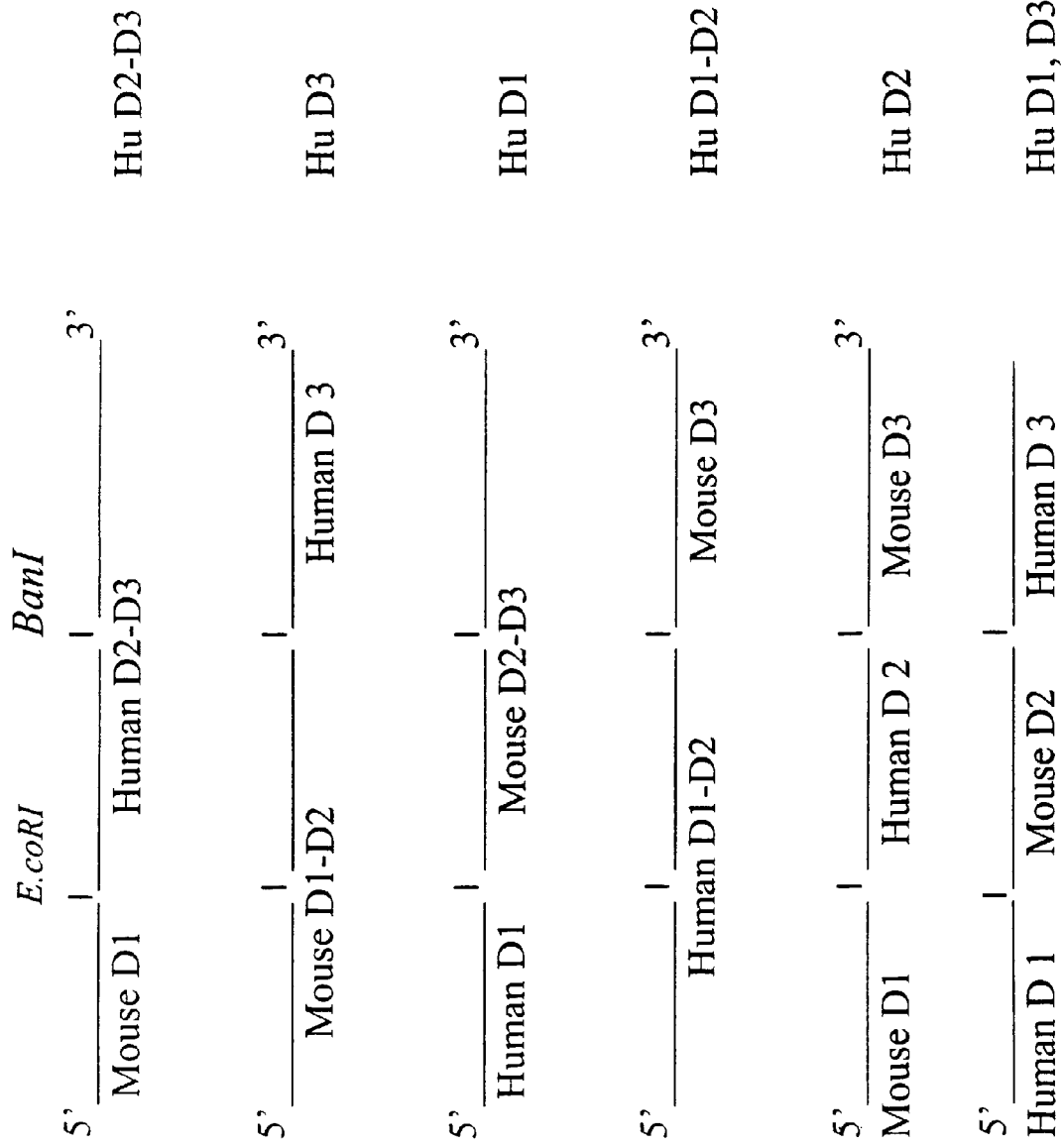
FIG. 18 is a group of schematic diagrams of the chimeric CD40 constructs.

Various CD40 domains were amplified by PCR and ligated. This approach allowed the replacement of various domains of the mouse CD40 by the homologous domains from the human CD40. The constructs obtained are shown in FIG. 18.

We then determined whether antibodies 21.4.1, 23.25.1, 23.29.1 and 24.2.1 were able to bind the mouse/human chimeric CD40 proteins by ELISA. The results of this experiment are shown in Table 37. As shown in Table 37, mAbs 21.4.1 and 23.25.1 recognize and epitope that is located partly in D1 and partly in D2; mAb 23.29.1 recognizes an epitope located mostly if not completely in D2; and mAb 24.2.1 recognizes an epitope located in D2 and D3.

TABLE 37

Antibody Binding to Chimeric CD40 Proteins

| Antibody | HuD1 | HuD2 | HuD3 | HuD1, D2 | HuD2, D3 | HuD1, D3 |
|---|---|---|---|---|---|---|
| 21.4.1 | No | No | No | Yes | No | No |
| 23.25.1 | No | No | No | Yes | No | No |
| 23.29.1 | No | Yes | No | Yes | Yes | No |
| 24.2.1 | No | No | No | No | Yes | No |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the invention.

What is claimed is:

1. A monoclonal antibody or an antigen-binding portion thereof that specifically binds to and activates human CD40, wherein said antibody or portion comprises:
   (a) a heavy chain CDR1 amino acid sequence, CDR2 amino acid sequence, and CDR3 amino acid sequence, respectively, of amino acid residues 26-35, 50-66, and 99-115 of SEQ ID NO: 42; and
   (b) a light chain CDR1 amino acid sequence, CDR2 amino acid sequence, and CDR3 amino acid sequence, respectively, of amino acid residues 24-34, 50-56, and 89-97 of SEQ ID NO: 44.

2. A monoclonal antibody or an antigen-binding portion thereof that specifically binds to and activates human CD40, wherein said antibody or portion comprises:
   (a) the light chain variable region amino acid sequence of SEQ ID NO: 44; and
   (b) the heavy chain variable region amino acid sequence of SEQ ID NO: 42.

3. The monoclonal antibody or antigen-binding portion thereof according to claim 1 or 2, wherein said antibody is an IgG molecule selected from the group consisting of an IgG1 subclass, an IgG2 subclass, and an IgG3 subclass.

4. The monoclonal antibody or antigen-binding portion thereof according to claim 3, wherein said antibody is an IgG2 subclass.

5. A monoclonal antibody or an antigen-binding portion thereof that specifically binds to and activates human CD40, wherein said antibody or portion comprises a light chain variable region amino acid sequence comprising SEQ ID NO: 44 and a heavy chain variable region amino acid sequence comprising SEQ ID NO: 42.

6. The monoclonal antibody according to claim 5, which is of the IgG2 subclass.

7. The monoclonal antibody according to claim 5, which is of the IgG1 subclass.

8. A monoclonal antibody that specifically binds to and activates human CD40, wherein said antibody comprises a light chain amino acid sequence comprising SEQ ID NO: 48 without amino acid residues 1-20, and a heavy chain amino acid sequence comprising SEQ ID NO:46 without amino acid residues 1-19.

9. The monoclonal antibody according to claim 8, wherein said antibody comprises a light chain with an amino acid sequence consisting of SEQ ID NO: 48 without amino acid residues 1-20, and a heavy chain with an amino acid sequence consisting of SEQ ID NO: 46 without amino acid residues 1-19.

10. A monoclonal antibody having the heavy and light chain amino acid sequences of the antibody produced by hybridoma 21.4.1 having American Type Culture Collection (ATCC) accession number PTA-3605.

11. A monoclonal antibody or an antigen-binding portion thereof that specifically binds to and activates human CD40, wherein said antibody or portion comprises:
   (a) a light chain variable region amino acid sequence encoded by a nucleic acid comprising the sequence of SEQ ID NO: 43; and
   (b) a heavy chain variable region amino acid sequence encoded by a nucleic acid comprising the sequence of SEQ ID NO: 41.

12. A monoclonal antibody that specifically binds to and activates human CD40, wherein said antibody comprises:
   (a) a light chain amino acid sequence encoded by a nucleic acid comprising the sequence of SEQ ID NO: 47 without nucleotides 1-60; and
   (b) a heavy chain amino acid sequence encoded by a nucleic acid comprising the sequence of SEQ ID NO: 45 without nucleotides 1-57.

13. A pharmaceutical composition comprising the monoclonal antibody or antigen-binding portion thereof according to claim 1 and a pharmaceutically acceptable carrier.

14. A pharmaceutical composition comprising the monoclonal antibody or antigen-binding portion thereof according to claim 5 and a pharmaceutically acceptable carrier.

15. A pharmaceutical composition comprising the monoclonal antibody according to claim 8 or an antigen-binding portion thereof and a pharmaceutically acceptable carrier.

16. A pharmaceutical composition comprising the monoclonal antibody or antigen-binding portion thereof according to claim 2 and a pharmaceutically acceptable carrier.

17. A pharmaceutical composition comprising the monoclonal antibody according to claim 9 or an antigen-binding portion thereof and a pharmaceutically acceptable carrier.

18. A pharmaceutical composition comprising the monoclonal antibody according to claim 10 or an antigen-binding portion thereof and a pharmaceutically acceptable carrier.

19. A pharmaceutical composition comprising the monoclonal antibody or antigen-binding portion thereof according to claim 11 and a pharmaceutically acceptable carrier.

20. A pharmaceutical composition comprising the monoclonal antibody according to claim 12 or an antigen-binding portion thereof and a pharmaceutically acceptable carrier.

21. A monoclonal antibody or an antigen-binding portion thereof comprising the CDR1, CDR2, and CDR3 of the heavy chain amino acid sequence and the CDR1, CDR2, and CDR3 of the light chain amino acid sequence of the antibody produced by hybridoma 21.4.1 having American Type Culture Collection (ATCC) accession number PTA-3605.

22. The monoclonal antibody or antigen-binding portion of claim 21, comprising the heavy chain variable region amino acid sequence and the light chain variable region amino acid sequence of the antibody produced by said hybridoma.

* * * * *